(12) United States Patent
Hannus et al.

(10) Patent No.: US 8,507,546 B2
(45) Date of Patent: Aug. 13, 2013

(54) USE OF INHIBITORS OF SCAVENGER RECEPTOR CLASS PROTEINS FOR THE TREATMENT OF INFECTIOUS DISEASES

(75) Inventors: Michael Hannus, Dresden (DE); Cecilie Martin, Dresden (DE); Maria M. Mota, Lisbon (PT); Miguel Prudencio, Lisbon (PT); Christina Dias Rodrigues, Povoa de Santa Iria (PT)

(73) Assignees: Instituto de Medicina Molecular, Faculdade de Medicina da Universidade de Lisboa, Lisboa (PT); Cenix Bioscience GmbH, Dresden (DE)

( * ) Notice: Subject to any disclaimer, the term of this patent is extended or adjusted under 35 U.S.C. 154(b) by 0 days.

(21) Appl. No.: 13/548,777

(22) Filed: Jul. 13, 2012

(65) Prior Publication Data

US 2012/0276121 A1 Nov. 1, 2012

Related U.S. Application Data

(63) Continuation of application No. 12/281,438, filed as application No. PCT/EP2007/002110 on Mar. 9, 2007, now abandoned.

(60) Provisional application No. 60/780,567, filed on Mar. 9, 2006.

(30) Foreign Application Priority Data

Mar. 9, 2006 (EP) .................................... 06004854

(51) Int. Cl.
*A01N 43/02* (2006.01)
*A01N 43/18* (2006.01)
*A61K 31/38* (2006.01)

(52) U.S. Cl.
USPC ......................................... 514/432; 514/430

(58) Field of Classification Search
None
See application file for complete search history.

(56) References Cited

U.S. PATENT DOCUMENTS

| 4,057,557 A | 11/1977 | Ascher et al. |
| 2003/0186993 A1 | 10/2003 | Ulrich et al. |
| 2004/0186168 A1 | 9/2004 | Vennerstrom et al. |

FOREIGN PATENT DOCUMENTS

| WO | WO 01/16357 | 3/2001 |
| WO | WO 02/095361 | 11/2002 |
| WO | WO 03/040726 | 5/2003 |
| WO | WO 2004/032716 | 4/2004 |
| WO | WO 2005/023305 | 3/2005 |
| WO | WO 2005/087211 | 9/2005 |

OTHER PUBLICATIONS

Melnyk, P. et al. "Design, synthesis and in vitro antimalarial activity" *Bioorganic & Medicinal Chemistry*, 2006, pp. 31-35, vol. 16.
Database CA, Chemical Abstracts Service, Columbus, OH; Draper, M. et al. "Substituted tetracycline compounds for the treatment of malaria" XP002393497, Database Accession No. 2004:1036703.
Database CA, Chemical Abstracts Service, Columbus, OH; Boss, C. et al. "Preparation of substituted alkyldiamines as inhibitors of *Plasmodium falciparum* protease plasmepsin II or related aspartic proteases" XP002393498, Database Accession No. 2002:368443.
Nieland, T.J. et al. "Discovery of chemical inhibitors of the selective transfer of lipids mediated by the HDI receptor SR-BI" *PNAS*, Nov. 26, 2002, pp. 15422-15427, vol. 99, No. 24, XP-002381179.
Seedorf, U. et al. "Cholesterol absorption inhibitor Ezetimibe blocks uptake of exidized LDL in human macrophages" *Biochemical and Biophysical Research Communications*, 2004, pp. 1337-1341, vol. 320.
Serghides, L. et al. "CD36 and malaria: friends or foes?" *Trends in Parasitology*, Oct. 2003, pp. 461-469, vol. 19, No. 10, XP-002393494.
Gupta, R. et al. "3-Aminooxy-1-Aminopropane and Derivatives Have an Antiproliferative Effect on Cultured *Plasmodium faciparum* by Decreasing Intracellular Polyamine Concentrations" *Antimicrobial Agents and Chemotherapy*, Jul. 2005, pp. 2857-2864, vol. 49, No. 7, XP-002433808.
Seebacher, W. et al. "Antiprotozoal activities of new bicycle [2.2.2] octan-2-imines and esters of bicycle [2.2.2] octan-2-ols" *European Journal of Pharmaceutical Sciences*, 2005, pp. 281-289, vol. 24.
Stanek, J. et al. "A-Amidinoindan-1-one 2'-Amidinohydrazone: A New Potent and Selective Inhibitor of S-Adenosylmethionine Decarboxylase" *Journal of Medicinal Chemistry*, 1993, pp. 2168-2171, vol. 36, No. 15, XP-002269173.
Bachelet, J. et al. "Research on Nitro Derivatives of Biological Interest 19. Nitro Derivatives of 4 5 6 7 Tetra Hybrid Benzo Furans and Benzo-B-Thiophenes" *European Journal of Medicinal Chemistry*, 1979, pp. 549-552, vol. 14, No. 6, XP-009083819.
Razdan, R. K. et al. "A New Class of Antimalarial Drugs: Derivatives of Benzothiopyrans" *Journal of Medicinal Chemistry*, 1978, pp. 643-649, vol. 21, No. 7, XP-009083817.
Jeney, E. et al. "Die antimikrobielle Wirkung von neueren Aminoguanidoen The Antimicrobial Action of New Aminoguanidones" Zentralblatt fur Bakteriologie, Parasitenkunde, Infektionskrankheiten und hygiene. Erste Abteilung, 1969, pp. 107-114, vol. 210, No. 1.
Cho, S. Y. et al. "PTP-1B inhibitors: Cyclopental[d][1,2]-oxazine derivatives" *Bioorganic & Medicinal Chemistry Letters*, 2006, pp. 499-502, vol. 16.

*Primary Examiner* — Sreeni Padmanabhan
*Assistant Examiner* — Svetlana M Ivanova
(74) *Attorney, Agent, or Firm* — Saliwanchik, Lloyd & Eisenschenk

(57) ABSTRACT

The present invention relates to the use of inhibitors of scavenger receptor class proteins, in particular ScarB1 for the production of a medicament for treatment of and/or prophylaxis against infections, involving liver cells and/or hematopoietic cells, in particular malaria.

5 Claims, 24 Drawing Sheets

Figure 1:
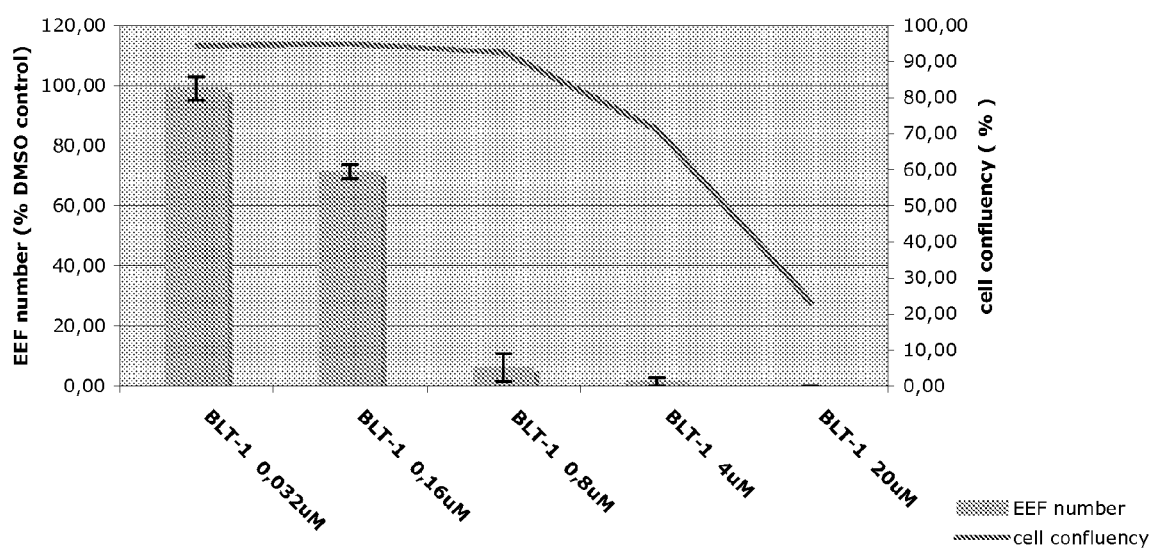

Fig. 6
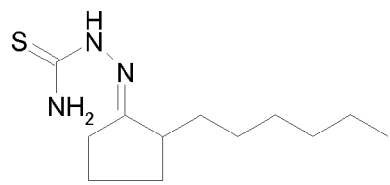
BLT-1
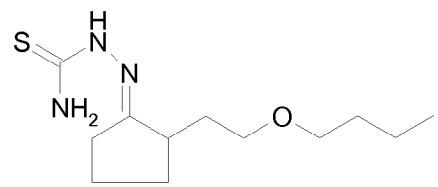
BLT-2
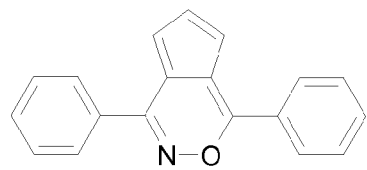
BLT-3
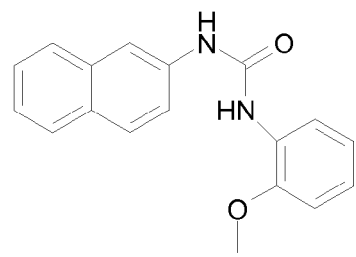
BLT-4
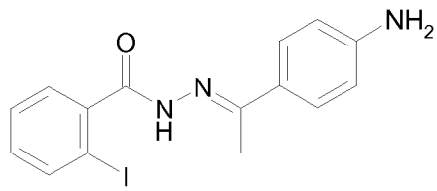
BLT-5
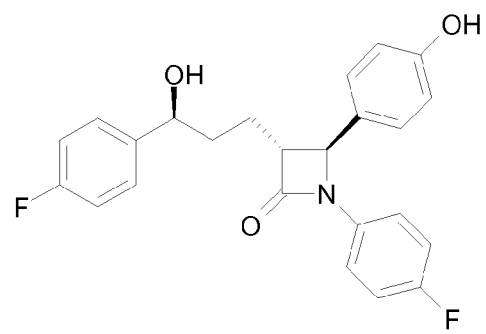
Ezetimibe

Fig. 9

| gene | siRNA id | siRNA sequence, sense strand | siRNA sequence, antisense strand |
|---|---|---|---|
| ScarB1 | 107731 | GGCAUUGGACAAACUGGGATT | UCCCAGUUUGUCCAAUGCCTG |
| ScarB1 | 111573 | GCUCAUCAUGACCUUGGCATT | UGCCAAGGUCAUGAUGAGCTT |
| ScarB1 | 111574 | GGACAAGUUCGGAUUAUUUTT | AAAUAAUCCGAACUUGUCCTT |

Fig. 10

```
   1  CGTCGCCGTC CCCGTCTCCT GCCAGGCGCG GAGCCCTGCG AGCCGCGGGT GGGCCCCAGG CGCGCAGACA    70
  71  TGGGCTGCTC CGCCAAAGCG CGCTGGGCTG CCGGGGCGCT GGGCGTCGCG GGGCTACTGT GCGCTGTGCT   140
 141  GGGCGCTGTC ATGATCGTGA TGGTGCCGTC GCTCATCAAG CAGCAGGTCC TTAAGAACGT GCGCATCGAC   210
 211  CCCAGTAGCC TGTCCTTCAA CATGTGGAAG GAGATCCCTA TCCCCTTCTA TCTCTCCGTC TACTTCTTTG   280
 281  ACGTCATGAA CCCCAGCGAG ATCCTGAAGG GCGAGAAGCC GCAGGTGCGG GAGCGCGGGC CCTACGTGTA   350
 351  CAGGGAGTCC AGGCACAAAA GCAACATCAC CTTCAACAAC AACGACACCG TGTCCTTCCT CGAGTACCGC   420
 421  ACCTTCCAGT TCCAGCCCTC CAAGTCCCAC GGCTCGGAGA GCGACTACAT CGTCATGCCC AACATCCTGG   490
 491  TCTTGGGTGC GGCGGTGATG ATGGAGAATA AGCCCATGAC CCTGAAGCTC ATCATGACCT TGGCATTCAC   560
 561  CACCCTCGGC GAACGTGCCT TCATGAACCG CACTGTGGGT GAGATCATGT GGGGCTACAA GGACCCCCTT   630
 631  GTGAATCTCA TCAACAAGTA CTTTCCAGGC ATGTTCCCCT TCAAGGACAA GTTCGGATTA TTTGCTGAGC   700
 701  TCAACAACTC CGACTCTGGG CTCTTCACGG TGTTCACGGG GGTCCAGAAC ATCAGCAGGA TCCACCTCGT   770
 771  GGACAAGTGG AACGGGCTGA GCAAGGTTGA CTTCTGGCAT TCCGATCAGT GCAACATGAT CAATGAAACT   840
 841  TCTGGGCAAA TGTGGCCGCC CTTCATGACT CCTGAGTCCT CGCTGGAGTT CTACAGCCCG GAGGCCTGCC   910
 911  GATCCATGAA GCTAATGTAC AAGGAGTCAG GGGTGTTTGA AGGCATCCCC ACCTATCGCT TCGTGGCTCC   980
 981  CAAAACCCTG TTTGCCAACG GGTCCATCTA CCCACCCAAC GAAGGCTTCT GCCCGTGCCT GGAGTCTGGA  1050
1051  ATTCAGAACG TCAGCACCTG CAGGTTCAGT GCCCCCTTGT TTCTCTCCCA TCCTCACTTC CTCAACGCCG  1120
1121  ACCCGGTTCT GGCAGAAGCG GTGACTGGCC TGCACCCTAA CCAGGAGGCA CACTCCTTGT TCCTGGACAT  1190
1191  CCACCCGGTC ACGGGAATCC CCATGAACTG CTCTGTGAAA CTGCAGCTGA GCCTCTACAT GAAATCTGTC  1260
1261  GCAGGCATTG ACAAACTGG GAAGATTGAG CCTGTGGTCC TGCCGCTGCT CTGGTTTGCA GAGAGCGGGG  1330
1331  CCATGGAGGG GGAGACTCTT CACACATTCT ACACTCAGCT GGTGTTGATG CCCAAGGTGA TGCACTATGC  1400
1401  CCAGTACGTC CTCCTGGCGC TGGGCTGCGT CCTGCTGCTG GTCCCTGTCA TCTGCCAAAT CCGGAGCCAA  1470
1471  GAGAAATGCT ATTTATTTTG GAGTAGTAGT AAAAAGGGCT CAAAGGATAA GGAGGCCATT CAGGCCTATT  1540
1541  CTGAATCCCT GATGACATCA GCTCCCAAGG GCTCTGTGCT GCAGGAAGCA AAACTGTAGG GTCCTGAGGA  1610
1611  CACCGTGAGC CAGCCAGGCC TGGCCGCTGG GCCTGACCGG CCCCCCAGCC CCTACACCCC GCTTCTCCCG  1680
1681  GACTCTCCCA GCAGACAGCC CCCCAGCCCC ACAGCCTGAG CCTCCCAGCT GCCATGTGCC TGTTCACACC  1750
1751  CTGCACACAC GCCCTGGCAC ACATACACAC ATGCGTGCAG GCTTGTGCAG ACACTCAGGG ATGGAGCTGC  1820
1821  TGCTGAAGGG ACTTGTAGGG AGAGGCTCGT CAACAAGCAC TGTTCTGGAA CCTTCTCTCC ACGTGGCCCA  1890
1891  CAGGCTGACC ACAGGGGCTG TGGGTCCTGC GTCCCCTTCC TCGGGTGAGC CTGGCCTGTC CCGTTCAGCC  1960
1961  GTTGGGCCAG GCTTCCTCCC CTCCAAGGTG AAACACTGCA GTCCCGGTGT GGTGGCTCCC CATGCAGGAC  2030
2031  GGGCCAGGCT GGGAGTGCCG CCTTCCTGTG CCAAATTCAG TGGGGACTCA GTGCCCAGGC CCTGGCACGA  2100
2101  GCTTTGGCCT TGGTCTACCT GCCAGGCCAG GCAAAGCGCC TTTACACAGG CCTCGGAAAA CAATGGAGTG  2170
2171  AGCACAAGAT GCCCTGTGCA GCTGCCCGAG GGTCTCCGCC CACCCCGGCC GGACTTTGAT CCCCCCGAAG  2240
2241  TCTTCACAGG CACTGCATCG GGTTGTCTGG CGCCCTTTTC CTCCAGCCTA AACTGACATC ATCCTATGGA  2310
2311  CTGAGCCGGC CACTCTCTGG CCGAAGTGGC GCAGGCTGTG CCCCCGAGCT GCCCCCACCC CCTCACAGGG  2380
2381  TCCCTCAGAT TATAGGTGCC CAGGCTGAGG TGAAGAGGCC TGGGGCCCCT GCCTTCCGGG CGCTCCTGGA  2450
2451  CCCTGGGGCA AACCTGTGAC CCTTTTCTAC TGGAATAGAA ATGAGTTTTA TCATCTTTGA AAAATAATTC  2520
2521  ACTCTTGAAG TAATAAACGT TTAAAAAAAT GGAAAAAAAA AAAAA                             2566
```

Fig. 11

```
  1   MGCSAKARWA AGALGVAGLL CAVLGAVMIV MVPSLIKQQV LKNVRIDPSS LSFNMWKEIP    60
 61   IPFYLSVYFF DVMNPSEILK GEKPQVRERG PYVYRESRHK SNITFNNNDT VSFLEYRTFQ   120
121   FQPSKSHGSE SDYIVMPNIL VLGAAVMMEN KPMTLKLIMT LAFTTLGERA FMNRTVGEIM   180
181   WGYKDPLVNL INKYFPGMFP FKDKFGLFAE LNNSDSGLFT VFTGVQNISR IHLVDKWNGL   240
241   SKVDFWHSDQ CNMINGTSGQ MWPPFMTPES SLEFYSPEAC RSMKLMYKES GVFEGIPTYR   300
301   FVAPKTLFAN GSIYPPNEGF CPCLESGIQN VSTCRFSAPL FLSHPHFLNA DPVLAEAVTG   360
361   LHPNQEAHSL FLDIHPVTGI PMNCSVKLQL SLYMKSVAGI GQTGKIEPVV LPLLWFAESG   420
421   AMEGETLHTF YTQLVLMPKV MHYAQYVLLA LGCVLLLVPV ICQIRSQEKC YLFWSSSKKG   490
481   SKDKEAIQAY SESLMTSAPK GSVLQEAKL                                    509
```

Fig. 13
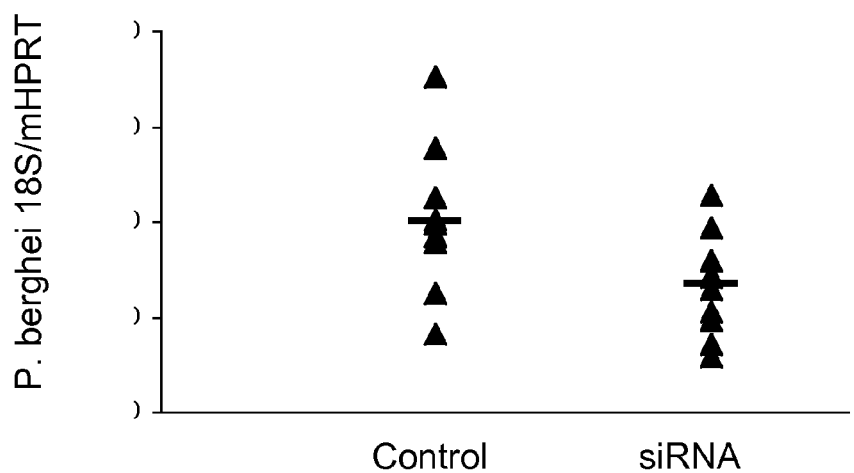
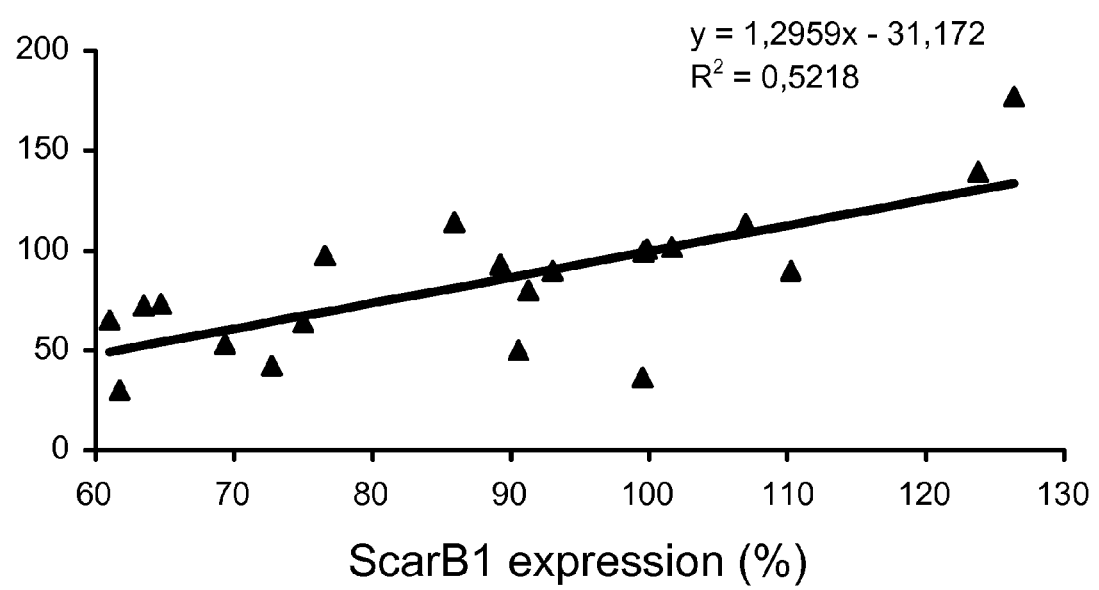

Fig. 16

| Compound No. | STRUCTURE | Molecular Formula | Molecular Weight | Infection score |
|---|---|---|---|---|
| 1 | 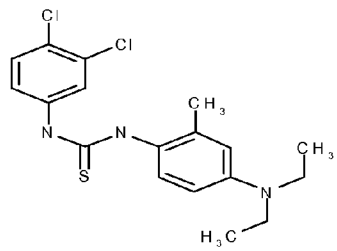 | C18H21Cl2N3S | 382,35817 | 4 |
| 97 | 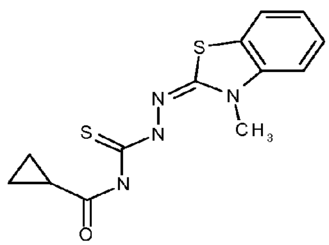 | C13H14N4OS2 | 306,41073 | 4 |
| 237 | 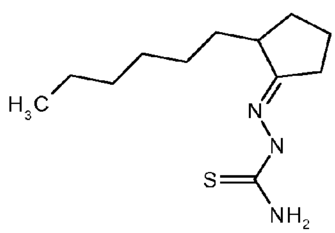 | C12H23N3S | 241,40121 | 4 |
| 217 | 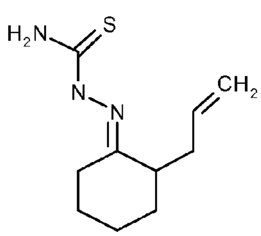 | C10H17N3S | 211,33109 | 4 |
| 5 | 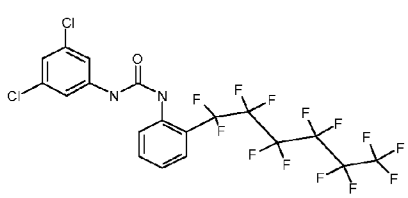 | C19H9Cl2F13N2O | 599,18158 | 3 |

Figure 16:
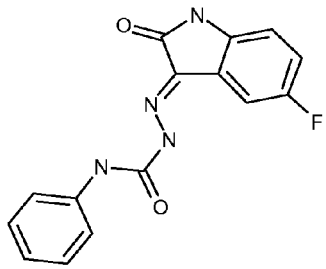

Fig. 16 (continued)
| | | C14H19N3S | 261,39163 | |
|---|---|---|---|---|
| 7 |  | | | 3 |
| 121 | 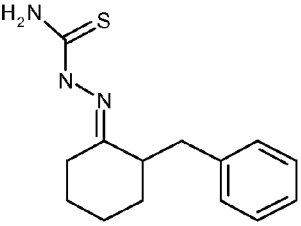 | C14H19N3S | 261,39163 | 3 |
| 234 | 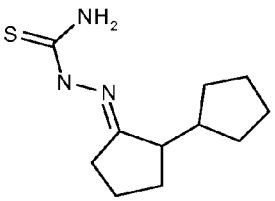 | C11H19N3S | 225,35818 | 3 |
| 2 | 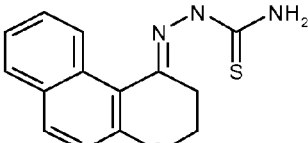 | C14H13N3OS | 271,34321 | 3 |
| 4 | 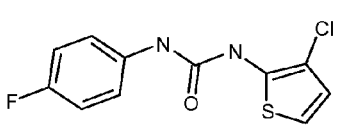 | C11H8ClFN2OS | 270,71461 | 3 |
| 3 | 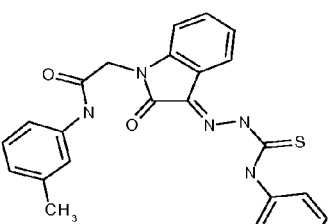 | C24H21N5O2S | 443,53127 | 3 |

Fig. 16 (continued)

| | | C19H11F13N2O | 530,29152 | |
|---|---|---|---|---|
| 6 | | | | 3 |
| 8 | | C18H16N4O | 304,35442 | 2 |
| 9 | | C17H26N2O | 274,40957 | 2 |
| 10 | | C19H26N2O | 298,43187 | 2 |
| 11 | | C18H26N2S | 302,48532 | 2 |
| 13 | | C19H16Cl2N2S | 375,32277 | 2 |

Fig. 16 (continued)

| | | | | |
|---|---|---|---|---|
| 85 | | C17H17N5OS | 339,42194 | 2 |
| 124 | | C8H16N4 | 168,24352 | 2 |
| 222 | | C11H20N4 | 208,30885 | 2 |
| 230 | | C9H17N3S | 199,31994 | 2 |
| 232 | | C13H21N3S | 251,39642 | 2 |

Fig. 16 (continued)

| | | | | |
|---|---|---|---|---|
| 12 | | C24H33N3S | 395,61471 | 2 |
| 14 | | C8H9N3S3 | 243,37303 | 2 |
| 16 | | C16H17N5OS | 327,41079 | 1 |
| 18 | | C20H24N2O | 308,42708 | 1 |
| 81 | | C18H19N3O2S | 341,43503 | 1 |

Fig. 16 (continued)

| | | | | |
|---|---|---|---|---|
| 92 | | C20H20N6OS2 | 424,55 | 1 |
| 99 | | C9H9N5S | 219,26958 | 1 |
| 106 | | C16H11F3N4OS | 364,35147 | 1 |
| 112 | | C13H18N4S | 262,37921 | 1 |
| 126 | | C13H26N4 | 238,37897 | 1 |
| 127 | | C13H22N4 | 234,34709 | 1 |

Fig. 16 (continued)

| | | | | |
|---|---|---|---|---|
| 164 | | C14H14N2OS | 258,34448 | 1 |
| 218 | | C8H15N3S | 185,29285 | 1 |
| 226 | | C13H17N3S | 247,36454 | 1 |
| 228 | | C13H25N3S | 255,4283 | 1 |
| 19 | | C16H20BrClN2S | 387,7722 | 1 |
| 94 | | C18H17N3S | 307,42029 | 1 |

Fig. 16 (continued)

| | | | | |
|---|---|---|---|---|
| 118 | | C17H14Cl2N4O2S | 409,29673 | 1 |
| 162 | | C17H20N2OS | 300,42575 | 1 |
| 75 | | CH5N3S | 91,1351 | 0 |
| 76 | | CH6ClN3O | 111,53147 | 0 |
| 236 | | C12H23N3O | 225,33661 | 0 |

| 41 |  | C15H11FN4O2 | 298,27892 | 0 |

SEQUENCE LISTING

<160> NUMBER OF SEQ ID NOS: 9

<210> SEQ ID NO 1
<211> LENGTH: 2555
<212> TYPE: DNA
<213> ORGANISM: Homo sapiens

<400> SEQUENCE: 1

-continued

```
gtcgccgtcc ccgtctcctg ccaggcgcgg agccctgcga gccgcgggtg ggccccaggc    60
gcgcagacat gggctgctcc gccaaagcgc gctgggctgc cggggcgctg ggcgtcgcgg   120
ggctactgtg cgctgtgctg ggcgctgtca tgatcgtgat ggtgccgtcg ctcatcaagc   180
agcaggtcct taagaacgtg cgcatcgacc ccagtagcct gtccttcaac atgtggaagg   240
agatccctat ccccttctat ctctccgtct acttctttga cgtcatgaac cccagcgaga   300
tcctgaaggg cgagaagccg caggtgcggg agcgcgggcc ctacgtgtac agggagttca   360
ggcacaaaag caacatcacc ttcaacaaca cgacaccgt gtccttcctc gagtaccgca    420
ccttccagtt ccagccctcc aagtcccacg gctcggagag cgactacatc gtcatgccca   480
acatcctggt cttgggtgcg gcggtgatga tggagaataa gcccatgacc ctgaagctca   540
tcatgacctt ggcattcacc accctcggcg aacgtgcctt catgaaccgc actgtgggtg   600
agatcatgtg gggctacaag gaccccttg tgaatctcat caacaagtac tttccaggca   660
tgttcccctt caaggacaag ttcggattat ttgctgagct caacaactcc gactctgggc   720
tcttcacggt gttcacgggg gtccagaaca tcagcaggat ccacctcgtg gacaagtgga   780
acgggctgag caaggttgac ttctggcatt ccgatcagtg caacatgatc aatgaaactt   840
ctgggcaaat gtggccgccc ttcatgactc ctgagtcctc gctggagttc tacagcccgg   900
aggcctgccg atccatgaag ctaatgtaca aggagtcagg ggtgtttgaa ggcatcccca   960
cctatcgctt cgtggctccc aaaaccctgt ttgccaacgg gtccatctac ccacccaacg  1020
aaggcttctg cccgtgcctg gagtctggaa ttcagaacgt cagcacctgc aggttcagtg  1080
cccccttgtt tctctcccat cctcacttcc tcaacgctga cccggttctg gcagaagcgg  1140
tgactggcct gcaccctaac caggaggcac actccttgtt cctggacatc cacccggtca  1200
cgggaatccc catgaactgc tctgtgaaac tgcagctgag cctctacatg aaatctgtcg  1260
caggcattgg acaaactggg aagattgagc ctgtggtcct gccgctgctc tggttttgcag  1320
agagcggggc catggagggg gagactcttc acacattcta cactcagctg gtgttgatgc  1380
ccaaggtgat gcactatgcc cagtacgtcc tcctggcgct gggctgcgtc ctgctgctgg  1440
tccctgtcat ctgccaaatc cggagccaag agaaatgcta tttatttgg agtagtagta  1500
aaaagggctc aaaggataag gaggccattc aggcctattc tgaatccctg atgacatcag  1560
ctcccaaggg ctctgtgctg caggaagcaa aactgtaggg tcctgaggac accgtgagcc  1620
agccaggcct ggccgctggg cctgaccggc ccccagccc ctacacccg cttctcccgg   1680
actctcccag cggacagccc cccagcccca cagcctgagc ctcccagctg ccatgtgcct  1740
gttgcacacc tgcacacacg ccctggcaca catacacaca tgcgtgcagg cttgtgcaga  1800
cactcaggga tggagctgct gctgaaggga cttgtaggga gaggctcgtc aacaagcact  1860
gttctggaac cttctctcca cgtggcccac aggcctgacc acaggggctg tgggtcctgc  1920
gtccccttcc tcgggtgagc ctggcctgtc ccgttcagcc gttgggccca ggcttcctcc  1980
cctccaaggt gaaacactgc agtcccggtg tggtggctcc ccatgcagga cgggccaggc  2040
tgggagtgcc gccttcctgt gccaaattca gtgggactc agtgcccagg ccctggccac  2100
gagctttggc cttggtctac ctgccaggcc aggcaaagcg cctttacaca ggcctcggaa  2160
aacaatggag tgagcacaag atgccctgtg cagctgcccg agggtctccg cccacccgg   2220
ccggactttg atcccccga agtcttcaca ggcactgcat cgggttgtct ggcgcccttt  2280
tcctccagcc taaactgaca tcatcctatg gactgagccg gccactctct ggccgaagtg  2340
gccgcaggct gtgcccccga gctgcccca ccccctcaca gggtccctca gattataggt  2400
```

-continued

```
gcccaggctg aggtgaagag gcctgggggc cctgccttcc gggcgctcct ggaccctggg    2460
gcaaacctgt gaccctttc tactggaata gaaatgagtt ttatcatctt tgaaaaataa     2520
ttcactcttg aagtaataaa cgtttaaaaa aatgg                               2555
```

<210> SEQ ID NO 2
<211> LENGTH: 1230
<212> TYPE: DNA
<213> ORGANISM: Homo sapiens

<400> SEQUENCE: 2

```
atgggctgct ccgccaaagc gcgctgggct gccggggcgc tgggcgtcgc ggggctactg    60
tgcgctgtgc tgggcgctgt catgatcgtg atggtgccgt cgctcatcaa gcagcaggtc   120
cttaagggtg cggcggtgat gatggagaat aagcccatga ccctgaagct catcatgacc   180
ttggcattca ccaccctcgg cgaacgtgcc ttcatgaacc gcactgtggg tgagatcatg   240
tggggctaca aggaccccct tgtgaatctc atcaacaagt actttccagg catgttcccc   300
ttcaaggaca agttcggatt atttgctgag ctcaacaact ccgactctgg gctcttcacg   360
gtgttcacgg gggtccagaa catcagcagg atccacctcg tggacaagtg aacgggctg    420 agcaaggttg acttctggca ttccgatcag tgcaacatga tcaatggaac ttctgggcaa   480
atgtggccgc ccttcatgac tcctgagtcc tcgctggagt tctacagccc ggaggcctgc   540
cgatccatga agctaatgta caaggagtca ggggtgtttg aaggcatccc cacctatcgc   600
ttcgtggctc ccaaaaccct gtttgccaac gggtccatct acccacccaa cgaaggcttc   660
tgcccgtgcc tggagtctgg aattcagaac gtcagcacct gcaggttcag tgccccttg    720 tttctctccc atcctcactt cctcaacgct gacccggttc tggcagaagc ggtgactggc   780
ctgcacccta ccaggaggc acactccttg ttcctggaca tccacccggt cacgggaatc    840
cccatgaact gctctgtgaa actgcagctg agcctctaca tgaaatctgt cgcaggcatt   900
ggacaaactg ggaagattga gcctgtggtc ctgccgctgc tctggtttgc agagagcggg   960 gccatgagg gggagactct tcacacattc tacactcagc tggtgttgat gcccaaggtg    1020
atgcactatg cccagtacgt cctcctggcg ctgggctgcg tcctgctgct ggtccctgtc   1080
atctgccaaa tccggagcca agagaaatgc tatttatttt ggagtagtag taaaaagggc   1140 tcaaggata aggaggccat tcaggcctat tctgaatccc tgatgacatc agctcccaag    1200
ggctctgtgc tgcaggaagc aaaactgtag                                     1230
```

<210> SEQ ID NO 3
<211> LENGTH: 21
<212> TYPE: DNA
<213> ORGANISM: Artificial
<220> FEATURE:
<223> OTHER INFORMATION: siRNA sequence, sense strand

<400> SEQUENCE: 3

```
ggcauuggac aaacugggau t                                              21
```

<210> SEQ ID NO 4
<211> LENGTH: 21
<212> TYPE: DNA
<213> ORGANISM: Artificial
<220> FEATURE:
<223> OTHER INFORMATION: siRNA sequence, antisense strand

<400> SEQUENCE: 4

```
ucccaguuug uccaaugcct g                                              21
```

```
<210> SEQ ID NO 5
<211> LENGTH: 21
<212> TYPE: DNA
<213> ORGANISM: Artificial
<220> FEATURE:
<223> OTHER INFORMATION: siRNA sequence, sense strand

<400> SEQUENCE: 5
gcucaucaug accuuggcat t                                              21

<210> SEQ ID NO 6
<211> LENGTH: 21
<212> TYPE: DNA
<213> ORGANISM: Artificial
<220> FEATURE:
<223> OTHER INFORMATION: siRNA sequence, antisense strand

<400> SEQUENCE: 6
ugccaagguc augaugagct t                                              21

<210> SEQ ID NO 7
<211> LENGTH: 21
<212> TYPE: DNA
<213> ORGANISM: Artificial
<220> FEATURE:
<223> OTHER INFORMATION: siRNA sequence, sense strand

<400> SEQUENCE: 7
ggacaaguuc ggauuauuut t                                              21

<210> SEQ ID NO 8
<211> LENGTH: 21
<212> TYPE: DNA
<213> ORGANISM: Artificial
<220> FEATURE:
<223> OTHER INFORMATION: siRNA sequence, antisense strand

<400> SEQUENCE: 8
aaauaauccg aacuugucct t                                              21

<210> SEQ ID NO 9
<211> LENGTH: 509
<212> TYPE: PRT
<213> ORGANISM: Homo sapiens

<400> SEQUENCE: 9
```

Met Gly Cys Ser Ala Lys Ala Arg Trp Ala Gly Ala Leu Gly Val
1               5                   10                  15

Ala Gly Leu Leu Cys Ala Val Leu Gly Ala Val Met Ile Val Met Val
                20                  25                  30

Pro Ser Leu Ile Lys Gln Gln Val Leu Lys Asn Val Arg Ile Asp Pro
        35                  40                  45

Ser Ser Leu Ser Phe Asn Met Trp Lys Glu Ile Pro Ile Pro Phe Tyr
    50                  55                  60

Leu Ser Val Tyr Phe Phe Asp Val Met Asn Pro Ser Glu Ile Leu Lys
65                  70                  75                  80

Gly Glu Lys Pro Gln Val Arg Glu Arg Gly Pro Tyr Val Tyr Arg Glu
                85                  90                  95

Ser Arg His Lys Ser Asn Ile Thr Phe Asn Asn Asn Asp Thr Val Ser
            100                 105                 110

Phe Leu Glu Tyr Arg Thr Phe Gln Phe Gln Pro Ser Lys Ser His Gly
        115                 120                 125

```
Ser Glu Ser Asp Tyr Ile Val Met Pro Asn Ile Leu Val Leu Gly Ala
130                 135                 140

Ala Val Met Met Glu Asn Lys Pro Met Thr Leu Lys Leu Ile Met Thr
145                 150                 155                 160

Leu Ala Phe Thr Thr Leu Gly Glu Arg Ala Phe Met Asn Arg Thr Val
                165                 170                 175

Gly Glu Ile Met Trp Gly Tyr Lys Asp Pro Leu Val Asn Leu Ile Asn
                180                 185                 190

Lys Tyr Phe Pro Gly Met Phe Pro Phe Lys Asp Lys Phe Gly Leu Phe
                195                 200                 205

Ala Glu Leu Asn Asn Ser Asp Ser Gly Leu Phe Thr Val Phe Thr Gly
210                 215                 220

Val Gln Asn Ile Ser Arg Ile His Leu Val Asp Lys Trp Asn Gly Leu
225                 230                 235                 240

Ser Lys Val Asp Phe Trp His Ser Asp Gln Cys Asn Met Ile Asn Gly
                245                 250                 255

Thr Ser Gly Gln Met Trp Pro Pro Phe Met Thr Pro Glu Ser Ser Leu
                260                 265                 270

Glu Phe Tyr Ser Pro Glu Ala Cys Arg Ser Met Lys Leu Met Tyr Lys
                275                 280                 285

Glu Ser Gly Val Phe Glu Gly Ile Pro Thr Tyr Arg Phe Val Ala Pro
                290                 295                 300

Lys Thr Leu Phe Ala Asn Gly Ser Ile Tyr Pro Pro Asn Glu Gly Phe
305                 310                 315                 320

Cys Pro Cys Leu Glu Ser Gly Ile Gln Asn Val Ser Thr Cys Arg Phe
                325                 330                 335

Ser Ala Pro Leu Phe Leu Ser His Pro His Phe Leu Asn Ala Asp Pro
                340                 345                 350

Val Leu Ala Glu Ala Val Thr Gly Leu His Pro Asn Gln Glu Ala His
                355                 360                 365

Ser Leu Phe Leu Asp Ile His Pro Val Thr Gly Ile Pro Met Asn Cys
370                 375                 380

Ser Val Lys Leu Gln Leu Ser Leu Tyr Met Lys Ser Val Ala Gly Ile
385                 390                 395                 400

Gly Gln Thr Gly Lys Ile Glu Pro Val Val Leu Pro Leu Leu Trp Phe
                405                 410                 415

Ala Glu Ser Gly Ala Met Glu Gly Glu Thr Leu His Thr Phe Tyr Thr
                420                 425                 430

Gln Leu Val Leu Met Pro Lys Val Met His Tyr Ala Gln Tyr Val Leu
                435                 440                 445

Leu Ala Leu Gly Cys Val Leu Leu Val Pro Val Ile Cys Gln Ile
450                 455                 460

Arg Ser Gln Glu Lys Cys Tyr Leu Phe Trp Ser Ser Lys Lys Gly
465                 470                 475                 480

Ser Lys Asp Lys Glu Ala Ile Gln Ala Tyr Ser Glu Ser Leu Met Thr
                485                 490                 495

Ser Ala Pro Lys Gly Ser Val Leu Gln Glu Ala Lys Leu
                500                 505
```

USE OF INHIBITORS OF SCAVENGER RECEPTOR CLASS PROTEINS FOR THE TREATMENT OF INFECTIOUS DISEASES

CROSS-REFERENCE TO RELATED APPLICATIONS

This application is a continuation of U.S. Ser. No. 12/281,438, filed Dec. 12, 2008, which is the U.S. national stage application of International Patent Application No. PCT/EP2007/002110, filed Mar. 9, 2007, which claims the benefit of U.S. Provisional Patent Application No. 60/780,567, filed Mar. 9, 2006, the disclosures of which are hereby incorporated by reference in their entireties, including all figures, tables and amino acid or nucleic acid sequences.

The Sequence Listing for this application is labeled "SeqList.txt" which was created on Jul. 13, 2012 and is 11 KB. The entire contents of the sequence listing is incorporated herein by reference in its entirety.

The present invention relates to the use of inhibitors of scavenger receptor class proteins, in particular ScarB1 for the production of a medicament for therapy of and/or prophylaxis against infections, involving liver cells and/or hematopoietic cells, in particular malaria.

Malaria is a major health problem, mainly in Sub-Saharan Africa and in some parts of Asia and South America. Each year there are about 600 million new clinical cases and at least one million individuals, mostly children, die from malaria. This reality is even more depressing realising that a death from malaria occurs every 30 seconds. Over 90% of the deaths occur in Africa. Within the last 10 to 15 years the burden of malaria has been increasing mainly because of the emergence of *Plasmodium falciparum* and *P. vivax* variants that are resistant to cheap drugs such as chloroquine, mefloquine, and pyrimethamine. In the light of the failure of the development of a malaria vaccine, despite intensive efforts, the development of novel anti-malarial drugs is crucial.

Death by malaria is almost exclusively caused by *P. falciparum*, transmitted by the vector *Anopheles gambiae*, which preferentially feeds on humans. As the mosquito bites, sporozoites are injected into the skin. After finding of a blood vessel, they travel directly to the liver. Once there, they migrate through several hepatocytes before they infect a final one, surrounded by a parasitophorous vacuole where the intrahepatic form of the parasite grows and multiplies. This asymptomatic phase is known as the liver or hepatic stage of disease. During this period there is an amazing parasite multiplication (each parasite gives rise to 10-30 thousand new parasites in 2-7 days depending on the parasite species). Eventually, the infected hepatocytes burst, releasing the parasites into the bloodstream, where they will target and invade the red blood cells (RBCs). The blood or erythrocytic stage of *Plasmodium*'s life cycle corresponds to the symptomatic phase of a malaria infection. The parasites invade and multiply within the RBCs and, upon rupturing the erythrocytic membrane, are released into the blood where they target new erythrocytes.

The hepatic stage of a *Plasmodium* infection constitutes an appealing target for the development of anti-malarial drugs since these would act before the onset of pathology. Despite the importance of such knowledge, little is known about the parasite's requirements and the strategies it developed in order to successfully invade and develop inside the liver cells.

*Plasmodium sporozoites* only develop in a very restricted type of cell, such as hepatocytes or hepatoma cell lines, strongly suggesting a crucial role of the host cell in sustaining the growth and development of this parasite.

To model this infection, the inventors have developed an assay monitoring infection and maturation of *Plasmodium berghei* ANKA, a mouse-pathogenic close relative of the human-pathogenic *Plasmodium falciparum* strain, in cultured human hepatoma cells.

This assay has also been used for the identification of new host factors required for sporozoit development by RNA interference (RNAi) screening. Surprisingly, it was found that a family of receptors termed "scavenger receptors" is required for development/proliferation of sporozoite in hepatic cells. The function of scavenger receptors B1 (ScarB1) was characterized in WO 96/00288, U.S. Pat. Nos. 6,359,859 and 6,429,289. It was reported by that ScarB1 is expressed principally in steroidogenic tissues and liver and appears to mediate HDL-transfer and uptake of cholesterol. Competitive binding studies showed that ScarB1 binds LDL, modified LDL, negatively charged phospholipid, and HDL. Direct binding studies show that ScarB1 expressed in mammalian cells (for example, a variant of CHO cells) binds HDL, without cellular degradation of the HDL-apoprotein, and lipid is accumulated within cells expressing the receptor. These studies indicated that ScarB1 might play a major role in transfer of cholesterol from peripheral tissues, via HDL, into the liver and steroidogenic tissues, and that increased or decreased expression in the liver or other tissues may be useful in regulating uptake of cholesterol by cells expressing ScarB1. Subsequent studies confirmed that ScarB1 not only binds to lipid, but also transfers cholesterol into and out of cells, (see, e.g. U.S. Pat. Nos. 5,962, 322 and 5,925, 333). Furthermore this receptor has been shown to affect female fertility, as described in WO 99/11288. Research on the role of scavenger family proteins, in particular on the role of ScarB1 have led to the identification of a large number of modulators of ScarB1 function (see, e.g. WO 2004/032716 A2). The function of ScarB1 first observed by the present inventors, which is entirely unrelated to the hitherto described functions of ScarB1 created the opportunity to test known inhibitors of ScarB1 function for their effect on infectious diseases, involving liver cells. It was observed that inhibitors of ScarB 1 function inhibit the growth of protozoa in liver cells, thus, that inhibitors of ScarB1 can be used to treat infectious diseases involving liver cells and since the ScarB 1 is expressed in erythrocytes, in hematopoietic cells, in particular malaria.

SUMMARY OF THE INVENTION

Accordingly, in a first aspect the present invention provides the use of inhibitors of a scavenger receptor class protein for the production of a medicament for the therapy of and/or prophylaxis against infections involving liver cells and/or hematopoietic cells, in particular protozoal infections, e.g. malaria.

In a preferred embodiment of the use of the present invention the inhibitor of the scavenger receptor class protein has a structure according to formula (I):

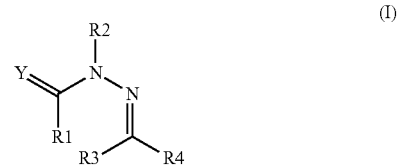

wherein, $R^1$ is $NR^5R^6$;

$R^2$ is hydrogen or alkyl, optionally substituted, preferably hydrogen;

$R^3$ and $R^4$ together form a cycloalkyl, heterocycloalkyl, cycloalkenyl or heterocycloalkenyl, optionally substituted;

$R^5$ is hydrogen or alkyl, optionally substituted, preferably hydrogen;

$R^6$ hydrogen, hydroxyl, halogen, alkyl, cycloalkyl, heteroalkyl, cycloheteroalkyl, aryl, aralkyl, heteroaryl, heteroaralkyl, alkenyl, cycloalkenyl, alkynyl, alkanoyl, alkoxyalkyl; or —CO—R'; optionally substituted, preferably hydrogen, aryl or —CO—R', wherein R' is hydrogen; alkyl; cycloalkyl; alkenyl; cycloalkenyl; aryl; aralkyl; heteroalkyl; cycloheteroalkyl; heteroaryl; heteroaralkyl; or alkynyl;

and

Y is S or N, preferably S;

or is a pharmaceutically acceptable salt thereof.

In a further preferred embodiment of the use of the present invention the inhibitor of the scavenger receptor class protein has a structure according to formula (XXXII):

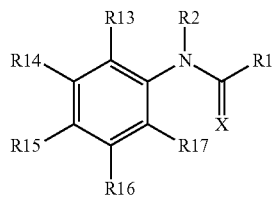

(XXXII)

wherein, $R^1$ is $NR^5R^6$;

$R^2$ is hydrogen or alkyl, optionally substituted;

$R^5$ is hydrogen, alkyl or alkenyl, optionally substituted;

$R^6$ is hydrogen, hydroxyl, halogen, alkyl, heteroalkyl, cycloalkyl, cycloheteroalkyl, aryl, aralkyl, heteroaryl, heteroaralkyl, alkenyl, cycloalkenyl, heteroalkenyl, cycloheteroalkenyl or alkynyl, optionally substituted, preferably cycloalkyl, cycloheteroalkyl, aryl or heteroaryl; and $R^{13}$, $R^{14}$, $R^{15}$, $R^{16}$, and $R^{17}$ are independent of each other hydrogen, hydroxyl, halogen, $SO_2$, $NO_2$, CN; alkyl, heteroalkyl, cycloalkyl, heterocycloalkyl, alicyclic system, aryl, aralkyl, aralkenyl, aralkynyl, heteroaryl, heteroaralkyl, heteroaralkenyl, heteroaralkynyl, alkenyl, cycloalkenyl, alkynyl, or $NR^{11}R^{12}$, optionally substituted;

$R^{11}$ is hydrogen or alkyl, optionally substituted;

$R^{12}$ is hydrogen, hydroxyl, halogen, alkyl, heteroalkyl, aryl, aralkyl, heteroaryl, heteroaralkyl, alkenyl, cycloalkenyl, or alkynyl, optionally substituted; and X is S or O;

or is a pharmaceutically acceptable salt thereof.

In a further preferred embodiment of the use of the present invention the inhibitor of the scavenger receptor class protein has a structure according to formula (IL):

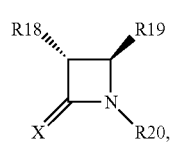

(IL)

wherein $R^{18}$ is alkyl, alkenyl, aryl, aralkyl, heteroaryl, or heteroaralkyl, optionally substituted;

$R^{19}$ and $R^{20}$ are independently alkyl, alkenyl, aryl or heteroaryl, optionally substituted;

and

X is O or S or is a pharmaceutically acceptable salt thereof.

In a preferred embodiment of the use of the present invention the inhibitor of the scavenger receptor class protein has a structure according to formula (LI):

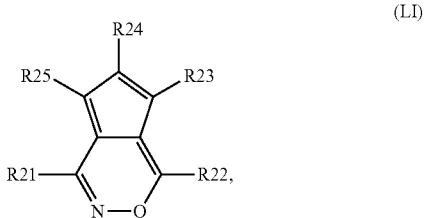

(LI)

wherein $R^{21}$ and $R^{22}$ are independent of each other aryl, aralkyl, heteroaryl or heteroaralkyl, optionally substituted; and $R^{23}$, $R^{24}$, and $R^{25}$ are independent of each other hydrogen, hydroxyl, F, Cl, Br, I, CN, $SO_2$, $NO_2$, alkyl, heteroalkyl, aryl, aralkyl, heteroaryl, heteroaralkyl, alkenyl, cycloalkenyl, or alkynyl, optionally substituted or a pharmaceutically acceptable salt thereof. Preferred salts comprise $Na^+$, $K^+$, $Mg^{2+}$, and $Ca^{2+}$.

In a preferred embodiment of the use of the present invention the inhibitor of the scavenger receptor class protein has a structure according to formula (LIII):

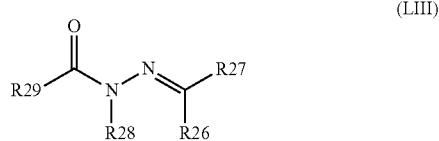

(LIII)

wherein $R^{26}$ is hydrogen, aryl, aralkyl, heteroaryl or heteroaralkyl, optionally substituted;

$R^{27}$ is aryl, aralkyl, heteroaryl or heteroaralkyl, optionally substituted;

$R^{28}$ is hydrogen or alkyl, optionally substituted; and $R^{29}$ is aryl, aralkyl, heteroaryl or heteroaralkyl, optionally substituted or is a pharmaceutically acceptable salt thereof.

In a preferred embodiment of the use of the present invention the inhibitor of the scavenger receptor class protein is a compound selected from Table I.

In a preferred embodiment of the use of the present invention the inhibitor of the scavenger receptor class protein is an antibody specifically binding to said scavenger receptor class protein.

In a preferred embodiment of the use of the present invention the inhibitor of the scavenger receptor class protein is a small interfering RNA (siRNA) capable of inhibiting expression of said scavenger receptor class protein.

In a preferred embodiment of the use of the present invention the scavenger receptor class protein is scavenger receptor class B 1 (ScarB1) or scavenger receptor class B 2 (ScarBII).

In a preferred embodiment of the use of the present invention the infectious disease is a protozoal infection.

In a preferred embodiment of the use of the present invention the protozoa is a member of the family of plasmodiidae.

In a preferred embodiment of the use of the present invention the plasmodiida is selected from the group consisting of *Plasmodium falciparum*, *Plasmodium vivax*, *Plasmodium ovale*, *Plasmodium malariae*, *Plasmodium semiovale* and *Plasmodium knowlesi*.

In a preferred embodiment of the use of the present invention the infectious disease is malaria.

In a further aspect the present invention relates to a method of identifying compounds for treatment and/or prophylaxis of infectious diseases involving liver or hematopoietic cells comprising the steps of:
(i) contacting a cell expressing a scavenger receptor class protein with a test compound,
(ii) measuring cholesterol transport into or out of said cell,
(iii) selecting test compound, which inhibits cholesterol transport into or out of said cells,
(iv) contacting liver or hematopoietic cell with selected test compound prior, during or after infection of said cell with an infectious agent, and
(v) selecting test compound inhibiting proliferation of the infectious agent by at least 10%.

In a further aspect the present invention relates to a method of identifying compounds for treatment and/or prophylaxis of infectious diseases involving liver or hematopoietic cells comprising the steps of:
(i) contacting a scavenger receptor class protein, functional variants, or soluble parts thereof with a test compound,
(ii) selecting a test compound, which specifically binds to ScarB1 or ScarBII,
(iii) contacting liver or hematopoietic cell with the selected test compound prior, during or after infection of said cell with an infectious agent, and
(iv) selecting a test compound inhibiting proliferation and/or development of the infectious agent by at least 10%.

In a further aspect the present invention relates to the use of test compound selected in step (v) of the method of the present invention for the production of a medicament for the therapy and/or prophylaxis of infectious diseases, which involve infection of liver and/or hematopoietic cells.

In a further aspect the present invention relates to a pharmaceutical composition comprising a compound usable according to the present invention and one or more of a compound selected from the group consisting of a chinine alkaloid, chloroquine-phosphate, hydroxychloroquine-sulfate, mefloquine, proguanil, di-aminopyrimidines: pyrimethamine, atovaquone, doxycycline, artemether, and lumefantrine and pharmaceutically acceptable additives and/or auxiliary substances.

In a further aspect the present invention relates to a method for the identification of molecules of pathogens, which are involved in the infection of liver and/or hematopoietic cells, comprising the following steps:
(i) contacting one or more scavenger receptor class proteins, functional variants, or soluble parts thereof with one or more molecules present in pathogens, which are involved in the infection of liver and/or hematopoietic cells,
(ii) selecting a molecule, which specifically binds to the scavenger receptor class protein.

Definitions

Before the present invention is described in detail below, it is to be understood that this invention is not limited to the particular methodology, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

Preferably, the terms used herein are defined as described in "A multilingual glossary of biotechnological terms: (IUPAC Recommendations)", Leuenberger, H. G. W, Nagel, B. and Klbl, H. eds. (1995), Helvetica Chimica Acta, CH-4010 Basel, Switzerland).

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step. In the following passages different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

Several documents are cited throughout the text of this specification. Each of the documents cited herein (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention.

In the following definitions of the terms: alkyl, heteroalkyl, cycloalkyl, heterocycloalkyl, aryl, aralkyl, heteroaryl, heteroaralkyl, alicyclic system, alkenyl, heteroalkenyl, cycloalkenyl, cycloheteroalkenyl, aralkenyl, aralkynyl, heteroaralkenyl, heteroaralkynyl and alkynyl are provided. These terms will in each instance of its use in the remainder of the specification have the respectively defined meaning and preferred meanings. Nevertheless in some instances of their use throughout the specification further or particular preferred meanings of these terms are indicated.

The term "alkyl" refers to a saturated straight or branched carbon chain. Preferably, the chain comprises from 1 to 16 carbon atoms, i.e. 1, 2, 3, 4, 5, 6, 7, 8, 9, 10, 11, 12, 13, 14, 15, or 16, e.g. methyl, ethyl, propyl, iso-propyl, butyl, iso-butyl, tert-butyl, pentyl, hexyl, heptyl, or octyl. Alkyl groups are optionally substituted.

The term "heteroalkyl" refers to a saturated straight or branched carbon chain. Preferably, the chain comprises from 1 to 16 carbon atoms, i.e. 1, 2, 3, 4, 5, 6, 7, 8, 9, 10, 11, 12, 13, 14, 15, or 16 e.g. methyl, ethyl, propyl, iso-propyl, butyl, iso-butyl, sec-butyl, tert-butyl, pentyl, hexyl, heptyl, octyl, which is interrupted one or more times, e.g. 1, 2, 3, 4, 5, with the same or different heteroatoms. Preferably the heteroatoms are selected from O, S, and N. A preferred heteroalkyl has the structure —$(CH_2)_n$—X—$(CH_2)_m CH_3$, with n=0, 1, 2, 3, 4, 5, 6, 7, 8, 9, 10, m=1, 2, 3, 4, 5, 6, 7, 8, 9, or 10 and X=S, O or NR' with R'=H or hydrocarbon, in particular —O—$CH_3$, —O$C_2H_5$, —$CH_2$—O—$CH_3$, —$CH_2$—O—$C_2H_5$, —$CH_2$—O—$C_3H_7$, —$CH_2$—O—$C_4H_9$, —$C_2$—O—$C_5H_{11}$, —$C_2H_4$—O—$CH_3$, —$C_2H_4$—O—$C_2H_5$, —$C_2H_4$—O—$C_3H_7$, —$C_2H_4$—O—$C_4H_9$ etc. Heteroalkyl groups are optionally substituted.

The terms "cycloalkyl" and "heterocycloalkyl", by themselves or in combination with other terms, represent, unless otherwise stated, cyclic versions of "alkyl" and "heteroalkyl", respectively, with preferably 3, 4, 5, 6, 7, 8, 9 or 10 atoms forming a ring, e.g. cyclopropyl, cyclobutyl, cyclopentyl, cyclohexyl, cycloheptyl, cyclooctyl etc. The terms "cycloalkyl" and "heterocycloalkyl" are also meant to include bicyclic, tricyclic and polycyclic versions thereof. If bicyclic, tricyclic or polycyclic rings are formed it is preferred that the respective rings are connected to each other at two adjacent carbon atoms, however, alternatively the two rings are connected via the same carbon atom, i.e. they form a spiro ring system or they form "bridged" ring systems. The term "heterocycloalkyl" preferably refers to a saturated ring having five members of which at least one member is a N, O or S atom and which optionally contains one additional O or one additional N; a saturated ring having six members of which at least one member is a N, O or S atom and which optionally contains one additional 0 or one additional N or two additional N atoms; or a saturated bicyclic ring having nine or ten members of which at least one member is a N, O or S atom and which optionally contains one, two or three additional N atoms. "Cycloalkyl" and "heterocycloalkyl" groups are optionally substituted. Additionally, for heterocycloalkyl, a heteroatom can occupy the position at which the heterocycle is attached to the remainder of the molecule. Examples of preferred cycloalkyl groups include cyclopropyl, cyclobutyl, cyclopentyl, cyclohexyl, cycloheptyl, spiro-[3,3]-heptyl, spiro-[3,4]-octyl, spiro-[4,3]-octyl, spiro-[3,5]-nonyl, spiro-[5,3]-nonyl, spiro-[3,6]-decyl, spiro-[6,3]-decyl, spiro-[4,5]-decyl, spiro-[5,4]-decyl, bicyclo-[2.2.1]-heptyl, bicyclo-[2.2.2]-octyl, or adamantyl. Examples of preferred heterocycloalkyl groups include 1,2,5,6-tetrahydropyridyl, e.g. 1-(1,2,5,6-tetrahydropyridyl), 2-(1,2,5,6-tetrahydropyridyl); piperidinyl, e.g. piperidin-1-yl, piperidin-2-yl, piperidin-3-yl, piperidin-4-yl; 1,2-diazacyclohexyl, 1,2-diazacyclohex-1-yl; 1,3-diazacyclohexyl; piperazinyl, e.g. 1-piperazinyl, 2-piperazinyl, 3-piperazinyl, or 4-piperazinyl; 1-oxo-2-azacyclohexyl; 1-oxo-3-azacyclohexyl; morpholinyl, e.g. 2-morpholinyl, 3-morpholinyl, or 4-morpholinyl; 1,8 diaza-spiro-[4,5]-decyl, 1,7 diaza-spiro-[4,5]-decyl, 1,6 diaza-spiro-[4,5]-decyl, 2,8 diaza-spiro[4,5]decyl, 2,7 diaza-spiro[4,5]-decyl, 2,6 diaza-spiro[4,5]decyl, 1,8 diaza-spiro-[5,4]decyl, 1,7 diaza-spiro-[5,4]-decyl, 2,8 diaza-spiro-[5,4]-decyl, 2,7 diaza-spiro-[5,4]-decyl, 3,8 diaza-spiro-[5,4]-decyl, 3,7 diaza-spiro-[5,4]-decyl, 1,4-d iazabicyclo-[2.2.2]-oct-2-yl; tetrahydrofuranyl, e.g. tetrahydrofuran-2-yl, or tetrahydrofuran-3-yl; tetrahydrothiophenyl, e.g. tetrahydrothiophen-2-yl, or tetrahydrothiophen-3-yl; or pyrrolidinyl, e.g. pyrrolidin-1-yl, pyrrolidin-2-yl, or pyrrolidin-3-yl; 2-diazacyclopentyl, e.g. 1,2-diazacyclopent-1-yl, or 1,2-diazacyclopent-3-yl; 1,3-diazacyclopentyl, e.g. 1,3-diazacyclopent-1-yl, or 1,3-diazacyclohex-2-yl; 1-oxo-2-azacyclopentyl, e.g. 1-oxo-2-azacyclopent-2-yl, 1-oxo-2-azacyclopent-3-yl, 1-oxo-2-azacyclopent-4-yl or 1-oxo-2-azacyclopent-5-yl; 1-oxo-3-azacyclopentyl, e.g. 1-oxo-3-azacyclopent-2-yl, 1-oxo-3-azacyclopent-3-yl, 1-oxo-3-azacyclopent-4-yl or 1-oxo-3azacyclopent-5-yl; 1-thio-2-azacyclopentyl, e.g. 1-thio-2-azacyclopent-2-yl, 1-thio-2-azacyclopent-3-yl, 1-thio-2-azacyclopent-4-yl or 1-thio-2-azacyclopent-5-yl; 1-thio-3-azacyclopentyl, e.g. 1-thio-3-azacyclopent-2-yl, 1-thio-3-azacyclopent-3-yl, 1-thio-3-azacyclopent-4-yl or 1-thio-3-azacyclopent-5-yl;.

The term "alicyclic system" refers to mono, bicyclic, tricyclic or polycyclic version of a cycloalkyl or heterocycloalkyl comprising at least one double and/or triple bond. However, an alicyclic system is not aromatic or heteroaromatic, i.e. does not have a system of conjugated double bonds/free electron pairs. Thus, the number of double and/or triple bonds maximally allowed in an alicyclic system is determined by the number of ring atoms, e.g. in a ring system with up to 5 ring atoms an alicyclic system comprises up to one double bond, in a ring system with 6 ring atoms the alicyclic system comprises up to two double bonds. Thus, the "cycloalkenyle" as defined below is a preferred embodiment of an alicyclic ring system. Alicyclic systems are optionally substituted.

The term "aryl" preferably refers to an aromatic monocyclic ring containing 6 carbon atoms, an aromatic bicyclic ring system containing 10 carbon atoms or an aromatic tricyclic ring system containing 14 carbon atoms. Examples are phenyl, naphthalenyl or anthracenyl. The aryl group is optionally substituted.

The term "aralkyl" refers to an alkyl moiety, which is substituted by aryl, wherein alkyl and aryl have the meaning as outlined above. An example is the benzyl radical. Preferably, in this context the alkyl chain comprises from 1 to 8 carbon atoms, i.e. 1, 2, 3, 4, 5, 6, 7, or 8, e.g. methyl, ethyl, propyl, iso-propyl, butyl, iso-butyl, sec-butenyl, tert-butyl, pentyl, hexyl, heptyl, or octyl. The aralkyl group is optionally substituted at the alkyl and/or aryl part of the group. Preferably the aryl attached to the alkyl has the meaning phenyl, naphtalenyl or anthracenyl.

The term "heteroaryl" preferably refers to a five or six-membered aromatic monocyclic ring wherein at least one of the carbon atoms are replaced by 1, 2, 3, or 4 (for the five membered ring) or 1, 2, 3, 4, or 5 (for the six membered ring) of the same or different heteroatoms, preferably selected from O, N and S; an aromatic bicyclic ring system wherein 1, 2, 3, 4, 5, or 6 carbon atoms of the 8, 9, 10, 11 or 12 carbon atoms have been replaced with the same or different heteroatoms, preferably selected from O, N and S; or an aromatic tricyclic ring system wherein 1, 2, 3, 4, 5, or 6 carbon atoms of the 13, 14, 15, or 16 carbon atoms have been replaced with the same or different heteroatoms, preferably selected from O, N and S. Examples are furanyl, thiophenyl, oxazolyl, isoxazolyl, 1,2,5-oxadiazolyl, 1,2,3-oxadiazolyl, pyrrolyl, imidazolyl, pyrazolyl, 1,2,3-triazolyl, thiazolyl, isothiazolyl, 1,2,3,-thiadiazolyl, 1,2,5-thiadiazolyl, pyridinyl, pyrimidinyl, pyrazinyl, 1,2,3-triazinyl, 1,2,4-triazinyl, 1,3,5-triazinyl, 1-benzofuranyl, 2-benzofuranyl, indolyl, isoindolyl, benzothiophenyl, 2-benzothiophenyl, 1H-indazolyl, benzimidazolyl, benzoxazolyl, indoxazinyl, 2,1-benzisoxazolyl, benzothiazolyl, 1,2-benzisothiazolyl, 2,1-benzisothiazolyl, benzotriazolyl, quinolinyl, isoquinolinyl, 2,3-benzodiazinyl, quinoxalinyl, quinazolinyl, quinolinyl, 1,2,3-benzotriazinyl, or 1,2,4-benzotriazinyl.

The term "heteroaralkyl" refers to an alkyl moiety, which is substituted by heteroaryl, wherein alkyl and heteroaryl have the meaning as outlined above. An example is the 2-alklypyridinyl, 3-alkylpyridinyl, or 2-methylpyridinyl. Preferably, in this context the alkyl chain comprises from 1 to 8 carbon atoms, i.e. 1, 2, 3, 4, 5, 6, 7, or 8, e.g. methyl, ethyl, propyl, iso-propyl, butyl, iso-butyl, sec-butenyl, tert-butyl, pentyl, hexyl, heptyl, octyl. The heteroaralkyl group is optionally substituted at the alkyl and/or heteroaryl part of the group. Preferably the heteroaryl attached to the alkyl has the meaning oxazolyl, isoxazolyl, 1,2,5-oxadiazolyl, 1,2,3-oxadiazolyl, pyrrolyl, imidazolyl, pyrazolyl, 1,2,3-triazolyl, thiazolyl, isothiazolyl, 1,2,3,-thiadiazolyl, 1,2,5-thiadiazolyl, pyridinyl, pyrimidinyl, pyrazinyl, 1,2,3-triazinyl, 1,2,4-triazinyl, 1,3,5-triazinyl, 1-benzofuranyl, 2-benzofuranyl, indolyl, isoindolyl, benzothiophenyl, 2-benzothiophenyl, 1H-indazolyl, benzimidazolyl, benzoxazolyl, indoxazinyl, 2,1-benzisoxazolyl, benzothiazolyl, 1,2-benzisothiazolyl, 2,1-benzisothiazolyl, 2,3-benzodiazinyl, quinolinyl, isoquinolinyl, quinoxalinyl, quinazolinyl, quinolinyl, 1,2,3-benzotriazinyl, or 1,2,4-benzotriazinyl.

Similarly the terms "aralkenyl", heteroaralkenyl", "aralkynyl" and "heteroaralkynyl" refer to an alkenyl or alkynyl moiety as defined above, which is substituted by an aryl and heteroaryl moiety, respectively, as defined above.

The term "alkenyl" refers to olefinic unsaturated carbon atoms containing chains with one or more double bonds. Preferably, the alkenyl chain comprises from 2 to 8 carbon atoms, i.e. 2, 3, 4, 5, 6, 7, or 8, e.g. ethenyl, 1-propenyl, 2-propenyl, iso-propenyl, 1-butenyl, 2-butenyl, 3-butenyl, iso-butenyl, sec-butenyl, 1-pentenyl, 2-pentenyl, 3-pentenyl, 4-pentenyl, hexenyl, pentenyl, octenyl.

The term "heteroalkenyl" refers to olefinic unsaturated carbon atoms containing chains with one or more double bonds, which is interrupted one or more times, e.g. 1, 2, 3, 4, 5, with the same or different heteroatoms. Preferably, the chain comprises from 2 to 12 carbon atoms, e.g. the alkenyl chain comprises from 2 to 12 carbon atoms, i.e. 2, 3, 4, 5, 6, 7, 8, 9, 10, 11, or 12 e.g. ethenyl, 1-propenyl, 2-propenyl, iso-propenyl, 1-butenyl, 2-butenyl, 3-butenyl, iso-butenyl, sec-butenyl, 1-pentenyl, 2-pentenyl, 3-pentenyl, 4-pentenyl, hexenyl, pentenyl, octenyl and is interrupted one or more times, e.g. 1, 2, 3, 4, 5, with the same or different heteroatoms. Preferably the heteroatoms are selected from O, S, and N. Preferred examples include —$(C_nH_{2n})$—X—$(C_mH_{2m-1})$, with n=0, 1, 2, 3, 4, 5, 6, 7, 8, 9, 10, m=2, 3, 4, 5, 6, 7, 8, 9, or 10 and X=S, O or NR' with R'=H or hydrocarbon, or —$(C_oH_{2o-2})$—X—$(C_pH_{2p+1})$, with o=2, 3, 4, 5, 6, 7, 8, 9, 10, m=1, 2, 3, 4, 5, 6, 7, 8, 9, or 10 and X=S, O or NR' with R'=H or hydrocarbon, in particular —$OC_2H_3$, —$CH_2$—O—$C_2H_3$, —$CH_2$—O—$C_3H_5$, —$CH_2$—O—$C_4H_7$, —$CH_2$—O—$C_5H_9$, —$C_2H_2$—O—$CH_3$, —$C_2H_2$—O—$C_2H_5$, —$C_2H_5$—O—$C_2H_3$, —$C_2H_2$—O—$C_3H_7$, —$C_2H_4$—O—$C_3H_5$, —$C_2H_2$—O—$C_4H_9$, —$C_2H_4$—O—$C_4H_7$ etc. heteroalkyl groups are optionally substituted. The terms "cycloalkenyl" and "heterocycloalkenyl", by themselves or in combination with other terms, represent, unless otherwise stated, cyclic versions of "alkenyl" and "heteroalkenyl", respectively, with preferably 3, 4, 5, 6, 7, 8, 9 or 10 atoms forming a ring, e.g. 1-cyclopropenyl, 2-cyclopropenyl, 1-cyclobutenyl, 2-cyclobutenyl, 1-cyclopentenyl, 2-cyclopentenyl, 3-cyclopentenyl, cyclohexenyl, cyclopentenyl, cyclooctenyl etc. The terms "cycloalkenyl" and "heterocycloalkenyl" are also meant to include bicyclic, tricyclic and polycyclic versions thereof. If bicyclic, tricyclic or polycyclic rings are formed it is preferred that the respective rings are connected to each other at two adjacent carbon atoms, however, alternatively the two rings are connected via the same carbon atom, i.e. they form a spiro ring system or they form "bridged" ring systems. The term "heterocycloalkenyl" preferably monounsaturated ring having five members of which at least one member is a N, O or S atom and which optionally contains one additional O or one additional N; a mono-unsaturated ring having six members of which at least one member is a N, O or S atom and which optionally contains one additional O or one additional N or two additional N atoms; or a mono or diunsaturated bicyclic ring having nine or ten members of which at least one member is a N, O or S atom and which optionally contains one, two or three additional N atoms. Preferred examples of cycloalkenyl include cyclopropenyl, cyclobutenyl, cyclopentenyl, cyclohexenyl, cyclopentenyl, and cyclooctenyl. Preferred examples of heterocycloalkenyl include 1,2,5,6-tetrahydropyridyl, e.g. 1-(1,2,5,6-tetrahydropyridyl), or 2-(1,2,5,6-tetrahydropyridyl).

The term "alkynyl" refers to unsaturated carbon atoms containing chains or rings with one or more triple bonds. Preferably, the alkynyl chain comprises from 2 to 8 carbon atoms, i.e. 2, 3, 4, 5, 6, 7, or 8, e.g. ethynyl, 1-propynyl, 2-propynyl, 1-butynyl, 2-butynyl, 3-butynyl, 1-pentynyl, 2-pentynyl, 3-pentynyl, 4-pentynyl, hexynyl, pentynyl, octynyl.

In preferred embodiments, carbon atoms or hydrogen atoms in alkyl, cycloalkyl, aryl, aralkyl, alkenyl, cycloalkenyl, alkynyl radicals may be substituted independently from each other with one or more elements selected from the group consisting of O, S, N or with groups containing one ore more elements, i.e. 1, 2, 3, 4, 5, 6, or more selected from the group consisting of O, S, and N.

Embodiments include alkoxy, alkyl-alkoxy, cycloalkoxy, aralkoxy, alkenyloxy, cycloalkenyloxy, alkynyloxy, alkylthio, cycloalkylthio, arylthio, aralkylthio, alkenylthio, cycloalkenylthio, alkynylthio, alkylamino, cycloalkylamino, arylamino, aralkylamino, alkenylamino, cycloalkenylamino, alkynylamino radicals.

Other embodiments include hydroxyalkyl, hydroxycloalkyl, hydroxyaryl, hydroxyaralkyl, hydroxyalkenyl, hydroxycycloalkenyl, hydroxyalinyl, mercaptoalkyl, mercaptocycloalkyl, mercaptoaryl, mercaptoaralkyl, mercaptoalkenyl, mercaptocycloalkenyl, mercaptoalkynyl, aminoalkyl, aminocycloalkyl, aminoaryl, aminoaralkyl, aminoalkenyl, aminocycloalkenyl, aminoalkynyl radicals.

In preferred embodiment, one or more hydrogen atoms, e.g. 1, 2, 3, 4, 5, 6, 7, or 8 hydrogen atoms in alkyl, heteroalkyl, cycloalkyl, heterocycloalkyl, aryl, heteroaryl, aralkyl, heteroaralkyl, alkenyl, heteroalkenyl cycloalkenyl, heterocycloalkenyl alkynyl radicals may be substituted independently from each other with one ore more halogen atoms, e.g. Cl, F, or Br. One preferred radical is the trifluoromethyl radical.

If two or more radicals can be selected independently from each other, then the term "independently" means that the radicals may be the same or may be different.

The term "pharmaceutically acceptable salt" refers to a salt of the compound of the present invention. Suitable pharmaceutically acceptable salts of the compound of the present invention include acid addition salts which may, for example, be formed by mixing a solution of choline or derivative thereof with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid. Furthermore, where the compound of the invention carries an acidic moiety, suitable pharmaceutically acceptable salts thereof may include alkali metal salts (e.g., sodium or potassium salts); alkaline earth metal salts (e.g., calcium or magnesium salts); and salts formed with suitable organic ligands (e.g., ammonium, quaternary ammonium and amine cations formed using counteranions such as halide, hydroxide, carboxylate, sulfate, phosphate, nitrate, alkyl sulfonate and aryl sulfonate). Illustrative examples of pharmaceutically acceptable salts include but are not limited to: acetate, adipate, alginate, ascorbate, aspartate, benzenesulfonate, benzoate, bicarbonate, bisulfate, bitartrate, borate, bromide, butyrate, calcium edetate, camphorate, camphorsulfonate, camsylate, carbonate, chloride, citrate, clavulanate, cyclopentanepropionate, digluconate, dihydrochloride, dodecylsulfate, edetate, edisylate, estolate, esylate, ethanesulfonate, formate, fumarate, gluceptate, glucoheptonate, gluconate, glutamate, glycerophosphate, glycolylarsanilate, hemisulfate, heptanoate, hexanoate, hexylresorcinate, hydrabamine, hydrobromide, hydrochloride, hydroiodide, 2-hydroxy-ethanesulfonate, hydroxynaphthoate, iodide, isothionate, lactate, lactobionate, laurate, lauryl sulfate, malate, maleate, malonate, mandelate, mesylate, methanesulfonate, methylsulfate, mucate, 2-naphthalenesulfonate, napsylate, nicotinate, nitrate, N-methylglucamine ammonium salt, oleate, oxalate, pamoate (embonate), palmitate, pantothenate, pectinate, persulfate, 3-phenylpropionate, phosphate/diphosphate, picrate, pivalate, polygalacturonate, propionate, salicylate, stearate, sulfate, subacetate, succinate, tannate, tartrate, teoclate, tosylate, triethiodide, undecanoate, valerate, and the like (see, for example, Berge, S. M., et al., "Pharmaceutical Salts", *Journal of Pharmaceutical Science*, 1977, 66, 1-19). Certain specific compounds of the present invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. Prodrugs of the compounds described herein are those compounds that readily undergo chemical changes under physiological conditions to provide a compound of formula (I). A prodrug is an active or inactive compound that is modified chemically through in vivo physiological action, such as hydrolysis, metabolism and the like, into a compound of this invention following administration of the prodrug to a patient. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme. The suitability and techniques involved in making and using prodrugs are well known by those skilled in the art. For a general discussion of prodrugs involving esters see Svensson and Tunek Drug Metabolism Reviews 16.5 (1988) and Bundgaard Design of Prodrugs, Elsevier (1985). Examples of a masked carboxylate anion include a variety of esters, such as alkyl (for example, methyl, ethyl), cycloalkyl (for example, cyclohexyl), aralkyl (for example, benzyl, p-methoxybenzyl), and alkylcarbonyloxyalkyl (for example, pivaloyloxymethyl). Amines have been masked as arylcarbonyloxymethyl substituted derivatives which are cleaved by esterases in vivo releasing the free drug and formaldehyde (Bungaard J. Med. Chem. 2503 (1989)). Also, drugs containing an acidic NH group, such as imidazole, imide, indole and the like, have been masked with N-acyloxymethyl groups (Bundgaard Design of Prodrugs, Elsevier (1985)). Hydroxy groups have been masked as esters and ethers. EP 0 039 051 (Sloan and Little, Apr. 11, 1981) discloses Mannich-base hydroxamic acid prodrugs, their preparation and use.

Compounds according to the invention can be synthesized by art known methods. It should be noted that the general procedures.

Certain compounds of the present invention can exist in unsolvated forms as well as in solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers and individual isomers are all intended to be encompassed within the scope of the present invention.

The compounds of the present invention may also contain unnatural proportions of atomic isotopes at one or more of the atoms that constitute such compounds. For example, the compounds may be radiolabeled with radioactive isotopes, such as for example tritium (3H), iodine-125 ($^{125}$I) or carbon-14 ($^{14}$C). All isotopic variations of the compounds of the present invention, whether radioactive or not, are intended to be encompassed within the scope of the present invention.

Specific Embodiments

Due to the surprising discovery that inhibitors of scavenger receptor class proteins, can interfere with the proliferation and/or development of infectious agents in liver cells and hematopoietic cells the invention provides in a first aspect the use of an inhibitor of a scavenger receptor class protein for the production of a medicament therapy of and/or prophylaxis against infections, involving liver cells and/or hematopoietic cells, in particular malaria. The term "inhibitor of scavenger receptor class proteins" within the present invention refers to compounds which can inhibit high density lipoprotein (HDL) uptake mediated by scavenger receptor class proteins, in particular ScarB1. Various assays to measure HDL uptake and its inhibition are known from the prior art. WO 2004/032716 to which specific reference is herewith made with respect to the high-throughput screening for inhibitors of ScarB1 disclosed therein. A compound is considered an inhibitor of scavenger receptor class proteins, if the compound has an $IC_{50}$ of <100 µM in a cholesterol transport assay preferably the one described below. Preferably the $IC_{50}$ is 90 µM, 80 µM, 70 µM, 60 µM, 50 µM, 40 µM, 30 µM, 20 µM, 10 µM, 9 µM, 8 µM, 7 µM, 6 µM, 5 µM, 4 µM, 3 µM, 2 µM, 1 µM, 0.9 µM, 0.8 µM, 0.7 µM, 0.6 µM, 0.5 µM, 0.4 µM, 0.3 µM, 0.2 µM, 0.1 µM or less. Preferably, the cholesterol transport assay measures the transport of cholesterol into and/or out of a given cell, preferably a hepatic cell. The measurement comprises the transport of "free" cholesterol, high density lipoproteins (HDL) and low density lipoproteins (LDL). Infections involving liver cells and/or hematopoietic cells are diseases wherein the pathogen in one or mores stages of its life cycle in the respective host attacks and/or enters liver cells and/or hematopoietic cells in order to, e.g. proliferate, develop or evade the immune system in those cells, in particular protozoal infections.

Of the various inhibitors of scavenger receptor class proteins those appear to be particular effective in the treatment of liver cell or hematopoietic cell infection, which comprise a urea or thiourea moiety. Accordingly, in a preferred use of the invention the inhibitor of the scavenger receptor class protein is a compound with the following formula (I):

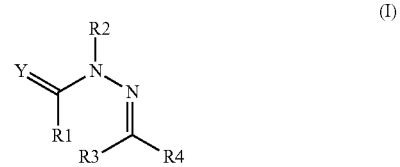

wherein,
$R^1$ is $NR^5R^6$;
$R^2$ is hydrogen or alkyl, optionally substituted, preferably hydrogen;
$R^3$ and $R^4$ together form a cycloalkyl, heterocycloalkyl, cycloalkenyl or heterocycloalkenyl, optionally substituted;

R⁵ is hydrogen or alkyl, optionally substituted, preferably hydrogen;

R⁶ hydrogen, hydroxyl, halogen, alkyl, cycloalkyl, heteroalkyl, cycloheteroalkyl, aryl, aralkyl, heteroaryl, heteroaralkyl, alkenyl, cycloalkenyl, alkynyl, alkanoyl, alkoxyalkyl; or —CO—R'; optionally substituted, preferably hydrogen, aryl or —CO—R',
wherein
R' is hydrogen; alkyl, in particular $C_1$-$C_6$ alkyl, e.g. $C_1$, $C_2$, $C_3$, $C_4$, $C_5$, or $C_6$ alkyl; cycloalkyl, in particular $(C_{3-10})$-cycloalkyl, preferably cyclopropyl, cyclobutyl, cyclopentyl, cyclohexyl, cycloheptyl; alkenyl; cycloalkenyl; aryl; aralkyl; heteroalkyl; cycloheteroalkyl; heteroaryl; heteroaralkyl; or alkynyl;
and
Y is S or N, preferably S
or a pharmaceutically acceptable salt thereof.

In a further preferred use of the invention the compound according to formula (I) has a structure wherein,
$R^1$ is $NR^5R^6$;
$R^2$ is hydrogen or alkyl, optionally substituted, preferably hydrogen; and/or
$R^3$ and $R^4$ together form a $(C_{3-10})$-cycloalkyl, i.e. $C_3$, $C_4$, $C_5$, $C_6$, $C_7$, $C_8$, $C_9$, or $C_{10}$-cycloalkyl, preferably cyclopropyl, cyclobutyl, cyclopentyl, cyclohexyl, cycloheptyl, $(C_{6-10})$-spiroalkyl, preferably spiro-[3,3]-heptyl, spiro-[3,4]-octyl, spiro-[4,3]-octyl, spiro-[3,5]-nonyl, spiro-[5,3]-nonyl, spiro-[3,6]-decyl, spiro-[6,3]-decyl, spiro-[4,5]-decyl, spiro-[5,4]-decyl, bicyclo-[2.2.1]-heptyl, bicyclo-[2.2.2]-octyl, or adamantyl or $C_3$ to $C_{10}$-heterocycloalkyl i.e. $C_3$, $C_4$, $C_5$, $C_6$, $C_7$, $C_8$, $C_9$, or $C_{10}$-cycloalkyl or $(C_{3-10})$-cycloheteroalkenyl, i.e. $C_3$, $C_4$, $C_5$, $C_6$, $C_7$, $C_8$, $C_9$, or $C_{10}$-cycloheteroalkenyl, preferably piperidinyl, e.g. piperidin-1-yl, piperidin-2-yl, piperidin-3-yl, piperidin-4-yl; 1,2-diazacyclohexyl, e.g. 1,2-diazacyclohex-1-yl, 1,2-diazacyclohex-2-yl or 1,2-diazacyclohex-4-yl; 1,3-diazacyclohexyl, e.g. 1,3-diazacyclohex-1-yl, 1,3-diazacyclohex-3-yl or 1,3-diazacyclohex-4-yl; piperazinyl, e.g. piperazin-1-yl, piperazin-2-yl, piperazin-3-yl, or piperazin-4-yl; 1-oxo-2-azacyclohexyl, e.g. 1-oxo-2-azacyclohexyl-2-yl, 1-oxo-2-azacyclohexyl-3-yl, 1-oxo-2-azacyclohexyl-4-yl, 1-oxo-2-azacyclohexyl-5-yl or 1-oxo-2-azacyclohexyl-6-yl; 1-oxo-3-azacyclohexyl, e.g. 1-oxo-3-azacyclohexyl-2-yl, 1-oxo-3-azacyclohexyl-3-yl, 1-oxo-3-azacyclohexyl-4-yl, 1-oxo-3-azacyclohexyl-5-yl, 1-oxo-3-azacyclohexyl-6-yl; morpholinyl, e.g. morpholin-2-yl, morpholin-3-yl, or morpholin-4-yl; $(C_{6-10})$.spiroheteroalkyl, e.g. 1,8 diaza-spiro-[4,5]-decyl, 1,7 diaza-spiro-[4,5]-decyl, 1,6 diaza-spiro-[4,5]-decyl, 2,8 diaza-spiro[4,5]decyl, 2,7 diaza-spiro[4,5]-decyl, 2,6 diaza-spiro[4,5]decyl, 1,8 diaza-spiro-[5,4]decyl, 1,7 diaza-spiro-[5,4]-decyl, 2,8 diaza-spiro-[5,4]-decyl, 2,7 diaza-spiro-[5,4]-decyl, 3,8 diaza-spiro-[5,4]-decyl, 3,7 diaza-spiro-[5,4]-decyl, 1,4-diazabicyclo-[2.2.2]-oct-2-yl; tetrahydrofuranyl, e.g. tetrahydrofuran-2-yl, or tetrahydrofuran-3-yl; tetrahydrothiophenyl, e.g. tetrahydrothiophen-2-yl, or tetrahydrothiophen-3-yl; or pyrrolidinyl, e.g. pyrrolidin-1-yl, pyrrolidin-2-yl, or pyrrolidin-3-yl; 1,2-diazacyclopentyl, e.g. 1,2-diazacyclopent-1-yl, or 1,2-diazacyclopent-3-yl; 1,3-diazacyclopentyl, e.g. 1,3-diazacyclopent-1-yl, or 1,3-diazacyclohex-2-yl; 1-oxo-2-azacyclopentyl, e.g. 1-oxo-2-azacyclopent-2-yl, 1-oxo-2-azacyclopent-3-yl, 1-oxo-2-azacyclopent-4-yl or 1-oxo-2-azacyclopent-5-yl; 1-oxo-3-azacyclopentyl, e.g. 1-oxo-3-azacyclopent-2-yl, 1-oxo-3-azacyclopent-3-yl, 1-oxo-3-azacyclopent-4-yl or 1-oxo-3-azacyclopent-5-yl; 1-thio-2-azacyclopentyl, e.g. 1-thio-2-azacyclopent-2-yl, 1-thio-2-azacyclopent-3-yl, 1-thio-2-azacyclopent-4-yl or 1-thio-2-azacyclopent-5-yl; 1-thio-3-azacyclopentyl, e.g. 1-thio-3-azacyclopent-2-yl, 1-thio-3-azacyclopent-3-yl, 1-thio-3-azacyclopent-4-yl or 1-thio-3-azacyclopent-5-yl; optionally substituted; and/or R⁵ is hydrogen or alkyl, optionally substituted, preferably hydrogen; and/or R⁶ is hydrogen, hydroxyl; halogen, F, Cl, Br or I; CN; $NO_2$; alkyl, in particular $(C_{1-6})$alkyl, e.g. $C_1$, $C_2$, $C_3$, $C_4$, $C_5$, or $C_6$ alkyl, preferably methyl, ethyl, propyl, iso-propyl, butyl, iso-butyl, tert-butyl, pentyl, hexyl; cycloalkyl, in particular $(C_{3-10})$-cycloalkyl, preferably cyclopropyl, cyclobutyl, cyclopentyl, cyclohexyl, cycloheptyl, heteroalkyl in particular $(C_1$-$C_6)$ heteroalkyl, e.g. $C_1$, $C_2$, $C_3$, $C_4$, $C_5$, or $C_6$ heteroalkyl, cycloheteroalkyl, in particular $(C_3$-$C_{10})$-cycloheteroalkyl; aryl, in particular phenyl, naphtalenyl or anthracenyl; aralkyl; heteroaryl, preferably oxazolyl, isoxazolyl, 1,2,5-oxadiazolyl, 1,2,3-oxadiazolyl, pyrrolyl, imidazolyl, pyrazolyl, 1,2,3-triazolyl, thiazolyl, isothiazolyl, 1,2,3,-thiadiazolyl, 1,2,5-thiadiazolyl, pyridinyl, pyrimidinyl, pyrazinyl, 1,2,3-triazinyl, 1,2,4-triazinyl, 1,3,5-triazinyl, 1-benzofuranyl, 2-benzofuranyl, indolyl, isoindolyl, benzothiophenyl, 2-benzothiophenyl, 1H-indazolyl, benzimidazolyl, benzoxazolyl, indoxazinyl, 2,1-benzisoxazolyl, benzothiazolyl, 1,2-benzisothiazolyl, 2,1-benzisothiazolyl, benzothiazolyl, 2,3-benzodiazinyl, quinolinyl, isoquinolinyl, quinoxalinyl, quinazolinyl, quinolinyl, 1,2,3-benzotriazinyl, benzotriazinyl; heteroaralkyl; alkenyl, in particular $C_2$-$C_6$ alkenyl, e.g. $C_2$, $C_3$, $C_4$, $C_5$, or $C_6$ alkenyl, preferably ethenyl, 1-propenyl, 2-propenyl, 1-iso-propenyl, 2-iso-propenyl, 1-butenyl, 2-butenyl, 3-butenyl; cycloalkenyl, in particular $(C_{3-10})$-cycloalkyl; or alkynyl, in particular $C_2$-$C_6$ alkynyl, e.g. $C_2$, $C_3$, $C_4$, $C_5$, or $C_6$ alkynyl; alkanoyl, preferably $C_1$-$C_6$ alkanoyl, e.g. $C_1$, $C_2$, $C_3$, $C_4$, $C_5$, or $C_6$ alkanoyl; alkenoyl, in particular $C_3$-$C_6$ alkenoyl, e.g. $C_3$, $C_4$, $C_5$, or $C_6$ alkenoyl, preferably propenoyl; alkynoyl, in particular $C_3$-$C_6$ alkynoyl, e.g. $C_3$, $C_4$, $C_5$, or $C_6$ alkynoyl, preferably propynoyl; alkoxy, in particular $C_1$-$C_6$ alkoxy, e.g. $C_1$, $C_2$, $C_3$, $C_4$, $C_5$, or $C_6$ alkoxy, preferably methoxy, ethoxy, propoxy, iso-propoxy, butoxy, iso-butoxy, tert-butoxy, pentoxy, or hexoxy; alkoxyalkyl, in particular $C_1$-$C_6$ alkoxy-$C_1$-$C_6$ alkyl, e.g. methoxymethyl, ethoxymethyl, propoxymethyl, methoxyethyl, ethoxyethyl, propoxyethyl, methoxypropyl, ethoxypropyl, or propoxypropyl; or —CO—R'; optionally substituted, preferably hydrogen, —CO—R' or aryl;
wherein
R' is hydrogen; alkyl, in particular $C_1$-$C_6$ alkyl, e.g. $C_1$, $C_2$, $C_3$, $C_4$, $C_5$, or $C_6$ alkyl; cycloalkyl, in particular $(C_{3-10})$-cycloalkyl, preferably cyclopropyl, cyclobutyl, cyclopentyl, cyclohexyl, cycloheptyl; alkenyl; cycloalkenyl; aryl; aralkyl; heteroalkyl; cycloheteroalkyl; heteroaryl; heteroaralkyl; or alkynyl.

If $R^3$ and $R^4$ form a $(C_{3-10})$-cycloalkyl, preferably cyclopropyl, cyclobutyl, cyclopentyl, cyclohexyl, cycloheptyl, $(C_{6-10})$.spiroalkyl, preferably spiro-[3,3]-heptyl, spiro-[3,4]-octyl, spiro-[4,3]-octyl, spiro-[3,5]-nonyl, spiro-[5,3]-nonyl, spiro-[3,6]-decyl, spiro-[6,3]-decyl, spiro-[4,5]-decyl, spiro-[5,4]-decyl, bicyclo-[2.2.1]-heptyl, bicyclo-[2.2.2]-octyl, or adamantyl or $C_3$ to $C_{10}$-heterocycloalkyl preferably piperidinyl, e.g. piperidin-1-yl, piperidin-2-yl, piperidin-3-yl, piperidin-4-yl; 1,2-diazacyclohexyl, e.g. 1,2-diazacyclohex-1-yl, 1,2-diazacyclohex-2-yl or 1,2-diazacyclohex-4-yl; 1,3-diazacyclohexyl, e.g. 1,3-diazacyclohex-1-yl, 1,3-diazacyclohex-3-yl or 1,3-diazacyclohex-4-yl; piperazinyl, e.g. piperazin-1-yl, piperazin-2-yl, piperazin-3-yl, or piperazin-4-yl; 1-oxo-2-azacyclohexyl, e.g. 1-oxo-2-azacyclohexyl-2-yl, 1-oxo-2-azacyclohexyl-3-yl, 1-oxo-2-azacyclohexyl-4-yl, 1-oxo-2-azacyclohexyl-5-yl or 1-oxo-2-azacyclohexyl-6-yl; 1-oxo-3-azacyclohexyl, e.g. 1-oxo-3-azacyclohexyl-2-yl, 1-oxo-3-azacyclohexyl-3-yl, 1-oxo-3-azacyclohexyl-4-yl, 1-oxo-3-azacyclohexyl-5-yl, 1-oxo-3-azacyclohexyl-6-yl; morpholinyl, e.g. morpholin-2-yl, morpholin-3-yl, or morpholin-4-yl; ($C_{6-10}$).spiroheteroalkyl, e.g. 1,8 diaza-spiro-[4,5]-decyl, 1,7 diaza-spiro-[4,5]-decyl, 1,6 diaza-spiro-[4,5]-decyl, 2,8 diaza-spiro[4,5]decyl, 2,7 diaza-spiro[4,5]-decyl, 2,6 diaza-spiro[4,5]decyl, 1,8 diaza-spiro-[5,4]decyl, 1,7 diaza-spiro-[5,4]-decyl, 2,8 diaza-spiro-[5,4]-decyl, 2,7 diaza-spiro-[5,4]-decyl, 3,8 diaza-spiro-[5,4]-decyl, 3,7 diaza-spiro-[5,4]-decyl, 1,4-diazabicyclo-[2.2.2]-oct-2-yl; tetrahydrofuranyl, e.g. tetrahydrofuran-2-yl,-or tetrahydrofuran-3-yl; tetrahydrothiophenyl, e.g. tetrahydrothiophen-2-yl, or tetrahydrothiophen-3-yl; or pyrrolidinyl, e.g. pyrrolidin-1-yl, pyrrolidin-2-yl, or pyrrolidin-3-yl; 1,2-diazacyclopentyl, e.g. 1,2-diazacyclopent-1-yl, or 1,2-diazacyclopent-3-yl; 1,3-diazacyclopentyl, e.g. 1,3-diazacyclopent-1-yl, or 1,3-diazacyclohex-2-yl; 1-oxo-2-azacyclopentyl, e.g. 1-oxo-2-azacyclopent-2-yl, 1-oxo-2-azacyclopent-3-yl, 1-oxo-2-azacyclopent-4-yl or 1-oxo-2-azacyclopent-5-yl; 1-oxo-3-azacyclopentyl, e.g. 1-oxo-3-azacyclopent-2-yl, 1-oxo-3-azacyclopent-3-yl, 1-oxo-3-azacyclopent-4-yl or 1-oxo-3-azacyclopent-5-yl; 1-thio-2-azacyclopentyl, e.g. 1-thio-2-azacyclopent-2-yl, 1-thio-2-azacyclopent-3-yl, 1-thio-2-azacyclopent-4-yl or 1-thio-2-azacyclopent-5-yl; 1-thio-3-azacyclopentyl, e.g. 1-thio-3-azacyclopent-2-yl, 1-thio-3-azacyclopent-3-yl, 1-thio-3-azacyclopent-4-yl or 1-thio-3-azacyclopent-5-yl; it is preferred that the $C_{3-10}$-cycloalkyl or $C_3$-$C_{10}$-cycloheteroalkyl is substituted with one, two, three or more substituents selected from the group consisting of hydrogen, hydroxyl, halogen, oxo, alkyl, heteroalkyl, cycloalkyl, heterocycloalkyl, alicyclic system, aryl, aralkyl, aralkenyl, aralkynyl, heteroaryl, heteroaralkyl, heteroaralkenyl, heteroaralkynyl, alkenyl, cycloalkenyl, alkynyl and/or two adjacent substituents are taken together to form an aryl or heteroaryl, preferably oxazolyl, isoxazolyl, 1,2,5-oxadiazolyl, 1,2,3-oxadiazolyl, pyrrolyl, imidazolyl, pyrazolyl, 1,2, 3-triazolyl, thiazolyl, isothiazolyl, 1,2,3,-thiadiazolyl, 1,2,5-thiadiazolyl, pyridinyl, pyrimidinyl, pyrazinyl, 1,2,3-triazinyl, 1,2,4-triazinyl, 1,3,5-triazinyl, 1-benzofuranyl, 2-benzofuranyl, indolyl, isoindolyl, benzothiophenyl, 2-benzothiophenyl, 1 H-indazolyl, benzimidazolyl, benzoxazolyl, indoxazinyl, 2,1-benzisoxazolyl, benzothiazolyl, 1,2-benzisothiazolyl, 2,1-benzisothiazolyl, benzotriazolyl, 2,3-benzodiazinyl, quinolinyl, isoquinolinyl, quinoxalinyl, quinazolinyl, quinolinyl, 1,2,3-benzotriazinyl, 1,2,4-benzotriazinyl, phenyl, naphtalenyl or antracenyl; optionally substituted. It is particularly preferred that one substituent is located in cis to the imin bound to the ring system. It is preferred that one substituent is oxo, alkyl, or heteroalkyl. A preferred ring system is 1-thio-3-azacyclopentyl, preferably 1-thio-3-azacyclopent-2-yl, 3-alkyl-(1-thio-3-azacyclopentyl) or 3-alkyl-(1-thio-3-azacyclopent-2-yl) and pyrrolidinyl, preferably pyrrolidin-3-yl, or 2-oxo-pyrrolidin-3-yl.

In a preferred use of the invention the compound according to formula (I) has a structure according to formula (II)

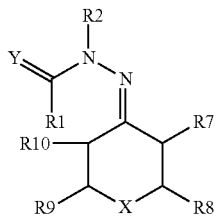

(II)

wherein,
$R^1$ is $NR^5R^6$;
$R^2$ is hydrogen or alkyl, optionally substituted, preferably hydrogen;

$R^5$ is hydrogen or alkyl, optionally substituted, preferably hydrogen;

$R^6$ hydrogen, hydroxyl, halogen, alkyl, cycloalkyl, heteroalkyl, cycloheteroalkyl, aryl, aralkyl, heteroaryl, heteroaralkyl, alkenyl, cycloalkenyl, alkynyl, alkanoyl, alkoxyalkyl; or —CO—R'; optionally substituted, preferably hydrogen, aryl or —CO—R', wherein
R' is hydrogen, alkyl, in particular $C_1$-$C_6$ alkyl, e.g. $C_1$, $C_2$, $C_3$, $C_4$, $C_5$, or $C_6$ alkyl cycloalkyl, in particular ($C_{3-10}$)-cycloalkyl, preferably cyclopropyl, cyclobutyl, cyclopentyl, cyclohexyl, cycloheptyl, alkenyl, cycloalkenyl, or alkynyl;

$R^7$, $R^8$, $R^9$, and $R^{10}$ are each independent of each other selected from the group consisting of hydrogen, hydroxyl, halogen, oxo, alkyl, heteroalkyl, cycloalkyl, heterocycloalkyl, alicyclic system, aryl, aralkyl, aralkenyl, aralkynyl, heteroaryl, heteroaralkyl, heteroaralkenyl, alkenyl, cycloalkenyl, heterocycloalkenyl, alkynyl, heteroaralkynyl, or $NR^{11}R^{12}$, optionally substituted and/or one or both of $R^7$ and $R^8$ or $R^9$ and $R^{10}$ are taken together to form an aryl or heteroaryl, optionally substituted; and $R^{11}$ is hydrogen or alkyl, optionally substituted;
$R^{12}$ hydrogen, hydroxyl, halogen, alkyl, heteroalkyl, aryl, aralkyl, heteroaryl, heteroaralkyl, alkenyl, cycloalkenyl, or alkynyl, optionally substituted;

X is not present, is $CH_2$, $C_2H_4$, N, S or O; and
Y is S or N, preferably S;
or a pharmaceutically acceptable salt thereof. It is preferred that $R^7$ and/or $R^8$ are non-polar side chains.

It is preferred that in a compound according to formula (II) $R^6$ is hydrogen, hydroxyl; halogen, F, Cl, Br or I; CN; $NO_2$; alkyl, in particular ($C_1$-$C_6$)alkyl, e.g. $C_1$, $C_2$, $C_3$, $C_4$, $C_5$, or $C_6$ alkyl, preferably methyl, ethyl, propyl, iso-propyl, butyl, iso-butyl, tert-butyl, pentyl, hexyl; cycloalkyl, in particular ($C_{3-10}$)-cycloalkyl, preferably cyclopropyl, cyclobutyl, cyclopentyl, cyclohexyl, cycloheptyl, heteroalkyl in particular ($C_1$-$C_6$)heteroalkyl, e.g. $C_1$, $C_2$, $C_3$, $C_4$, $C_5$, or $C_6$ heteroalkyl, cycloheteroalkyl, in particular ($C_3$-$C_{10}$)-cycloheteroalkyl; aryl, in particular phenyl, naphtalenyl or anthracenyl; aralkyl; heteroaryl, preferably oxazolyl, isoxazolyl, 1,2,5-oxadiazolyl, 1,2,3-oxadiazolyl, pyrrolyl, imidazolyl, pyrazolyl, 1,2,3-triazolyl, thiazolyl, isothiazolyl, 1,2, 3,-thiadiazolyl, 1,2,5-thiadiazolyl, pyridinyl, pyrimidinyl, pyrazinyl, 1,2,3-triazinyl, 1,2,4-triazinyl, 1,3,5-triazinyl, 1-benzofuranyl, 2-benzofuranyl, indolyl, isoindolyl, benzothiophenyl, 2-benzothiophenyl, 1H-indazolyl, benzimidazolyl, benzoxazolyl, indoxazinyl, 2,1-benzisoxazolyl, benzothiazolyl, 1,2-benzisothiazolyl, 2,1-benzisothiazolyl, benzotriazolyl, 2,3-benzodiazinyl, quinolinyl, isoquinolinyl, quinoxalinyl, quinazolinyl, quinolinyl, 1,2,3-benzotriazinyl, 1,2,4-benzotriazinyl; heteroalkyl; alkenyl, in particular $C_2$-$C_6$ alkenyl, e.g. $C_2$, $C_3$, $C_4$, $C_5$, or $C_6$ alkenyl, preferably ethenyl, 1-propenyl, 2-propenyl, 1-iso-propenyl, 2-iso-propenyl, 1-butenyl, 2-butenyl, 3-butenyl; cycloalkenyl, in particular ($C_{3-10}$)-cycloalkyl; or alkynyl, in particular $C_2$-$C_6$ alkynyl, e.g. $C_2$, $C_3$, $C_4$, $C_5$, or $C_6$ alkynyl; alkanoyl, preferably $C_1$-$C_6$ alkanoyl, e.g. $C_1$, $C_2$, $C_3$, $C_4$, $C_5$, or $C_6$ alkanoyl; alkenoyl, in particular $C_3$-$C_6$ alkenoyl, e.g. $C_3$, $C_4$, $C_5$, or $C_6$ alkenoyl, preferably propenoyl; alkynoyl, in particular $C_3$-$C_6$ alkynoyl, e.g. $C_3$, $C_4$, $C_5$, or $C_6$ alkynoyl, preferably propynoyl; alkoxy, in particular $C_1$-$C_6$ alkoxy, e.g. $C_1$, $C_2$, $C_3$, $C_4$, $C_5$, or $C_6$ alkoxy, preferably methoxy, ethoxy, propoxy, iso-propoxy, butoxy, iso-butoxy, tert-butoxy, pentoxy, or hexoxy; alkoxyalkyl, in particular $C_1$-$C_6$ alkoxy-$C_1$-$C_6$ alkyl, e.g. methoxymethyl, ethoxymethyl, propoxymethyl, methoxyethyl, ethoxyethyl, propoxyethyl, methoxypropyl, ethoxypropyl, or propoxypropyl; and —CO—R'''; optionally substituted, preferably hydrogen, —CO—R'or aryl;
wherein
R' is hydrogen, alkyl, in particular $C_1$-$C_6$ alkyl, e.g. $C_1$, $C_2$, $C_3$, $C_4$, $C_5$, or $C_6$ alkyl; cycloalkyl, in particular ($C_{3-10}$)-cycloalkyl, preferably cyclopropyl, cyclobutyl, cyclopentyl, cyclohexyl, cycloheptyl, alkenyl, cycloalkenyl; or alkynyl; and/or $R^7$ is ($C_{1-16}$)alkyl, e.g. $C_1$, $C_2$, $C_3$, $C_4$, $C_5$ $C_6$, $C_7$, $C_8$, $C_9$, $C_{10}$, $C_{11}$, $C_{,2}$, $C_{13}$, $C_{,4}$, $C_{15}$, or $C_{16}$-alkyl, in particular methyl, ethyl, n-propyl, iso-propyl, n-butyl, sec-butyl, tert-butyl, pentyl, n-hexyl, iso-hexyl, n-heptyl, n-octyl; ($C_{2-16}$)alkenyl, e.g. $C_2$, $C_3$, $C_4$, $C_5$ $C_6$, $C_7$, $C_8$, $C_9$, $C_{10}$, $C_{11}$, $C_{12}$, $C_{13}$, $C_{14}$, $C_{15}$, or $C_{16}$-alkenyl, in particular ethenyl, propenyl, butenyl, pentenyl, hexenyl; ($C_{1-6}$)alkoxy, e.g. methoxy, ethoxy, propoxy, butoxy, pentoxy or hexoxy; ($C_{1-6}$)alkoxy-($C_{1-6}$)alkyl, e.g. methoxymethyl, ethoxymethyl, propoxymethyl, butoxymethyl, pentoxymethyl, hexoxymethyl, methoxyethyl, ethoxyethyl, propoxyethy, butoxyethyl, pentoxyethyl, hexoxyethyl, methoxypropyl, ethoxypropyl, propoxypropyl, butoxypropyl, pentoxypropyl, hexoxypropyl, methoxybutyl, ethoxybutyl, propoxybutyl, butoxybutyl, pentoxybutyl, hexoxybutyl, methoxypentyl, ethoxypentyl, propoxypentyl, butoxypentyl, pentoxypentyl, hexoxypentyl, methoxyhexyl, ethoxyhexyl, propoxyhexyl, butoxyhexyl, pentoxyhexyl, hexoxyhexyl; ($C_{1-6}$)aralkyl, e.g. $C_1$, $C_2$, $C_3$, $C_4$, $C_5$ or $C_6$-aralkyl, wherein the aryl residue is preferably selected from phenyl or naphthalenyl; or ($C_{1-6}$)heteroaralkyl, e.g. $C_1$, $C_2$, $C_3$, $C_4$, $C_5$ or $C_6$-heteroaralkyl, wherein the heteroaryl residue is preferably selected from the group consisting of oxazolyl, isoxazolyl, 1,2,5-oxadiazolyl, 1,2,3-oxadiazolyl, pyrrolyl, imidazolyl, pyrazolyl, 1,2,3-triazolyl, thiazolyl, isothiazolyl, 1,2,3,-thiadiazolyl, 1,2,5-thiadiazolyl, pyridinyl, pyrimidinyl, pyrazinyl, 1,2,3-triazinyl, 1,2,4-triazinyl, 1,3,5-triazinyl, 1-benzofuranyl, 2-benzofuranyl, indolyl, isoindolyl, benzothiophenyl, 2-benzothiophenyl, 1H-indazolyl, benzimidazolyl, benzoxazolyl, indoxazinyl, 2,1-benzisoxazolyl, benzothiazolyl, 1,2-benzisothiazolyl, 2,1-benzisothiazolyl, benzotriazolyl, 2,3-benzodiazinyl, quinolinyl, isoquinolinyl, quinoxalinyl, quinazolinyl, quinolinyl, 1,2,3-benzotriazinyl, 1,2,4-benzotriazinyl; cycloalkyl, in particular ($C_{3-10}$)-cycloalkyl, preferably cyclopropyl, cyclobutyl, cyclopentyl, cyclohexyl, cycloheptyl; cycloalkenyl, in particular ($C_{3-10}$)-cycloalkenyl; heterocycloalkyl, in particular ($C_{3-10}$)-hetercycloalkenyl; or oxo; optionally substituted; preferably $R^7$ is a non-polar side chain;

$R^8$, $R^9$ and $R^{10}$ are independent of each other selected from the group consisting of hydrogen, Cl, Br, F, ($C_{1-6}$)alkyl, e.g. $C_1$, $C_2$, $C_3$, $C_4$, $C_5$ or $C_6$-alkyl, in particular methyl, ethyl, n-propyl, iso-propyl, n-butyl, sec-butyl, tert-butyl, pentyl, n-hexyl, iso-hexyl; ($C_{2-6}$)alkenyl e.g. $C_2$, $C_3$, $C_4$, $C_5$ or $C_6$-alkenyl, in particular ethenyl, propenyl, butenyl, pentenyl, hexenyl; ($C_{1-6}$)alkoxy; ($C_{1-6}$)alkyl-($C_{1-6}$)alkoxy; ($C_{1-6}$)aralkyl; ($C_{1-6}$)heteroaralkyl.

In the above preferred embodiment of $R^7$ the respective substituent is preferably substituted with hydroxyl; halogen, F, Cl, Br or I; CN; $NO_2$; alkyl, in particular ($C_{1-6}$)alkyl, e.g. $C_1$, $C_2$, $C_3$, $C_4$, $C_5$, or $C_6$ alkyl, preferably methyl, ethyl, propyl, iso-propyl, butyl, iso-butyl, tert-butyl, pentyl, hexyl; cycloalkyl, in particular ($C_{3-10}$)-cycloalkyl, preferably cyclopropyl, cyclobutyl, cyclopentyl, cyclohexyl, cycloheptyl, heteroalkyl in particular ($C_{1-6}$)heteroalkyl, e.g. $C_1$, $C_2$, $C_3$, $C_4$, $C_5$, or $C_6$ heteroalkyl, cycloheteroalkyl, in particular ($C_{3-10}$)-cycloheteroalkyl; aryl, in particular phenyl, naphtalenyl or anthracenyl; aralkyl; heteroaryl, preferably oxazolyl, isoxazolyl, 1,2,5-oxadiazolyl, 1,2,3-oxadiazolyl, pyrrolyl, imidazolyl, pyrazolyl, 1,2,3-triazolyl, thiazolyl, isothiazolyl, 1,2, 3,-thiadiazolyl, 1,2,5-thiadiazolyl, pyridinyl, pyrimidinyl, pyrazinyl, 1,2,3-triazinyl, 1,2,4-triazinyl, 1,3,5-triazinyl, 1-benzofuranyl, 2-benzofuranyl, indolyl, isoindolyl, benzothiophenyl, 2-benzothiophenyl, 1H-indazolyl, benzimidazolyl, benzoxazolyl, indoxazinyl, 2,1-benzisoxazolyl, benzothiazolyl, 1,2-benzisothiazolyl, 2,1-benzisothiazolyl, benzotriazolyl, 2,3-benzodiazinyl, quinolinyl, isoquinolinyl, quinoxalinyl, quinazolinyl, quinolinyl, 1,2,3-benzotriazinyl, 1,2,4-benzotriazinyl; heteroalkyl; alkenyl, in particular $C_2$-$C_6$ alkenyl, e.g. $C_2$, $C_3$, $C_4$, $C_5$, or $C_6$ alkenyl, preferably ethenyl, 1-propenyl, 2-propenyl, 1-iso-propenyl, 2-iso-propenyl, 1-butenyl, 2-butenyl, 3-butenyl; cycloalkenyl, in particular ($C_{3-10}$)-cycloalkyl; or alkynyl, in particular $C_2$-$C_6$ alkynyl, e.g. $C_2$, $C_3$, $C_4$, $C_5$, or $C_6$ alkynyl; alkanoyl, preferably $C_1$-$C_6$ alkanoyl, e.g. $C_1$, $C_2$, $C_3$, $C_4$, $C_5$, or $C_6$ alkanoyl; alkenoyl, in particular $C_3$-$C_6$ alkenoyl, e.g. $C_3$, $C_4$, $C_5$, or $C_6$ alkenoyl, preferably propenoyl; alkynoyl, in particular $C_3$-$C_6$ alkynoyl, e.g. $C_3$, $C_4$, $C_5$, or $C_6$ alkynoyl, preferably propynoyl; alkoxy, in particular $C_1$-$C_6$ alkoxy, e.g. $C_1$, $C_2$, $C_3$, $C_4$, $C_5$, or $C_6$ alkoxy, preferably methoxy, ethoxy, propoxy, iso-propoxy, butoxy, iso-butoxy, tert-butoxy, pentoxy, or hexoxy; alkoxyalkyl, in particular $C_1$-$C_6$ alkoxy-$C_1$-$C_6$ alkyl, e.g. methoxymethyl, ethoxymethyl, propoxymethyl, methoxyethyl, ethoxyethyl, propoxyethyl, methoxypropyl, ethoxypropyl, or propoxypropyl; and —CO—R'''; optionally substituted, preferably hydrogen, —CO—R'' or aryl;
wherein
R'' is hydrogen, alkyl, in particular $C_1$-$C_6$ alkyl, e.g. $C_1$, $C_2$, $C_3$, $C_4$, $C_5$, or $C_6$ alkyl; cycloalkyl, in particular ($C_{3-10}$)-cycloalkyl, preferably cyclopropyl, cyclobutyl, cyclopentyl, cyclohexyl, cycloheptyl, alkenyl, cycloalkenyl; or alkynyl.

In a preferred embodiment the compound of formula (I) has the structure according to formula (III):

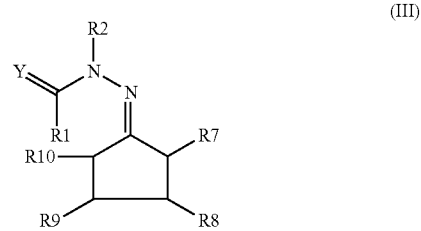

(III)

wherein,
$R^1$ is $NR^5R^6$;
$R^2$ is hydrogen or alkyl, optionally substituted, preferably hydrogen;
$R^5$ is hydrogen or alkyl, optionally substituted, preferably hydrogen;
$R^6$ hydrogen, hydroxyl, halogen, alkyl, heteroalkyl, aryl, aralkyl, heteroaryl, heteroaralkyl, alkenyl, cycloalkenyl, or alkynyl, optionally substituted, preferably hydrogen; and
$R^7$ is hydrogen, hydroxyl, halogen, alkyl, heteroalkyl, cycloalkyl, heterocycloalkyl, alicyclic system, aryl, aralkyl, aralkenyl, aralkynyl, heteroaryl, heteroaralkyl, heteroaralkenyl, heteroaralkynyl, alkenyl, cycloalkenyl, alkynyl, or $NR^{11}R^{12}$, optionally substituted, preferably $R^7$ is alkyl or alkyl interrupted one or more times by O, S, or N;
$R^8$, $R^9$ and $R^{10}$ are independent of each other hydrogen, hydroxyl, halogen, alkyl, heteroalkyl, aryl, aralkyl, heteroaryl, heteroaralkyl, alkenyl, cycloalkenyl, or alkynyl, optionally substituted, preferably hydrogen;
$R^{11}$ is hydrogen or alkyl, optionally substituted;

R¹² is hydrogen, hydroxyl, halogen, alkyl, heteroalkyl, aryl, aralkyl, heteroaryl, heteroaralkyl, alkenyl, cycloalkenyl, or alkynyl, optionally substituted; and Y is S or N, preferably S;
or a pharmaceutically acceptable salt thereof. Preferred salts comprise Na⁺, K⁺, Mg²⁺, and Ca²⁺. It is preferred that R⁷ is a non-polar side chain.

In a preferred use of the embodiment of the invention wherein the compound has a structure according to formula (II) or (III)

R⁷ is substituted, preferably 1, 2, or 3 times with a radical selected from the group consisting of halogen; hydroxyl; SO₂; NO₂; CN; $(C_{1-16})$alkyl, e.g. $C_1$, $C_2$, $C_3$, $C_4$, $C_5$ $C_6$, $C_7$, $C_8$, C9, $C_{10}$, $C_{11}$, $C_{12}$, $C_{13}$, $C_{14}$, $C_{15}$, or $C_{16}$, in particular methyl, ethyl, propyl, butyl, pentyl hexyl, heptyl, or octyl ; $(C_{2-16})$alkenyl, e.g. $C_2$, $C_3$, $C_4$, $C_5$ $C_6$, $C_7$, $C_8$, $C_9$, $C_{10}$, $C_{11}$, $C_{12}$, $C_{13}$, $C_{14}$, $C_{15}$, or $C_{16}$, in particular ethenyl, propenyl, butenyl, pentenyl, hexenyl, heptenyl, or octenyl; $(C_{1-6})$ alkoxy, e.g. methoxy, ethoxy, propoxy, butoxy, pentoxy or hexoxy; $(C_{1-6})$alkyl-$(C_{1-6})$alkoxy; amino, optionally mono- or disubstituted by $(C_{1-6})$alkoxy, $(C_{1-6})$alkyl, $(C_{2-6})$alkenyloxyl, $(C_{2-6})$alkenyl, $(C_{1-6})$alkyl, $(C_{2-6})$alkenyl, $(C_{1-6})$alkylsulphonyl, and $(C_{2-6})$alkenylsulphonyl;
or two adjacent substituents are taken together to form a 4, 5, 6, or 7 membered cycloalkyl or cycloalkenyl; and/or R⁸, R⁹, and R¹⁰ are each independent of each other substituted, preferably 1, 2, or 3 times with a radical selected from the group consisting of halogen, e.g. F, Cl, Br; hydroxyl; SO₂; NO₂; CN; $(C_{1-6})$alkyl, e.g. $C_1$, $C_2$, $C_3$, $C_4$, $C_5$, or $C_6$-alkyl, in particular methyl, ethyl, propyl, butyl, pentyl or hexyl; $(C_{2-6})$alkenyl, e.g. $C_2$, $C_3$, $C_4$, $C_5$, or $C_6$-alkenyl, in particular ethenyl, propenyl, butenyl, pentenyl, hexenyl; $(C_{1-6})$ alkoxy, e.g. methoxy, ethoxy, propoxy, butoxy, pentoxy or hexoxy; and/or R², R⁵, R⁶, R¹¹ and R¹² are each independent of each other substituted, preferably 1, 2, or 3 times with a radical selected from the group consisting of halogen, e.g. F, Cl, Br; hydroxyl; SO₂; NO₂, CN; $(C_{1-6})$alkyl, e.g. $C_1$, $C_2$, $C_3$, $C_4$, $C_5$, or $C_6$-alkyl, in particular methyl, ethyl, propyl, butyl, pentyl or hexyl; $(C_{2-6})$alkenyl, e.g. $C_2$, $C_3$, $C_4$, $C_5$, or $C_6$-alkenyl, in particular ethenyl, propenyl, butenyl, pentenyl, hexenyl; $(C_{1-6})$alkoxy, e.g. methoxy, ethoxy, propoxy, butoxy, pentoxy or hexoxy.

In a preferred use of this embodiment of the invention wherein the compound has a structure according to formula (II) or (III)

R² is hydrogen or $(C_{1-6})$alkyl, e.g. $C_1$, $C_2$, $C_3$, $C_4$, $C_5$ or $C_6$-alkyl, in particular methyl, ethyl, n-propyl, iso-propyl, n-butyl, sec-butyl, tert-butyl, pentyl, n-hexyl, iso-hexyl;

R⁵ is hydrogen;

R⁶ is hydrogen, $(C_{1-6})$alkyl, e.g. $C_1$, $C_2$, $C_3$, $C_4$, $C_5$ or $C_6$-alkyl, in particular methyl, ethyl, n-propyl, iso-propyl, n-butyl, sec-butyl, tert-butyl, pentyl, n-hexyl, iso-hexyl or $(C_{2-6})$alkenyl;

R⁷ is $(C_{1-16})$alkyl, e.g. $C_1$, $C_2$, $C_3$, $C_4$, $C_5$ $C_6$, $C_7$, $C_8$, $C_9$, $C_{10}$, $C_{11}$, $C_{12}$, $C_{13}$, $C_{14}$, $C_{15}$, or $C_{16}$-alkyl, in particular methyl, ethyl, n-propyl, iso-propyl, n-butyl, sec-butyl, tert-butyl, pentyl, n-hexyl, iso-hexyl, n-heptyl, n-octyl; $(C_{2-16})$alkenyl, e.g. $C_2$, $C_3$, $C_4$, $C_5$ $C_6$, $C_7$, $C_8$, $C_9$, $C_{10}$, $C_{11}$, $C_{12}$, $C_{13}$, $C_{14}$, $C_{15}$, or $C_{16}$-alkenyl, in particular ethenyl, propenyl, butenyl, pentenyl, hexenyl; $(C_{1-6})$alkoxy, e.g. methoxy, ethoxy, propoxy, butoxy, pentoxy or hexoxy; $(C_{1-6})$alkoxy-$(C_{1-6})$alkyl, e.g. methoxymethyl, ethoxymethyl, propoxymethyl, butoxymethyl, pentoxymethyl, hexoxymethyl, methoxyethyl, ethoxyethyl, propoxyethy, butoxyethyl, pentoxyethyl, hexoxyethyl, methoxypropyl, ethoxypropyl, propoxypropyl, butoxypropyl, pentoxypropyl, hexoxypropyl, methoxybutyl, ethoxybutyl, propoxybutyl, butoxybutyl, pentoxybutyl, hexoxybutyl, methoxypentyl, ethoxypentyl, propoxypentyl, butoxypentyl, pentoxypentyl, hexoxypentyl, methoxyhexyl, ethoxyhexyl, propoxyhexyl, butoxyhexyl, pentoxyhexyl, hexoxyhexyl; $(C_{1-6})$aralkyl, e.g. $C_1$, $C_2$, $C_3$, $C_4$, $C_5$ or $C_6$-aralkyl; or $(C_{1-6})$heteroaralkyl, e.g. $C_1$, $C_2$, $C_3$, $C_4$, $C_5$ or $C_6$-heteroaralkyl, preferably R⁷ is a non-polar side chain;

R⁸, R⁹ and R¹⁰ are independent of each other selected from the group consisting of hydrogen, Cl, Br, F, $(C_{1-6})$alkyl, e.g. $C_1$, $C_2$, $C_3$, $C_4$, $C_5$ or $C_6$-alkyl, in particular methyl, ethyl, n-propyl, iso-propyl, n-butyl, sec-butyl, tert-butyl, pentyl, n-hexyl, iso-hexyl; $(C_{2-6})$alkenyl e.g. $C_2$, $C_3$, $C_4$, $C_5$ or $C_o$-alkenyl, in particular ethenyl, propenyl, butenyl, pentenyl, hexenyl; $(C_{1-6})$alkoxy; $(C_{1-6})$alkyl-$(C_{1-6})$alkoxy; $(C_{1-6})$aralkyl; $(C_{1-6})$heteroaralkyl.

In a preferred use of the invention the compound according to formula (III) has a structure selected from the structures according to formulas (IV) to (VII)

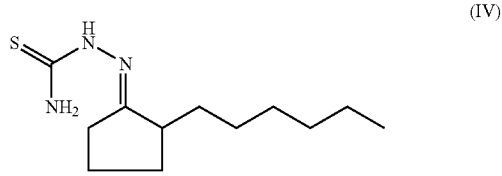

(IV)

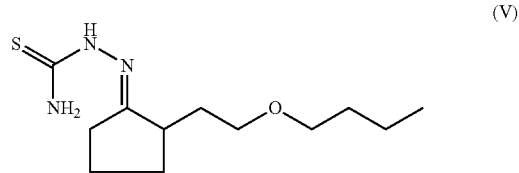

(V)

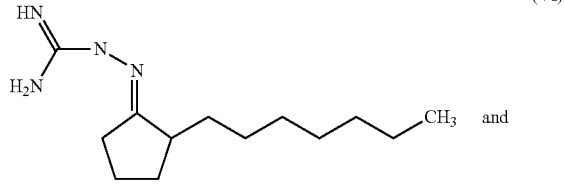

(VI)

and

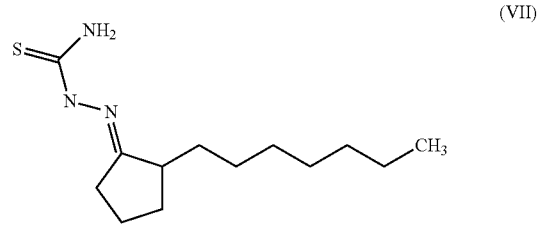

(VII)

or a pharmaceutically acceptable salt thereof. Preferred salts comprise Na⁺, K⁺, Mg²⁺, and Ca²⁺.

In a preferred embodiment of the use of the present invention wherein the compound has a structure according to formula (II) one, two or three of R⁷, R⁸, R⁹, and R¹⁰ are each independent of each other selected from the group consisting of $(C_{1-16})$alkyl, e.g. $C_1$, $C_2$, $C_3$, $C_4$, $C_5$ $C_6$, $C_7$, $C_8$, $C_9$, $C_{10}$, $C_{11}$, $C_{12}$, $C_{13}$, $C_{14}$, $C_{15}$, or $C_{16}$-alkyl, in particular methyl, ethyl, n-propyl, iso-propyl, n-butyl, sec-butyl, tert-butyl, pentyl, n-hexyl, iso-hexyl, n-heptyl, n-octyl; $(C_{2-16})$alkenyl, e.g. $C_2$, $C_3$, $C_4$, $C_5$ $C_6$, $C_7$, $C_8$, $C_9$, $C_{10}$, $C_{11}$, $C_{12}$, $C_{13}$, $C_{14}$, $C_{15}$, or $C_6$-alkenyl, in particular ethenyl, propenyl, butenyl, pentenyl, hexenyl; oxo; $(C_{1-6})$alkoxy, e.g. methoxy, ethoxy, propoxy, butoxy, pentoxy or hexoxy; $(C_{1-6})$alkoxy-$(C_{1-6})$alkyl, e.g. methoxymethyl, ethoxymethyl, propoxymethyl, butoxymethyl, pentoxymethyl, hexoxymethyl, methoxyethyl, ethoxyethyl, propoxyethy, butoxyethyl, pentoxyethyl, hexoxyethyl, methoxypropyl, ethoxypropyl, propoxypropyl, butoxypropyl, pentoxypropyl, hexoxypropyl, methoxybutyl, ethoxybutyl, propoxybutyl, butoxybutyl, pentoxybutyl, hexoxybutyl, methoxypentyl, ethoxypentyl, propoxypentyl, butoxypentyl, pentoxypentyl, hexoxypentyl, methoxyhexyl, ethoxyhexyl, propoxyhexyl, butoxyhexyl, pentoxyhexyl, hexoxyhexyl; $(C_{1-6})$aralkyl, e.g. $C_1$, $C_2$, $C_3$, $C_4$, $C_5$ or $C_6$-aralkyl; or $(C_{1-6})$heteroaralkyl, e.g. $C_1$, $C_2$, $C_3$, $C_4$, $C_5$ or $C_6$-heteroaralkyl, optionally substituted. The other substituent(s) in this case are preferably hydrogen.

In a preferred embodiment of the use of the present invention wherein the compound has a structure according to formula (II) one or both of $R^7$ and $R^8$ or $R^9$ and $R^{10}$, preferably $R^9$ and $R^{10}$, together form an oxazolyl, isoxazolyl, 1,2,5-oxadiazolyl, 1,2,3-oxadiazolyl, pyrrolyl, imidazolyl, pyrazolyl, 1,2,3-triazolyl, thiazolyl, isothiazolyl, 1,2,3,-thiadiazolyl, 1,2,5-thiadiazolyl, pyridinyl, pyrimidinyl, pyrazinyl, 1,2,3-triazinyl, 1,2,4-triazinyl, 1,3,5-triazinyl, 1-benzofuranyl, 2-benzofuranyl, indolyl, isoindolyl, benzothiophenyl, 2-benzothiophenyl, 1H-indazolyl, benzimidazolyl, benzoxazolyl, indoxazinyl, 2,1-benzisoxazolyl, benzothiazolyl, 1,2-benzisothiazolyl, 2,1-benzisothiazolyl, benzotriazolyl, 2,3-benzodiazinyl, quinolinyl, isoquinolinyl, quinoxalinyl, quinazolinyl, quinolinyl, 1,2,3-benzotriazinyl, 1,2,4-benzotriazinyl, phenyl, naphtalenyl or antracenyl, optionally substituted. The other substituents $R^7$ and $R^8$ or $R^9$ and $R^{10}$ as the case may be, are each independent of each other selected from the group consisting of hydrogen, $(C_{1-16})$alkyl, e.g. $C_1$, $C_2$, $C_3$, $C_4$, $C_5$ $C_6$, $C_7$, $C_8$, $C_9$, $C_{10}$, $C_{11}$, $C_{12}$, $C_{13}$, $C_{14}$, $C_{15}$, or $C_{16}$-alkyl, in particular methyl, ethyl, n-propyl, iso-propyl, n-butyl, sec-butyl, tert-butyl, pentyl, n-hexyl, iso-hexyl, n-heptyl, n-octyl; $(C_{2-16})$alkenyl, e.g. $C_2$, $C_3$, $C_4$, $C_5$ $C_6$, $C_7$, $C_8$, $C_9$, $C_{10}$, $C_{11}$, $C_{12}$, $C_{13}$, $C_{14}$, $C_{15}$, or $C_{16}$-alkenyl, in particular ethenyl, propenyl, butenyl, pentenyl, hexenyl; oxo; $(C_{1-6})$alkoxy, e.g. methoxy, ethoxy, propoxy, butoxy, pentoxy or hexoxy; $(C_{1-6})$alkoxy-$(C_{1-6})$alkyl, e.g. methoxymethyl, ethoxymethyl, propoxymethyl, butoxymethyl, pentoxymethyl, hexoxymethyl, methoxyethyl, ethoxyethyl, propoxyethy, butoxyethyl, pentoxyethyl, hexoxyethyl, methoxypropyl, ethoxypropyl, propoxypropyl, butoxypropyl, pentoxypropyl, hexoxypropyl, methoxybutyl, ethoxybutyl, propoxybutyl, butoxybutyl, pentoxybutyl, hexoxybutyl, methoxypentyl, ethoxypentyl, propoxypentyl, butoxypentyl, pentoxypentyl, hexoxypentyl, methoxyhexyl, ethoxyhexyl, propoxyhexyl, butoxyhexyl, pentoxyhexyl, hexoxyhexyl; $(C_{1-6})$aralkyl, e.g. $C_1$, $C_2$, $C_3$, $C_4$, $C_5$ or $C_6$-aralkyl; or $(C_{1-6})$heteroaralkyl, e.g. $C_1$, $C_2$, $C_3$, $C_4$, $C_5$ or $C_6$-heteroaralkyl, optionally substituted.

In a preferred use of the invention the compound according to formula (II) has a structure selected from the structures according to formulas (VIII) to (XXXI)

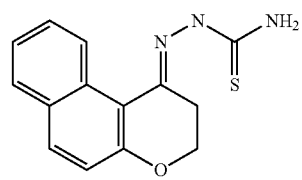
(VIII)

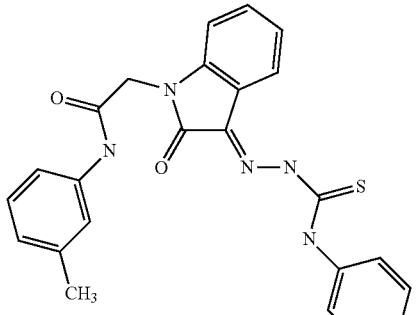
(IX)

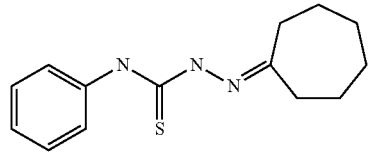
(X)

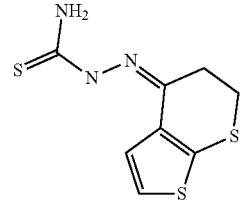
(XI)

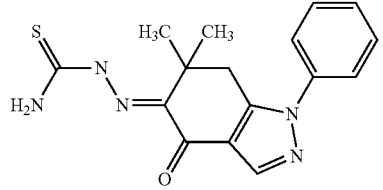
(XII)

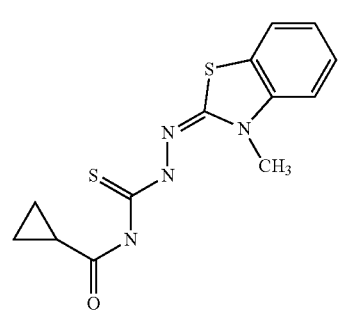
(XIII)

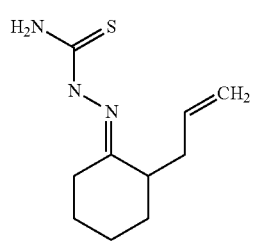
(XIV)

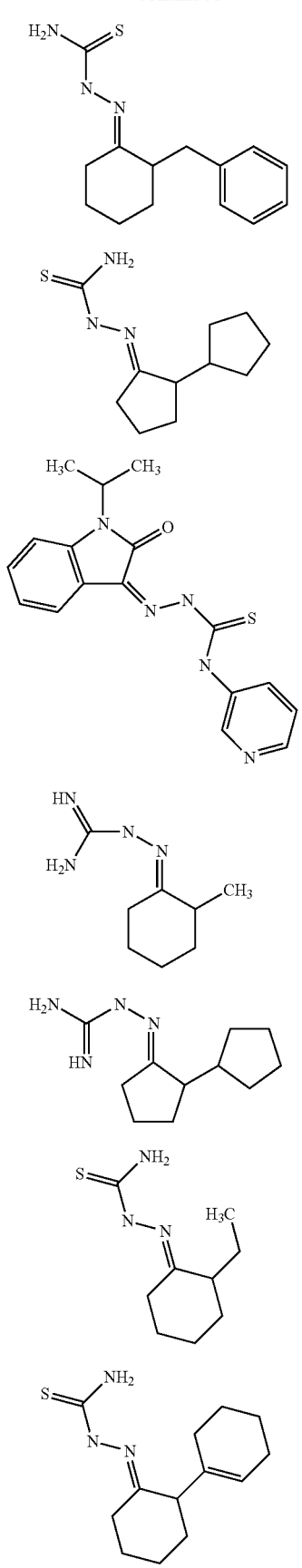
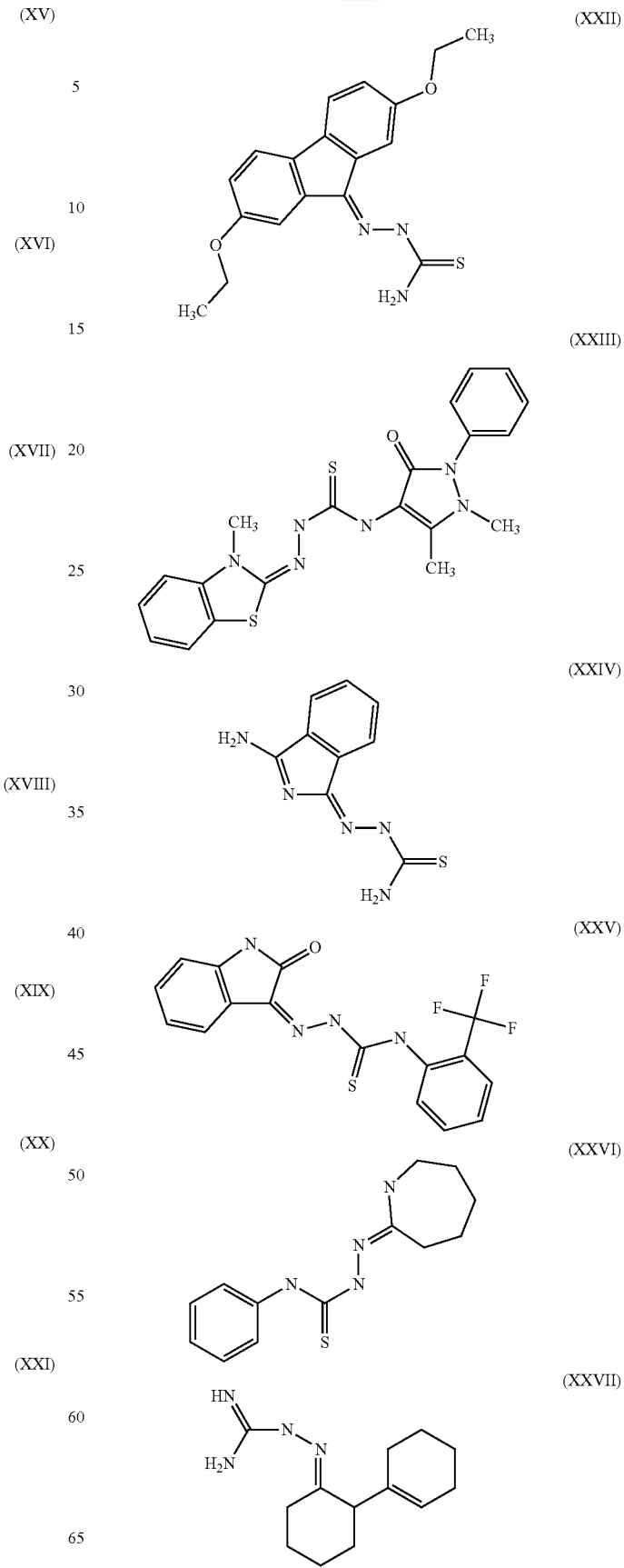

(XXVIII)

(XXIX)

(XXX)

(XXXI)

optionally substituted or a pharmaceutically acceptable salt thereof.

In a preferred embodiment the compound usable according to the present invention having a structure according to formula (VI) to (XXXI) is substituted, preferably 1, 2, or 3 times with a radical selected from the group consisting of halogen, e.g. F, Cl, Br, or I; hydroxyl; $SO_2$; $NO_2$; CN; $(C_{1-16})$alkyl, e.g. $C_1, C_2, C_3, C_4, C_5, C_6, C_7, C_8, C_9, C_{10}, C_{11}, C_{12}, C_{13}, C_{14}, C_{15}$, or $C_{16}$, in particular methyl, ethyl, propyl, butyl, pentyl hexyl, heptyl, or octyl; $(C_{2-16})$alkenyl, e.g. $C_2, C_3, C_4, C_5 C_6, C_7, C_8, C_9, C_{10}, C_{11}, C_{12}, C_{13}, C_{14}, C_{15}$, or $C_{16}$, in particular ethenyl, propenyl, butenyl, pentenyl, hexenyl, heptenyl, or octenyl; $(C_{1-6})$alkoxy, e.g. methoxy, ethoxy, propoxy, butoxy, pentoxy or hexoxy; $(C_{1-6})$alkyl-$(C_{1-6})$alkoxy; amino, optionally mono- or disubstituted by $(C_{1-6})$alkoxy, $(C_{1-6})$alkyl, $(C_{2-6})$alkenyloxy, $(C_{2-6})$alkenyl, $(C_{1-6})$alkyl, $(C_{2-6})$alkenyl, $(C_{1-6})$alkylsulphonyl; $(C_{2-6})$alkenylsulphonyl; and $NR^{11'}R^{12'}$; or two adjacent substituents are taken together to form a 4, 5, 6, or 7 membered cycloalkyl or cycloalkenyl, optionally substituted;

wherein $R^{11'}$ and $R^{12'}$ are independent of each other selected from hydrogen, hydroxyl; halogen; alkyl, preferably $(C_{1-6})$alkyl, e.g. $C_1, C_2, C_3, C_4, C_5$, or $C_6$-alkyl, in particular methyl, ethyl, propyl, butyl, pentyl or hexyl; heteroalkyl, preferably $(C_{1-6})$heteroalkyl, e.g. $C_1, C_2, C_3, C_4, C_5$, or $C_6$-heteroalkyl, wherein preferably one or two carbon atoms are replaced by a heteroatom selected from the group consisting of N, S, and O; $(C_{1-6})$alkoxy; $(C_{1-6})$alkylsulphonyl; alkenyl, preferably $(C_{2-6})$alkenyl, $(C_{2-6})$alkenyloxy, cycloalkenyl, $(C_{2-6})$alkenylsulphonyl; alkynyl; aryl; aralkyl; heteroaryl; or heteroaralkyl, optionally substituted.

In a preferred use of the invention the inhibitor of the scavenger receptor class protein is a compound having a structure according to the following formula (XXXII):

(XXXII)

wherein, $R^1$ is $NR^5R^6$;

$R^2$ is hydrogen or alkyl, optionally substituted;

$R^5$ is hydrogen, alkyl or alkenyl, optionally substituted;

$R^6$ is hydrogen; hydroxyl; halogen; alkyl, preferably $(C_{1-8})$alkyl, e.g. $C_1, C_2, C_3, C_4, C_5, C_6, C_7$ or $C_8$-alkyl; heteroalkyl, preferably $(C_{1-8})$heteroalkyl, e.g. $C_1, C_2, C_3, C_4, C_5, C_6, C_7$ or $C_8$-alkyl; cycloalkyl, preferably $(C_{3-10})$-cycloalkyl, e.g. $C_1, C_2, C_3, C_4, C_5, C_6, C_7, C_8, C_9$, or $C_{10}$; cycloheteroalkyl, preferably $(C_{3-10})$-cycloheteroalkyl, e.g. $C_1, C_2, C_3, C_4, C_5, C_6, C_7, C_8, C_9$, or $C_{10}$, wherein preferably one or two carbon atoms are substituted by heteroatoms, preferably selected from the group consisting of S, N, and O; aralkyl, preferably $(C_{1-6})$-aralkyl, e.g. $C_1, C_2, C_3, C_4, C_5$, or $C_6$-aralkyl; heteroaryl, preferably mono or bicyclic heteroaryl, preferably comprising one, two or three heteroatoms selected from the group consisting of S, N, and O; heteroaralkyl, preferably $(C_{1-6})$-heteroaralkyl, e.g. $C_1, C_2, C_3, C_4, C_5$, or $C_6$-heteroaralkyl, wherein the heteroaryl preferably is a mono or bicyclic heteroaryl, preferably comprising one, two or three heteroatoms selected from the group consisting of S, N, and O; alkenyl, preferably $(C_{2-6})$-alkenyl e.g. $C_2, C_3, C_4, C_5$, or $C_6$-alkenyl, preferably ethenyl, 1-propenyl, 2-propenyl, 1-iso-propenyl, 2-iso-propenyl, 1-butenyl, 2-butenyl, 3-butenyl; cycloalkenyl, preferably $C_{3-10}$-cycloalkenyl, e.g. $C_1, C_2, C_3, C_4, C_5, C_6, C_7, C_8, C_9$, or $C_{10}$-cycloalkenyl; cycloheteroalkenyl, preferably $(C_{3-10})$-cycloheteroalkenyl, e.g. $C_1, C_2, C_3, C_4, C_5, C_6, C_7, C_8, C_9$, or $C_{10}$-cycloheteroalkenyl; or alkynyl, preferably $(C_{2-6})$-alkynyl e.g. $C_2, C_3, C_4, C_5$, or $C_6$-alkynyl; optionally substituted, preferably cycloalkyl, cycloheteroalykl, aryl or heteroaryl;

$R^{13}, R^{14}, R^{15}, R^{16}$, and $R^{17}$ are independent of each other hydrogen, hydroxyl, halogen, $SO_2$, $NO_2$, CN; alkyl, heteroalkyl, cycloalkyl, heterocycloalkyl, alicyclic system, aryl, aralkyl, aralkenyl, aralkynyl, heteroaryl, heteroaralkyl, heteroaralkenyl, heteroaralkynyl, alkenyl, cycloalkenyl, alkynyl, or $NR^{11}R^{12}$, optionally substituted;

$R^{11}$ is hydrogen or alkyl, optionally substituted;

$R^{12}$ is hydrogen, hydroxyl, halogen, alkyl, heteroalkyl, aryl, aralkyl, heteroaryl, heteroaralkyl, alkenyl, cycloalkenyl, or alkynyl, optionally substituted; and X is S or O;

or a pharmaceutically acceptable salt thereof. Preferred salts comprise $Na^+$, $K^+$, $Mg^{2+}$, and $Ca^{2+}$.

In a preferred embodiment of the use of the present invention the compound has a structure according to formula (XXXII) wherein $R^2$ and $R^5$ are independent of each other substituted preferably 1 to 3 time with a radical selected from the group consisting of halogen, e.g. F, Cl, Br; hydroxyl; $SO_2$; $NO_2$; CN; $(C_{1-6})$alkyl, e.g. $C_1$, $C_2$, $C_3$, $C_4$, $C_5$, or $C_6$-alkyl, in particular methyl, ethyl, propyl, butyl, pentyl or hexyl; $(C_{2-6})$alkenyl, e.g. $C_2$, $C_3$, $C_4$, $C_5$, or $C_6$-alkenyl, in particular ethenyl, propenyl, butenyl, pentenyl, hexenyl; $(C_{1-6})$alkoxy, e.g. methoxy, ethoxy, propoxy, butoxy, pentoxy or hexoxy; and/or $R^6$ is substituted preferably 1 to 3 time with a radical selected from the group consisting of halogen, e.g. F, Cl, Br; hydroxyl; $SO_2$; $NO_2$; CN; $(C_{1-6})$alkyl, e.g. $C_1$, $C_2$, $C_3$, $C_4$, $C_5$, or $C_6$-alkyl, in particular methyl, ethyl, propyl, butyl, pentyl or hexyl; $(C_{2-6})$alkenyl, e.g. $C_2$, $C_3$, $C_4$, $C_5$, or $C_6$-alkenyl, in particular ethenyl, propenyl, butenyl, pentenyl, hexenyl; $(C_{1-6})$alkoxy, e.g. methoxy, ethoxy, propoxy, butoxy, pentoxy or hexoxy; $(C_{1-6})$alkoxy-$(C_{1-6})$alkyl; $NR^{11'}R^{12'}$; or two adjacent substituents are taken together to form a 4, 5, 6, or 7 membered cycloalkyl or cycloalkenyl, optionally substituted;

wherein $R^{11'}$ and $R^{12'}$ are independent of each other selected from hydrogen, hydroxyl; halogen; alkyl, preferably $(C_{1-6})$alkyl, e.g. $C_1$, $C_2$, $C_3$, $C_4$, $C_5$, or $C_6$-alkyl, in particular methyl, ethyl, propyl, butyl, pentyl or hexyl; heteroalkyl, preferably $(C_{1-6})$heteroalkyl, e.g. $C_1$, $C_2$, $C_3$, $C_4$, $C_5$, or $C_6$-heteroalkyl, wherein preferably one or two carbon atoms are replaced by a heteroatom selected from the group consisting of N, S, and O; $(C_{1-6})$alkoxy; $(C_{1-6})$alkylsulphonyl; alkenyl, preferably $(C_{2-6})$alkenyl, $(C_{2-6})$alkenyloxy, cycloalkenyl, $(C_{2-6})$alkenylsulphonyl; alkynyl; aryl; aralkyl; heteroaryl; or heteroaralkyl, optionally substituted; and/or $R^{13}$, $R^{14}$, $R^{15}$, $R^{16}$, and $R^{17}$ are independent of each other substituted preferably 1 to 3 time with a radical selected from the group consisting of halogen, e.g. F, Cl, Br; hydroxyl; $SO_2$; $NO_2$; CN; $(C_{1-6})$alkyl, e.g. $C_1$, $C_2$, $C_3$, $C_4$, $C_5$, or $C_6$-alkyl, in particular methyl, ethyl, propyl, butyl, pentyl or hexyl; $(C_{2-6})$alkenyl, e.g. $C_2$, $C_3$, $C_4$, $C_5$, or $C_6$-alkenyl, in particular ethenyl, propenyl, butenyl, pentenyl, hexenyl; $(C_{1-6})$alkoxy, e.g. methoxy, ethoxy, propoxy, butoxy, pentoxy or hexoxy; $(C_{1-6})$alkoxy$(C_{1-6})$alkyl; amino, optionally mono- or disubstituted by $(C_{1-6})$alkoxy, e.g. $C_1$, $C_2$, $C_3$, $C_4$, $C_5$ or $C_6$-alkoxy, in particular methoxy, ethoxy, propxy, butoxy, pentoxy, hexoxy, $(C_{1-6})$alkyl, $(C_{2-6})$alkenyloxy, $(C_{2-6})$alkenyl, $(C_{1-6})$alkyl, $(C_{2-6})$alkenyl, $(C_{1-6})$alkylsulphonyl, and $(C_{2-6})$alkenylsulphonyl.

In a preferred embodiment of the use of the present invention the compound has a structure according to formula (XXXII) wherein $R^2$ is hydrogen or $(C_{1-6})$alkyl, e.g. $C_1$, $C_2$, $C_3$, $C_4$, $C_5$ or $C_6$-alkyl, in particular methyl, ethyl, n-propyl, iso-propyl, n-butyl, sec-butyl, tert-butyl, pentyl, n-hexyl, iso-hexyl; and/or $R^5$ is hydrogen, $(C_{1-6})$alkyl, e.g. $C_1$, $C_2$, $C_3$, $C_4$, $C_5$, or $C_6$-alkyl, in particular methyl, ethyl, propyl, butyl, pentyl or hexyl; $(C_{2-6})$alkenyl, e.g. $C_2$, $C_3$, $C_4$, $C_5$, or $C_6$-alkenyl, in particular ethenyl, propenyl, butenyl, pentenyl, hexenyl; and/or $R^6$ is phenyl; naphthalenyl; anthracenyl; furanyl; thiophenyl; oxazolyl; isoxazolyl; 1,2,5-oxadiazolyl; 1,2,3-oxadiazolyl; pyrrolyl; imidazolyl; pyrazolyl; 1,2,3-triazolyl; thiazolyl; isothiazolyl; 1,2,3,-thiadiazolyl; 1,2,5-thiadiazolyl; pyridinyl; pyrimidinyl; pyrazinyl; 1,2,3-triazinyl; 1,2,4-triazinyl; 1,3,5-triazinyl; 1-benzofuranyl; 2-benzofuranyl; indolyl; isoindolyl; benzothiophenyl; 2-benzothiophenyl; 1H-indazolyl; benzimidazolyl; benzoxazolyl; indoxazinyl; 2,1-benzisoxazolyl; benzothiazolyl; 1,2-benzisothiazolyl; 2,1-benzisothiazolyl; benzotriazolyl; quinolinyl; isoquinolinyl; 2,3-benzodiazinyl; quinoxalinyl; quinazolinyl; quinolinyl; 1,2,3-benzotriazinyl; 1,2,4-benzotriazinyl; cyclopropyl; cyclobutyl; cyclopentyl; cyclohexyl; cycloheptyl; spiro-[3,3]-heptyl; spiro-[3,4]-octyl; spiro-[4,3]-octyl; spiro-[3,5]-nonyl; spiro-[5,3]-nonyl; spiro-[3,6]-decyl; spiro-[6,3]-decyl; spiro-[4,5]-decyl, spiro-[5,4]-decyl, bicyclo-[2.2.1]-heptyl, bicyclo-[2.2.2]-octyl, adamantyl, piperidinyl; 1,2-diazacyclohexyl; 1,3-diazacyclohexyl; piperazinyl; 1-oxo-2-azacyclohexyl; 1-oxo-3-azacyclohexyl; 1,8-diaza-spiro-[4,5]-decyl; 1,7-diaza-spiro-[4,5]-decyl; 1,6-diaza-spiro-[4,5]-decyl; 2,8-diaza-spiro[4,5]decyl; 2,7-diaza-spiro[4,5]-decyl; 2,6-diaza-spiro[4,5]decyl; 1,8-diaza-spiro-[5,4]decyl; 1,7-diaza-spiro-[5,4]-decyl; 2,8-diaza-spiro-[5,4]-decyl; 2,7-diaza-spiro-[5,4]-decyl; 3,8-diaza-spiro-[5,4]-decyl; 3,7-diaza-spiro-[5,4]-decyl; 1,4-diazabicyclo-[2.2.2]-oct-2-yl morpholinyl; tetrahydrofuranyl; tetrahydrothiophenyl; pyrrolidinyl; $(C_{1-6})$aralkyl; $(C_1-C_6)$heteroaralkyl; $(C_{1-6})$alkyl or $(C_{2-6})$alkenyl; optionally substituted; and/or $R^{13}$ is $(C_{1-6})$alkyl, e.g. $C_1$, $C_2$, $C_3$, $C_4$, $C_5$ or $C_6$-alkyl, in particular methyl, ethyl, n-propyl, iso-propyl, n-butyl, sec-butyl, tert-butyl, pentyl, n-hexyl, iso-hexyl; $(C_{2-6})$alkenyl; $(C_{1-6})$alkoxy; $(C_{1-6})$alkoxy$(C_{1-6})$alkyl; $(C_{1-o})$aralkyl; or $(C_{1-6})$heteroaralkyl; and/or $R^{13}$, $R^{14}$, $R^{15}$, $R^{16}$, and $R^{17}$ are independent of each other selected from the group consisting of hydrogen, halogen, e.g. F, Cl, Br; hydroxyl; $SO_2$; $NO_2$, CN; $(C_{1-6})$alkyl, e.g. $C_1$, $C_2$, $C_3$, $C_4$, $C_5$, or $C_6$-alkyl, in particular methyl, ethyl, propyl, butyl, pentyl or hexyl; $(C_{2-6})$alkenyl, e.g. $C_2$, $C_3$, $C_4$, $C_5$, or $C_6$-alkenyl, in particular ethenyl, propenyl, butenyl, pentenyl, hexenyl; $(C_{1-6})$alkoxy, e.g. methoxy, ethoxy, propoxy, butoxy, pentoxy or hexoxy; $(C_{1-6})$alkoxy$(C_{1-6})$alkyl; $(C_{1-6})$aralkyl; $(C_{1-6})$heteroaralkyl.

In a preferred embodiment of the use of the present invention the compound has a structure according to formula (XXXII) wherein $R^2$ is hydrogen or $(C_{1-6})$alkyl, e.g. $C_1$, $C_2$, $C_3$, $C_4$, $C_5$ or $C_6$-alkyl, in particular methyl, ethyl, n-propyl, iso-propyl, n-butyl, sec-butyl, tert-butyl, pentyl, n-hexyl, iso-hexyl;

$R^5$ is hydrogen, $(C_{1-6})$alkyl, e.g. $C_1$, $C_2$, $C_3$, $C_4$, $C_5$, or $C_6$-alkyl, in particular methyl, ethyl, propyl, butyl, pentyl or hexyl; $(C_{2-6})$alkenyl, e.g. $C_2$, $C_3$, $C_4$, $C_5$, or $C_6$-alkenyl, in particular ethenyl, propenyl, butenyl, pentenyl, hexenyl;

$R^6$ is phenyl; naphthalenyl; anthracenyl; furanyl; thiophenyl; oxazolyl; isoxazolyl; 1,2,5-oxadiazolyl; 1,2,3-oxadiazolyl; pyrrolyl; imidazolyl; pyrazolyl; 1,2,3-triazolyl; thiazolyl; isothiazolyl; 1,2,3,-thiadiazolyl; 1,2,5-thiadiazolyl; pyridinyl; pyrimidinyl; pyrazinyl; 1,2,3-triazinyl; 1,2,4-triazinyl; 1,3,5-triazinyl; 1-benzofuranyl; 2-benzofuranyl; indolyl; isoindolyl; benzothiophenyl; 2-benzothiophenyl; 1H-indazolyl; benzimidazolyl; benzoxazolyl; indoxazinyl; 2,1-benzisoxazolyl; benzothiazolyl; 1,2-benzisothiazolyl; 2,1-benzisothiazolyl; benzotriazolyl; quinolinyl; isoquinolinyl; 2,3-benzodiazinyl; quinoxalinyl; quinazolinyl; quinolinyl; 1,2,3-benzotriazinyl; 1,2,4-benzotriazinyl; cyclopropyl;

cyclobutyl; cyclopentyl; cyclohexyl; cycloheptyl; Spiro-[3,3]-heptyl; spiro-[3,4]-octyl; spiro-[4,3]-octyl; spiro-[3,5]-nonyl; spiro-[5,3]-nonyl; spiro-[3,6]-decyl; spiro-[6,3]-decyl; spiro-[4,5]-decyl, spiro-[5,4]-decyl, bicyclo-[2.2.1]-heptyl, bicyclo-[2.2.2]-octyl, adamantyl, piperidinyl; 1,2-diazacyclohexyl; 1,3-diazacyclohexyl; piperazinyl; 1-oxo-2-azacyclohexyl; 1-oxo-3-azacyclohexyl; 1,8-diaza-spiro-[4,5]-decyl; 1,7-diaza-spiro-[4,5]-decyl; 1,6-diaza-spiro-[4,5]-decyl; 2,8-diaza-spiro[4,5]decyl; 2,7-diaza-spiro[4,5]-decyl; 2,6-diaza-spiro[4,5]decyl; 1,8-diaza-spiro-[5,4]decyl; 1,7-diaza-spiro-[5,4]-decyl; 2,8-diaza-spiro-[5,4]-decyl; 2,7-diaza-spiro-[5,4]-decyl; 3,8-diaza-spiro-[5,4]-decyl; 3,7-diaza-spiro-[5,4]-decyl; 1,4-diazabicyclo-[2.2.2]-oct-2-ylmorpholinyl; tetrahydrofuranyl; tetrahydrothiophenyl; pyrrolidinyl; $(C_{1-6})$aralkyl; $(C_1-C_6)$heteroaralkyl; $(C_{1-6})$alkyl or $(C_{2-6})$alkenyl; optionally substituted and $R^{13}$, $R^{14}$, $R^{15}$, $R^{16}$, and $R^{17}$ are independent of each other selected from the group consisting of hydrogen, halogen, e.g. F, Cl, Br; hydroxyl; $SO_2$; $NO_2$; CN; $(C_{1-6})$alkyl, e.g. $C_1$, $C_2$, $C_3$, $C_4$, $C_5$, or $C_6$-alkyl, in particular methyl, ethyl, propyl, butyl, pentyl or hexyl; $(C_{2-6})$alkenyl, e.g. $C_2$, $C_3$, $C_4$, $C_5$, or $C_6$-alkenyl, in particular ethenyl, propenyl, butenyl, pentenyl, hexenyl; $(C_{1-6})$alkoxy, e.g. methoxy, ethoxy, propoxy, butoxy, pentoxy or hexoxy; $(C_{1-6})$alkoxy$(C_{1-6})$alkyl; $(C_{1-6})$aralkyl; $(C_{1-6})$heteroaralkyl.

In a further preferred embodiment $R^6$ is mono or disubstituted aryl or heteroaryl, preferably phenyl; naphthalenyl; anthracenyl; furanyl; thiophenyl; oxazolyl; isoxazolyl; 1,2,5-oxadiazolyl; 1,2,3-oxadiazolyl; pyrrolyl; imidazolyl; pyrazolyl; 1,2,3-triazolyl; thiazolyl; isothiazolyl; 1,2,3-thiadiazolyl; 1,2,5-thiadiazolyl; pyridinyl; pyrimidinyl; pyrazinyl; 1,2,3-triazinyl; 1,2,4-triazinyl; 1,3,5-triazinyl; 1-benzofuranyl; 2-benzofuranyl; indolyl; isoindolyl; benzothiophenyl; 2-benzothiophenyl; 1H- indazolyl; benzimidazolyl; benzoxazolyl; indoxazinyl; 2,1-benzisoxazolyl; benzothiazolyl; 1,2-benzisothiazolyl; 2,1-benzisothiazolyl; benzotriazolyl; quinolinyl; isoquinolinyl; 2,3-benzodiazinyl; quinoxalinyl; quinazolinyl; quinolinyl; 1,2,3-benzotriazinyl; or 1,2,4-benzotriazinyl. In this preferred embodiment the one or two substituents are preferably independently selected from the group consisting of F, Cl, Br, $(C_{1-6})$alkoxy, e.g. $C_1$, $C_2$, $C_3$, $C_4$, $C_5$ or $C_6$-alkoxy, in particular methoxy, ethoxy, propxy, butoxy, pentoxy, hexoxy, $(C_{1-6})$alkyl, e.g. $C_1$, $C_2$, $C_3$, $C_4$, $C_5$ or $C_6$-alkyl, in particular methyl, ethyl, n-propyl, iso-propyl, n-butyl, sec-butyl, tert-butyl, pentyl, n-hexyl, or iso-hexyl and $NR^{11'}R^{12'}$, wherein $R^{11'}R^{12'}$, wherein $R^{11'}R^{12'}$ are independent of each other selected from hydrogen, hydroxyl, halogen, alkyl, heteroalkyl, aryl, aralkyl, heteroaryl, heteroaralkyl, alkenyl, cycloalkenyl, or alkynyl, optionally substituted.

Preferably $R^6$ is phenyl substituted with one or two $(C_{1-6})$alkyl, e.g. $C_1$, $C_2$, $C_3$, $C_4$, $C_5$ or $C_6$-alkyl, in particular methyl, ethyl, n-propyl, iso-propyl, n-butyl, sec-butyl, tert-butyl, pentyl, n-hexyl, or iso-hexyl and/or one or two $NR^{11'}R^{12'}$, wherein $R^{11'}R^{12'}$, wherein $R^{11'}R^{12'}$ are independent of each other selected from hydrogen, hydroxyl, halogen, alkyl, heteroalkyl, aryl, aralkyl, heteroaryl, heteroaralkyl, alkenyl, cycloalkenyl, or alkynyl.

In a preferred use of the invention the compound according to formula (XXXII) has a structure according to formula (XXXIII) to (XLVIII):

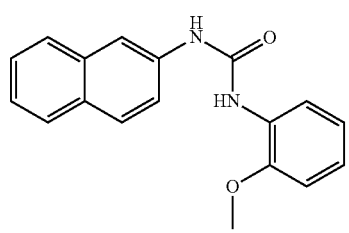

(XXXIII)

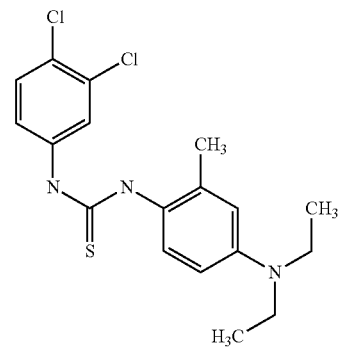

(XXXIV)

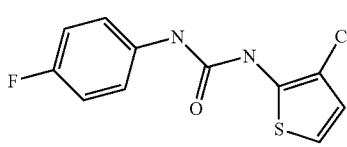

(XXXV)

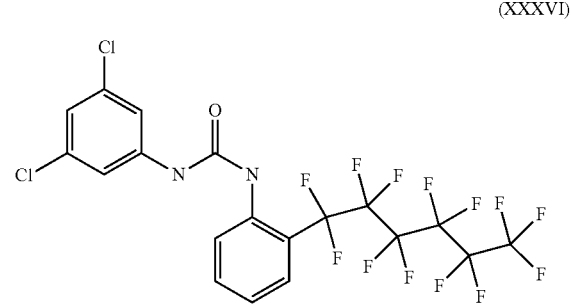

(XXXVI)

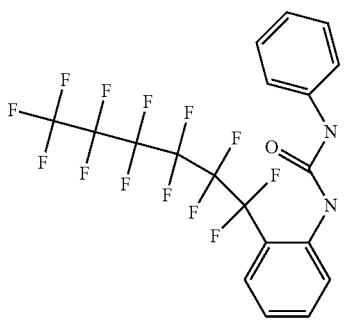

(XXXVII)

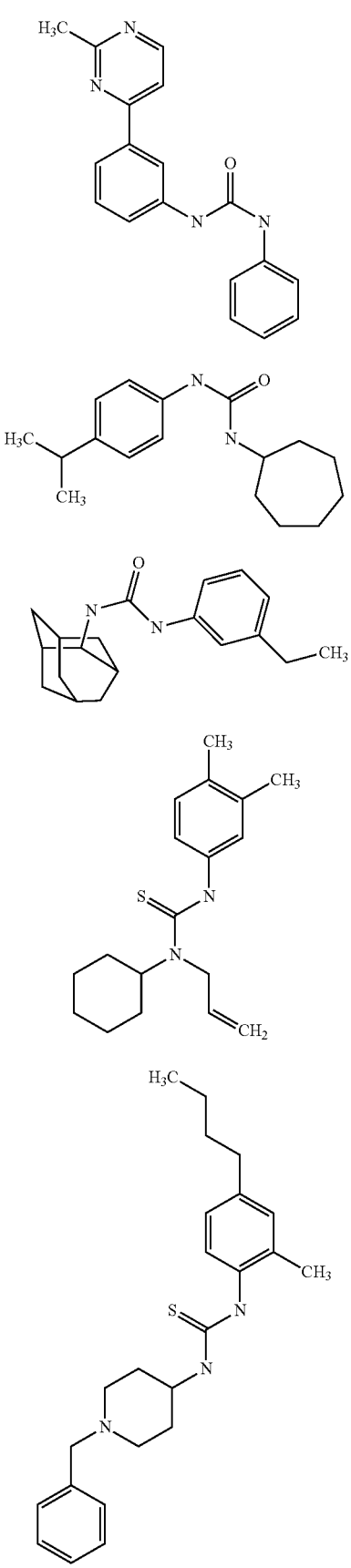
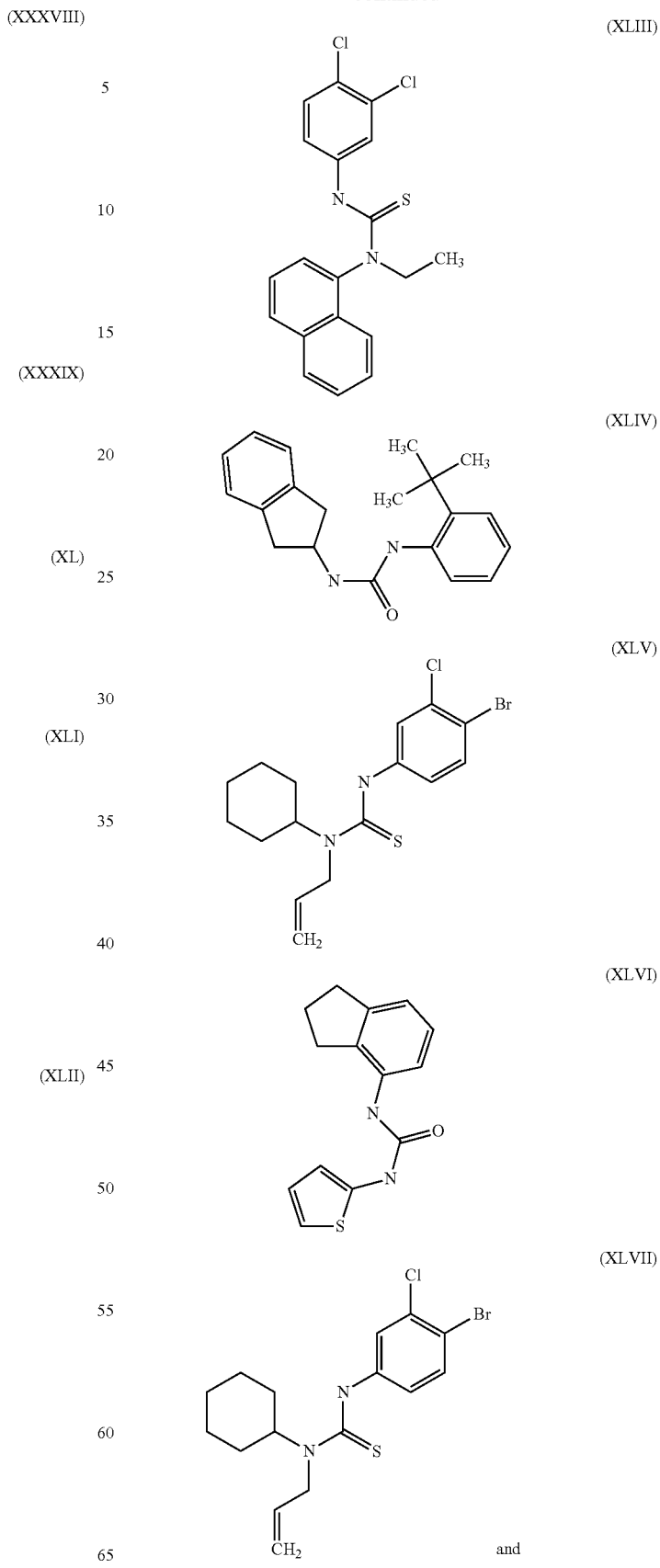

(XLVIII)

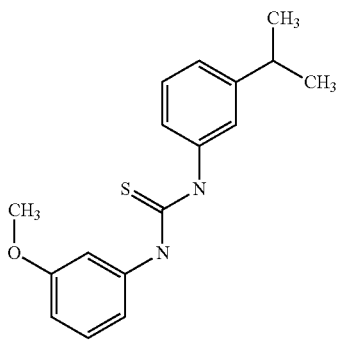

optionally substituted or a pharmaceutically acceptable salt thereof. Preferred salts comprise $Na^+$, $K^+$, $Mg^{2+}$, and $Ca^{2+}$.

In a preferred embodiment the compound usable according to the present invention having a structure according to formula (XXXIII) to (XLVIII) is substituted, preferably 1, 2, or 3 times with a radical selected from the group consisting of halogen, e.g. F, Cl, Br, or I; hydroxyl; $SO_2$, $NO_2$; CN; $(C_{1-6})$ alkyl, e.g. $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, or $C_{16}$, in particular methyl, ethyl, propyl, butyl, pentyl hexyl, heptyl, or octyl ; $(C_{2-16})$alkenyl, e.g. $C_2$, $C_3$, $C_4$, $C_5$ $C_6$, $C_7$, $C_8$, $C_9$, $C_{10}$, $C_{11}$, $C_{12}$, $C_{13}$, $C_{14}$, $C_{15}$, or $C_{16}$, in particular ethenyl, propenyl, butenyl, pentenyl, hexenyl, heptenyl, or octenyl; $(C_{1-6})$ alkoxy, e.g. methoxy, ethoxy, propoxy, butoxy, pentoxy or hexoxy; $(C_{1-6})$alkyl-$(C_{1-6})$alkoxy; amino, optionally mono- or disubstituted by $(C_{1-6})$alkoxy, $(C_{1-6})$alkyl, $(C_{2-6})$alkenyloxy, $(C_{2-6})$alkenyl, $(C_{1-6})$alkyl, $(C_{2-6})$alkenyl, $(C_{1-6})$alkylsulphonyl; $(C_{2-6})$alkenylsulphonyl; and $NR^{11'}R^{12'}$; or two adjacent substituents are taken together to form a 4, 5, 6, or 7 membered cycloalkyl or cycloalkenyl, optionally substituted;
wherein $R^{11'}$ and $R^{12'}$ are independent of each other selected from hydrogen, hydroxyl; halogen; alkyl, preferably $(C_{1-6})$alkyl, e.g. $C_1$, $C_2$, $C_3$, $C_4$, $C_5$, or $C_6$-alkyl, in particular methyl, ethyl, propyl, butyl, pentyl or hexyl; heteroalkyl, preferably $(C_{1-6})$heteroalkyl, e.g. $C_1$, $C_2$, $C_3$, $C_4$, $C_5$, or $C_6$-heteroalkyl, wherein preferably one or two carbon atoms are replaced by a heteroatom selected from the group consisting of N, S, and O; $(C_{1-6})$alkoxy; $(C_{1-6})$alkylsulphonyl; alkenyl, preferably $(C_{2-6})$alkenyl, $(C_{2-6})$alkenyloxy, cycloalkenyl, $(C_{2-6})$alkenylsulphonyl; alkynyl; aryl; aralkyl; heteroaryl; or heteroaralkyl, optionally substituted.

In a preferred use of the invention the inhibitor of the scavenger receptor class protein is a compound with the following formula (IL):

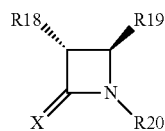

(IL)

wherein,
$R^{18}$ is alkyl, alkenyl, aryl, aralkyl, heteroaryl, or heteroaralkyl, optionally substituted;
$R^{19}$ and $R^{20}$ are independently alkyl, alkenyl, aryl or heteroaryl, optionally substituted; and
X is O or S or a pharmaceutically acceptable salt thereof. Preferred salts comprise $Na^+$, $K^+$, $Mg^{2+}$, and $Ca^{2+}$.

In a preferred use of the invention
$R^{18}$ is substituted preferably 1 to 3 time with a radical selected from the group consisting of F; Cl; Br; I; hydroxyl; $SO_2$, $NO_2$; CN; $(C_{1-6})$alkyl, e.g. $C_1$, $C_2$, $C_3$, $C_4$, $C_5$ or $C_6$-alkyl, in particular methyl, ethyl, n-propyl, iso-propyl, n-butyl, sec-butyl, tert-butyl, pentyl, n-hexyl, iso-hexyl; $(C_{2-6})$alkenyl; $(C_{1-6})$alkoxy; in particular methoxy, $(C_{1-6})$alkoxy$(C_{1-6})$alkyl; amino, optionally mono- or disubstituted by $(C_{1-6})$alkoxy, $(C_{1-6})$alkyl, e.g. $C_1$, $C_2$, $C_3$, $C_4$, $C_5$ or $C_6$-alkyl, in particular methyl, ethyl, n-propyl, iso-propyl, n-butyl, sec-butyl, tert-butyl, pentyl, n-hexyl, iso-hexyl, $(C_{2-6})$alkenyloxy, $(C_{2-6})$alkenyl, $(C_{1-6})$alkyl, $(C_{2-6})$alkenyl, $(C_{1-6})$alkylsulphonyl, and $(C_{2-6})$alkenylsulphonyl; or two adjacent substituents are taken together to form a 4, 5, 6, or 7 membered cycloalkyl or cycloalkenyl; and/or $R^{19}$ and $R^{20}$ are independently substituted preferably 1 to 3 time with a radical selected from the group consisting of F; Cl; Br; I; hydroxyl; $SO_2$, $NO_2$; CN; $(C_{1-6})$alkyl, e.g. $C_1$, $C_2$, $C_3$, $C_4$, $C_5$ or $C_6$-alkyl, in particular methyl, ethyl, n-propyl, iso-propyl, n-butyl, sec-butyl, tert-butyl, pentyl, n-hexyl, iso-hexyl; $(C_{2-6})$alkenyl; $(C_{2-6})$alkenyl; $(C_{1-6})$ alkoxy, e.g. $C_1$, $C_2$, $C_3$, $C_4$, $C_5$ or $C_6$-alkoxy, in particular methoxy, ethoxy, propxy, butoxy, pentoxy, hexoxy;

In a preferred use of the invention
$R^{18}$ is $(C_{1-6})$aralkyl, in particular $(C_{1-6})$phenylalkyl, e.g. $C_1$, $C_2$, $C_3$, $C_4$, $C_5$, or $C_6$, phenylalkyl, more particularly phenylmethyl, phenylethyl, phenylpropyl, phenylbutyl, phenylpentyl, phenylhexyl; $(C_{1-6})$heteroaralkyl, phenyl; naphthalenyl; anthracenyl; furanyl; thiophenyl; oxazolyl; isoxazolyl; 1,2,5-oxadiazolyl; 1,2,3-oxadiazolyl; pyrrolyl; imidazolyl; pyrazolyl; 1,2,3-triazolyl; thiazolyl; isothiazolyl; 1,2,3-thiadiazolyl; 1,2,5-thiadiazolyl; pyridinyl; pyrimidinyl; pyrazinyl; 1,2,3-triazinyl; 1,2,4-triazinyl; 1,3,5-triazinyl; 1-benzofuranyl; 2-benzofuranyl; indolyl; isoindolyl; benzothiophenyl; 2-benzothiophenyl; 1H-indazolyl; benzimidazolyl; benzoxazolyl; indoxazinyl; 2,1-benzisoxazolyl; benzothiazolyl; 1,2-benzisothiazolyl; 2,1-benzisothiazolyl; benzotriazolyl; quinolinyl; isoquinolinyl; 2,3-benzodiazinyl; quinoxalinyl; quinazolinyl; quinolinyl; 1,2,3-benzotriazinyl; or 1,2,4-benzotriazinyl; and/or $R^{19}$ and $R^{20}$ are independently phenyl, naphthalenyl; anthracenyl; furanyl; thiophenyl; oxazolyl; isoxazolyl; 1,2,5-oxadiazolyl; 1,2,3-oxadiazolyl; pyrrolyl; imidazolyl; pyrazolyl; 1,2,3-triazolyl; thiazolyl; isothiazolyl; 1,2,3-thiadiazolyl; 1,2,5-thiadiazolyl; pyridinyl; pyrimidinyl; pyrazinyl; 1,2,3-triazinyl; 1,2,4-triazinyl; 1,3,5-triazinyl; 1-benzofuranyl; 2-benzofuranyl; indolyl; isoindolyl; benzothiophenyl; 2-benzothiophenyl; 1H-indazolyl; benzimidazolyl; benzoxazolyl; indoxazinyl; 2,1-benzisoxazolyl; benzothiazolyl; 1,2-benzisothiazolyl; 2,1-benzisothiazolyl; benzotriazolyl; quinolinyl; isoquinolinyl; 2,3-benzodiazinyl; quinoxalinyl; quinazolinyl; quinolinyl; 1,2,3-benzotriazinyl; or 1,2,4-benzotriazinyl.

In a preferred embodiment $R^{18}$ is aralkyl, in particular phenylmethyl, phenylethyl, phenylpropyl, phenylbutyl, phenylpentyl, phenylhexyl wherein both the alkyl and the aryl, in particular the phenyl radical are substituted one or more times with a substituent independently selected from the group consisting of F, Cl, Br, hydroxyl. In this context it is preferred that X is O.

In a preferred use of the invention the compound according to formula (IL) has a structure according to formula (L):

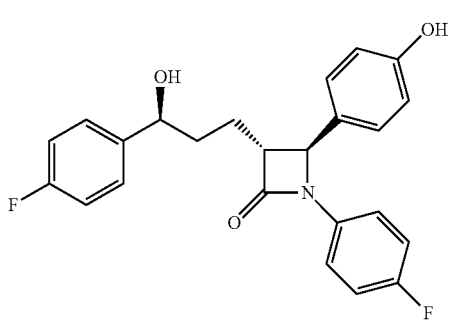

(L)

optionally substituted or a pharmaceutically acceptable salt thereof. Preferred salts comprise Na⁺, K⁺, Mg²⁺, and Ca²⁺.

In a preferred embodiment the compound usable according to the present invention having a structure according to formula (L) is substituted, preferably 1, 2, or 3 times with a radical selected from the group consisting of halogen, e.g. F, Cl, Br, or I; hydroxyl; $SO_2$, $NO_2$. CN; $(C_{1-16})$alkyl, e.g. $C_1$, $C_2$, $C_3$, $C_4$, $C_5$ $C_6$, $C_7$, $C_8$, $C_9$, $C_{10}$, $C_{11}$, $C_{12}$, $C_{13}$, $C_{14}$, $C_{15}$, or $C_{16}$, in particular methyl, ethyl, propyl, butyl, pentyl hexyl, heptyl, or octyl; $(C_{2-16})$alkenyl, e.g. $C_2$, $C_3$, $C_4$, $C_5$ $C_6$, $C_7$, $C_8$, $C_9$, $C_{10}$, $C_{11}$, $C_{12}$, $C_{13}$, $C_{14}$, $C_{15}$, or $C_{16}$, in particular ethenyl, propenyl, butenyl, pentenyl, hexenyl, heptenyl, or octenyl; $(C_{1-6})$ alkoxy, e.g. methoxy, ethoxy, propoxy, butoxy, pentoxy or hexoxy; $(C_{1-6})$alkyl-$(C_{1-6})$alkoxy; amino, optionally mono- or disubstituted by $(C_{1-6})$alkoxy, $(C_{1-6})$alkyl, $(C_{2-6})$alkenyloxy, $(C_{2-6})$alkenyl, $(C_{1-6})$alkyl, $(C_{2-6})$alkenyl, $(C_{1-6})$alkylsulphonyl; $(C_{2-6})$alkenylsulphonyl; and $NR^{11'}R^{12'}$; or two adjacent substituents are taken together to form a 4, 5, 6, or 7 membered cycloalkyl or cycloalkenyl, optionally substituted;

wherein $R^{11'}$ and $R^{12'}$ are independent of each other selected from hydrogen, hydroxyl; halogen; alkyl, preferably $(C_{1-6})$alkyl, e.g. $C_1$, $C_2$, $C_3$, $C_4$, $C_5$, or $C_6$-alkyl, in particular methyl, ethyl, propyl, butyl, pentyl or hexyl; heteroalkyl, preferably $(C_{1-6})$heteroalkyl, e.g. $C_1$, $C_2$, $C_3$, $C_4$, $C_5$, or $C_6$-heteroalkyl, wherein preferably one or two carbon atoms are replaced by a heteroatom selected from the group consisting of N, S, and O; $(C_{1-6})$alkoxy; $(C_{1-6})$alkylsulphonyl; alkenyl, preferably $(C_{2-6})$alkenyl, $(C_{2-6})$alkenyloxy, cycloalkenyl, $(C_{2-6})$alkenylsulphonyl; alkynyl; aryl; aralkyl; heteroaryl; or heteroaralkyl, optionally substituted.

In a preferred use of the invention the inhibitor of the scavenger receptor class protein has a structure according to formula (LI):

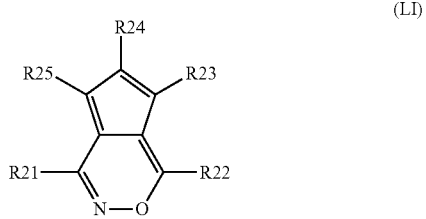

(LI)

wherein,
$R^{21}$ and $R^{22}$ are independent of each other aryl, aralkyl, heteroaryl or heteroaralkyl, optionally substituted; and
$R^{23}$, $R^{24}$, and $R^{25}$ are independent of each other hydrogen, hydroxyl, F, Cl, Br, I, CN, $SO_2$, $NO_2$, alkyl, heteroalkyl, aryl, aralkyl, heteroaryl, heteroaralkyl, alkenyl, cycloalkenyl, or alkynyl, optionally substituted, preferably hydrogen.

In a preferred use of the invention
$R^{21}$ and $R^{22}$ are independent of each other substituted preferably with 1 to 3 radicals selected from the group consisting of F; Cl; Br; I; hydroxyl; $SO_2$, $NO_2$; CN; $(C_{1-6})$alkyl, e.g. $C_1$, $C_2$, $C_3$, $C_4$, $C_5$, or $C_6$-alkyl, in particular methyl, ethyl, propyl, butyl, pentyl or hexyl; $(C_{2-6})$alkenyl, e.g. $C_2$, $C_3$, $C_4$, $C_5$, or $C_6$-alkenyl, in particular ethenyl, propenyl, butenyl, pentenyl, hexenyl; $(C_{1-6})$ alkoxy, e.g. methoxy, ethoxy, propoxy, butoxy, pentoxy or hexoxy, $(C_{1-6})$alkoxy-$(C_{1-6})$alkyl; amino, optionally mono- or disubstituted by $(C_{1-6})$alkoxy, $(C_{1-6})$alkyl, $(C_{2-6})$alkenyloxy, $(C_{2-6})$alkenyl, $(C_{1-6})$alkylsulphonyl, and $(C_{2-6})$alkenylsulphonyl; and/or
$R_{23}$, $R_{24}$, and $R^{25}$ are independent of each substituted preferably with 1 to 3 radicals selected from the group consisting of F; Cl; Br; I; hydroxyl; $SO_2$; $NO_2$; CN; $(C_{1-6})$alkyl, e.g. $C_1$, $C_2$, $C_3$, $C_4$, $C_5$, or $C_6$-alkyl, in particular methyl, ethyl, propyl, butyl, pentyl or hexyl; $(C_{2-6})$alkenyl, e.g. $C_2$, $C_3$, $C_4$, $C_5$, or $C_6$-alkenyl, in particular ethenyl, propenyl, butenyl, pentenyl, hexenyl; $(C_{1-6})$alkoxy, e.g. methoxy, ethoxy, propoxy, butoxy, pentoxy or hexoxy or a pharmaceutically acceptable salt thereof. Preferred salts comprise Na⁺, K⁺; Mg²⁺, and Ca²⁺.

In a preferred use of the invention $R^{21}$ and $R^{22}$ are independent of each other phenyl; naphthalenyl; anthracenyl; furanyl; thiophenyl; oxazolyl; isoxazolyl; 1,2,5-oxadiazolyl; 1,2,3-oxadiazolyl; pyrrolyl; imidazolyl; pyrazolyl; 1,2,3-triazolyl; thiazolyl; isothiazolyl; 1,2,3-thiadiazolyl; 1,2,5-thiadiazolyl; pyridinyl; pyrimidinyl; pyrazinyl; 1,2,3-triazinyl; 1,2,4-triazinyl; 1,3,5-triazinyl; 1-benzofuranyl; 2-benzofuranyl; indolyl; isoindolyl; benzothiophenyl; 2-benzothiophenyl; 1H-indazolyl; benzimidazolyl; benzoxazolyl; indoxazinyl; 2,1-benzisoxazoly l; benzothiazolyl; 1,2-benzisothiazolyl; 2,1-benzisothiazolyl; benzotriazolyl; quinolinyl; isoquinolinyl; 2,3-benzodiazinyl; quinoxalinyl; quinazolinyl; quinolinyl; 1,2,3-benzotriazinyl; or 1,2,4-benzotriazinyl. If $R^{21}$ and $R^{22}$ have this preferred meaning it is preferred that $R^{23}$, $R^{24}$, and $R^{25}$ are independent of each other hydrogen, hydroxyl, F, Cl, Br, I, CN, $SO_2$, $NO_2$, alkyl, heteroalkyl, aryl, aralkyl, heteroaryl, heteroaralkyl, alkenyl, cycloalkenyl, or alkynyl, optionally substituted, preferably hydrogen.

In a preferred use of the invention the compound according to formula (LI) has a structure according to formula (LII):

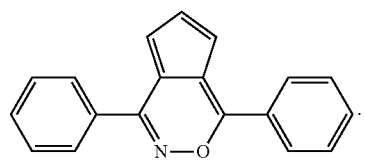

(LII)

In a preferred embodiment the compound usable according to the present invention having a structure according to formula (LII) is substituted, preferably 1, 2, or 3 times with a radical selected from the group consisting of halogen, e.g. F, Cl, Br, or I; hydroxyl; $SO_2$; $NO_2$; CN; $(C_{1-16})$alkyl, e.g. $C_1$, $C_2$, $C_3$, $C_4$, $C_5$ $C_6$, $C_7$, $C_8$, $C_9$, $C_{10}$, $C_{11}$, $C_{12}$, $C_{13}$, $C_{14}$, $C_{15}$, or $C_{16}$, in particular methyl, ethyl, propyl, butyl, pentyl hexyl, heptyl, or octyl; $(C_{2-16})$alkenyl, e.g. $C_2, C_3, C_4, C_5, C_6, C_7, C_8, C_9, C_{10}, C_{11}, C_{12}, C_{13}, C_{14}, C_{15}$, or $C_{16}$, in particular ethenyl, propenyl, butenyl, pentenyl, hexenyl, heptenyl, or octenyl; $(C_{1-6})$alkoxy, e.g. methoxy, ethoxy, propoxy, butoxy, pentoxy or hexoxy; $(C_{1-6})$alkyl-$(C_{1-6})$alkoxy; amino, optionally mono- or disubstituted by $(C_{1-6})$alkoxy, $(C_{1-6})$alkyl, $(C_{2-6})$alkenyloxy, $(C_{2-6})$alkenyl, $(C_{1-6})$alkyl, $(C_{2-6})$alkenyl, $(C_{1-6})$alkylsulphonyl; $(C_{2-6})$alkenylsulphonyl; and $NR^{11'}R^{12'}$; or two adjacent substituents are taken together to form a 4, 5, 6, or 7 membered cycloalkyl or cycloalkenyl, optionally substituted;

wherein $R^{11'}$ and $R^{12'}$ are independent of each other selected from hydrogen, hydroxyl; halogen; alkyl, preferably $(C_{1-6})$alkyl, e.g. $C_1, C_2, C_3, C_4, C_5$, or $C_6$-alkyl, in particular methyl, ethyl, propyl, butyl, pentyl or hexyl; heteroalkyl, preferably $(C_{1-6})$heteroalkyl, e.g. $C_1, C_2, C_3, C_4, C_5$, or $C_6$-heteroalkyl, wherein preferably one or two carbon atoms are replaced by a heteroatom selected from the group consisting of N, S, and O; $(C_{1-6})$alkoxy; $(C_{1-6})$alkylsulphonyl; alkenyl, preferably $(C_{2-6})$alkenyl, $(C_{2-6})$alkenyloxy, cycloalkenyl, $(C_{2-6})$alkenylsulphonyl; alkynyl; aryl; aralkyl; heteroaryl; or heteroaralkyl, optionally substituted.

In a preferred use of the invention the inhibitor of the scavenger receptor class protein has a structure according to formula (LIII):

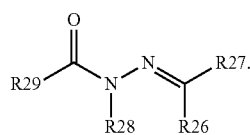

(LIII)

In a preferred use of the invention $R^{26}$ is hydrogen, alkyl, aryl, aralkyl, heteroaryl or heteroaralkyl, optionally substituted;

$R^{27}$ is aryl, aralkyl, heteroaryl or heteroaralkyl, optionally substituted;

$R^{28}$ is hydrogen or alkyl, optionally substituted; and $R^{29}$ is aryl, aralkyl, heteroaryl or heteroaralkyl, optionally substituted or a pharmaceutically acceptable salt thereof. Preferred salts comprise $Na^+, K^+, Mg^{2+}$, and $Ca^{2+}$.

In a preferred use of the invention $R^{27}$ and $R^{29}$ are independent of each other substituted preferably with one to three radicals selected from the group consisting of F; Cl; Br; I; hydroxyl; $SO_2$, $NO_2$, CN; $(C_{1-6})$alkyl, e.g. $C_1, C_2, C_3, C_4, C_5$, or $C_6$-alkyl, in particular methyl, ethyl, propyl, butyl, pentyl or hexyl; $(C_{2-6})$alkenyl, e.g. $C_2, C_3, C_4, C_5$, or $C_6$-alkenyl, in particular ethenyl, propenyl, butenyl, pentenyl, hexenyl; $(C_{1-6})$alkoxy, e.g. methoxy, ethoxy, propoxy, butoxy, pentoxy or hexoxy, $(C_{1-6})$alkoxy $(C_{1-6})$alkyl; amino, optionally mono- or disubstituted by $(C_{1-6})$alkoxy, $(C_{2-6})$alkenyloxy, $(C_{1-6})$alkyl, $(C_{2-6})$alkenyl, $(C_{1-6})$alkylsulphonyl, and $(C_{2-6})$alkenylsulphonyl; and/or $R^{26}$ and $R^{28}$ are independent of each other substituted preferably with one to three radicals selected from the group consisting of F; Cl; Br; I; hydroxyl; $SO_2$; $NO_2$; CN; $(C_{1-6})$alkyl, e.g. $C_1, C_2, C_3, C_4, C_5$, or $C_6$-alkyl, in particular methyl, ethyl, propyl, butyl, pentyl or hexyl; $(C_{2-6})$alkenyl, e.g. $C_2, C_3, C_4, C_5$, or $C_6$-alkenyl, in particular ethenyl, propenyl, butenyl, pentenyl, hexenyl; $(C_{1-6})$alkoxy, e.g. methoxy, ethoxy, propoxy, butoxy, pentoxy or hexoxy.

In a preferred use of the invention $R^{27}$ and $R^{29}$ are independent of each other phenyl; naphthalenyl; anthracenyl; furanyl; thiophenyl; oxazolyl; isoxazolyl; 1,2,5-oxadiazolyl; 1,2,3-oxadiazolyl; pyrrolyl; imidazolyl; pyrazolyl; 1,2,3-triazolyl; thiazolyl; isothiazolyl; 1,2,3-thiadiazolyl; 1,2,5-thiadiazolyl; pyridinyl; pyrimidinyl; pyrazinyl; 1,2,3-triazinyl; 1,2,4-triazinyl; 1,3,5-triazinyl; 1-benzofuranyl; 2-benzofuranyl; indolyl; isoindolyl; benzothiophenyl; 2-benzothiophenyl; 1H-indazolyl; benzimidazolyl; benzoxazolyl; indoxazinyl; 2,1-benzisoxazolyl; benzothiazolyl; 1,2-benzisothiazolyl; 2,1-benzisothiazolyl; benzotriazolyl; quinolinyl; isoquinolinyl; 2,3-benzodiazinyl; quinoxalinyl; quinazolinyl; quinolinyl; 1,2,3-benzotriazinyl; or 1,2,4-benzotriazinyl; and/or $R^{26}$ and $R^{28}$ are independent of each other hydrogen, $(C_{1-6})$alkyl, e.g. $C_1, C_2, C_3, C_4, C_5$, or $C_6$-alkyl, in particular methyl, ethyl, propyl, butyl, pentyl or hexyl; $(C_{2-6})$alkenyl, e.g. $C_2, C_3, C_4, C_5$, or $C_6$-alkenyl, in particular ethenyl, propenyl, butenyl, pentenyl, hexenyl; $(C_{1-6})$aralkyl or $(C_{1-6})$heteroaralkyl.

In a preferred use of the invention $R^{27}$ and $R^{29}$ are independent of each other phenyl; naphthalenyl; anthracenyl; furanyl; thiophenyl; oxazolyl; isoxazolyl; 1,2,5-oxadiazolyl; 1,2,3-oxadiazolyl; pyrrolyl; imidazolyl; pyrazolyl; 1,2,3-triazolyl; thiazolyl; isothiazolyl; 1,2,3-thiadiazolyl; 1,2,5-thiadiazolyl; pyridinyl; pyrimidinyl; pyrazinyl; 1,2,3-triazinyl; 1,2,4-triazinyl; 1,3,5-triazinyl; 1-benzofuranyl; 2-benzofuranyl; indolyl; isoindolyl; benzothiophenyl; 2-benzothiophenyl; 1H-indazolyl; benzimidazolyl; benzoxazolyl; indoxazinyl; 2,1-benzisoxazolyl; benzothiazolyl; 1,2-benzisothiazolyl; 2,1-benzisothiazolyl; benzotriazolyl; quinolinyl; isoquinolinyl; 2,3-benzodiazinyl; quinoxalinyl; quinazolinyl; quinolinyl; 1,2,3-benzotriazinyl; or 1,2,4-benzotriazinyl; and $R^{26}$ and $R^{28}$ are independent of each other hydrogen, $(C_{1-6})$alkyl, e.g. $C_1, C_2, C_3, C_4, C_5$, or $C_6$-alkyl, in particular methyl, ethyl, propyl, butyl, pentyl or hexyl; $(C_{2-6})$alkenyl, e.g. $C_2, C_3, C_4, C_5$, or $C_6$-alkenyl, in particular ethenyl, propenyl, butenyl, pentenyl, hexenyl; $(C_{1-6})$aralkyl or $(C_{1-6})$heteroaralkyl.

It is particularly preferred that both $R^{27}$ and $R^{29}$ are aryl, preferably phenyl, substituted preferably with one to three substituents selected from the group consisting of F; Cl; Br; I; hydroxyl; $SO_2$, $NO_2$, CN; $(C_{1-6})$alkyl, e.g. $C_1, C_2, C_3, C_4, C_5$, or $C_6$-alkyl, in particular methyl, ethyl, propyl, butyl, pentyl or hexyl; $(C_{2-6})$alkenyl, e.g. $C_2, C_3, C_4, C_5$, or $C_6$-alkenyl, in particular ethenyl, propenyl, butenyl, pentenyl, hexenyl; $(C_{1-6})$alkoxy, e.g. methoxy, ethoxy, propoxy, butoxy, pentoxy or hexoxy, $(C_{1-6})$alkoxy$(C_{1-6})$alkyl; amino, optionally mono- or disubstituted by $(C_{1-6})$alkoxy, $(C_{2-6})$alkenyloxy, $(C_{1-6})$alkyl, $(C_{2-6})$alkenyl, $(C_{1-6})$alkylsulphonyl, and $(C_{2-6})$alkenylsulphonyl. Preferably $R^{29}$ is phenyl substituted with 1, 2, or 3 halogen radicals, preferably I. Preferably, $R^{27}$ is phenyl substituted with 1, 2, or 3 amino radicals or substituted amino radicals.

In a preferred use of the invention the compound according to formula (LIII) has a structure according to formula (LIV):

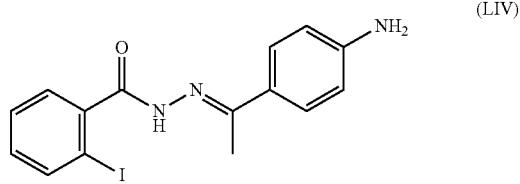 [SMILES: C/C(=N\NC(=O)c1ccccc1I)c1ccc(N)cc1]

(LIV)

optionally substituted or a pharmaceutically acceptable salt thereof. Preferred salts comprise Na$^+$, K$^+$, Mg$^{2+}$, and Ca$^{2+}$.

In a preferred embodiment the compound usable according to the present invention having a structure according to formula (LIV) is substituted, preferably 1, 2, or 3 times with a radical selected from the group consisting of halogen, e.g. F, Cl, Br, or I; hydroxyl; SO$_2$; NO$_2$; CN; (C$_{1-16}$)alkyl, e.g. C$_1$, C$_2$, C$_3$, C$_4$, C$_5$, C$_6$, C$_7$, C$_8$, C$_9$, C$_{10}$, C$_{11}$, C$_{12}$, C$_{13}$, C$_{14}$, C$_{15}$, or C$_{16}$, in particular methyl, ethyl, propyl, butyl, pentyl hexyl, heptyl, or octyl; (C$_{2-16}$)alkenyl, e.g. C$_2$, C$_3$, C$_4$, C$_5$ C$_6$, C$_7$, C$_8$, C$_9$, C$_{10}$, C$_{11}$, C$_{12}$, C$_{13}$, C$_{14}$, C$_{15}$, or C$_{16}$, in particular ethenyl, propenyl, butenyl, pentenyl, hexenyl, heptenyl, or octenyl; (C$_{1-4}$)alkoxy, e.g. methoxy, ethoxy, propoxy, butoxy, pentoxy or hexoxy; (C$_{1-6}$)alkyl-(C$_{1-6}$)alkoxy; amino, optionally mono- or disubstituted by (C$_{1-6}$)alkoxy, (C$_{1-6}$)alkyl, (C$_{2-6}$)alkenyloxy, (C$_{2-6}$)alkenyl, (C$_{1-6}$)alkyl, (C$_{2-6}$)alkenyl, (C$_{1-6}$)alkylsulphonyl; (C$_{2-6}$)alkenylsulphonyl; and NR$^{11'}$R$^{12'}$; or two adjacent substituents are taken together to form a 4, 5, 6, or 7 membered cycloalkyl or cycloalkenyl, optionally substituted;

wherein R$^{11'}$ and R$^{12'}$ are independent of each other selected from hydrogen, hydroxyl; halogen; alkyl, preferably (C$_{1-6}$)alkyl, e.g. C$_1$, C$_2$, C$_3$, C$_4$, C$_5$, or C$_6$-alkyl, in particular methyl, ethyl, propyl, butyl, pentyl or hexyl; heteroalkyl, preferably (C$_{1-6}$)heteroalkyl, e.g. C$_1$, C$_2$, C$_3$, C$_4$, C$_5$, or C$_6$-heteroalkyl, wherein preferably one or two carbon atoms are replaced by a heteroatom selected from the group consisting of N, S, and O; (C$_{1-6}$)alkoxy; (C$_{1-6}$)alkylsulphonyl; alkenyl, preferably (C$_{2-6}$)alkenyl, (C$_{2-6}$)alkenyloxy, cycloalkenyl, (C$_{2-6}$)alkenylsulphonyl; alkynyl; aryl; aralkyl; heteroaryl; or heteroaralkyl, optionally substituted.

A further aspect of the present invention is directed at inhibitors of scavenger receptor type proteins the use of which has been disclosed herein, specifically at all inhibitors of scavenger receptor type proteins according to formulas (I) to (LIV) and according to all of the above indicated preferred and particularly preferred embodiments of compounds having structures according to these formulas.

A further aspect of the present invention is a pharmaceutical composition comprising any of the compounds usable according to the present invention.

Various inhibitors of scavenger receptor type proteins are known from the prior art. Specifically, WO 2004/032716 A2 describes a large number of different compounds specifically inhibiting cholesterol transport activity of ScarB1. For the purpose of this opinion it is specifically referred to these compounds, which can also be used in the uses of the present invention. Accordingly, a further aspect of the present invention is the use of one or more of the compounds selected from Table I below.

TABLE I

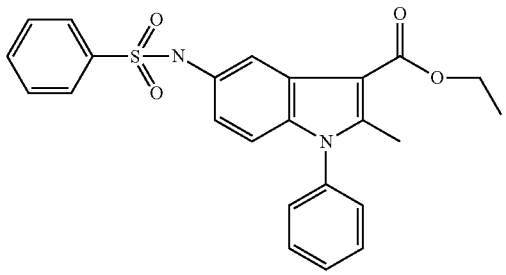 [SMILES: CCOC(=O)c1c(C)n(-c2ccccc2)c2ccc(NS(=O)(=O)c3ccccc3)cc12]

MIT 9952-1

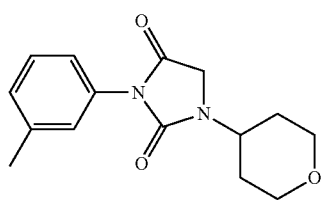 [SMILES: Cc1cccc(N2C(=O)CN(C3CCOCC3)C2=O)c1]

MIT 9952-2

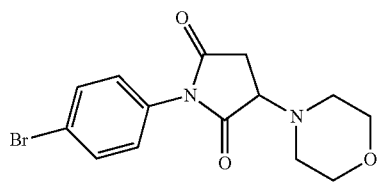

MIT 9952-3

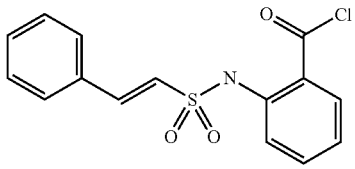 [SMILES: O=C(Cl)c1ccccc1NS(=O)(=O)/C=C/c1ccccc1]

MIT 9952-4

TABLE I-continued
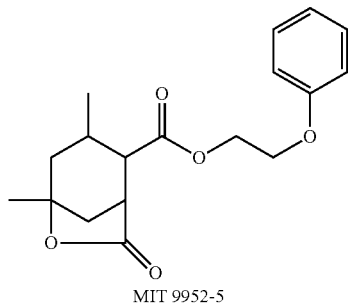
MIT 9952-5
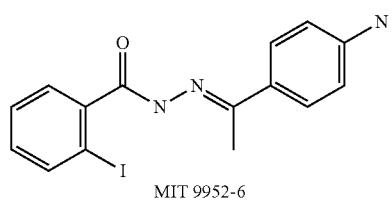
MIT 9952-6
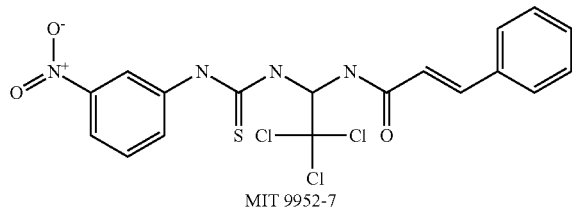
MIT 9952-7
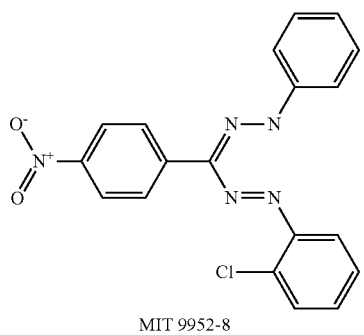
MIT 9952-8
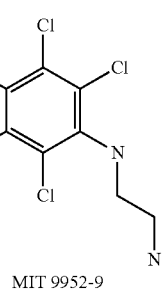
MIT 9952-9
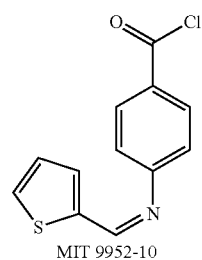
MIT 9952-10

TABLE I-continued
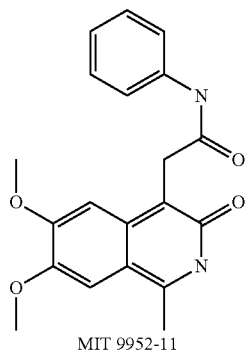
MIT 9952-11
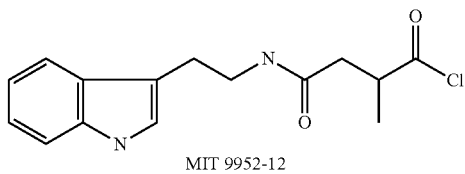
MIT 9952-12
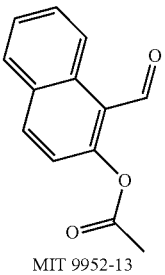
MIT 9952-13
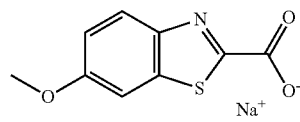
MIT 9952-14
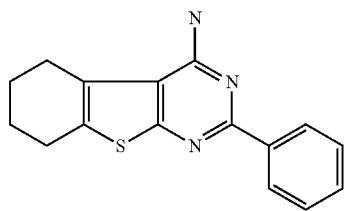 [SMILES: Nc1nc(-c2ccccc2)nc2sc3c(c12)CCCC3]
MIT 9952-15
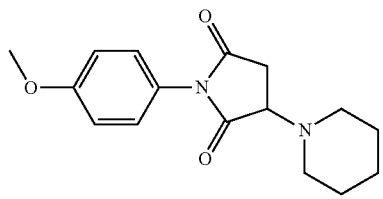 [SMILES: COc1ccc(N2C(=O)CC(N3CCCCC3)C2=O)cc1]
MIT 9952-16
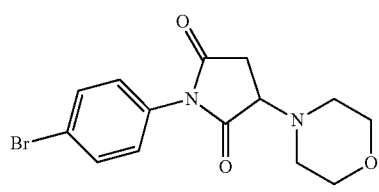 [SMILES: O=C1CC(N2CCOCC2)C(=O)N1c1ccc(Br)cc1]
MIT 9952-17

TABLE I-continued
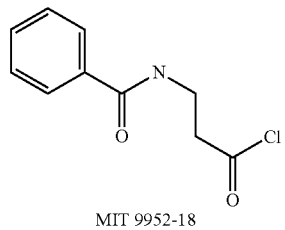
MIT 9952-18
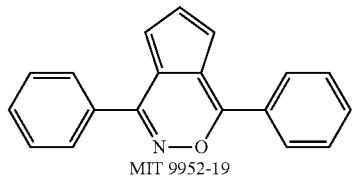
MIT 9952-19
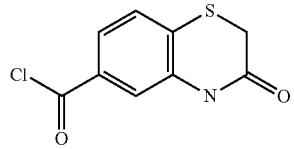 [SMILES: O=C1CSc2ccc(C(=O)Cl)cc2N1]
MIT 9952-20
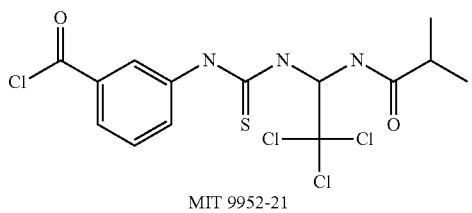
MIT 9952-21
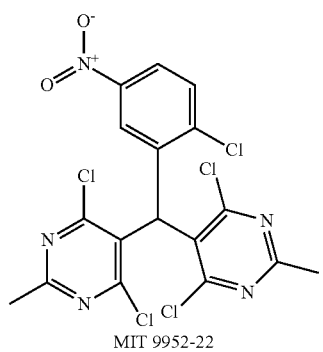
MIT 9952-22
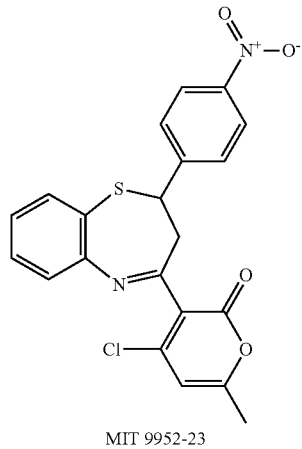
MIT 9952-23

TABLE I-continued
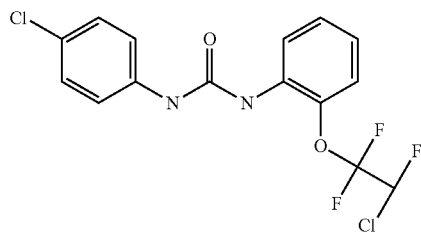 [SMILES: O=C(Nc1ccc(Cl)cc1)Nc1ccccc1OC(F)(F)C(F)Cl]
MIT 9952-24
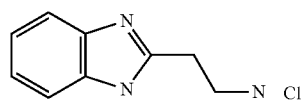 [SMILES: NCCc1nc2ccccc2[nH]1 ; Cl]
MIT 9952-25
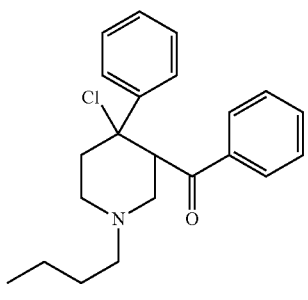
MIT 9952-26
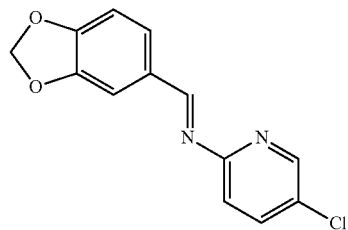 [SMILES: Clc1ccc(/N=C/c2ccc3c(c2)OCO3)nc1]
MIT 9952-27
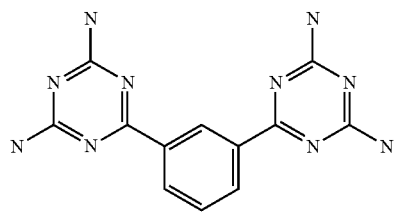 [SMILES: Nc1nc(N)nc(-c2cccc(-c3nc(N)nc(N)n3)c2)n1]
MIT 9952-28
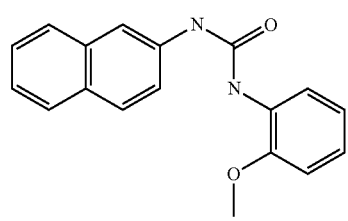 [SMILES: COc1ccccc1NC(=O)Nc1ccc2ccccc2c1]
MIT 9952-29

TABLE I-continued
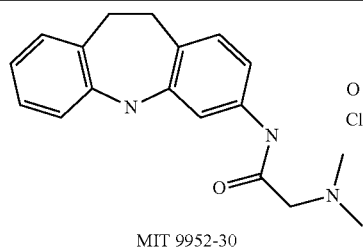
MIT 9952-30
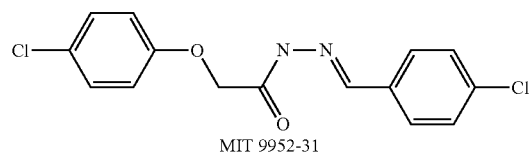
MIT 9952-31
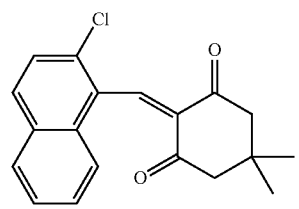 [SMILES: CC1(C)CC(=O)C(=Cc2c(Cl)ccc3ccccc23)C(=O)C1]
MIT 9952-32
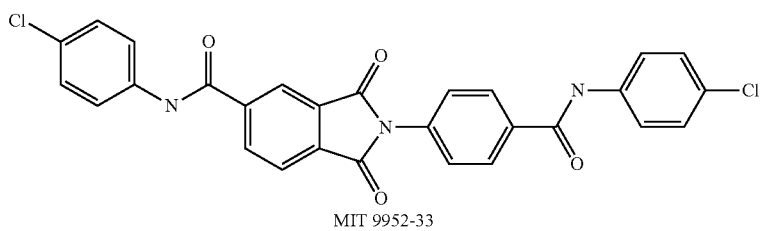
MIT 9952-33
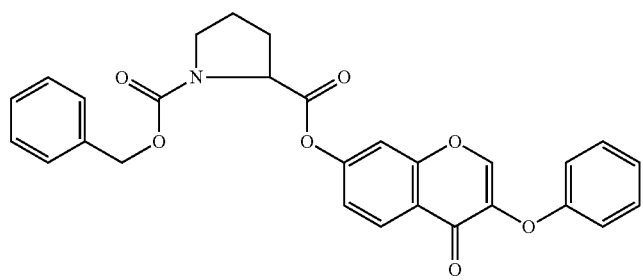 [SMILES: O=C(Oc1ccc2c(=O)c(Oc3ccccc3)coc2c1)C1CCCN1C(=O)OCc1ccccc1]
MIT 9952-34
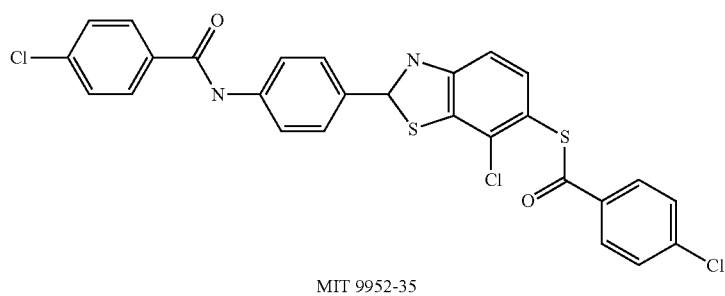
MIT 9952-35
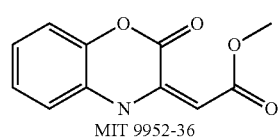
MIT 9952-36

TABLE I-continued
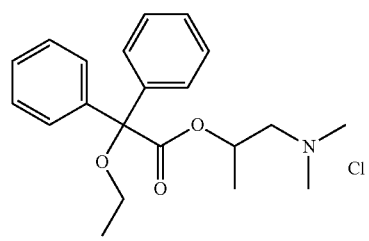 [SMILES: CCOC(C(=O)OC(C)CN(C)C)(c1ccccc1)c1ccccc1 ; Cl]
MIT 9952-37
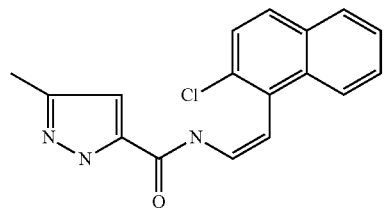 [SMILES: Cc1cc(C(=O)N/C=C\c2c(Cl)ccc3ccccc23)[nH]n1]
MIT 9952-38
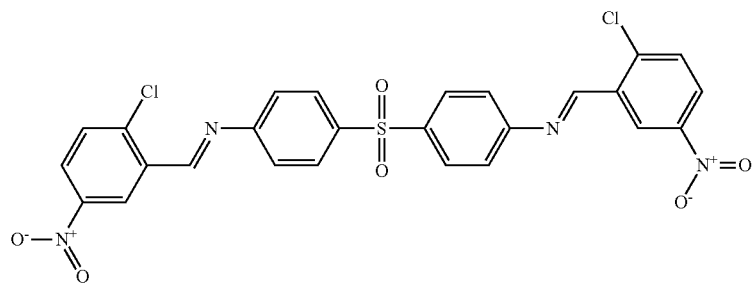 [SMILES: O=[N+]([O-])c1ccc(Cl)c(/C=N/c2ccc(S(=O)(=O)c3ccc(/N=C/c4cc([N+](=O)[O-])ccc4Cl)cc3)cc2)c1]
MIT 9952-39
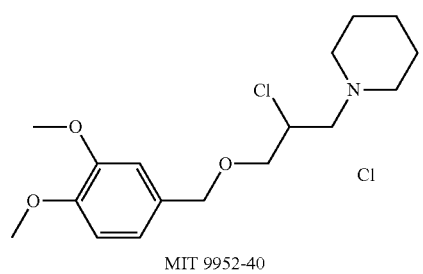
MIT 9952-40
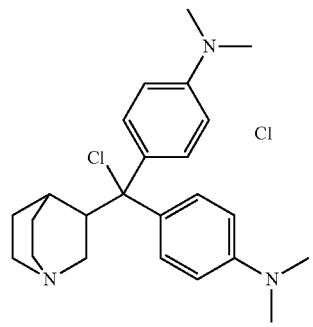 [SMILES: CN(C)c1ccc(C(Cl)(c2ccc(N(C)C)cc2)C2CN3CCC2CC3)cc1 ; Cl]
MIT 9952-41

TABLE I-continued
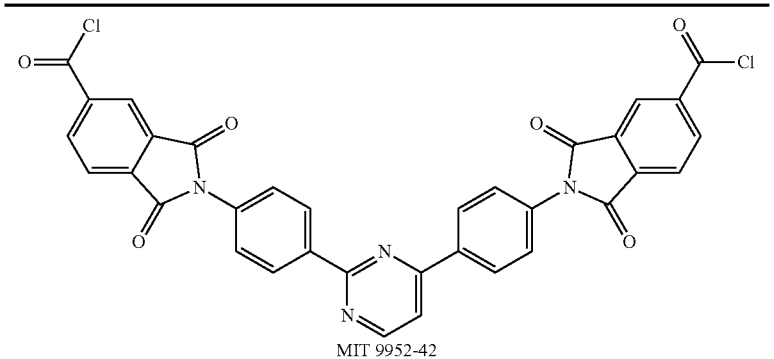
MIT 9952-42
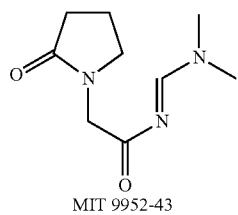
MIT 9952-43
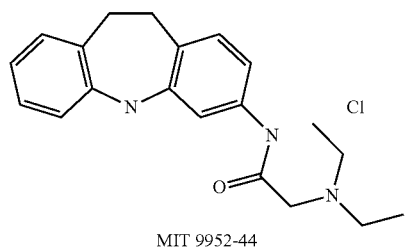
MIT 9952-44
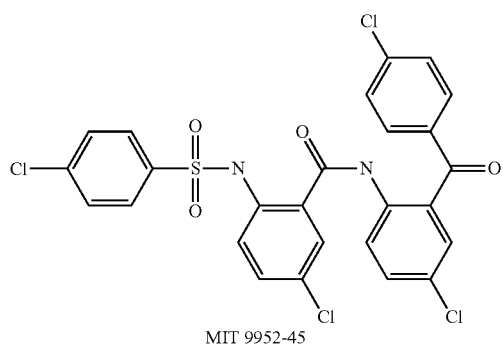
MIT 9952-45
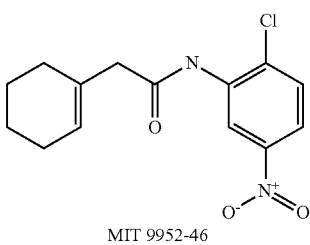
MIT 9952-46
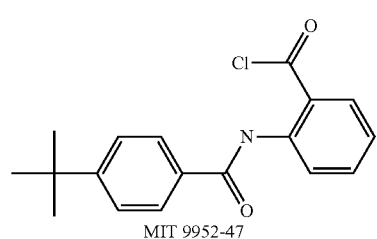
MIT 9952-47

TABLE I-continued
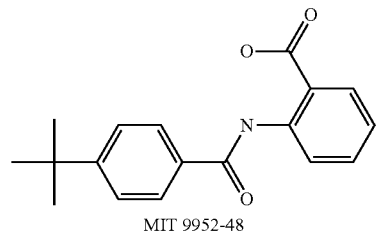
MIT 9952-48
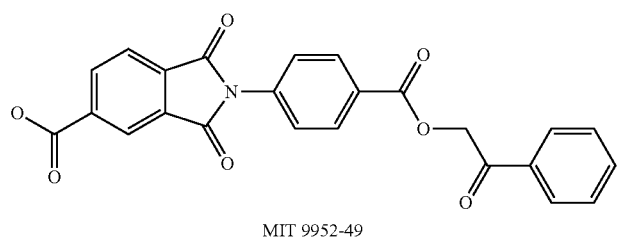
MIT 9952-49
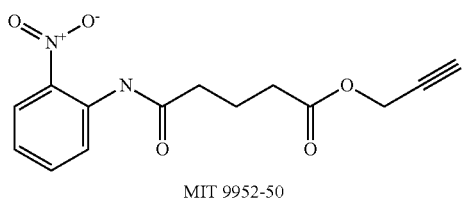
MIT 9952-50
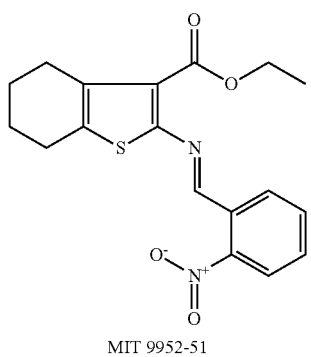
MIT 9952-51
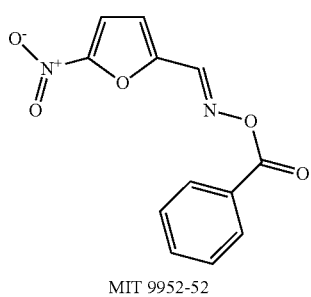
MIT 9952-52
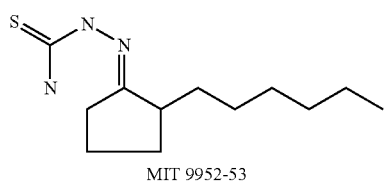
MIT 9952-53

TABLE I-continued
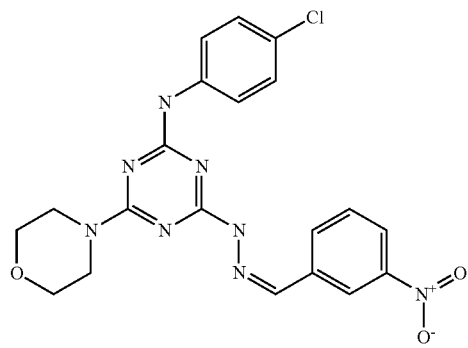 [SMILES: O=[N+]([O-])c1cccc(/C=N\Nc2nc(Nc3ccc(Cl)cc3)nc(N3CCOCC3)n2)c1]
MIT 9952-54
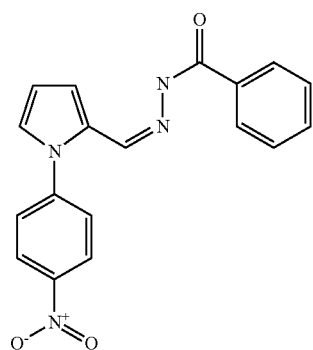 [SMILES: O=C(N/N=C\c1cccn1-c1ccc([N+](=O)[O-])cc1)c1ccccc1]
MIT 9952-55
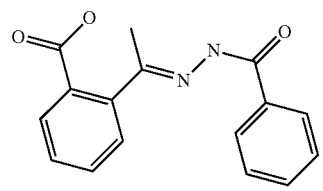 [SMILES: C/C(=N\NC(=O)c1ccccc1)c1ccccc1C(=O)O]
MIT 9952-56
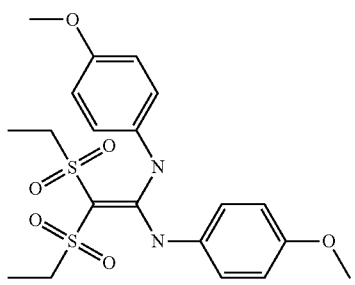 [SMILES: CCS(=O)(=O)C(=C(Nc1ccc(OC)cc1)Nc1ccc(OC)cc1)S(=O)(=O)CC]
MIT 9952-57
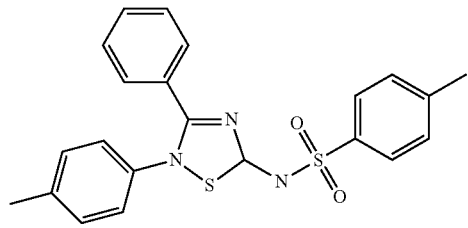
MIT 9952-58

TABLE I-continued
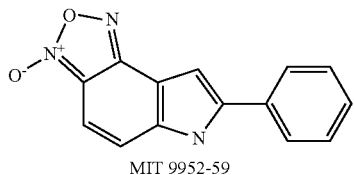
MIT 9952-59
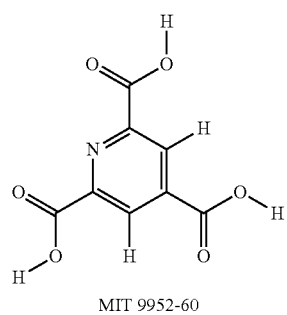
MIT 9952-60
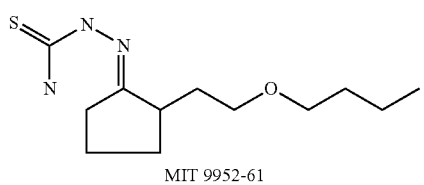
MIT 9952-61
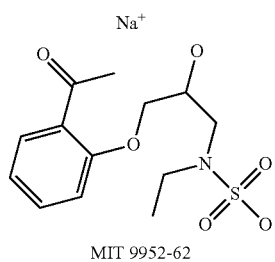
MIT 9952-62
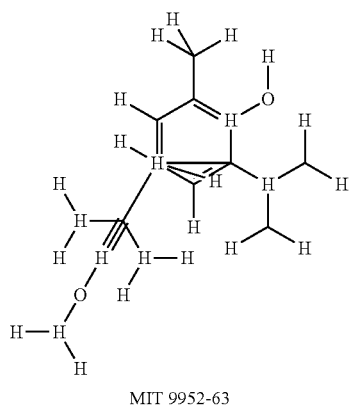
MIT 9952-63

TABLE I-continued
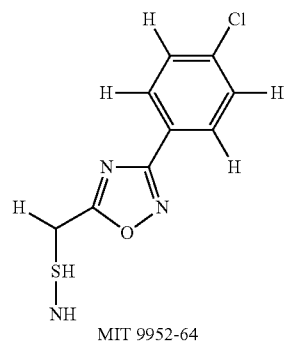
MIT 9952-64
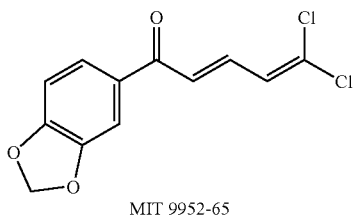
MIT 9952-65
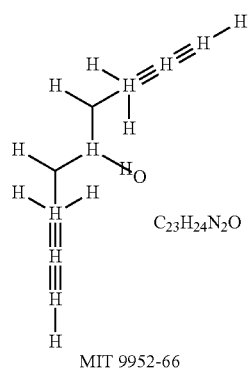
C₂₃H₂₄N₂O
MIT 9952-66
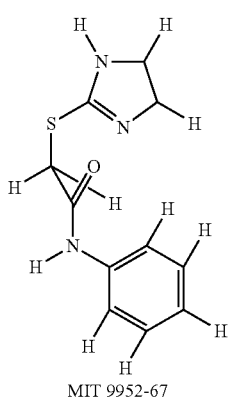
MIT 9952-67
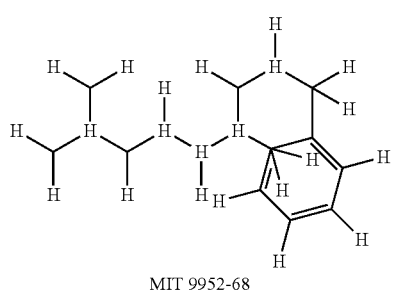
MIT 9952-68

TABLE I-continued
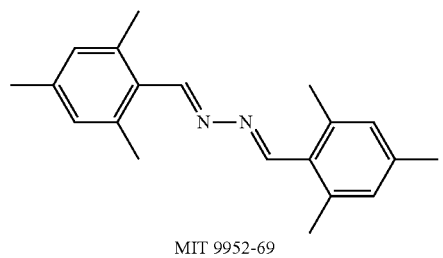
MIT 9952-69
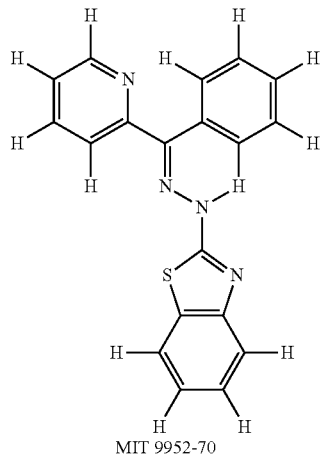
MIT 9952-70
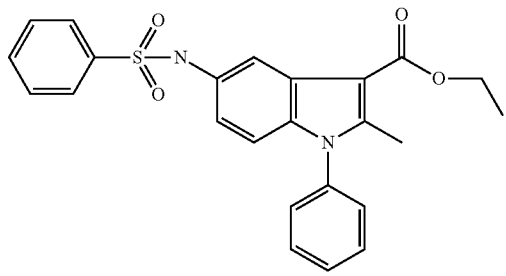 [SMILES: CCOC(=O)c1c(C)n(-c2ccccc2)c2ccc(NS(=O)(=O)c3ccccc3)cc12]
MIT 9952-71
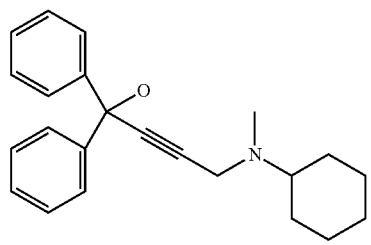 [SMILES: CN(CC#CC(O)(c1ccccc1)c1ccccc1)C1CCCCC1]
MIT 9952-72
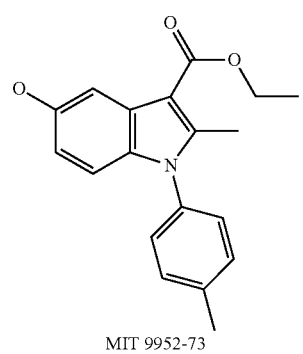
MIT 9952-73

TABLE I-continued
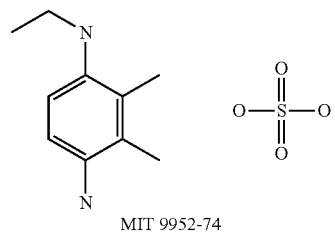
MIT 9952-74
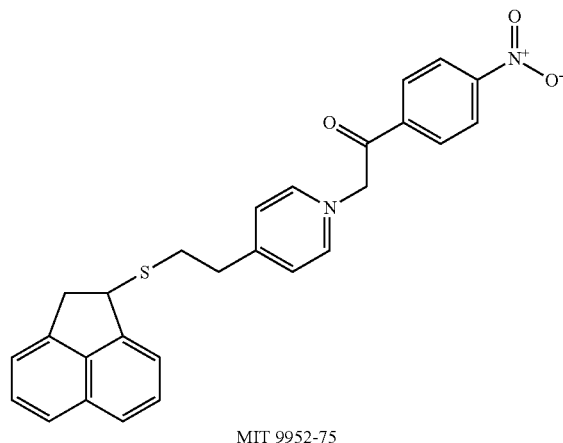
MIT 9952-75
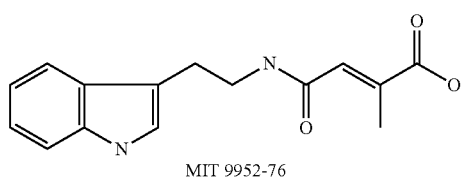
MIT 9952-76
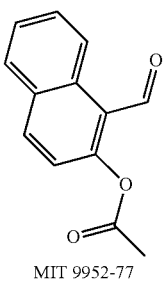
MIT 9952-77
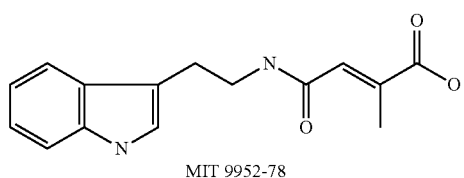
MIT 9952-78
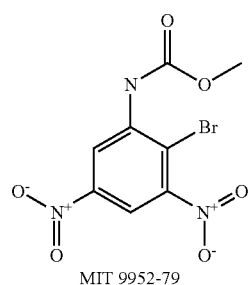
MIT 9952-79

TABLE I-continued
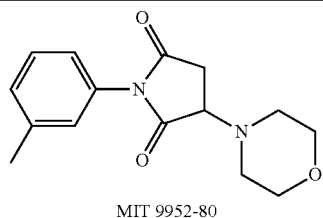
MIT 9952-80
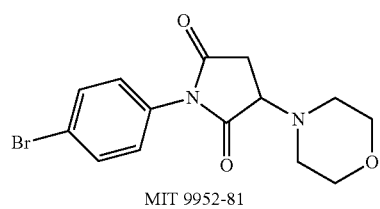
MIT 9952-81
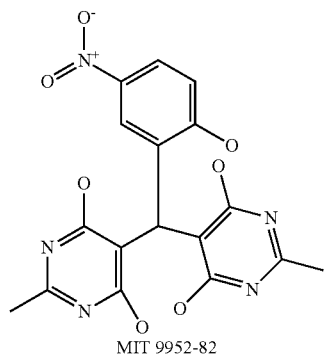
MIT 9952-82
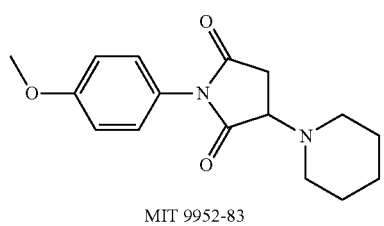
MIT 9952-83
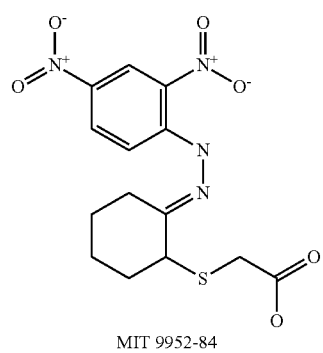
MIT 9952-84
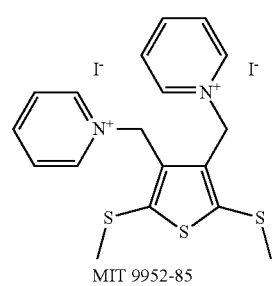
MIT 9952-85

TABLE I-continued
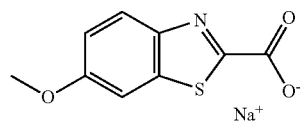
MIT 9952-86
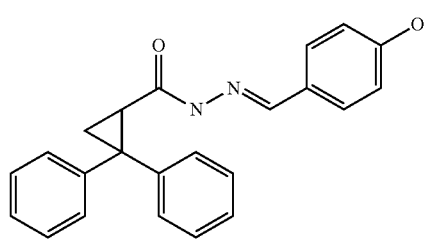 [SMILES: O=C(N/N=C/c1ccc(O)cc1)C1CC1(c1ccccc1)c1ccccc1]
MIT 9952-87
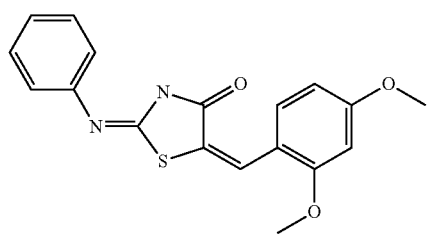 [SMILES: COc1ccc(/C=C2/S/C(=N/c3ccccc3)NC2=O)c(OC)c1]
MIT 9952-88
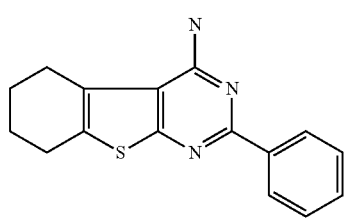 [SMILES: Nc1nc(-c2ccccc2)nc2sc3c(c12)CCCC3]
MIT 9952-89
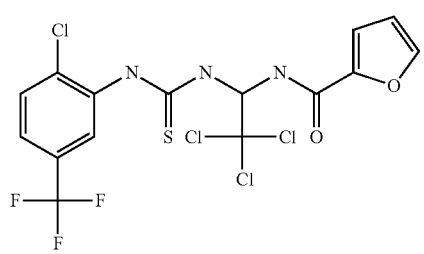 [SMILES: O=C(NC(NC(=S)Nc1cc(C(F)(F)F)ccc1Cl)C(Cl)(Cl)Cl)c1ccco1]
MIT 9952-90
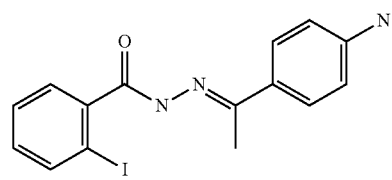 [SMILES: C/C(=N\NC(=O)c1ccccc1I)c1ccc(N)cc1]
MIT 9952-91

TABLE I-continued
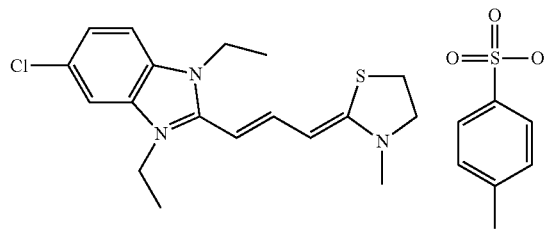
MIT 9952-92
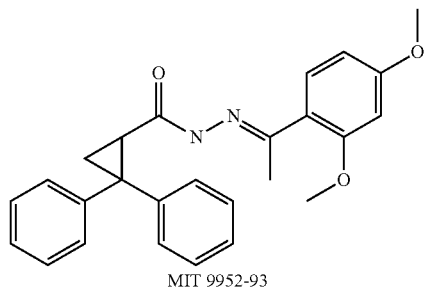
MIT 9952-93
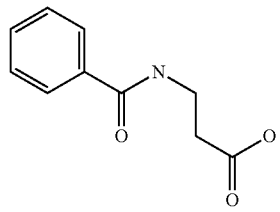 [SMILES: O=C(O)CCNC(=O)c1ccccc1]
MIT 9952-94
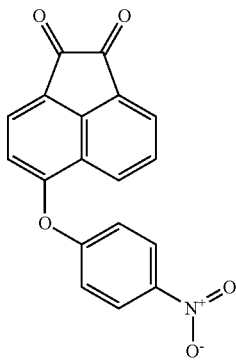 [SMILES: O=C1C(=O)c2ccc(Oc3ccc([N+](=O)[O-])cc3)c3cccc1c23]
MIT 9952-95
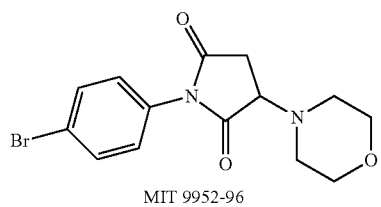
MIT 9952-96
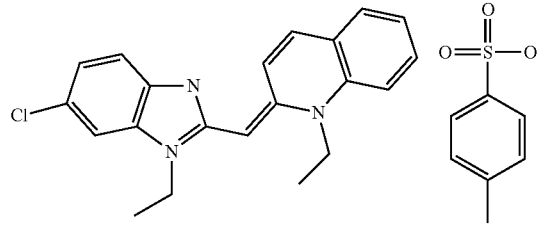
MIT 9952-97

TABLE I-continued
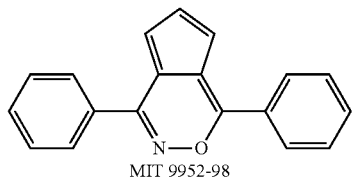
MIT 9952-98
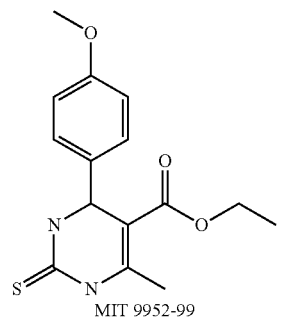
MIT 9952-99
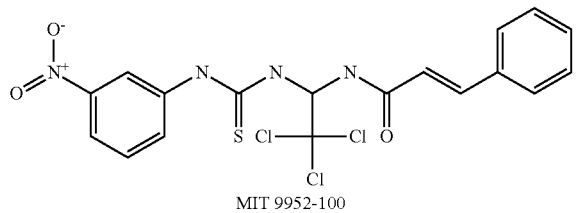
MIT 9952-100
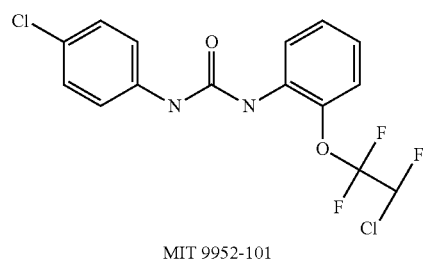
MIT 9952-101
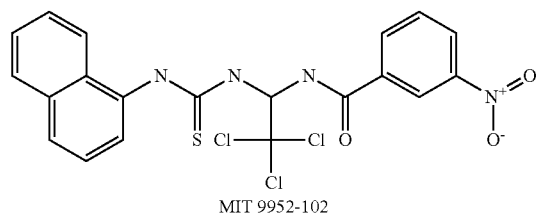
MIT 9952-102
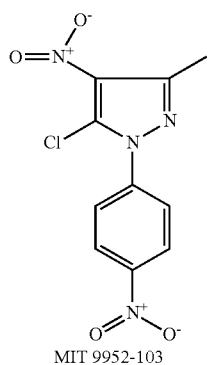
MIT 9952-103

TABLE I-continued
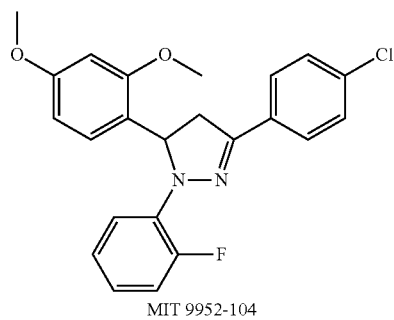
MIT 9952-104
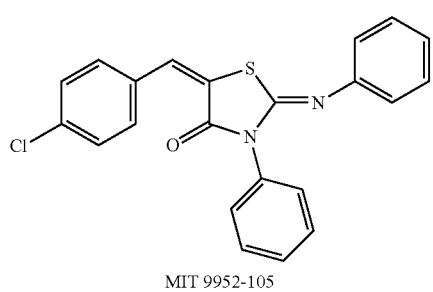
MIT 9952-105
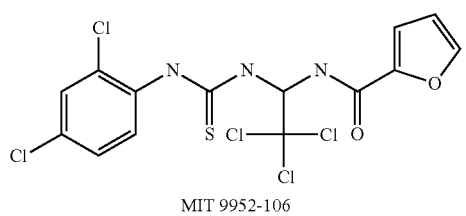
MIT 9952-106
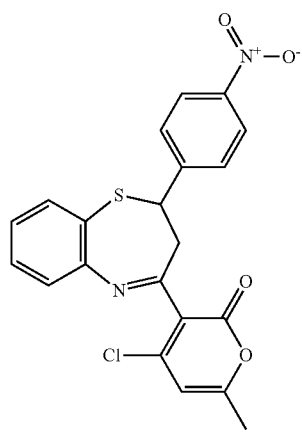 [SMILES: Cc1cc(Cl)c(C2=Nc3ccccc3SC(c3ccc([N+](=O)[O-])cc3)C2)c(=O)o1]
MIT 9952-107
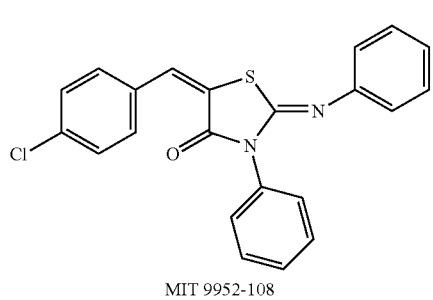
MIT 9952-108

TABLE I-continued
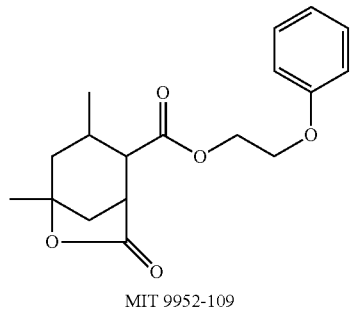
MIT 9952-109
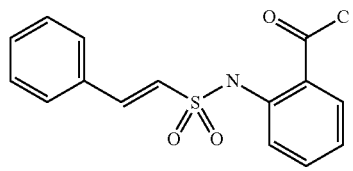 [SMILES: CC(=O)c1ccccc1NS(=O)(=O)/C=C/c1ccccc1]
MIT 9952-110
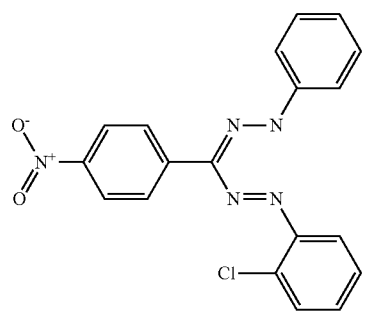 [SMILES: O=[N+]([O-])c1ccc(C(=N/Nc2ccccc2)/N=N/c2ccccc2Cl)cc1]
MIT 9952-111
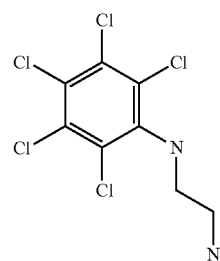 [SMILES: NCCNc1c(Cl)c(Cl)c(Cl)c(Cl)c1Cl]
MIT 9952-112
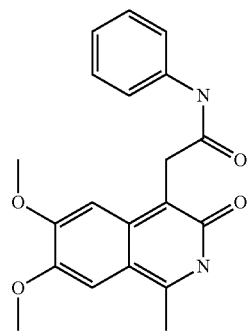 [SMILES: COc1cc2c(C)[nH]c(=O)c(CC(=O)Nc3ccccc3)c2cc1OC]
MIT 9952-113

TABLE I-continued
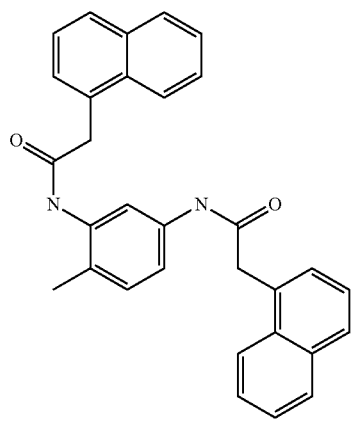 [SMILES: Cc1ccc(NC(=O)Cc2cccc3ccccc23)cc1NC(=O)Cc1cccc2ccccc12]
MIT 9952-114
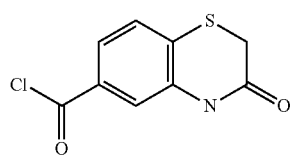 [SMILES: O=C1CSc2ccc(C(=O)Cl)cc2N1]
MIT 9952-115
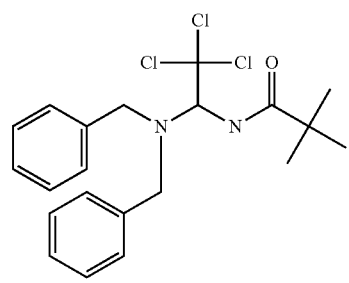 [SMILES: CC(C)(C)C(=O)NC(N(Cc1ccccc1)Cc1ccccc1)C(Cl)(Cl)Cl]
MIT 9952-116
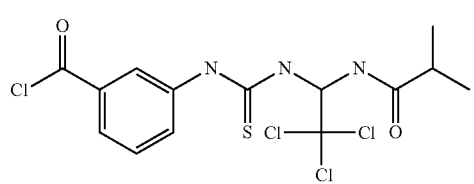 [SMILES: CC(C)C(=O)NC(NC(=S)Nc1cccc(C(=O)Cl)c1)C(Cl)(Cl)Cl]
MIT 9952-117
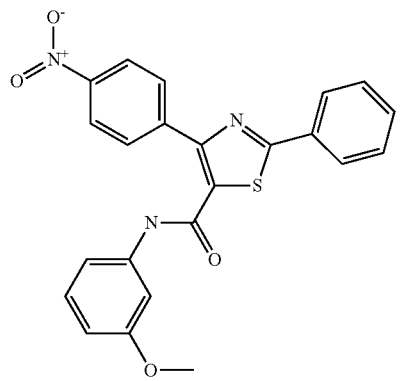 [SMILES: COc1cccc(NC(=O)c2sc(-c3ccccc3)nc2-c2ccc([N+](=O)[O-])cc2)c1]
MIT 9952-118

TABLE I-continued
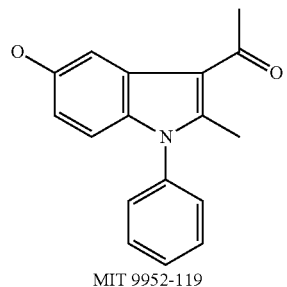
MIT 9952-119
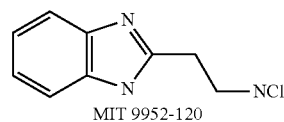
MIT 9952-120
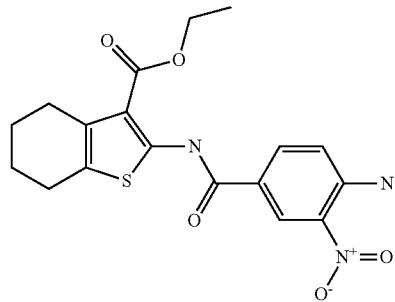 [SMILES: CCOC(=O)c1c(NC(=O)c2ccc(N)c([N+](=O)[O-])c2)sc2c1CCCC2]
MIT 9952-121
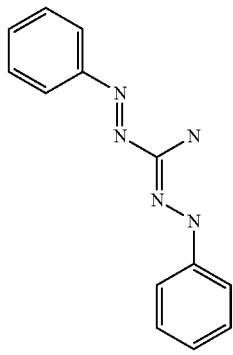 [SMILES: NC(/N=N/c1ccccc1)=N\Nc1ccccc1]
MIT 9952-122
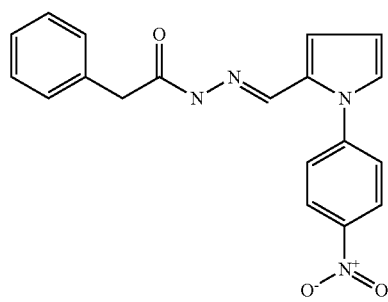 [SMILES: O=C(Cc1ccccc1)N/N=C/c1cccn1-c1ccc([N+](=O)[O-])cc1]
MIT 9952-123
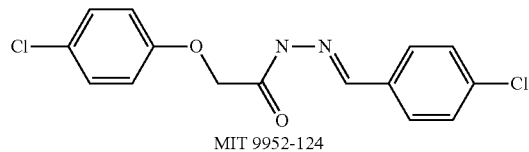
MIT 9952-124

TABLE I-continued
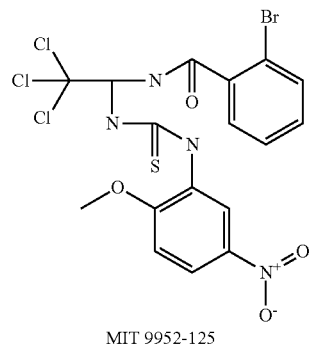
MIT 9952-125
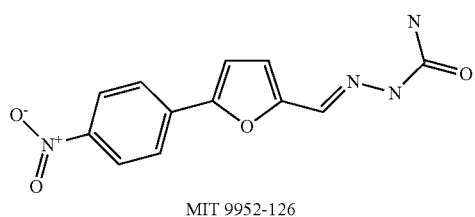
MIT 9952-126
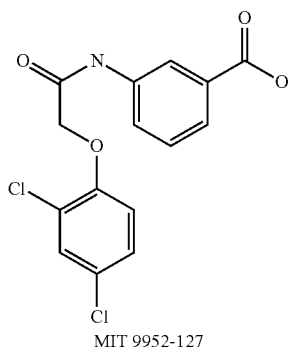
MIT 9952-127
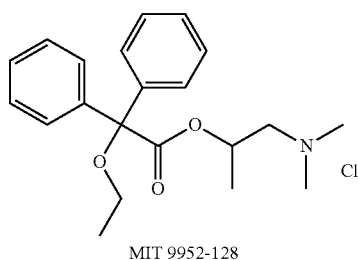
MIT 9952-128
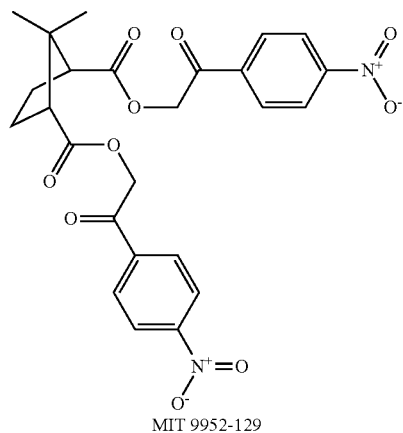
MIT 9952-129

TABLE I-continued
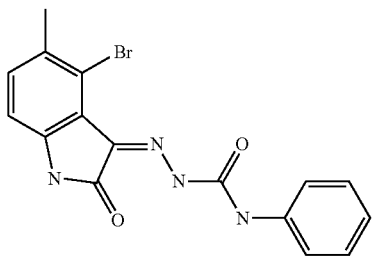 [SMILES: Cc1ccc2c(c1Br)/C(=N/NC(=O)Nc1ccccc1)C(=O)N2]
MIT 9952-130
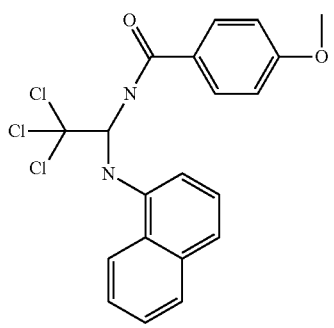 [SMILES: COc1ccc(C(=O)NC(Nc2cccc3ccccc23)C(Cl)(Cl)Cl)cc1]
MIT 9952-131
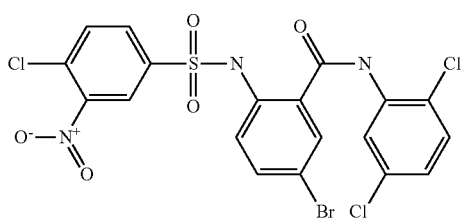 [SMILES: O=C(Nc1cc(Cl)ccc1Cl)c1cc(Br)ccc1NS(=O)(=O)c1ccc(Cl)c([N+](=O)[O-])c1]
MIT 9952-132
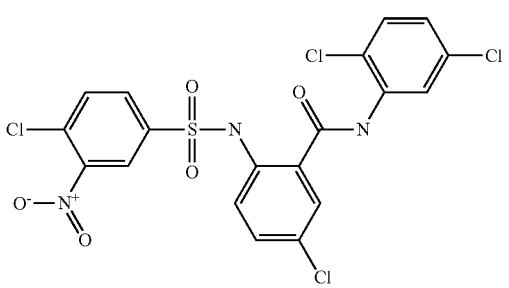 [SMILES: O=C(Nc1cc(Cl)ccc1Cl)c1cc(Cl)ccc1NS(=O)(=O)c1ccc(Cl)c([N+](=O)[O-])c1]
MIT 9952-133
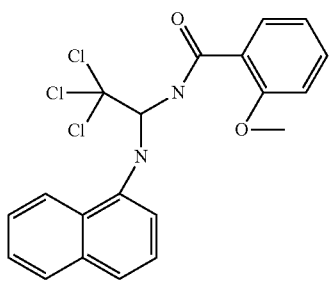 [SMILES: COc1ccccc1C(=O)NC(Nc1cccc2ccccc12)C(Cl)(Cl)Cl]
MIT 9952-134

TABLE I-continued
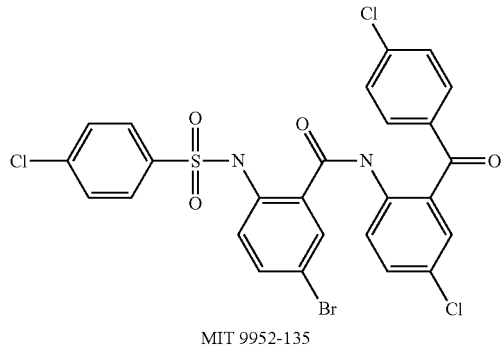
MIT 9952-135
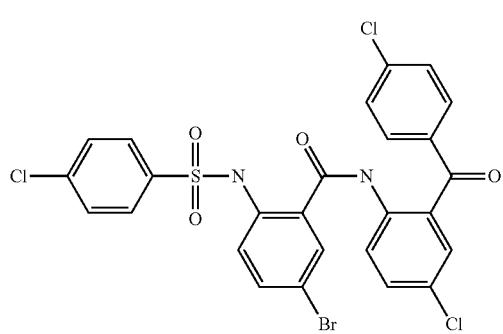
MIT 9952-136
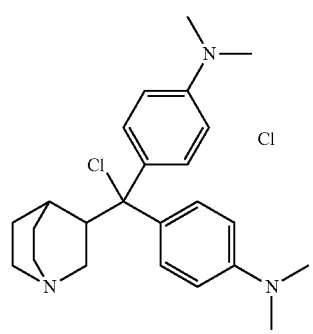 [SMILES: CN(C)c1ccc(C(Cl)(c2ccc(N(C)C)cc2)C2CN3CCC2CC3)cc1 ; Cl]
MIT 9952-137
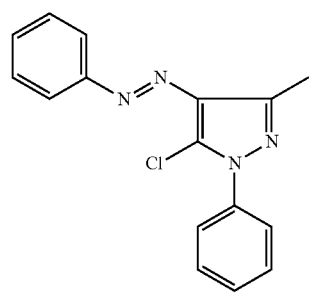 [SMILES: Cc1nn(-c2ccccc2)c(Cl)c1/N=N/c1ccccc1]
MIT 9952-138

TABLE I-continued
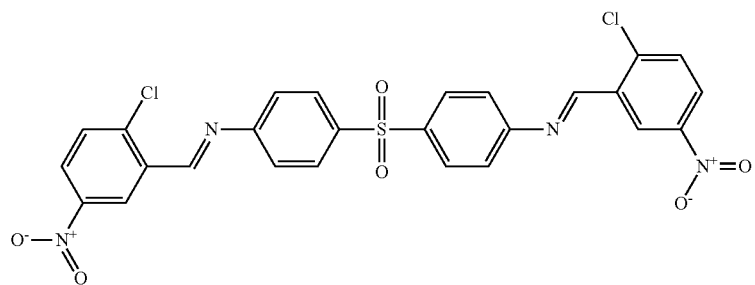 [SMILES: O=[N+]([O-])c1ccc(Cl)c(/C=N/c2ccc(S(=O)(=O)c3ccc(/N=C/c4cc([N+](=O)[O-])ccc4Cl)cc3)cc2)c1]
MIT 9952-139
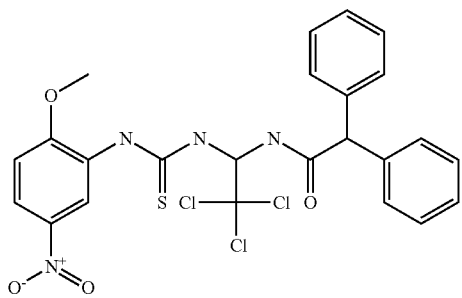 [SMILES: COc1ccc([N+](=O)[O-])cc1NC(=S)NC(NC(=O)C(c1ccccc1)c1ccccc1)C(Cl)(Cl)Cl]
MIT 9952-140
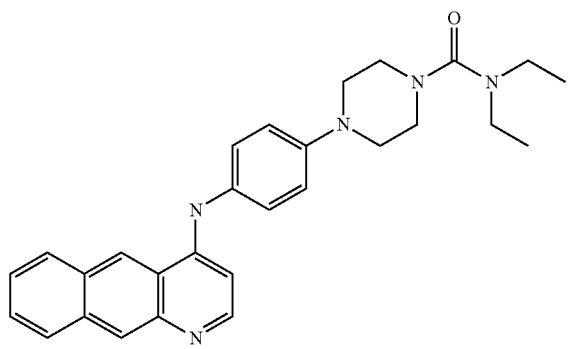 [SMILES: CCN(CC)C(=O)N1CCN(c2ccc(Nc3ccnc4cc5ccccc5cc34)cc2)CC1]
MIT 9952-141
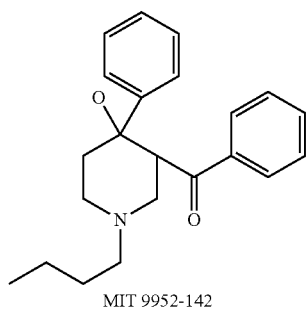
MIT 9952-142
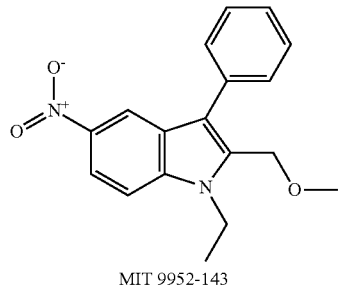
MIT 9952-143

TABLE I-continued
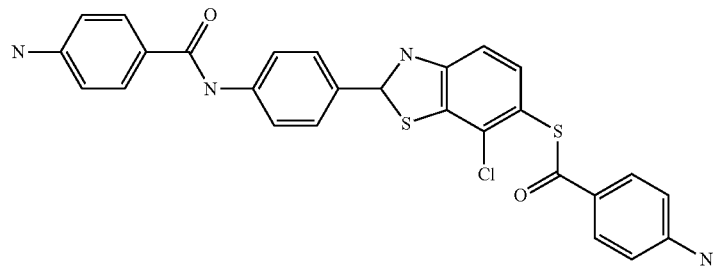 [SMILES: Nc1ccc(C(=O)Nc2ccc(C3Nc4ccc(SC(=O)c5ccc(N)cc5)c(Cl)c4S3)cc2)cc1]
MIT 9952-144
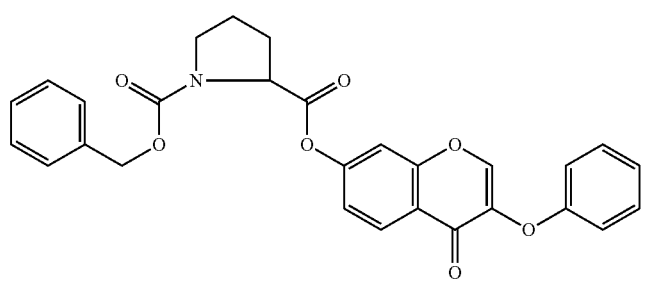 [SMILES: O=C(Oc1ccc2c(=O)c(Oc3ccccc3)coc2c1)C1CCCN1C(=O)OCc1ccccc1]
MIT 9952-145
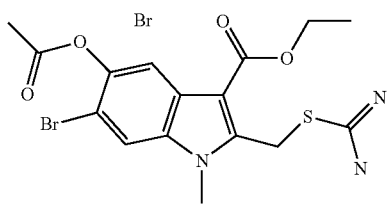 [SMILES: Br ; CCOC(=O)c1c(CSC(=N)N)n(C)c2cc(Br)c(OC(C)=O)cc12]
MIT 9952-146
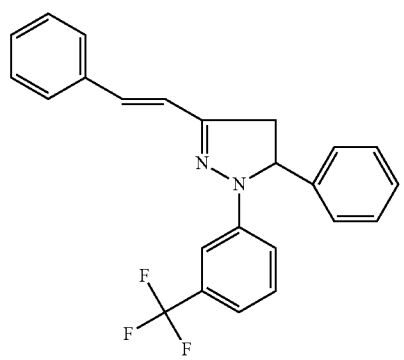 [SMILES: FC(F)(F)c1cccc(N2N=C(/C=C/c3ccccc3)CC2c2ccccc2)c1]
MIT 9952-147
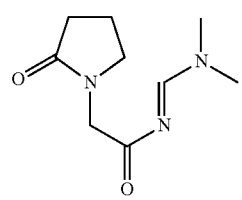
MIT 9952-148

TABLE I-continued
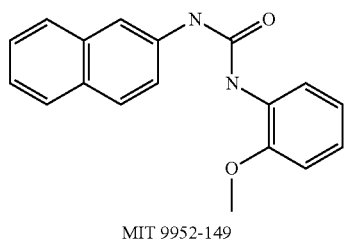
MIT 9952-149
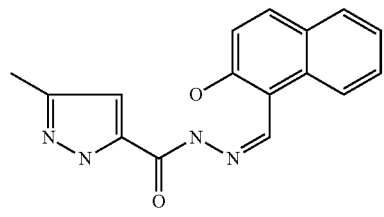 [SMILES: Cc1cc(C(=O)N/N=C\c2c(O)ccc3ccccc23)[nH]n1]
MIT 9952-150
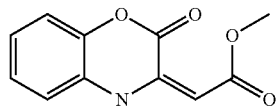 [SMILES: COC(=O)/C=C1/Nc2ccccc2OC1=O]
MIT 9952-151
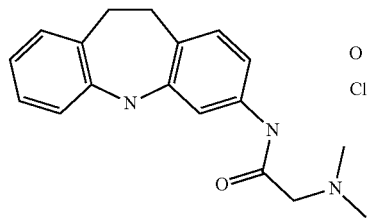 [SMILES: CN(C)CC(=O)Nc1ccc2c(c1)Nc1ccccc1CC2 ; Cl ; O]
MIT 9952-152
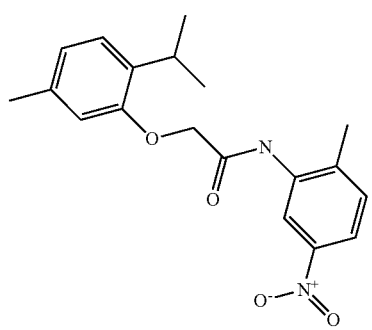 [SMILES: Cc1ccc(C(C)C)c(OCC(=O)Nc2cc([N+](=O)[O-])ccc2C)c1]
MIT 9952-153
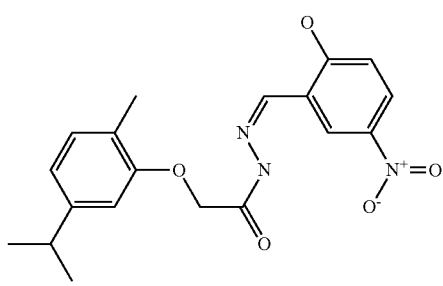 [SMILES: Cc1ccc(C(C)C)cc1OCC(=O)N/N=C\c1cc([N+](=O)[O-])ccc1O]
MIT 9952-154

TABLE I-continued
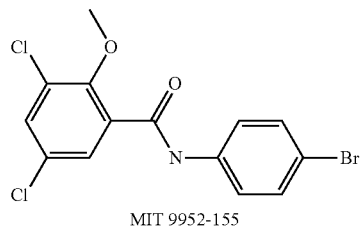
MIT 9952-155
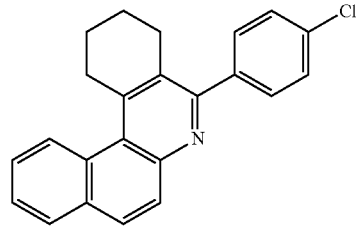 [SMILES: Clc1ccc(-c2nc3ccc4ccccc4c3c3c2CCCC3)cc1]
MIT 9952-156
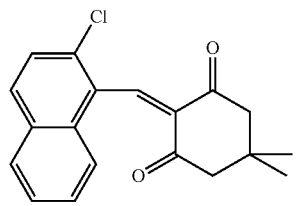 [SMILES: CC1(C)CC(=O)C(=Cc2c(Cl)ccc3ccccc23)C(=O)C1]
MIT 9952-157
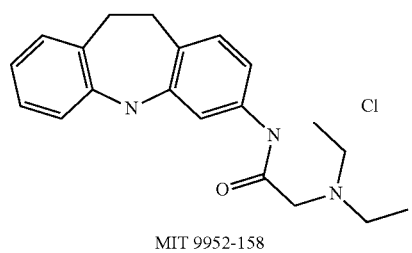
MIT 9952-158
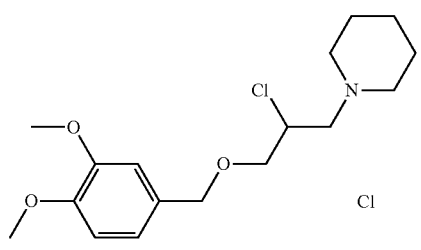 [SMILES: COc1ccc(COCC(Cl)CN2CCCCC2)cc1OC ; Cl]
MIT 9952-159
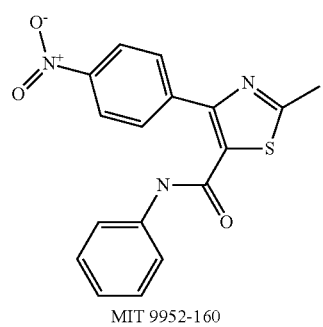
MIT 9952-160

TABLE I-continued
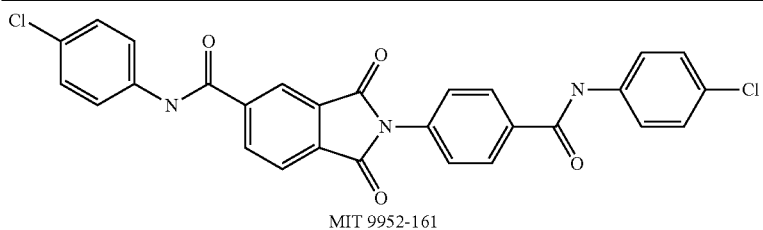
MIT 9952-161
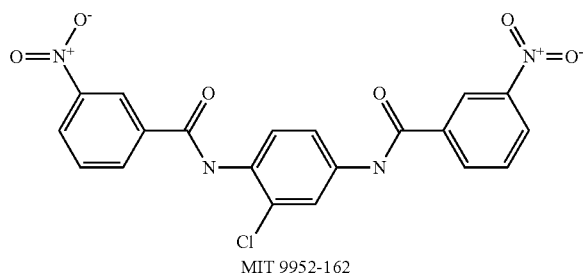
MIT 9952-162
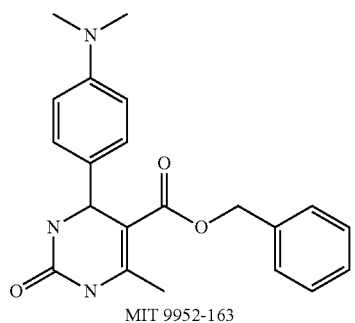
MIT 9952-163
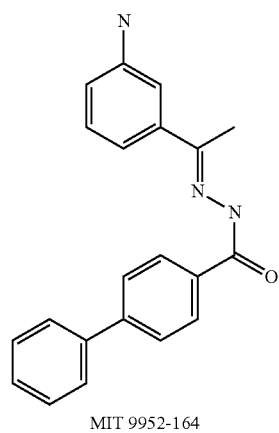
MIT 9952-164
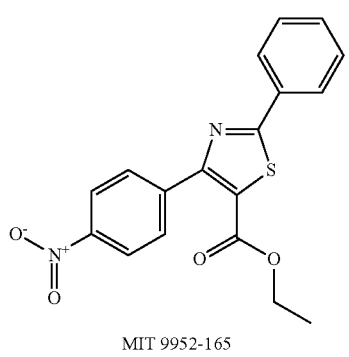
MIT 9952-165

TABLE I-continued
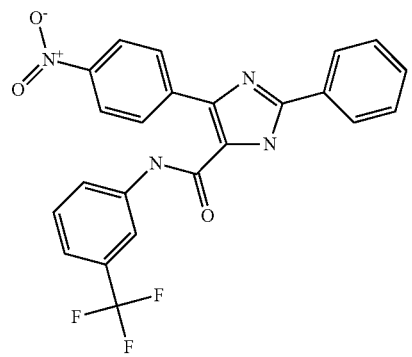 [SMILES: O=C(Nc1cccc(C(F)(F)F)c1)c1[nH]c(-c2ccccc2)nc1-c1ccc([N+](=O)[O-])cc1]
MIT 9952-166
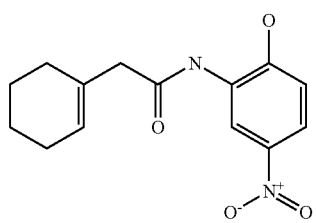 [SMILES: O=C(CC1=CCCCC1)Nc1cc([N+](=O)[O-])ccc1O]
MIT 9952-167
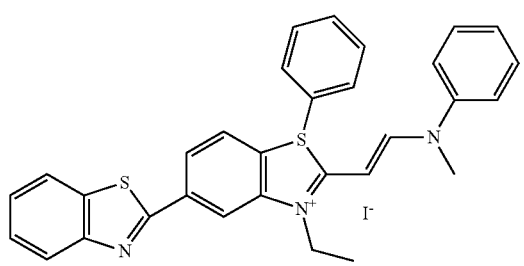
MIT 9952-168
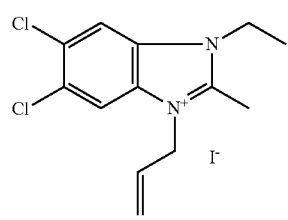 [SMILES: C=CC[n+]1c(C)n(CC)c2cc(Cl)c(Cl)cc21 ; [I-]]
MIT 9952-169
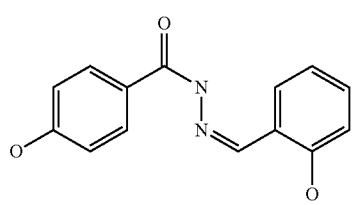 [SMILES: O=C(N/N=C\c1ccccc1O)c1ccc(O)cc1]
MIT 9952-170

TABLE I-continued
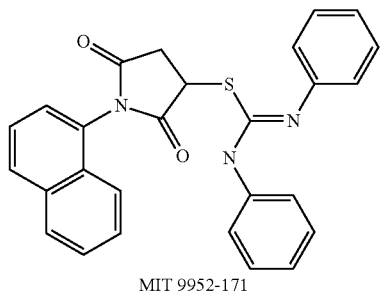
MIT 9952-171
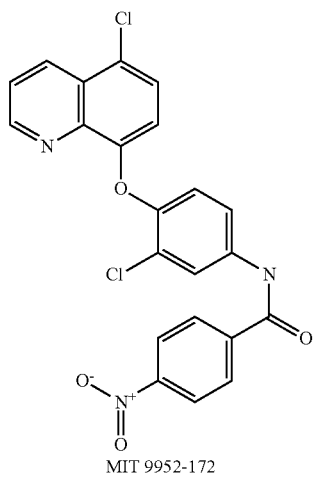
MIT 9952-172
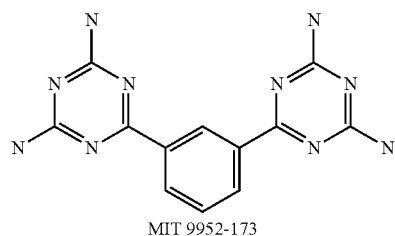
MIT 9952-173
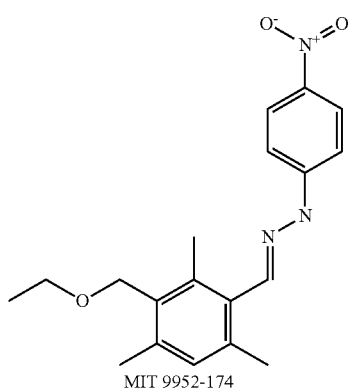
MIT 9952-174
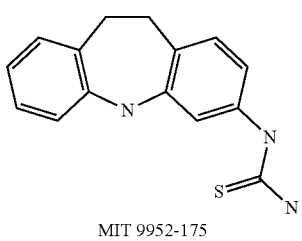
MIT 9952-175

TABLE I-continued
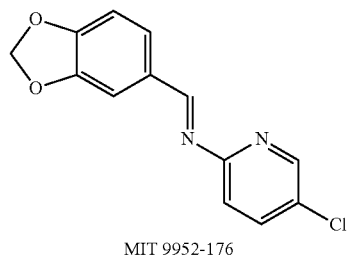
MIT 9952-176
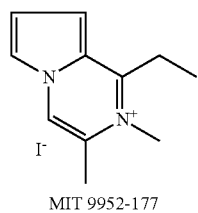
MIT 9952-177
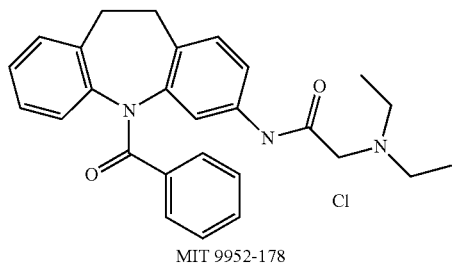
MIT 9952-178
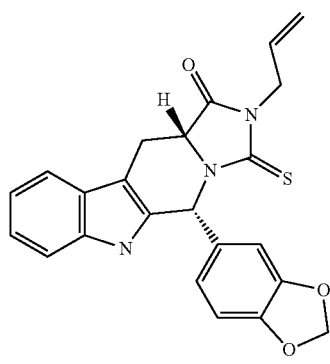 [SMILES: C=CCN1C(=O)[C@H]2Cc3c([nH]c4ccccc34)[C@@H](c3ccc4c(c3)OCO4)N2C1=S]
MIT 9952-179
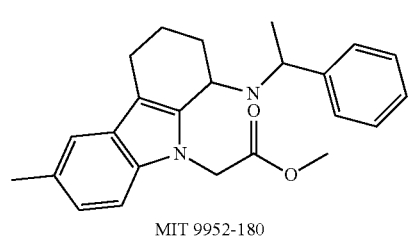
MIT 9952-180
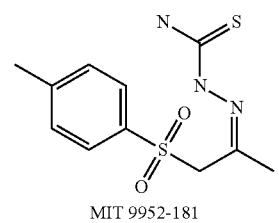
MIT 9952-181

TABLE I-continued
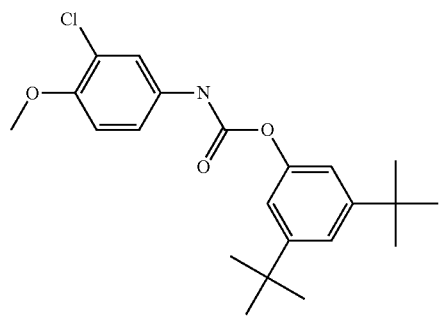 [SMILES: COc1ccc(NC(=O)Oc2cc(C(C)(C)C)cc(C(C)(C)C)c2)cc1Cl]
MIT 9952-182
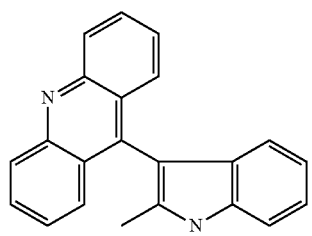 [SMILES: Cc1[nH]c2ccccc2c1-c1c2ccccc2nc2ccccc12]
MIT 9952-183
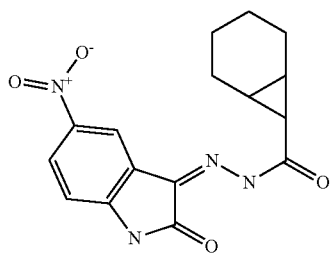 [SMILES: O=C1Nc2ccc([N+](=O)[O-])cc2/C1=N/NC(=O)C1C2CCCCC21]
MIT 9952-184
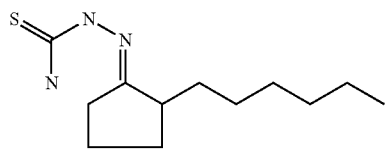 [SMILES: CCCCCCC1CCC/C1=N\NC(N)=S]
MIT 9952-185
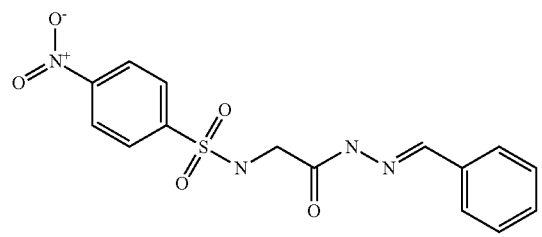 [SMILES: O=C(CNS(=O)(=O)c1ccc([N+](=O)[O-])cc1)N/N=C/c1ccccc1]
MIT 9952-186

TABLE I-continued
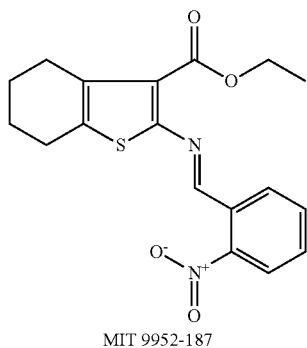
MIT 9952-187
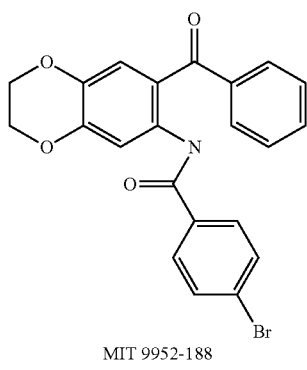
MIT 9952-188
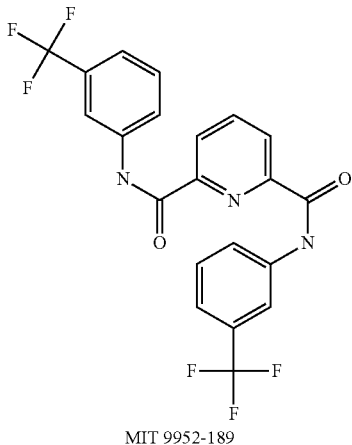
MIT 9952-189
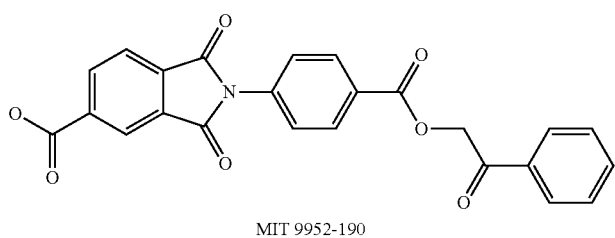
MIT 9952-190
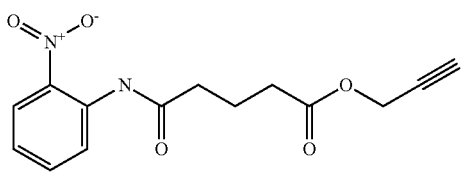 [SMILES: C#CCOC(=O)CCCC(=O)Nc1ccccc1[N+](=O)[O-]]
MIT 9952-191

TABLE I-continued
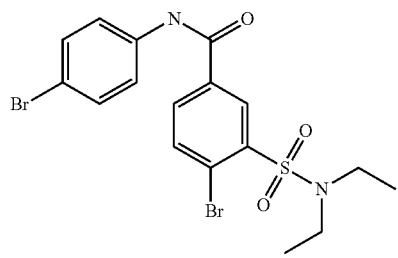 [SMILES: CCN(CC)S(=O)(=O)c1cc(C(=O)Nc2ccc(Br)cc2)ccc1Br]
MIT 9952-192
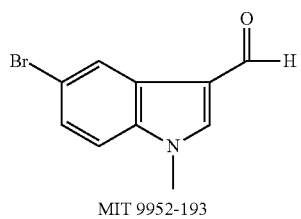
MIT 9952-193
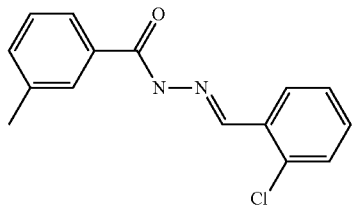 [SMILES: Cc1cccc(C(=O)N/N=C/c2ccccc2Cl)c1]
MIT 9952-194
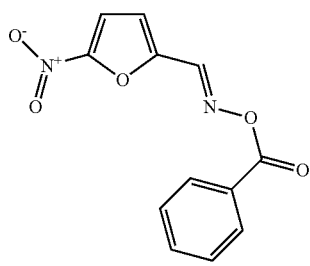 [SMILES: O=C(O/N=C/c1ccc([N+](=O)[O-])o1)c1ccccc1]
MIT 9952-195
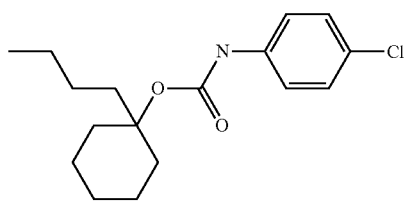 [SMILES: CCCCC1(OC(=O)Nc2ccc(Cl)cc2)CCCCC1]
MIT 9952-196
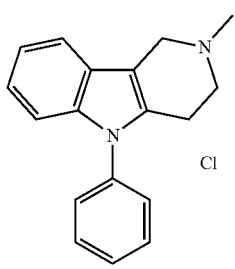 [SMILES: CN1CCc2c(c3ccccc3n2-c2ccccc2)C1 ; Cl]
MIT 9952-197

TABLE I-continued
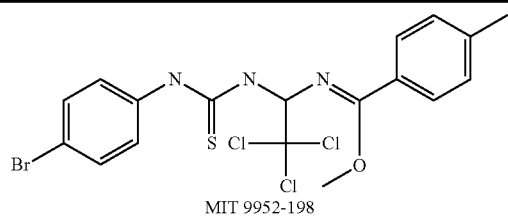
MIT 9952-198
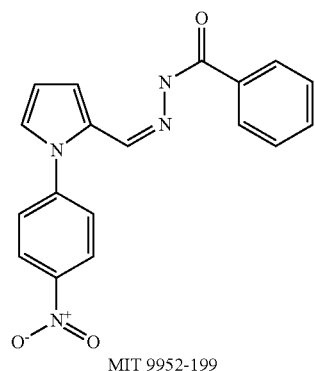
MIT 9952-199
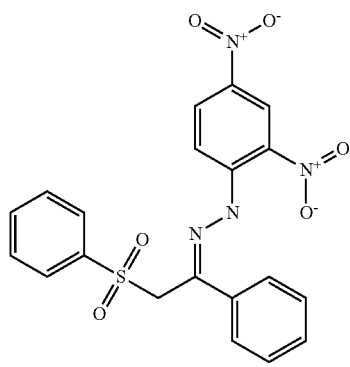 [SMILES: O=[N+]([O-])c1ccc(N/N=C(/CS(=O)(=O)c2ccccc2)c2ccccc2)c([N+](=O)[O-])c1]
MIT 9952-200
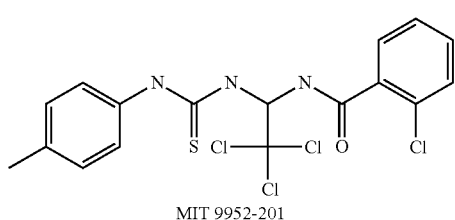
MIT 9952-201
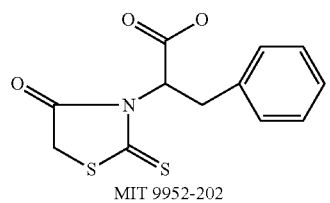
MIT 9952-202
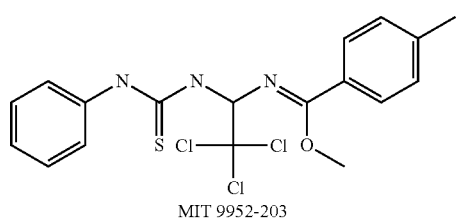
MIT 9952-203

TABLE I-continued
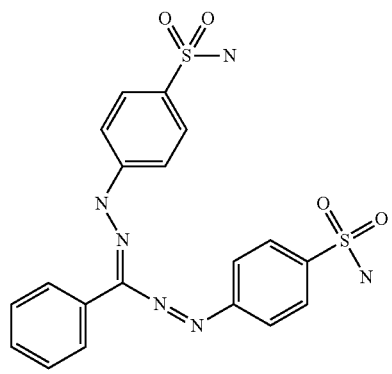 [SMILES: NS(=O)(=O)c1ccc(N=N/C(=N/Nc2ccc(S(N)(=O)=O)cc2)c2ccccc2)cc1]
MIT 9952-204
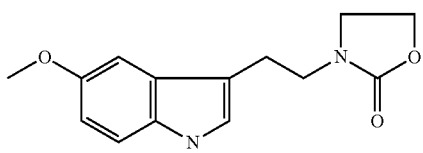 [SMILES: COc1ccc2[nH]cc(CCN3CCOC3=O)c2c1]
MIT 9952-205
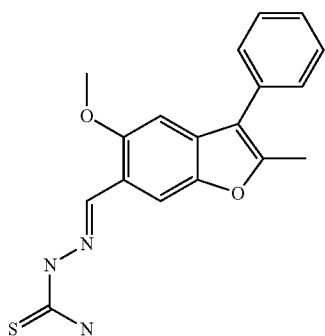 [SMILES: COc1cc2c(-c3ccccc3)c(C)oc2cc1/C=N/NC(N)=S]
MIT 9952-206
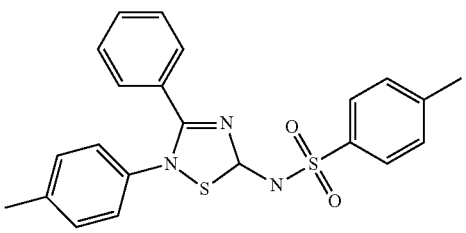
MIT 9952-207
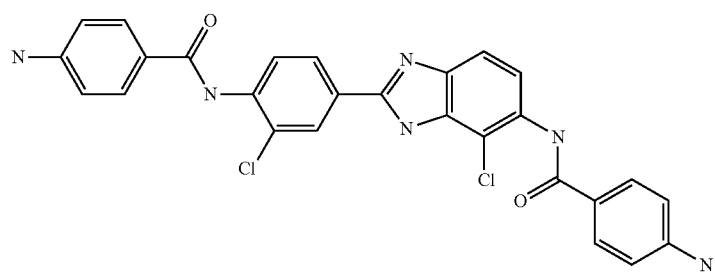 [SMILES: Nc1ccc(C(=O)Nc2ccc(-c3nc4ccc(NC(=O)c5ccc(N)cc5)c(Cl)c4[nH]3)cc2Cl)cc1]
MIT 9952-208

TABLE I-continued
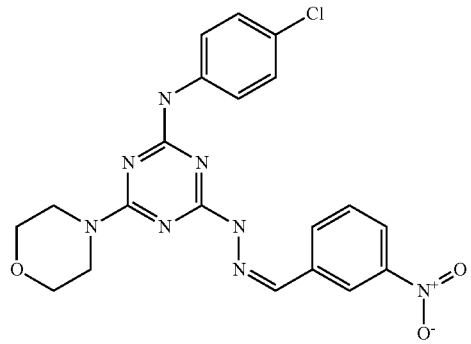 [SMILES: O=[N+]([O-])c1cccc(/C=N\Nc2nc(Nc3ccc(Cl)cc3)nc(N3CCOCC3)n2)c1]
MIT 9952-209
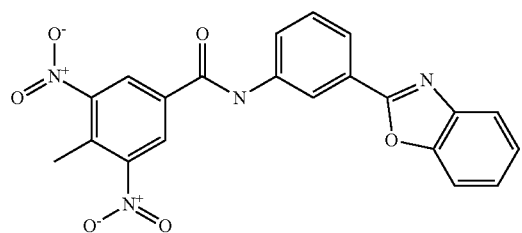 [SMILES: Cc1c([N+](=O)[O-])cc(C(=O)Nc2cccc(-c3nc4ccccc4o3)c2)cc1[N+](=O)[O-]]
MIT 9952-210
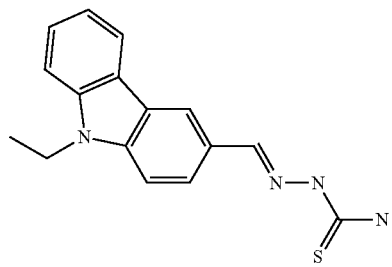 [SMILES: CCn1c2ccccc2c2cc(/C=N/NC(N)=S)ccc21]
MIT 9952-211
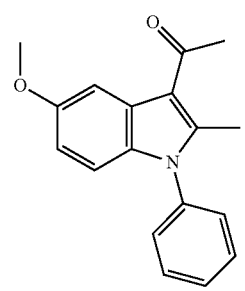 [SMILES: COc1ccc2c(c1)c(C(C)=O)c(C)n2-c1ccccc1]
MIT 9952-212
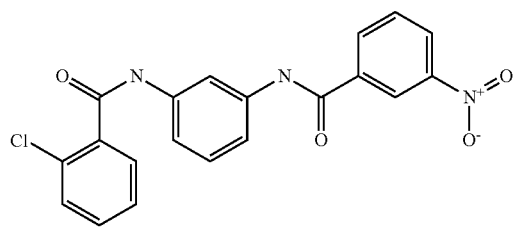 [SMILES: O=C(Nc1cccc(NC(=O)c2ccccc2Cl)c1)c1cccc([N+](=O)[O-])c1]
MIT 9952-213

TABLE I-continued
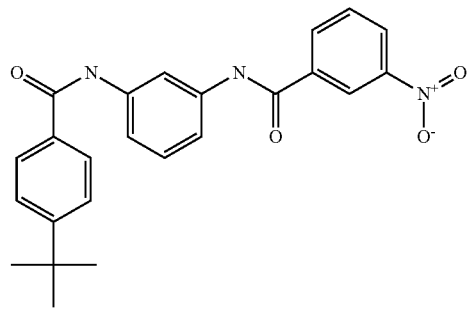 [SMILES: CC(C)(C)c1ccc(C(=O)Nc2cccc(NC(=O)c3cccc([N+](=O)[O-])c3)c2)cc1]
MIT 9952-214
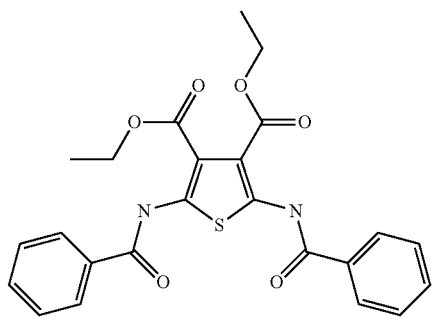 [SMILES: CCOC(=O)c1c(NC(=O)c2ccccc2)sc(NC(=O)c2ccccc2)c1C(=O)OCC]
MIT 9952-215
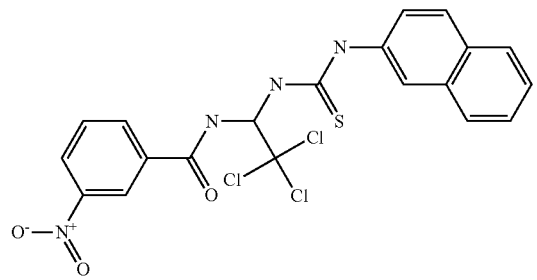 [SMILES: O=C(NC(NC(=S)Nc1ccc2ccccc2c1)C(Cl)(Cl)Cl)c1cccc([N+](=O)[O-])c1]
MIT 9952-216
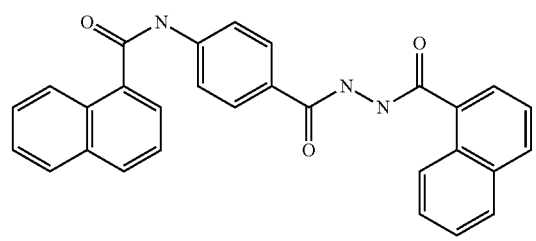 [SMILES: O=C(NNC(=O)c1cccc2ccccc12)c1ccc(NC(=O)c2cccc3ccccc23)cc1]
MIT 9952-217
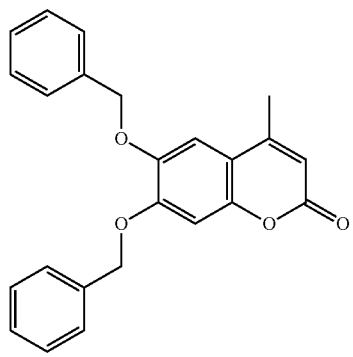 [SMILES: Cc1cc(=O)oc2cc(OCc3ccccc3)c(OCc3ccccc3)cc12]
MIT 9952-218

TABLE I-continued
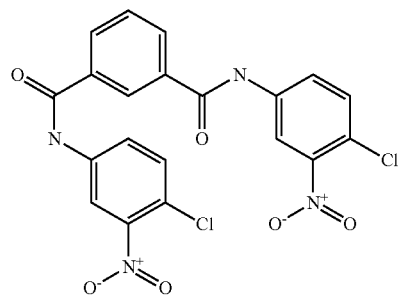 [SMILES: O=C(Nc1ccc(Cl)c([N+](=O)[O-])c1)c1cccc(C(=O)Nc2ccc(Cl)c([N+](=O)[O-])c2)c1]
MIT 9952-219
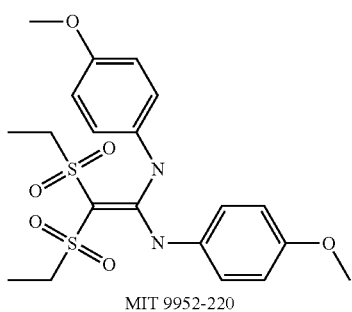
MIT 9952-220
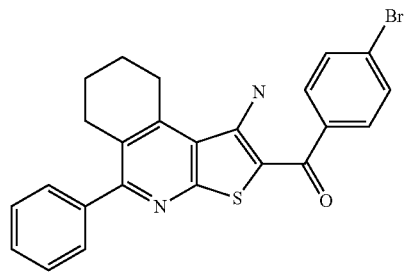 [SMILES: Nc1c(C(=O)c2ccc(Br)cc2)sc2nc(-c3ccccc3)c3c(c12)CCCC3]
MIT 9952-221
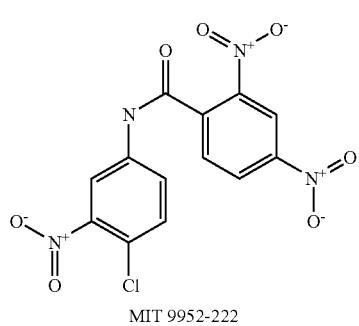
MIT 9952-222
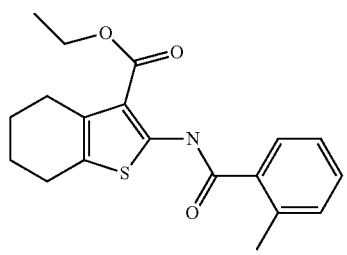 [SMILES: CCOC(=O)c1c(NC(=O)c2ccccc2C)sc2c1CCCC2]
MIT 9952-223

TABLE I-continued
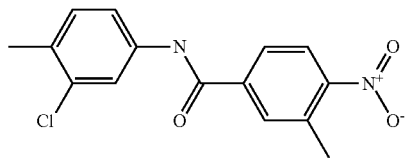 [SMILES: Cc1ccc(NC(=O)c2ccc([N+](=O)[O-])c(C)c2)cc1Cl]
MIT 9952-224
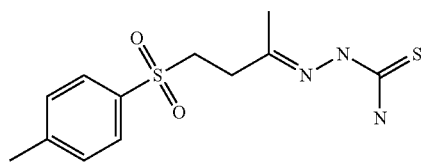 [SMILES: C/C(CCS(=O)(=O)c1ccc(C)cc1)=N\NC(N)=S]
MIT 9952-225
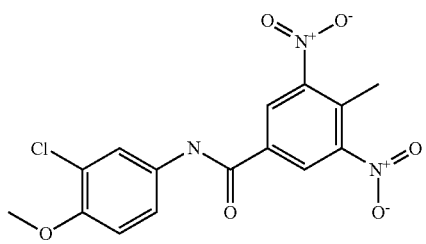 [SMILES: COc1ccc(NC(=O)c2cc([N+](=O)[O-])c(C)c([N+](=O)[O-])c2)cc1Cl]
MIT 9952-226
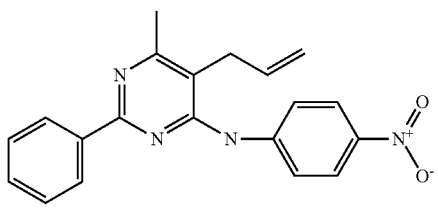 [SMILES: C=CCc1c(C)nc(-c2ccccc2)nc1Nc1ccc([N+](=O)[O-])cc1]
MIT 9952-227
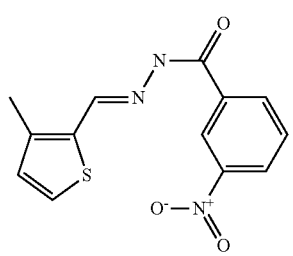 [SMILES: Cc1ccsc1/C=N/NC(=O)c1cccc([N+](=O)[O-])c1]
MIT 9952-228
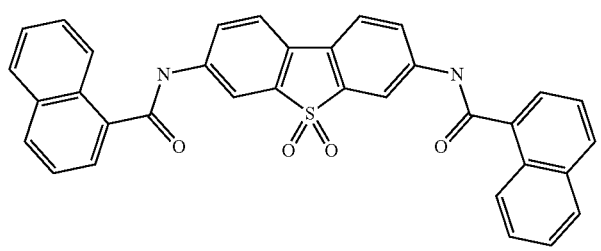 [SMILES: O=C(Nc1ccc2c(c1)S(=O)(=O)c1cc(NC(=O)c3cccc4ccccc34)ccc1-2)c1cccc2ccccc12]
MIT 9952-229

TABLE I-continued
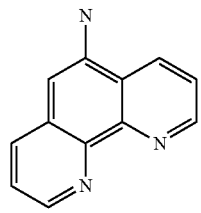 [SMILES: Nc1cc2cccnc2c2ncccc12]
MIT 9952-230
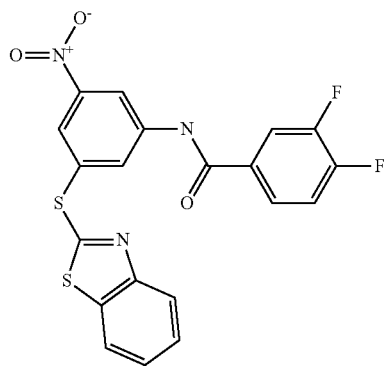 [SMILES: O=C(Nc1cc(Sc2nc3ccccc3s2)cc([N+](=O)[O-])c1)c1ccc(F)c(F)c1]
MIT 9952-231
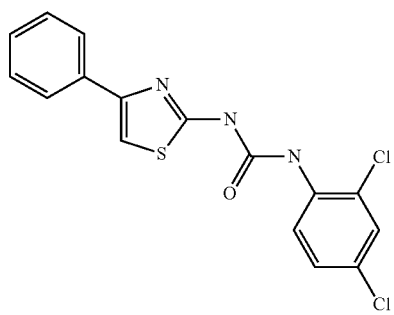 [SMILES: O=C(Nc1nc(-c2ccccc2)cs1)Nc1ccc(Cl)cc1Cl]
MIT 9952-232
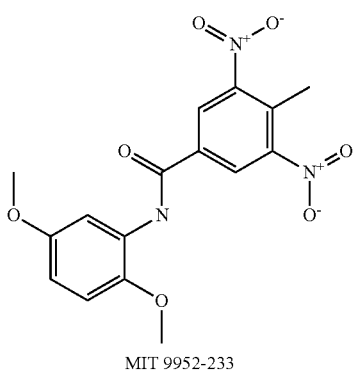
MIT 9952-233
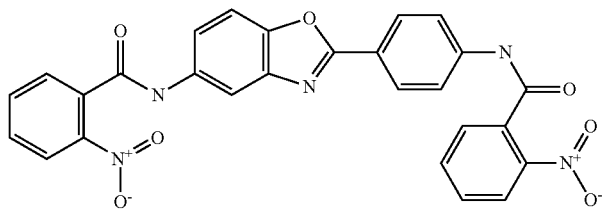 [SMILES: O=C(Nc1ccc(-c2nc3cc(NC(=O)c4ccccc4[N+](=O)[O-])ccc3o2)cc1)c1ccccc1[N+](=O)[O-]]
MIT 9952-234

TABLE I-continued
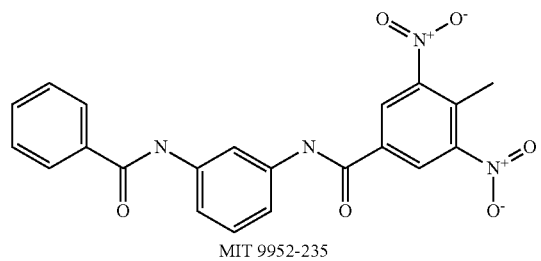
MIT 9952-235
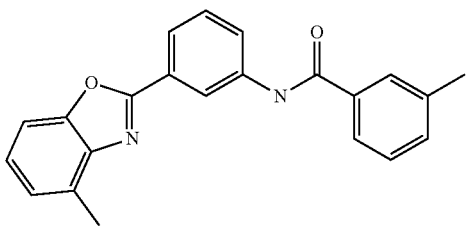 [SMILES: Cc1cccc(C(=O)Nc2cccc(-c3nc4c(C)cccc4o3)c2)c1]
MIT 9952-236
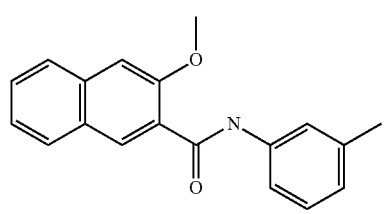 [SMILES: COc1cc2ccccc2cc1C(=O)Nc1cccc(C)c1]
MIT 9952-237
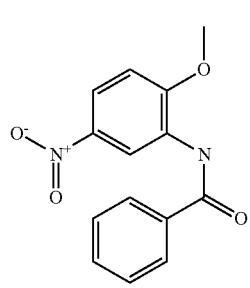 [SMILES: COc1ccc([N+](=O)[O-])cc1NC(=O)c1ccccc1]
MIT 9952-238
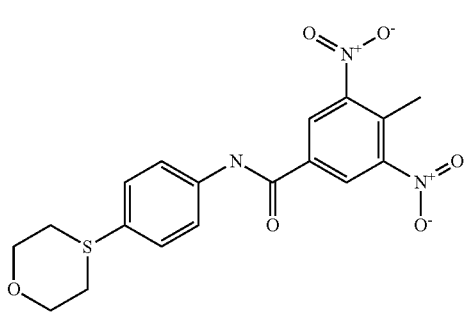
MIT 9952-239
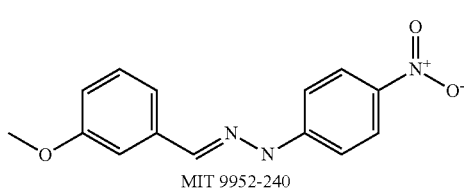
MIT 9952-240

TABLE I-continued
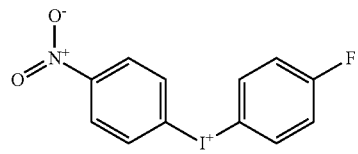
MIT 9952-241
MIT 9952-242
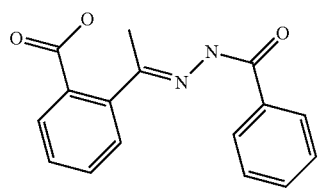 [SMILES: C/C(=N\NC(=O)c1ccccc1)c1ccccc1C(=O)O]
MIT 9952-243
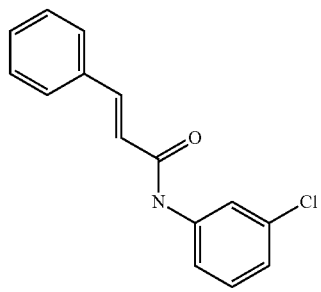 [SMILES: O=C(/C=C/c1ccccc1)Nc1cccc(Cl)c1]
MIT 9952-244
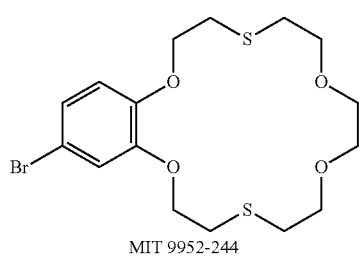
MIT 9952-245
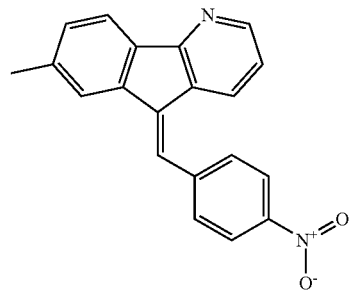 [SMILES: Cc1ccc2c(c1)/C(=C/c1ccc([N+](=O)[O-])cc1)c1cccnc1-2]
MIT 9952-246

TABLE I-continued
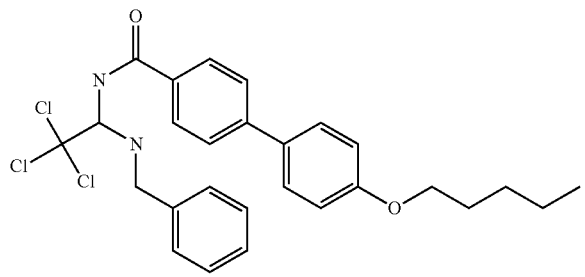 [SMILES: CCCCCOc1ccc(-c2ccc(C(=O)NC(NCc3ccccc3)C(Cl)(Cl)Cl)cc2)cc1]
MIT 9952-247
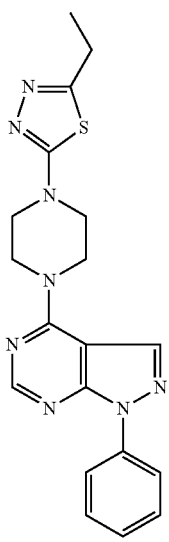 [SMILES: CCc1nnc(N2CCN(c3ncnc4c3cnn4-c3ccccc3)CC2)s1]
MIT 9952-248
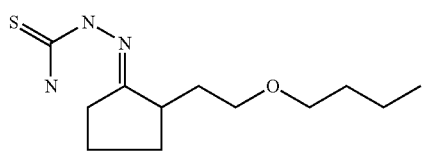 [SMILES: CCCCOCCC1CCC/C1=N\NC(N)=S]
MIT 9952-249
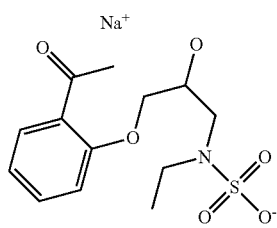 [SMILES: [Na+] ; CCN(CC(O)COc1ccccc1C(C)=O)S(=O)(=O)[O-]]
MIT 9952-250
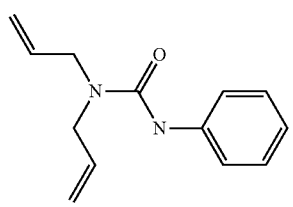 [SMILES: C=CCN(CC=C)C(=O)Nc1ccccc1]
MIT 9952-251

TABLE I-continued
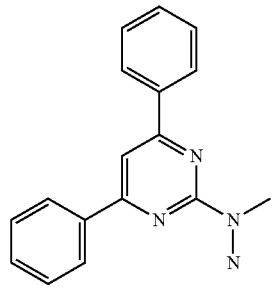 [SMILES: CN(N)c1nc(-c2ccccc2)cc(-c2ccccc2)n1]
MIT 9952-252
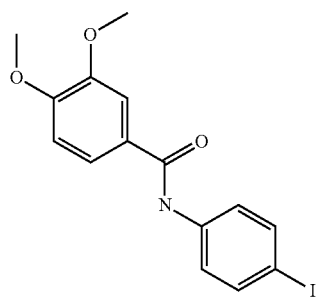 [SMILES: COc1ccc(C(=O)Nc2ccc(I)cc2)cc1OC]
MIT 9952-253
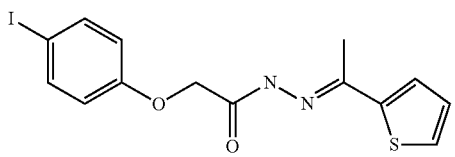 [SMILES: C/C(=N\NC(=O)COc1ccc(I)cc1)c1cccs1]
MIT 9952-254
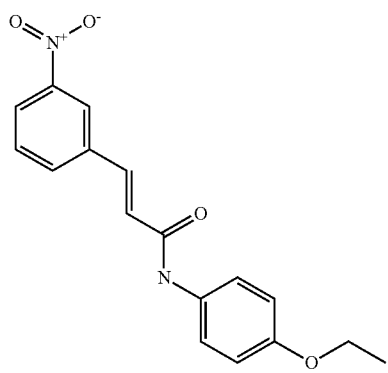 [SMILES: CCOc1ccc(NC(=O)/C=C/c2cccc([N+](=O)[O-])c2)cc1]
MIT 9952-255
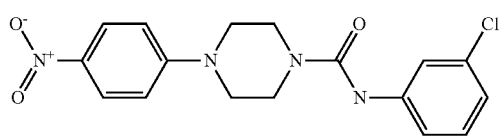 [SMILES: O=C(Nc1cccc(Cl)c1)N1CCN(c2ccc([N+](=O)[O-])cc2)CC1]
MIT 9952-256

TABLE I-continued
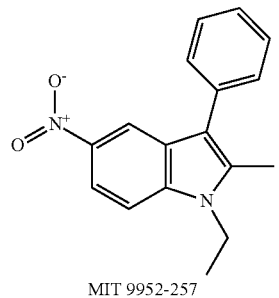
MIT 9952-257
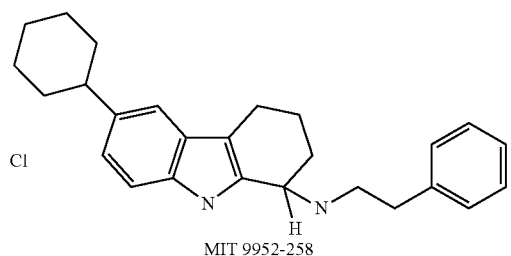
MIT 9952-258
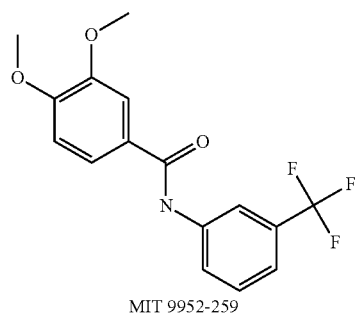
MIT 9952-259
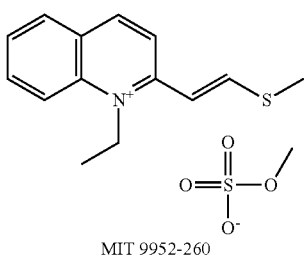
MIT 9952-260
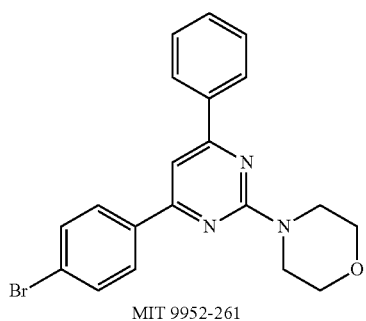
MIT 9952-261
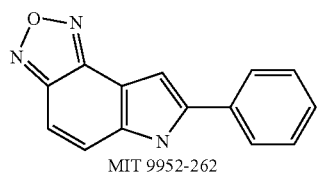
MIT 9952-262

TABLE I-continued
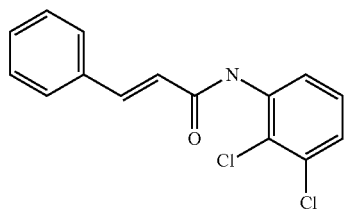 [SMILES: O=C(/C=C/c1ccccc1)Nc1cccc(Cl)c1Cl]
MIT 9952-263
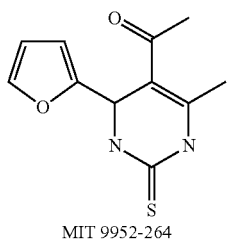
MIT 9952-264
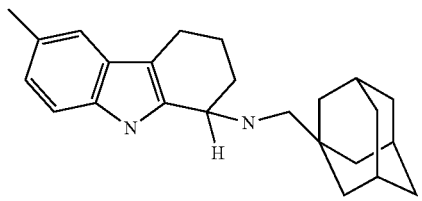 [SMILES: Cc1ccc2[nH]c3c(c2c1)CCCC3NCC12CC3CC(CC(C3)C1)C2]
MIT 9952-265
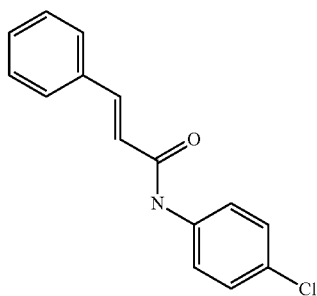 [SMILES: O=C(/C=C/c1ccccc1)Nc1ccc(Cl)cc1]
MIT 9952-266
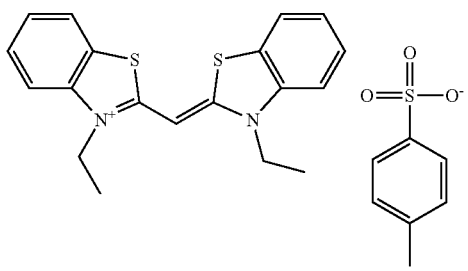 [SMILES: CCN1/C(=C/c2sc3ccccc3[n+]2CC)Sc2ccccc21 ; Cc1ccc(S(=O)(=O)[O-])cc1]
MIT 9952-267
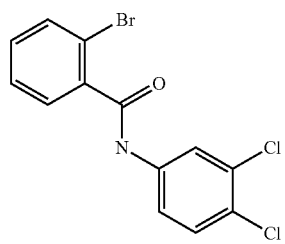 [SMILES: O=C(Nc1ccc(Cl)c(Cl)c1)c1ccccc1Br]
MIT 9952-268

TABLE I-continued
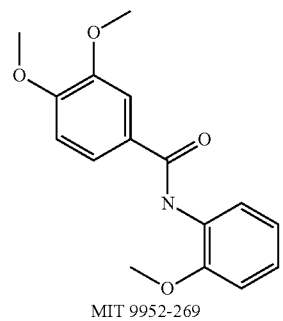
MIT 9952-269
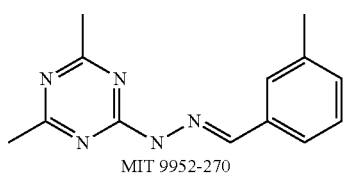
MIT 9952-270
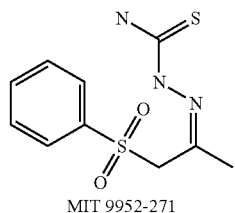
MIT 9952-271
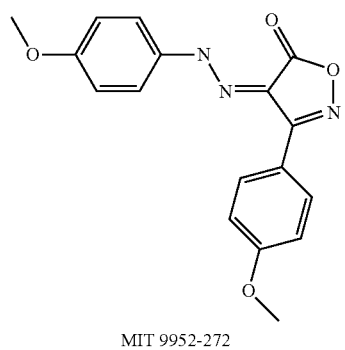
MIT 9952-272
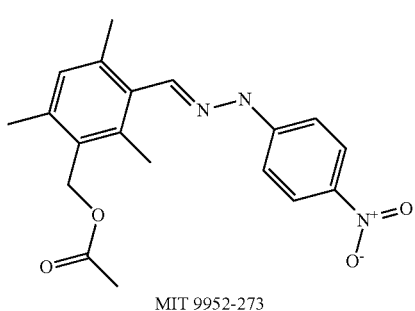
MIT 9952-273
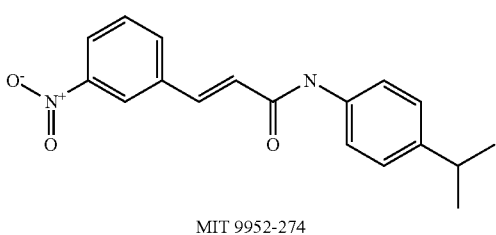
MIT 9952-274

TABLE I-continued
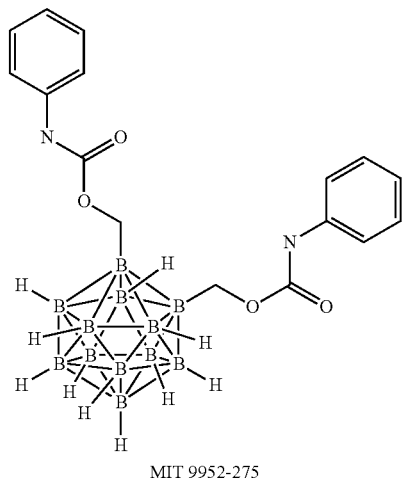
MIT 9952-275
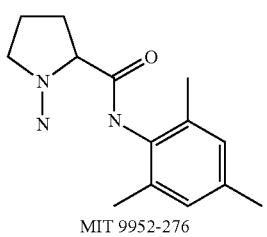
MIT 9952-276
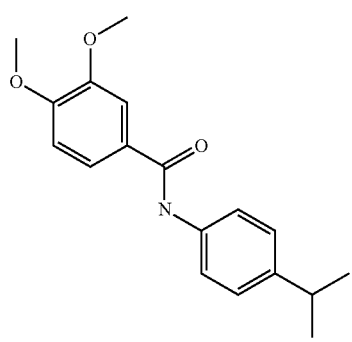 [SMILES: COc1ccc(C(=O)Nc2ccc(C(C)C)cc2)cc1OC]
MIT 9952-277
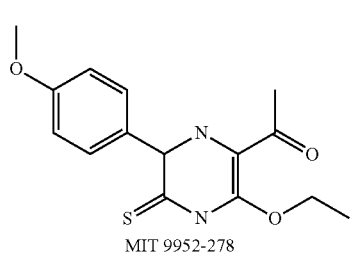
MIT 9952-278
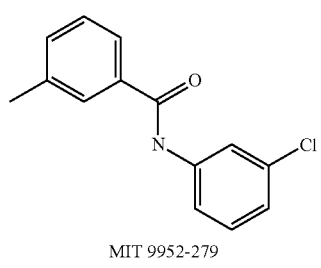
MIT 9952-279

TABLE I-continued
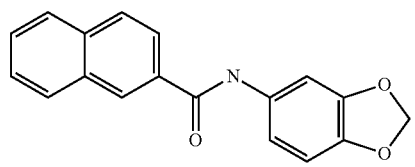 [SMILES: O=C(Nc1ccc2c(c1)OCO2)c1ccc2ccccc2c1]
MIT 9952-280
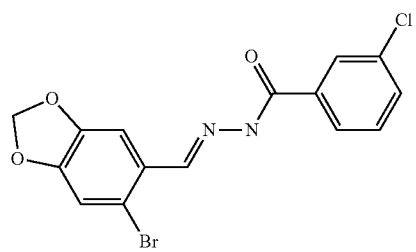 [SMILES: O=C(N/N=C/c1cc2c(cc1Br)OCO2)c1cccc(Cl)c1]
MIT 9952-281
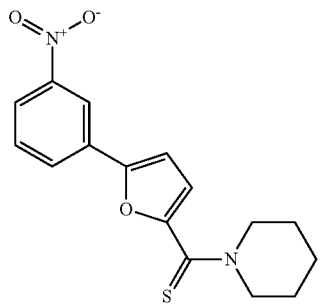 [SMILES: O=[N+]([O-])c1cccc(-c2ccc(C(=S)N3CCCCC3)o2)c1]
MIT 9952-282
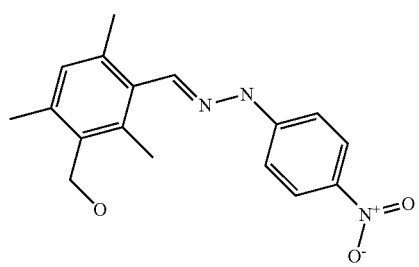 [SMILES: Cc1cc(C)c(CO)c(C)c1/C=N/Nc1ccc([N+](=O)[O-])cc1]
MIT 9952-283
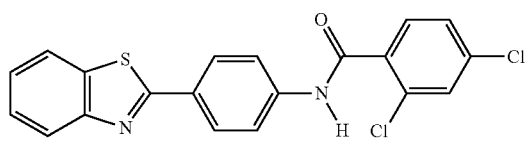 [SMILES: O=C(Nc1ccc(-c2nc3ccccc3s2)cc1)c1ccc(Cl)cc1Cl]
MIT 9952-284
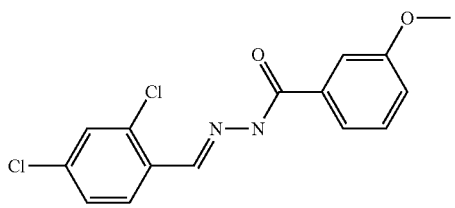 [SMILES: COc1cccc(C(=O)N/N=C/c2ccc(Cl)cc2Cl)c1]
MIT 9952-285

TABLE I-continued
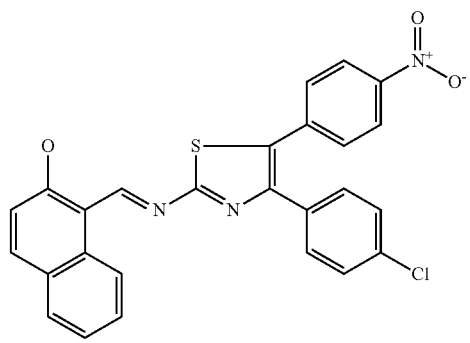 [SMILES: O=[N+]([O-])c1ccc(-c2sc(/N=C/c3c(O)ccc4ccccc34)nc2-c2ccc(Cl)cc2)cc1]
MIT 9952-286
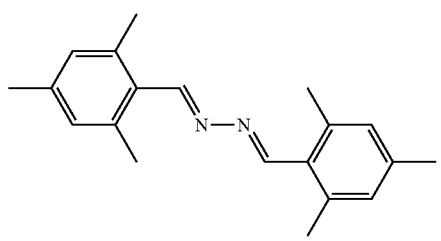
MIT 9952-287
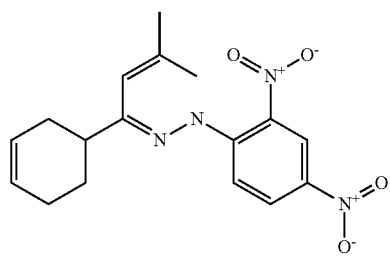 [SMILES: CC(C)=C/C(=N\Nc1ccc([N+](=O)[O-])cc1[N+](=O)[O-])C1CC=CCC1]
MIT 9952-288
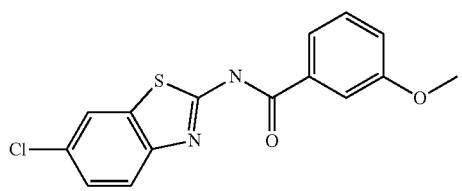 [SMILES: COc1cccc(C(=O)Nc2nc3ccc(Cl)cc3s2)c1]
MIT 9952-289
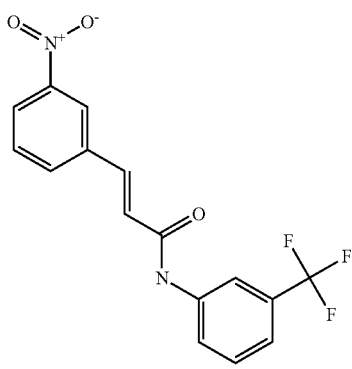 [SMILES: O=C(/C=C/c1cccc([N+](=O)[O-])c1)Nc1cccc(C(F)(F)F)c1]
MIT 9952-290

TABLE I-continued
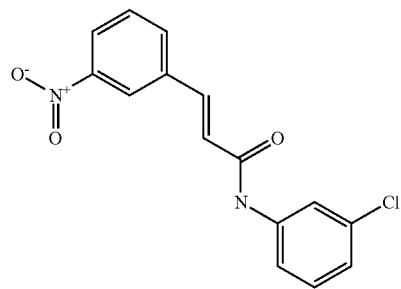 [SMILES: O=C(/C=C/c1cccc([N+](=O)[O-])c1)Nc1cccc(Cl)c1]
MIT 9952-291
MIT 9952-292
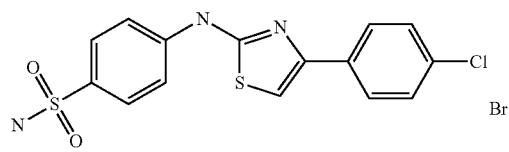 [SMILES: NS(=O)(=O)c1ccc(Nc2nc(-c3ccc(Cl)cc3)cs2)cc1 ; Br]
MIT 9952-293
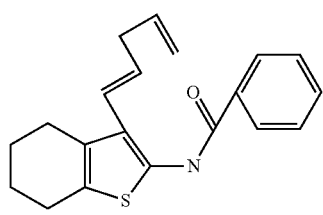 [SMILES: C=CC/C=C/c1c(NC(=O)c2ccccc2)sc2c1CCCC2]
MIT 9952-294
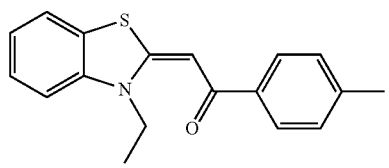 [SMILES: CCN1/C(=C\C(=O)c2ccc(C)cc2)Sc2ccccc21]
MIT 9952-295
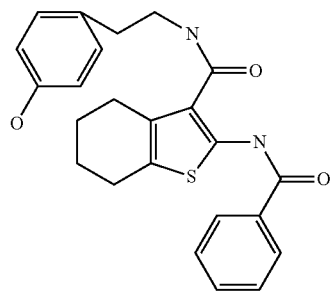 [SMILES: O=C(Nc1sc2c(c1C(=O)NCCc1ccc(O)cc1)CCCC2)c1ccccc1]
MIT 9952-296

TABLE I-continued

MIT 9952-297

MIT 9952-298

MIT 9952-299

MIT 9952-300

MIT 9952-301

TABLE I-continued
MIT 9952-302
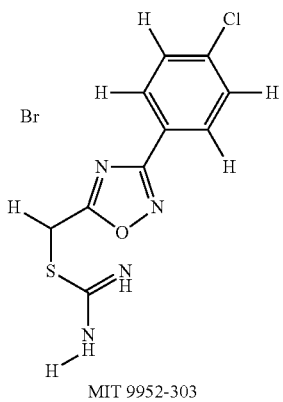
MIT 9952-303
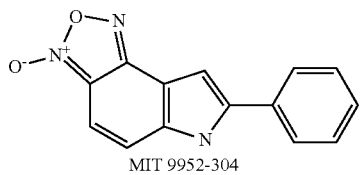
MIT 9952-304
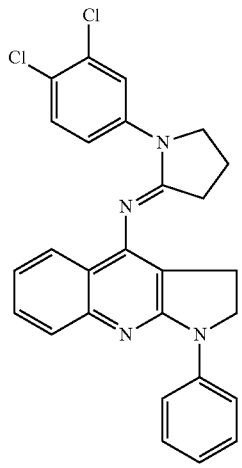 [SMILES: Clc1ccc(N2CCC/C2=N\c2c3c(nc4ccccc24)N(c2ccccc2)CC3)cc1Cl]
MIT 9952-305
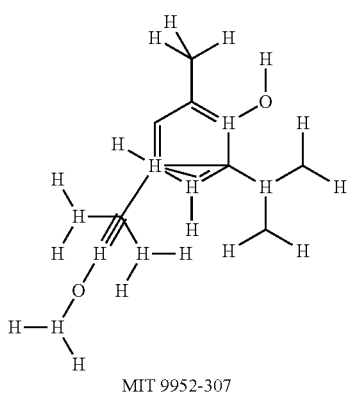
MIT 9952-307

TABLE I-continued
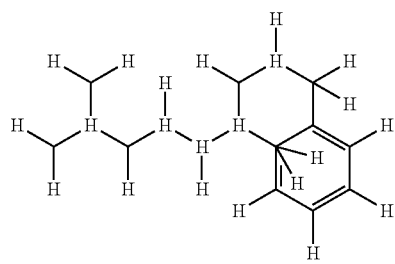
MIT 9952-308
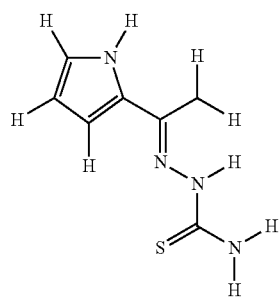 [SMILES: C/C(=N\NC(N)=S)c1ccc[nH]1]
MIT 9952-309
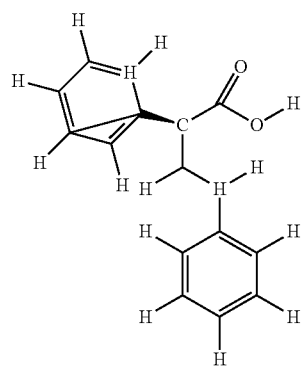
MIT 9952-310
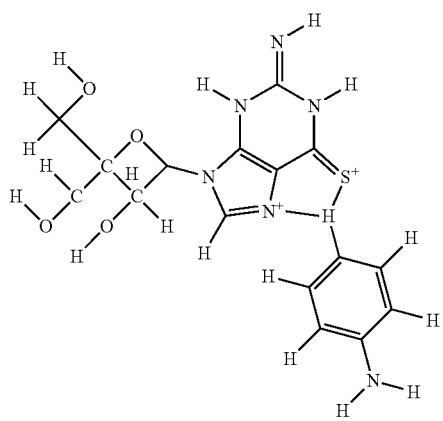
MIT 9952-311

TABLE I-continued
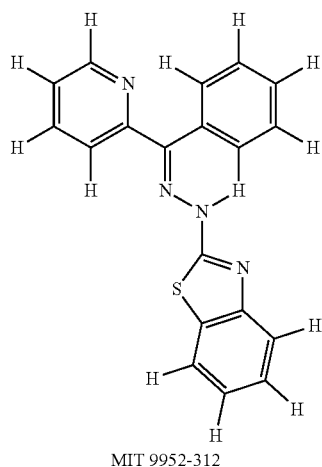
MIT 9952-312
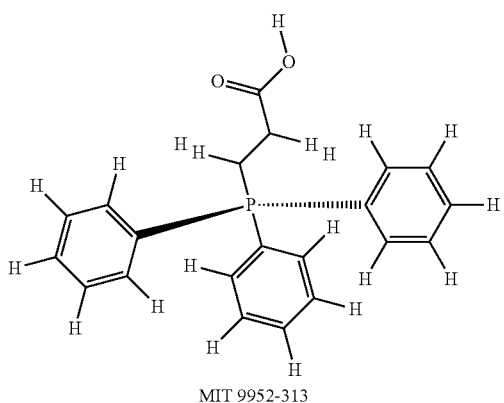
MIT 9952-313
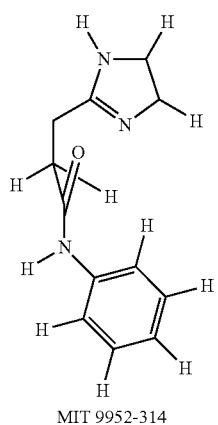
MIT 9952-314
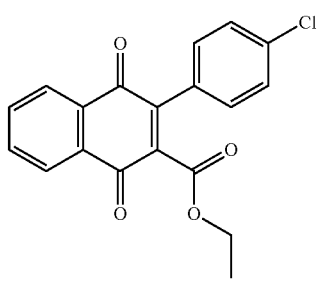 [SMILES: CCOC(=O)C1=C(c2ccc(Cl)cc2)C(=O)c2ccccc2C1=O]
MIT 9952-315

TABLE I-continued
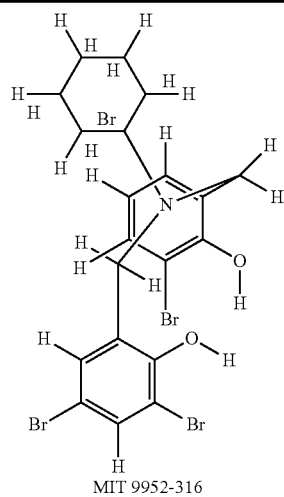
MIT 9952-316
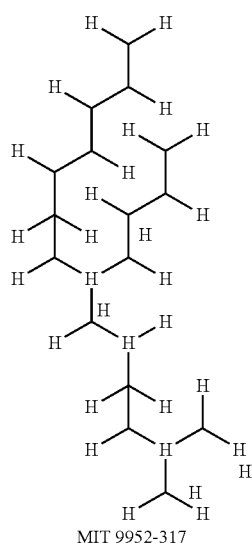
MIT 9952-317
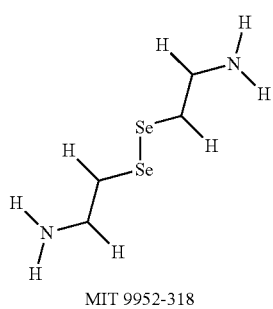
MIT 9952-318
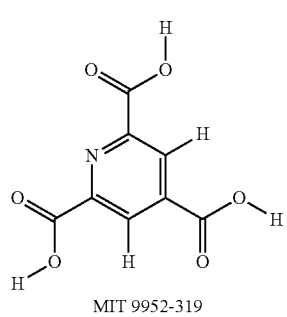
MIT 9952-319

TABLE I-continued
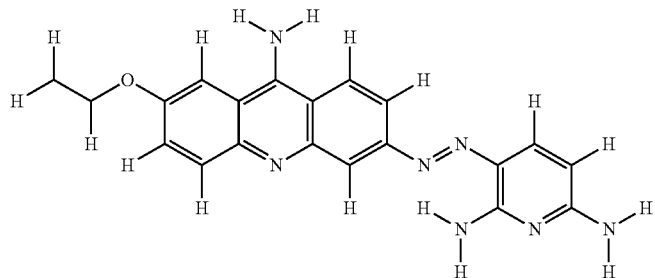 [SMILES: CCOc1ccc2nc3cc(/N=N/c4ccc(N)nc4N)ccc3c(N)c2c1]
MIT 9952-320
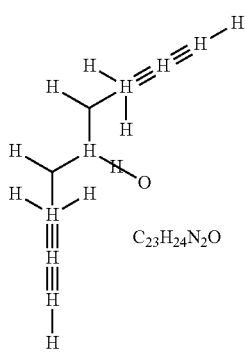
$C_{23}H_{24}N_2O$
MIT 9952-321
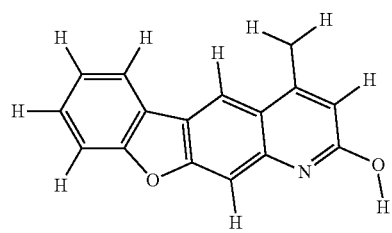 [SMILES: Cc1cc(O)nc2cc3oc4ccccc4c3cc12]
MIT 9952-322
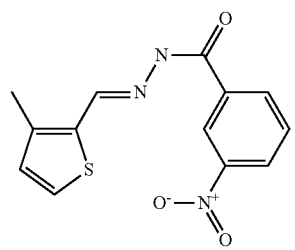 [SMILES: Cc1ccsc1/C=N/NC(=O)c1cccc([N+](=O)[O-])c1]
MIT 9952-323

TABLE I-continued
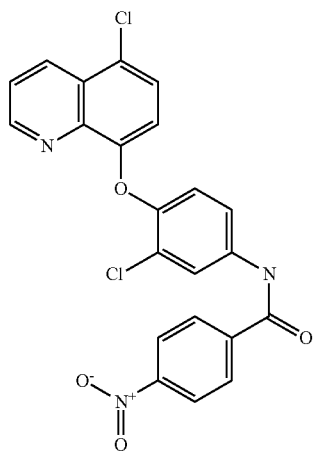 [SMILES: O=C(Nc1ccc(Oc2ccc(Cl)c3cccnc23)c(Cl)c1)c1ccc([N+](=O)[O-])cc1]
MIT 9952-324
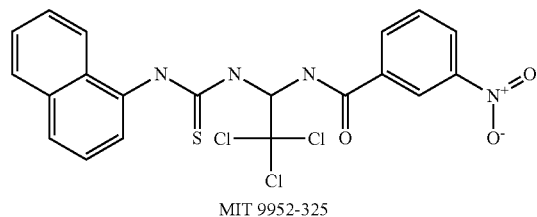
MIT 9952-325
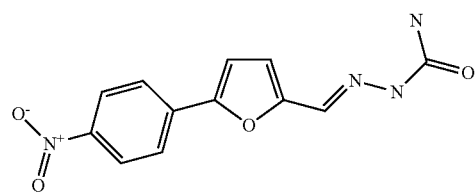 [SMILES: NC(=O)N/N=C/c1ccc(-c2ccc([N+](=O)[O-])cc2)o1]
MIT 9952-326
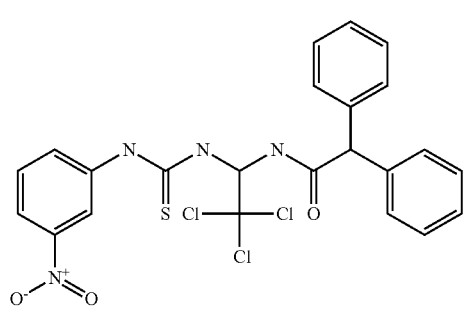 [SMILES: O=C(NC(NC(=S)Nc1cccc([N+](=O)[O-])c1)C(Cl)(Cl)Cl)C(c1ccccc1)c1ccccc1]
MIT 9952-327
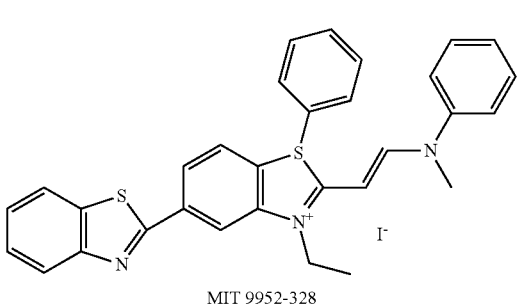
MIT 9952-328

TABLE I-continued
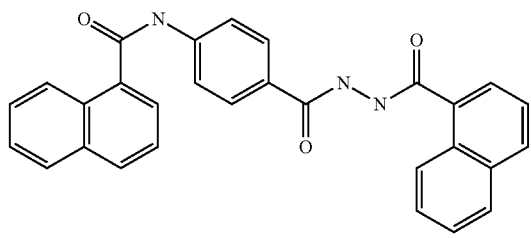 [SMILES: O=C(NNC(=O)c1cccc2ccccc12)c1ccc(NC(=O)c2cccc3ccccc23)cc1]
MIT 9952-329
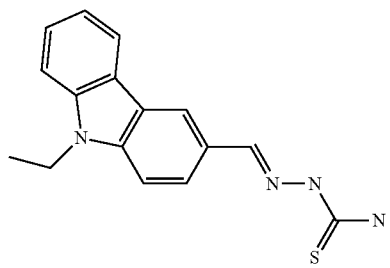 [SMILES: CCn1c2ccccc2c2cc(/C=N/NC(N)=S)ccc21]
MIT 9952-330
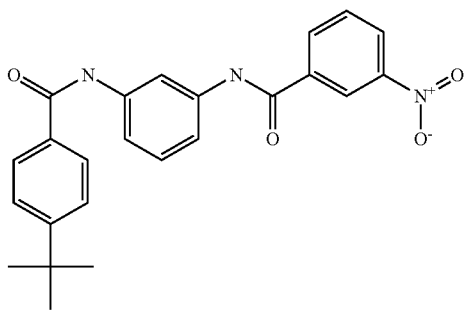 [SMILES: CC(C)(C)c1ccc(C(=O)Nc2cccc(NC(=O)c3cccc([N+](=O)[O-])c3)c2)cc1]
MIT 9952-331
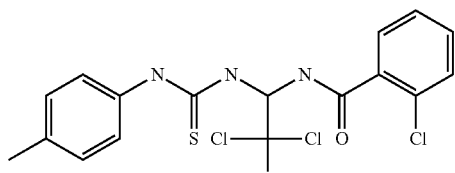
MIT 9952-332
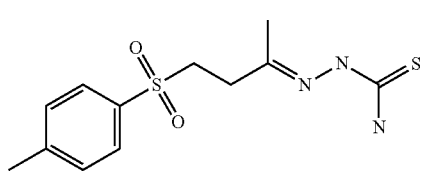 [SMILES: C/C(CCS(=O)(=O)c1ccc(C)cc1)=N\NC(N)=S]
MIT 9952-333
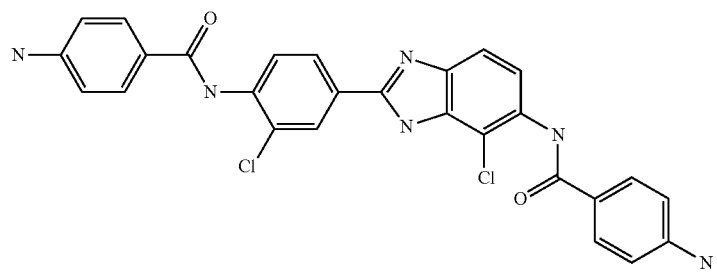 [SMILES: Nc1ccc(C(=O)Nc2ccc(-c3nc4ccc(NC(=O)c5ccc(N)cc5)c(Cl)c4[nH]3)cc2Cl)cc1]
MIT 9952-334

TABLE I-continued
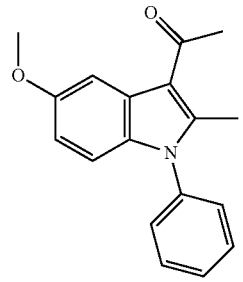 [SMILES: COc1ccc2c(c1)c(C(C)=O)c(C)n2-c1ccccc1]
MIT 9952-335
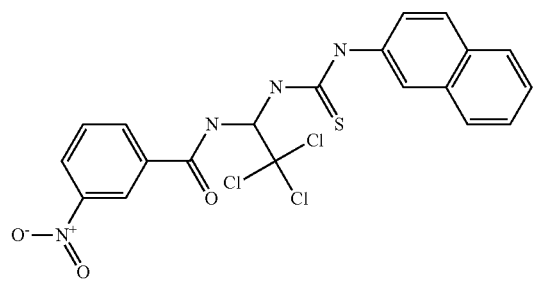 [SMILES: O=C(NC(NC(=S)Nc1ccc2ccccc2c1)C(Cl)(Cl)Cl)c1cccc([N+](=O)[O-])c1]
MIT 9952-336
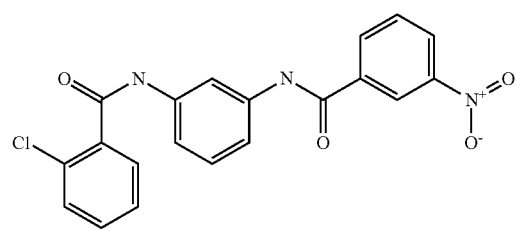 [SMILES: O=C(Nc1cccc(NC(=O)c2ccccc2Cl)c1)c1cccc([N+](=O)[O-])c1]
MIT 9952-337
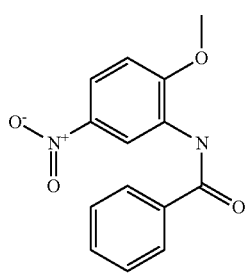 [SMILES: COc1ccc([N+](=O)[O-])cc1NC(=O)c1ccccc1]
MIT 9952-338
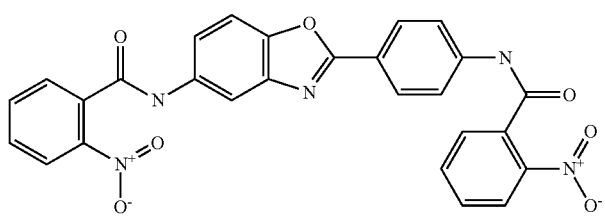 [SMILES: O=C(Nc1ccc(-c2nc3cc(NC(=O)c4ccccc4[N+](=O)[O-])ccc3o2)cc1)c1ccccc1[N+](=O)[O-]]
MIT 9952-339

TABLE I-continued

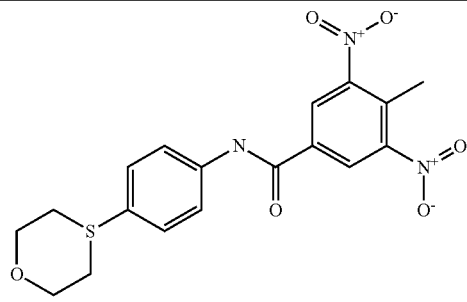

MIT 9952-340

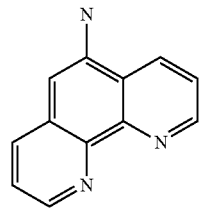 [SMILES: Nc1cc2cccnc2c2ncccc12]

MIT 9952-341 optionally substituted or pharmaceutically acceptable salts thereof. Preferred salts comprise $Na^+$, $K^+$, $Mg^{2+}$, and $Ca^{2+}$.

Since the present inventors have surprisingly found that scavenger receptor class proteins, in particular ScarB1, have a role in the life cycle of pathogens, which proliferate, develop and/or hide in liver or haematopoietic cells another preferred use of the present invention relates to the use of one or more antibodies specifically binding to said scavenger receptor class protein for the treatment and/or prophylaxis of infections involving liver and/or haematopoietic cells. Preferably, the antibody binds to the extracellular part of the scavenger receptor class protein thereby interfering with the interaction of the pathogen with the receptor. The term "antibody" as used herein comprises monoclonal and polyclonal antibodies and binding fragments thereof, in particular Fc-fragments as well as so called "single-chain-antibodies" (Bird R. E. et al (1988) Science 242:423-6), chimeric, humanized, in particular CDR-grafted antibodies, and dia or tetrabodies (Holliger P. et al (1993) Proc. Natl. Acad. Sci. U.S.A. 90:6444-8). Also comprised are immunoglobulin like proteins that are selected through techniques including, for example, phage display to specifically bind to scavenger receptor class proteins.

A mechanism termed "RNA interference" (RNAi) was discovered through the observation that injection of double stranded RNA (dsRNA) into the nematode C. elegans led to specific silencing of genes highly homologous in sequence to the delivered dsRNA (Fire A. et al. (1998) Nature 391: 806-811). RNAi was subsequently also observed in insects, frogs (Oelgeschlager M. et al. (2000) Nature 405: 757-763), and other animals including mice (Svoboda P. et al. (2000) Development 127: 4147-4156; Wianny F. and Zernicka-Goetz M. (2000) Nat. Cell Biol 2: 70-75). It was then described that this effect could also be obtained with short RNA doublexes termed "small interfering RNA" (siRNA) (Elbashir S. M. et al. (2001) Nature 411: 428-9 and WO02/044321). As set out below siRNAs were also used to identify scavenger receptor class proteins as a potential target to interfere with the proliferation and/or development of pathogens, in particular malaria. Accordingly, in a further preferred use of the present invention the inhibitor of the scavenger receptor class protein is a small interfering RNA (siRNA) capable of inhibiting expression of a scavenger receptor class protein. It is preferred that each RNA strand of the siRNA has a length from 19 to 30, particularly from 19 to 23 nucleotides, wherein said RNA molecule is capable of mediating target-specific nucleic acid modifications, particularly RNA interference and/or DNA methylation. It is further preferred that at least one strand has a 3' overhang from 1 to 5 nucleotides, more preferably from 1 to 3 nucleotides and most preferably of 2 nucleotides. The other strand may be blunt-ended or may have up to 6 nucleotides 3' overhang. Preferably the siRNA is designed to inhibit expression of scavenger receptor class B 1 (ScarB1) and ScarBII. To that end various short, e.g. 19 to 25 nucleotides dsRNAs are designed on the basis of the sequence of either ScarB1 (SEQ ID NO: 1) or ScarBII (SEQ ID NO: 2) It is particularly preferred that the siRNA is a double stranded RNA each comprised of the RNAs according to SEQ ID NO: 3 and SEQ ID NO: 4; SEQ ID NO: 5 and SEQ ID NO: 6; and SEQ ID NO: 7 and SEQ ID NO: 8, respectively.

In a preferred use of the invention the scavenger receptor class protein is scavenger receptor class B 1 (ScarB1) or scavenger receptor class B 2 (ScarBII).

A large number of protozoal pathogens are known, which require during their life cycle in their host, e.g. a human, to attach to and/or enter scavenger receptor expressing cells, in particular hepatic and haematopoietic cells. These diseases are all amenable to the treatment and/or prophylaxis with inhibitors of scavenger receptor class proteins. Accordingly, in a preferred use of the invention the infectious disease is a protozoal infection. Preferably the pathogenic protozoa is selected from the group consisting of *Entomoeba histolytica, Trichomonas tenas, Trichomonas hominis, Trichomonas vaginalis, Trypanosoma gambiense, Trypanosoma rhodesiense, Trypanosoma cruzi, Leishmania donovani, Leishmania tropica, Leishmania braziliensis, Pneumocystis pneumonia, Toxoplasma gondii, Theileria lawrenci, Theileria parva, Plasmodium vivax, Plasmodium falciparum*, and *Plasmodium malaria*. In a particular preferred use of the invention the protozoa is a member of the family of plasmodiidae, preferably *Plasmodium falciparum, Plasmodium vivax, Plasmodium ovale, Plasmodium malariae, Plasmodium semiov-*

*ale* and *Plasmodium knowlesi*. In the most preferred use of the invention the infectious disease for which treatment and/or prophylaxis is provided is malaria.

As set out above a large number of inhibitors of scavenger receptor class proteins, in particular ScarB1 is known from the prior art. In order to identify further compounds suitable for the use of the present invention the present invention relates in another aspect to a method of identifying compounds for treatment and/or prophylaxis of infectious diseases involving liver or hematopoietic cells comprising the steps of:
(i) contacting a cell comprising a scavenger receptor class protein, in particular ScarB1 or ScarBII, or a functional variant thereof, with a test compound,
(ii) measuring cholesterol transport into or out of said cell,
(iii) selecting a test compound, which inhibits cholesterol transport into or out of said cells,
(iv) contacting liver or hematopoietic cell with the selected test compound prior, during or after infection of said cell with an infectious agent, and
(v) selecting a test compound inhibiting proliferation and/or development of the infectious agent by at least 10%.

In the context of the present invention the term "contacting" refers to the process of allowing the compound to bind to, preferably to bind to and enter the cell and comprises mixing as well as transfecting, transducing and/or electroporating. A cell "comprising" a scavenger receptor class protein, preferably ScarB1 or ScarBII, may have been stably or transiently transfected with a nucleic acid encoding a scavenger receptor class protein or functional variant thereof, by e.g. viral infection, electroporation, $CaCl_2$ precipitation or the protein may have been directly introduced into the cell by, e.g. electroporation, or liposomal delivery etc. A "functional variant" of a scavenger receptor class protein is a protein, which has been modified by N-terminal, C-terminal and/or internal deletions and/or amino acid additions and or mutations, preferably conservative mutations and which has at least 10%, preferably at least 20%, 30%, 40%, 50%, 60%, 70% or more of the cholesterol transport activity into or out of the cell, if compared to the respective wild type scavenger receptor class protein on which the variant is based. The measuring of the cholesterol transport is preferably carried out by providing some type of labelled cholesterol to the cell, e.g. free cholesterol, LDL or HDL, which might be labelled by any art known label, in particular radioactive, or fluorescent label. The selected test compound preferably inhibits the cholesterol transport into or out of the cells by at least 10%, preferably by at least 20%, preferably by at least 30%, preferably by at least 40%, preferably by at least 50%, preferably by at least 60%, preferably by at least 70%, preferably by at least 80%, preferably by at least 90% or more, if compared to an untreated cell, which is kept under otherwise similar conditions. Methods of propagating/maintaining infectious agents in cell culture systems, in particular in liver and/or haematopoietic cells are known from the prior art and are also described herein. The test compounds are contacted with such cellular systems, which can be in vitro or in vivo, e.g. in animal models of the infectious agent.

Test compounds that can be used in the context of the methods of the present invention are not particularly limited and comprise without limitation peptides, proteins, peptidomimetics, small molecules, and/or nucleic acids. Peptides in this sense are chains of naturally and/or non-naturally occurring amino acids with 1 to 50 amino acids connected by peptide bonds. Chains with 50 or more naturally and/or non-naturally occurring amino acids are referred to as proteins. Preferred peptides used in the methods of the present invention are peptides interfering with the interaction of the scavenger receptor class protein(s), in particular ScarB1 and/or ScarBII, with the structure on the respective pathogen, e.g. pasmodiidae, preferably *Plasmodium falciparum, Plasmodium vivax, Plasmodium ovale, Plasmodium malariae, Plasmodium semiovale* and *Plasmodium knowlesi*, required for binding to the scavenger receptor class protein(s). Accordingly, in a preferred embodiment peptides are fragments of scavenger receptor type proteins, in particular of ScarB1 and/or ScarBII. Particularly preferred fragments are fragments of the extracellular domain of these receptors. Peptidomimetics are well known in the art and refer to compounds, which are designed based on the primary structure of a given peptide to be modelled, e.g. like one of the peptides mentioned above, and which take on a similar secondary structure. Thus, peptidomimetics can be designed to be, e.g. more protease resistant, have a different half life, improved pharmacokinetics or pharmacodynamics etc. Small molecules within the meaning of the present invention are non peptidly (no peptide bonds), non nucleic acid compounds, of a molecular weight lower than 1.000 g/mol, preferably lower than 500 g/mol. In most cases the small molecules used in the methods of the present invention are hydrocarbons or mixtures thereof, e.g. plant extracts. The term "nucleic acids" comprises without limitation, DNA and RNA, e.g. siRNA etc.

The selecting of a test compound inhibiting proliferation or development of the infectious agent is based on its activity in inhibiting proliferation and/or development of the infectious agent. It is expected that any compound showing an activity in step (iii) will also be active in inhibiting the infectious agent. However, in some instances a compound with a high activity in step (iii) will be less active than in step (v) as another drug having the same activity in step (iii) and vice versa. Accordingly, the further step of assessing the activity of the preselected compounds in a further selection step leads to compounds more active in therapy and/or prophylaxis of infectious diseases, in particular malaria. The infectious agents are those, which are outlined above in particular plasmodiidae, preferably *Plasmodium falciparum, Plasmodium vivax, Plasmodium ovale, Plasmodium malariae, Plasmodium semiovale* and *Plasmodium knowlesi*.

In order to identify further compounds suitable for the use of the present invention the present invention also relates in another aspect to a method of identifying compounds for treatment and/or prophylaxis of infectious diseases involving liver or hematopoietic cells comprising the steps of:
(i) contacting one or more scavenger receptor class protein, in particular ScarB1 and/or ScarBII protein, functional variants, or soluble parts thereof with a test compound,
(ii) selecting a test compound, which specifically binds to the scavenger receptor class protein(s), in particular ScarB1 or ScarBII,
(iii) contacting liver or hematopoietic cell with the selected test compound prior, during or after infection of said cell with an infectious agent, and
(iv) selecting a test compound inhibiting proliferation and/or development of the infectious agent by at least 10%.

The term "functional variant" in the context of this method has the same meaning as outlined above. Soluble parts are fragments, which preferably do not comprise the hydrophobic membrane spanning regions of the protein. A test compound is considered to specifically bind to a scavenger receptor class protein, in particular ScarB1 or ScarBII, if it has a binding constant to the respective scavenger receptor class protein of 100 μM or less, preferably 50 μM or less, preferably 30 μM or less, and preferably 20 μM or less.

It is preferred that the scavenger receptor class proteins, in particular ScarB1 or ScarBII protein, used in above assay is recombinantly expressed. Various suitable expression systems are known, which include without limitation baculovirus systems using cells like Hi5 or Sf9, bacterial expression systems using E. coli, yeas systems using cells like P. pastori or S. cerevisiae or mammalian systems using cell like CHO, HeLa, NIH 3T3, or Swiss 3T3. It is further preferred that the proteins, the variants or parts thereof are purified prior to their use in above assay.

In a further preferred method the present invention comprises the additional step of formulating the test compound selected in step (v) and (iv), respectively, of either method with pharmaceutically acceptable additives and/or auxiliary substances. Auxiliary substances comprise liposomes, virosomes, microsphere, niosomes, dendrimeres, stabilizers, buffers, and carriers. Stabilizers are known in the art and comprise, for example, α-tocopherol and various carbohydrates.

In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as saline solutions in water and oils, including those of petroleum, animal, vegetable or synthetic origin, such as peanut oil, soybean oil, mineral oil, sesame oil and the like. A saline solution is a preferred carrier when the composition comprising the scavenger receptor class inhibitor is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, alginates, calcium carbonate, dextrose, fructose, maltose, maltodextrin, sodium stearate, glycerol monostearate, talc, sodium chloride, dried skim milk, glycerol, propylene, glycol, water, ethanol and the like. The composition comprising the scavenger receptor class inhibitor, if desired, can also contain minor amounts of wetting or emulsifying agents, or pH buffering agents. These compositions can take the form of solutions, suspensions, emulsion, tablets, pills, capsules, powders, sustained-release formulations and the like. The composition comprising the scavenger receptor class inhibitor can be formulated as a suppository, with traditional binders and carriers such as triglycerides. The compounds usable according to the invention can be formulated as neutral or salt forms. Pharmaceutically acceptable salts include in particular those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc. Examples of suitable pharmaceutical carriers are described in "Remington's Pharmaceutical Sciences" by E. W. Martin. Such compositions will contain a therapeutically effective amount of the compound, preferably in purified form, together with a suitable amount of carrier so as to provide the form for proper administration to the patient. The formulation should suit the mode of administration.

Pharmaceutical compositions comprising the scavenger receptor class inhibitor(s) may be adapted for oral administration and can be provided as capsules or tablets; as powders or granules; as solutions, syrups or suspensions (in aqueous or non-aqueous liquids); as edible foams or whips; or as emulsions. Tablets or hard gelatine capsules may comprise lactose, starch or derivatives thereof, magnesium stearate, sodium saccharine, cellulose, magnesium carbonate, stearic acid or salts thereof. Soft gelatine capsules may comprise vegetable oils, waxes, fats, semi-solid, or liquid polyols etc. Solutions and syrups may comprise water, polyols and sugars.

The scavenger receptor class inhibitor usable according to the present invention may be coated with or admixed with a material that delays disintegration and/or absorption of the active agent in the gastrointestinal tract (e.g., glyceryl monostearate or glyceryl distearate may be used). Thus, the sustained release of an active agent may be achieved over many hours and, if necessary, the active agent can be protected from being degraded within the stomach. Pharmaceutical compositions for oral administration may be formulated to facilitate release of an active agent at a particular gastrointestinal location due to specific pH or enzymatic conditions.

The scavenger receptor class inhibitor may be adapted for transdermal administration and can be provided as discrete patches intended to remain in intimate contact with the epidermis of the recipient for a prolonged period of time. They may be adapted for topical administration and can be provided as ointments, creams, suspensions, lotions, powders, solutions, pastes, gels, sprays, aerosols or oils. For topical administration to the skin, mouth, eye or other external tissues a topical ointment or cream is preferably used. When formulated in an ointment, the active ingredient may be employed with either a paraffinic or a water-miscible ointment base. Alternatively, the active ingredient may be formulated in a cream with an oil-in-water base or a water-in-oil base. Pharmaceutical compositions adapted for topical administration to the eye include eye drops. In these compositions, the active ingredient can be dissolved or suspended in a suitable carrier, e.g., in an aqueous solvent. Pharmaceutical compositions adapted for topical administration in the mouth include lozenges, pastilles and mouthwashes.

The scavenger receptor class inhibitor may be adapted for nasal administration and can comprise solid carriers such as powders (preferably having a particle size in the range of 20 to 500 microns). Powders can be administered in the manner in which snuff is taken, i.e., by rapid inhalation through the nose from a container of powder held close to the nose. Alternatively, compositions adopted for nasal administration may comprise liquid carriers, e.g., nasal sprays or nasal drops. These compositions may comprise aqueous or oil solutions of the active ingredient. Compositions for administration by inhalation may be supplied in specially adapted devices including, but not limited to, pressurized aerosols, nebulizers or insufflators, which can be constructed so as to provide predetermined dosages of the active ingredient. In a preferred embodiment, pharmaceutical compositions of the invention are administered via the nasal cavity to the lungs.

The scavenger receptor class inhibitor may be adapted for rectal administration may be provided as suppositories or enemas. Pharmaceutical compositions adapted for vaginal administration may be provided as pessaries, tampons, creams, gels, pastes, foams or spray formulations.

The scavenger receptor class inhibitor may be adapted for parenteral administration and can include aqueous and non-aqueous sterile injectable solutions or suspensions, which may contain antioxidants, buffers, bacteriostats and solutes that render the compositions substantially isotonic with the blood of an intended recipient. Other components that may be present in such compositions include water, alcohols, polyols, glycerine and vegetable oils, for example. Compositions adapted for parenteral administration may be presented in unit-dose or multi-dose containers, for example sealed ampules and vials, and may be stored in a freeze-dried (lyophilized) condition requiring only the addition of a sterile liquid carrier, e.g., sterile saline solution for injections, immediately prior to use.

In a further aspect the present invention relates to the use of a test compound selected in step (v) of the method of the present invention for the production of a medicament for the therapy and/or prophylaxis of infectious diseases, which involve infection of liver and/or hematopoietic cells.

The increasing speed of the development of resistance of protozoal pathogens, in particular malaria to the various medicaments used to treat these disease makes it necessary to efficiently eradicate the pathogen without giving it a chance to develop a resistance. To that end it is desirable to interfere with distinct pathways required for the lifecycle of a given pathogen. Since the present inventors have for the first time shown that inhibitors of ScarB1 can interfere with development/proliferation of malaria the compounds present a hitherto unknown route of attack on pathogens, in particular pathogens causing malaria, which can beneficially combined with the known treatments of malaria. Accordingly the present invention in a further aspect relates to pharmaceutical compositions comprising one or more of compound usable according to the present invention and one or more of a known malaria therapeutic including in particular one or more selected from the group consisting of chinine alkaloids, chloroquine (-phosphate, hydroxychloroquinesulfate), mefloquine (Lariam), bi-guanides: proguanil (Paludrine), di-aminopyrinriidines: pyrimethamine, atovaquone, doxycycline, artemether, and lumefantrine and suitable carriers. Accordingly, the present invention also relates to the use of the compounds usable according to the present invention and one or more malaria medicament, preferably chinine alkaloids, chloroquine (-phosphate, hydroxychloroquinesulfate), mefloquine (Lariam), bi-guanides: proguanil (Paludrine), di-aminopyrimidines: pyrimethamine, atovaquone, doxycycline, artemether, and lumefantrine for the manufacture of a medicament for the treatment of diseases involving liver and/or hematopoeitc cells, preferably malaria. Preferably, the two medicaments are administered simultaneously, e.g. combined in one administration form or simultaneously or subsequently in separate administration forms.

The surprising discovery underlying the present invention that scavenger receptor class proteins, in particular ScarB1 and ScarBII, are involved in mediating entry of pathogens into liver and hematopoietic cells also provides the possibility to identify those structures on the pathogens, which interact with the scavenger receptor class proteins and which are, thus, also potential targets in order to interfere with the live cycle of those pathogens. Therefore, the present invention in a further aspect relates to a method of identifying molecules, which are present in, in particular on the surface, of pathogens capable of infecting liver and hematopoietic cells and which interact with one or more scavenger receptor class protein, in particular ScarB1 and/or ScarBII. The method preferably comprises the following steps:

(i) contacting one or more scavenger receptor class proteins, in particular ScarB1 and/or ScarBII protein, functional variants, or soluble parts thereof with one or more molecules present in, in particular on the surface of pathogens, which are involved in the infection of liver and/or hematopoietic cells, (ii) selecting a molecule, which specifically binds to the scavenger receptor class protein, in particular ScarB1 or ScarBII.

The terms "functional variants" and "soluble parts thereof" have the above outlined meaning. Preferred molecules of pathogens, which can be tested for their binding to scavenger receptor class proteins comprise proteins, lipids and carbohydrates, preferably proteins. In many cases cell surface receptors of pathogens are involved in a specific interaction with a corresponding receptor on a host cell. Accordingly, it is particularly preferred that the molecules tested for binding to scavenger receptor class proteins are cell surface receptors of the particular pathogen. All pathogens outlined above can be the source for molecules tested in this method of the invention, preferably, however, the pathogens are selected from the group consisting *Entomoeba histolytica*, *Trichomonas tenas*, *Trichomonas hominis*, *Trichomonas vaginalis*, *Trypanosoma gambiense*, *Trypanosoma rhodesiense*, *Trypanosoma cruzi*, *Leishmania donovani*, *Leishmania tropica*, *Leishmania braziliensis*, *Pneumocystis pneumonia*, *Toxoplasma gondii*, *Theileria lawrenci*, *Theileria parva*, *Plasmodium vivax*, *Plasmodium falciparum*, *Plasmodium ovale*, *Plasmodium malariae*, *Plasmodium semiovale* and *Plasmodium knowlesi*, in particular *Plasmodium vivax* and *Plasmodium falciparum*.

The contacting between the scavenger receptor class protein and the molecule(s) derived from the pathogen can be carried out in vivo or in vitro. For example, (i) both the scavenger receptor class protein(s), functional variants, or soluble parts thereof and the potentially interacting molecule(s) can be present together in a cell, (ii) either the scavenger receptor class protein(s), functional variants, or soluble parts thereof or the potentially interacting molecule(s) can be expressed in a cell, e.g. on the surface of a cell, which is then contacted with the respective other entity in, e.g. solution or (iii) both scavenger receptor class protein(s), functional variants, or soluble parts thereof and the potentially interacting molecule(s) are contacted in vitro.

A molecule comprised in a pathogen is considered to specifically bind to a scavenger receptor class protein, in particular ScarB1 or ScarBII, if it has a binding constant to the respective scavenger receptor class protein of 100 µM or less, preferably 50 µM or less, preferably 30 µM or less, and preferably 20 µM or less.

It is preferred that the method comprises the further step of determining the molecule, which specifically binds to the scavenger receptor class protein(s). Various methods of determining the nature of an interaction molecule are known in the prior art, which in part depend on the respective method used to select the specifically binding molecule as discussed below. Preferably the determining of the molecule comprises MS, peptide or nucleic acid sequencing, ELISA etc.

Several methods are known in the prior art to determine molecules interacting with a given target molecule. These methods comprise without limitation co-immunoprecipitation, affinity purification, cross-linking, phage display and so called "two-hybrid" assays. In co-immunoprecipitation experiments usually the target, i.e. the scavenger receptor class protein can be immobilized on, e.g. beads or another matrix, and will be contacted with a cellular extract of the respective pathogen or recombinant proteins derived from an expression library. Alternatively, the target is contacted with the molecules derived from the pathogens in a homogenous system, i.e. in solution, and only after binding has occurred the target is bound "pulled down" by interaction with a molecule specifically binding the target, e.g. a scavenger receptor specific antibody, which has been attached to a bead or matrix. To assure specific binding the beads or matrix will be washed to remove unbound and/or unspecifically bound molecules, the specifically bound molecules are then eluted and analyzed by e.g. MS, peptide sequencing or Western blot. The affinity purification is similar to co-immunoprecipitation, however, the binding is carried out by applying the molecules of the pathogens to a column loaded with a matrix to which the scavenger receptor class protein has'been attached. Cross-linking typically involves the labelling of the target, which may or may not be further modified to include a cross-linking moiety, the contacting of the labelled target with the molecules of the pathogen, preferably with the intact pathogen and effecting crosslinking between the target and whatever molecule the target has bound to. The complex which is formed between the target and the molecule of the pathogen can then be purified away from the other molecules of the pathogen on the basis of the label and/or analyzed by art known methods, involving MS, peptide sequencing and the like. Phage display is a method wherein proteins or protein fragments are fused to phage coat proteins and, thus, displayed on the surface of the resulting phage. It is possible to express protein libraries derived from the pathogens of interest on phage and then select those phages displaying proteins of the pathogens, which are capable of specifically interacting with the respective scavenger receptor class protein(s). The identity of the interacting molecule can then be determined easily by sequencing of the phage DNA. A further well known method to identify proteins, which interact with a given target molecule is the so called "two-hybrid" assay (first described by Fields S. and Song O. (1989) Nature 340:245-6). This assay has been modified in the past to improve sensitivity and specificity and to adapt the assay to the specific requirements of the target protein (reviewed in, e.g. Piehler J. (2005) Curr. Opin. Struct. Biol. 15(1):4-14 and Fields S. 2005) FEBS J. 272(21):5391-9). For example, LaCount D J, et al. (Nature (2005) 438:103-7) describe a high-throughput version of the yeast two-hybrid assay that circumvents the difficulties in expressing *P. falciparum* proteins in *Saccharomyces cerevisiae*. This assay could be adapted to isolate scavenger receptor class protein, in particular ScarB1 and ScarBII, interacting proteins from the pathogens indicated above, in particular from *P. falciparum*.

Above indicated assays and variations thereof can be used to identify proteins of pathogens interacting with scavenger receptor class proteins present on liver and hematopoietic cells. The identification will then facilitate the isolation of compounds specifically interfering with the interaction between the molecules of the pathogens and the scavenger receptor class proteins.

DESCRIPTION OF THE TABLES AND FIGURES

FIG. 1: Inhibition of EEF (Exo-Erythrocytic Forms) development in Huh-7 human hepatoma cells by BLT-1. Light grey bars represent EEF number (values on the left side of the graph) and the dark grey line represents percentage of cell confluency (values on the right side of the graph).

Figure 2:
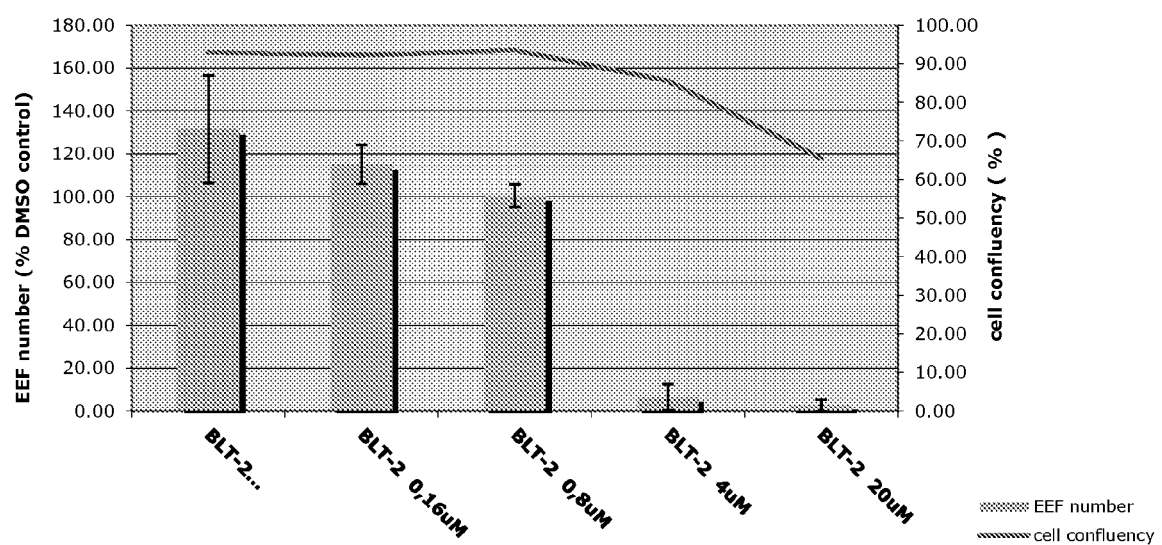

FIG. 2: Inhibition of EEF development in Huh-7 human hepatoma cells by BLT-2. Light grey bars represent EEF number (values on the left side of the graph) and the dark grey line represents percentage of cell confluency (values on the right side of the graph).

Figure 3:
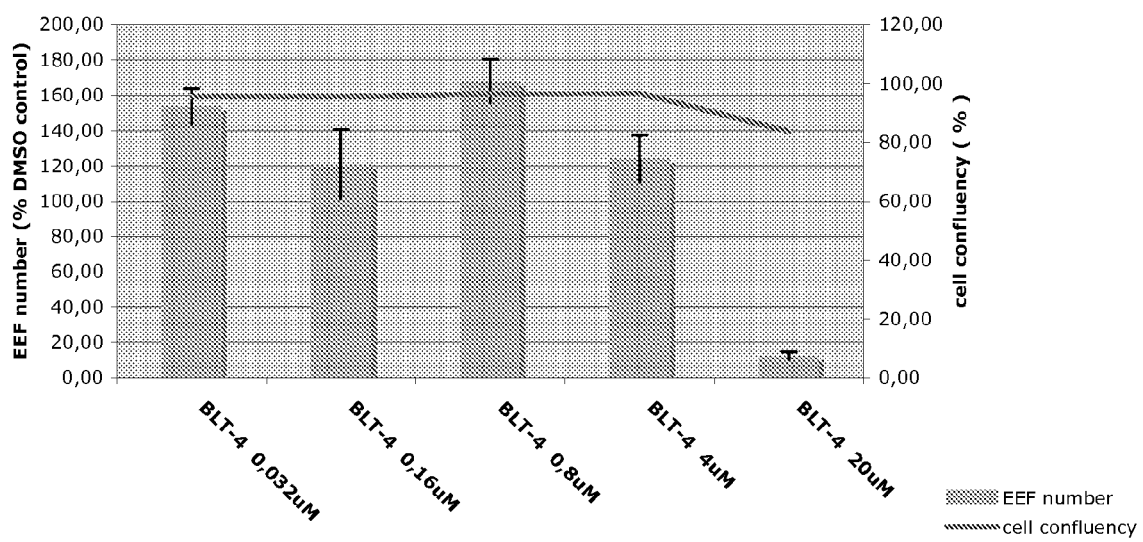

FIG. 3: Inhibition of EEF development in Huh-7 human hepatoma cells by BLT-4. Light grey bars represent EEF number (values on the left side of the graph) and the dark grey line represents percentage of cell confluency (values on the right side of the graph).

Figure 4:
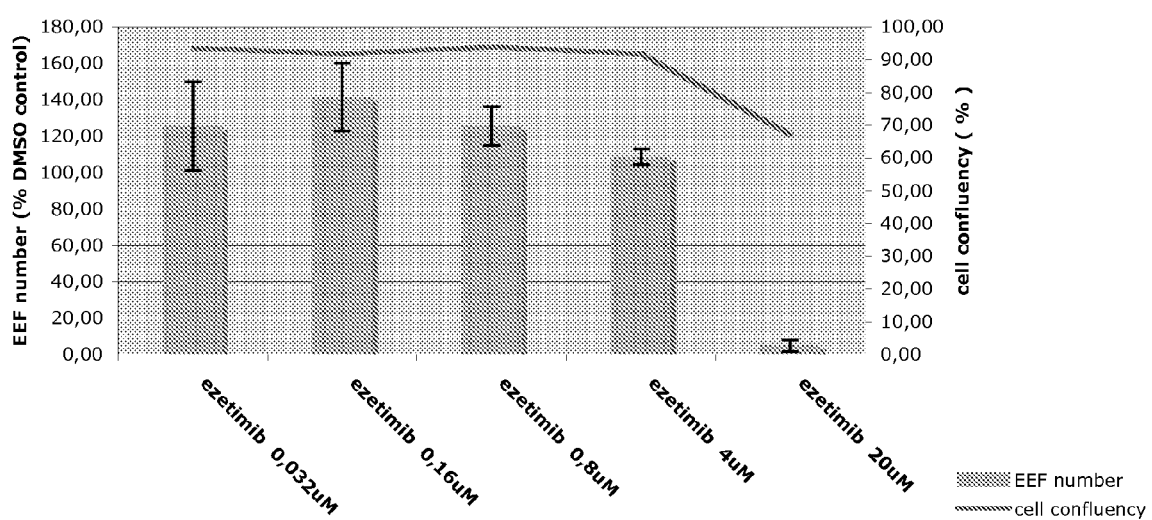

FIG. 4: Inhibition of EEF development in Huh-7 human hepatoma cells by Ezetimibe. Light grey bars represent EEF number (values on the left side of the graph) and the dark grey line represents percentage of cell confluency (values on the right side of the graph).

Figure 5:
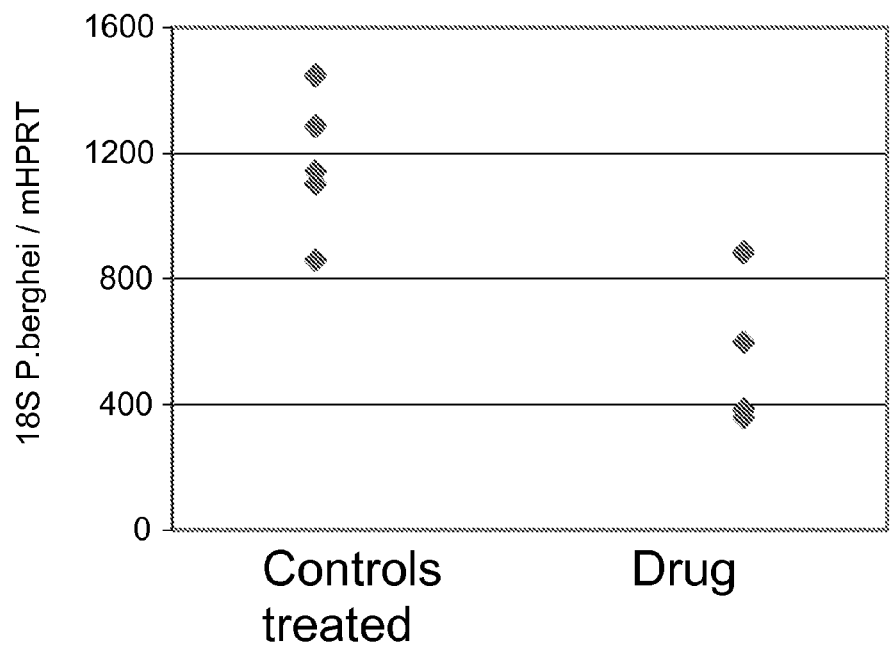

FIG. 5: Ezetimibe reduces infection rate for liver in mice.

FIG. 6: Structures of preferred compounds usable to treat infection by plasmodiidae.

Figure 7:
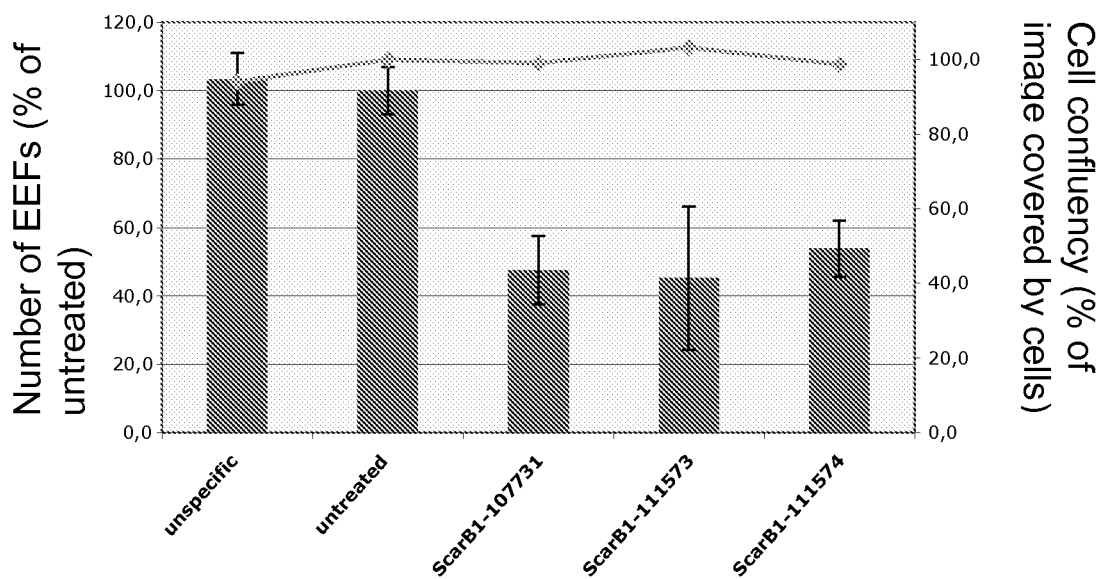

FIG. 7: Knock down of ScarB1 by RNAi reduces EEF development in human hepatoma cells.

Figure 8:
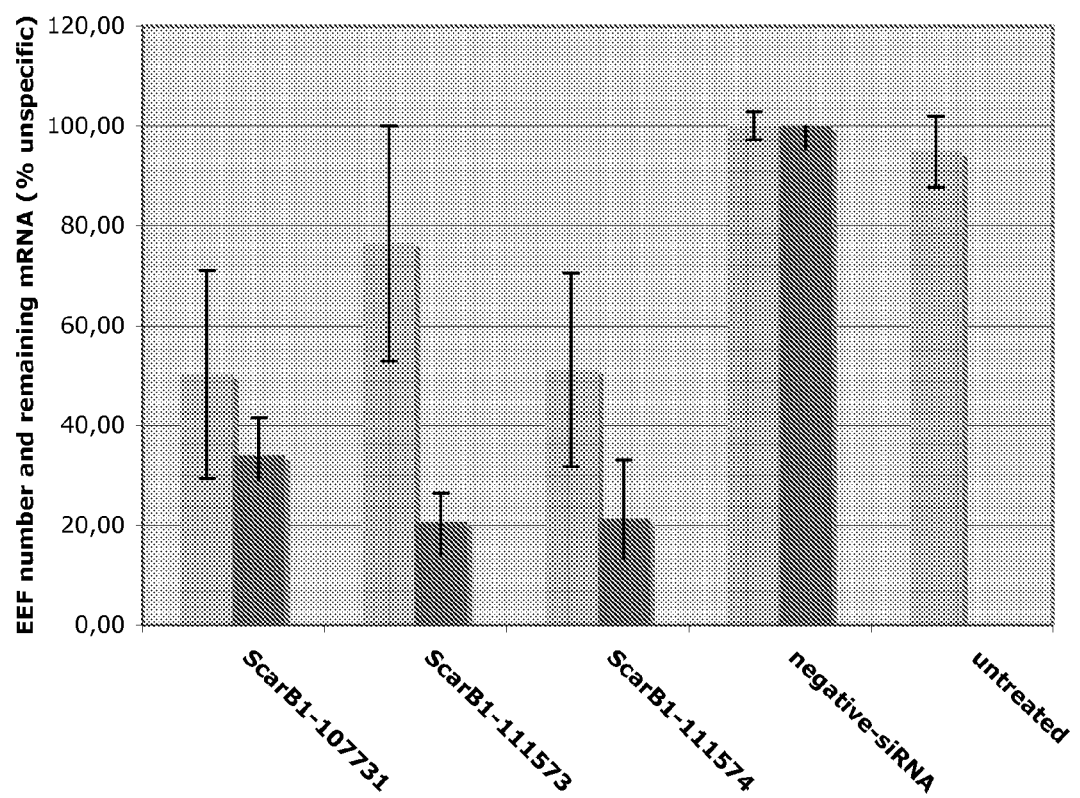

FIG. 8: Inhibitory effect on EEF development correlates with knock down of ScarB1. Dark bars depict the remaining mRNA and light bars depict the numbers of EEF.

FIG. 9: siRNAs sequences targeting ScarB1 (SEQ ID NO: 3 to SEQ ID NO: 8)

FIG. 10: Nucleic acid sequence of Homo sapiens scavenger receptor class B, member 1 (SCARB1), NM_005505.3 (SEQ ID NO: 1).

FIG. 11: Scavenger receptor class B, member 1 [*Homo sapiens*], amino acid sequence, NP_005496.3 (SEQ ID NO: 9).

Figure 12:
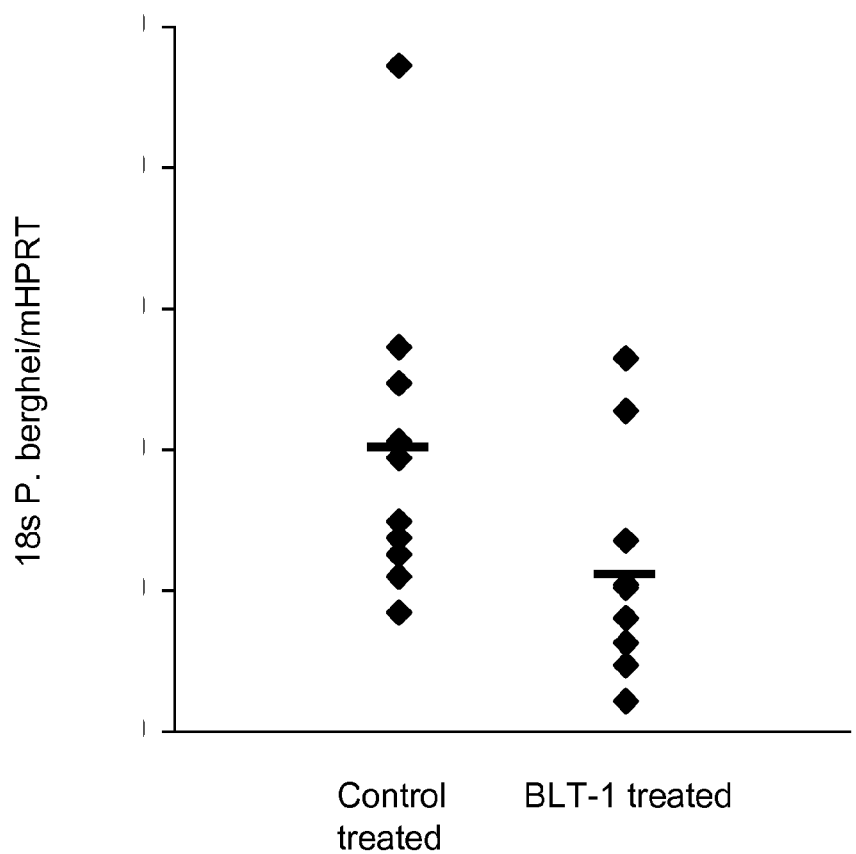

FIG. 12: BLT-1 reduces infection rate for liver in mice.

FIG. 13: Inhibitory effect on EEF development correlates with knock down of ScarB1 in living mice.

Figure 14:
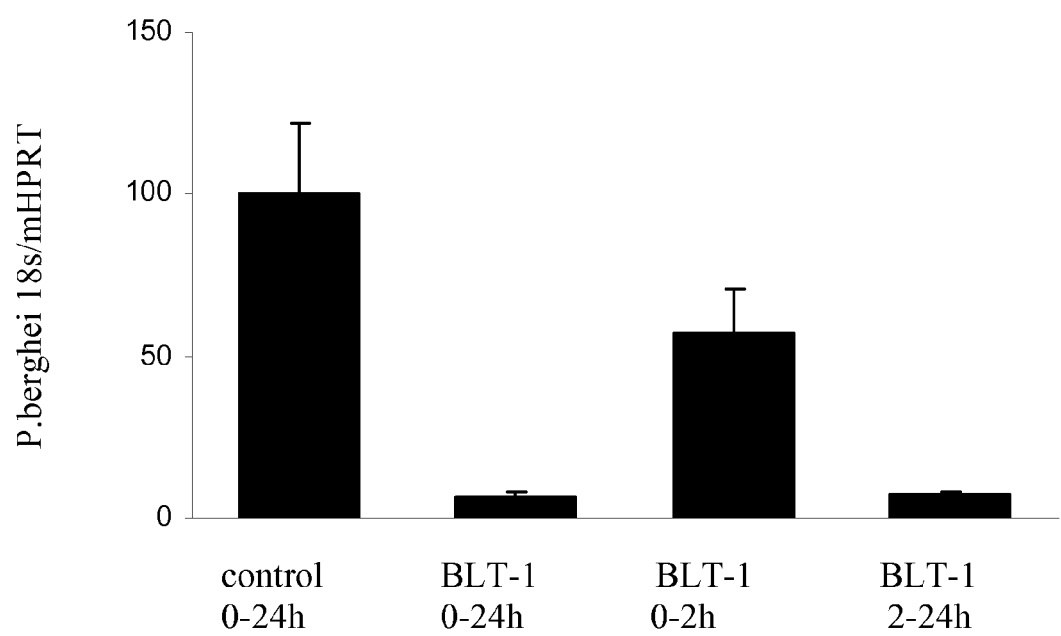

FIG. 14: Inhibition of EEF development in Mouse Primary Hepatocytes by BLT-1.

Figure 15:
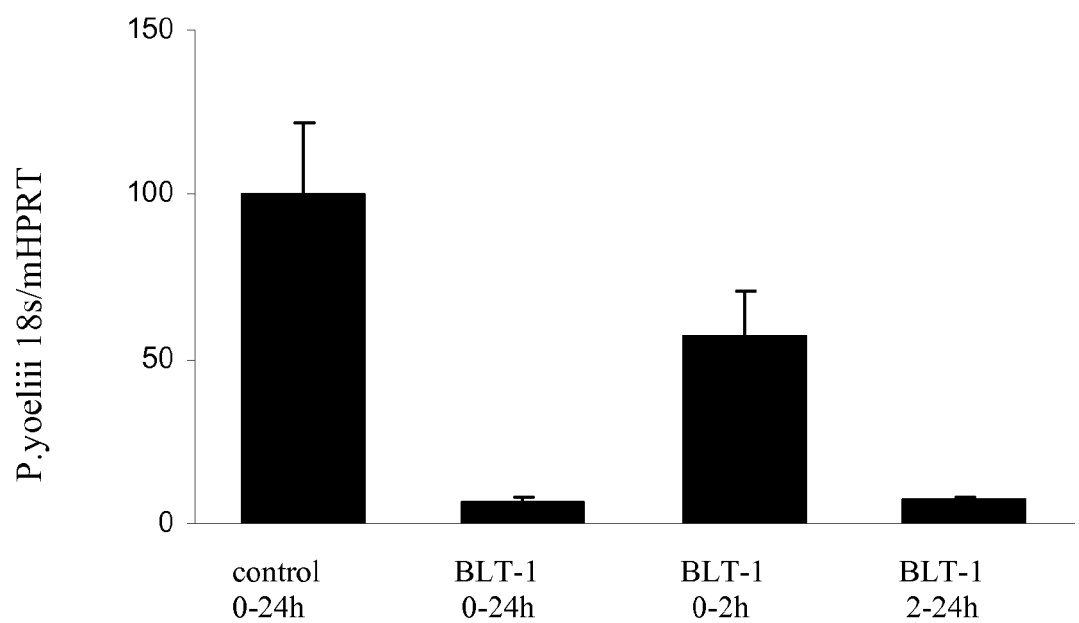

FIG. 15: Inhibition of *P. Yoelii* EEF development in Hepa 1-6 cells by BLT-1. The time period given indicates the length of the presence of 10 µM BLT-1 during infection.

FIG. 16: Infection Score for preferred compounds usable in the present invention and for comparative compounds.

EXAMPLES

Example 1

Cell Cultivation and Seeding

Huh human hepatoma cells, were cultivated in RPMI (Gibco/Invitrogen) medium containing 10% FBS, 1% nonessential amino acid solution (Gibco/Invitrogen), 1% penicillin/streptomycin solution (Gibco/Invitrogen), 1% glutamine (Gibco/Invitrogen) and 1% Hepes pH 8 (Gibco/Invitrogen).

Hepa 1-6 cells were cultured in complete DMEM medium (Gibco/Invitrogen) supplemented with 10% fetal calf serum (Gibco/Invitrogen) and 1% penicillin/streptomycin (Gibco/Invitrogen) incubated at 37° C. and 5% $CO_2$.

Cells were split twice per week by seeding $10^6$ cells in 15 ml complete medium in 75 ml culture flasks (Nunc). For passaging, cells were detached from the flask by incubation with 3 ml Trypsin solution (Gibco/Invitrogen) for 5 min at 37° C. Trypsin was inactivated by adding 10 ml of complete medium to the flask.

Cell based experiments were performed in black, optical 96 well plates (Costar/Corning).

4000-6000 cells per well were seeded in a volume of 100 µl/well.

To allow homogenous settling of the cells, the plates were left for 30 min at RT before they were transferred to an incubator with 37° C. and 5% $CO_2$.

Example 2

Isolation of Sporozoites of *Plasmodium Berghei* Anka or *Plasmodium Yoelii* from Mosquitoes Sporozoites were obtained from *Anopheles stephensi* mosquitoes infected with *P. berghei* ANKA or *P. yoelii*. Salivary glands were dissected and collected in RPMI medium (GIBCO) on ice. Collected tissues were gently ground in the medium to release sporozoites. Tissue fragments were removed by centrifugation at 40×g for 3 min, and sporozoites were collected from the supernatant.

Example 3

Treatment of Cells with Chemical Compounds Prior to Infection

Blt-1, Blt-2, and Blt-4 were purchased from ChemBridge Corporation (San Diego, USA). Ezetimibe (for chemical structure see FIG. 6 and structure (XXVI)) was derived from powdered Ezeterol tablets (Essex Pharma, UK). Each compound was dissolved in DMSO at a final concentration of 50 mM. 48 hours after seeding of 6000 Huh-7 cells per well, growth medium was replaced by fresh complete culture medium, containing the compounds in 4 different concentrations, generated by dilution series of the compound stock solutions in complete growth medium: 8 µM; 1.6 µM; 320 nM; 64 nM. Controls media were prepared according to DMSO concentrations in the 4 compound dilutions, i.e. 0.016%; 0.0032%; 0.00064%; 0.000128%. Huh-7 cells were equilibrated for 1 h with compound/DMSO-containing medium at 37° C. before infection with 10,000 sporozoites per well (FIGS. 1 to 4).

Example 4

Immuno-Staining of Cells and Fluorescence Microscopy Based Quantification of Infection Rate Cell Staining:

For the microscopy based analysis of sporozoite infection, cell proliferation and cell viability, experimental plates were subjected to the following fixation and antibody staining procedure:

Culture medium was completely removed by inverting the plates and replaced by 100 µl of 3% PFA in phosphate buffered saline (PBS). After an incubation step of 30 min at RT, experimental plates were washed 3 times with 500 µl of PBS per well.

Next, unspecific binding sites were blocked for 45 min at RT in PBS substituted with 0.1% saponin, 3% BSA 100 mM glycine and 10% FCS (blocking buffer).

After washing with 500 µl PBS/well, cells were incubated with a 1:500 dilution of a mouse monoclonal antibody, 2E6, targeting the parasite heat shock protein 70 (Tsuji et al., 1994) in blocking buffer for 45 min at RT. Complete removal of non-bound primary antibody was assured by extensive washing with PBS.

The secondary antibody solution consisting of blocking buffer, substituted with an alexa-555 labeled goat anti mouse secondary antibody (Molecular Probes/Invitrogen) in a final dilution of 1/1000, Phalloidin coupled to alexa-488 in a final dilution of 1/500 and Hoechst-33342 in a final dilution of 1:2000, was applied to the cells for 45 min at RT followed by extensive washing with PBS.

Finally, experimental plates were sealed with each well containing 100 µl of PBS and stored at 4° C. in the dark until image acquisition.

Image Acquisition:

Cells were imaged using a fully automated fluorescence microscope from MDC (Molecular Devices Corporation, CA, USA). Per experimental well 9 fields with a dimension of approx. 2×1.5 mm were acquired using excitation/emission conditions, optimized to the spectral properties of the three chromophores, alexa-488, alexa-555 and Hoechst-33342.

Image Analysis:

An automated image analysis routine based on Metamorph (Molecular Devices Corporation, CA, USA) was applied to the image sets from each well, consisting of 3 images, representing the channels for alexa 488, alexa 555 and Hoechst respectively, for each of the 9 fields acquired. Numerical readouts comprised of cell proliferation as measured by the number of nuclei per imaged field (Hoechst staining), cell confluency as measured by the percentage of the imaged field covered by cells (actin/Phalloidin staining), and number of EEFs per imaged field. EEFs were identified as bright, round objects in the 2E6 staining. Objects in a size range of 16-150 pixels were quantified.

Furthermore, visual analysis of the cellular and nuclear morphology using the actin/Phalloidin and Hoechst images allowed a manual evaluation of cell toxicity.

Data Normalization:

EEF numbers were normalized to the cell confluency (see above).

Next, EEF numbers, normalized to cell confluency, were averaged between the 9 fields imaged per well and normalized to the corresponding mean value from 3 untreated wells present on the same experimental plate.

Finally, for each treatment, mean value and standard deviation were calculated from the normalized average values of 3 replicate wells.

Example 5

Treatment of Mice with Ezetimibe or Blt-1 Prior to Infection

Ezeterol tablets were used to prepare a 0.3 mg/ml solution of Ezetimibe in water. Experimental C5781/6 mice were treated by oral gavage with 200 µl of Ezetimibe solution (3 mg/kg) 2 hours prior to infection with sporozoites. To control mice, 200 µl of water were administered by oral gavage. Infection with *Plasmodium berghei* was performed by i.v. injection of 30 000 sporozoites (see FIG. 5). For BLT-1 treatment of C57Bl/6 mice (male, 6-8 weeks old), intra-peritoneal injections of 50 mg/kg of BLT-1 in DMSO were carried out prior to infection. Control mice were treated with DMSO only. Two hours later, mice were infected by intravenous injection with 3×10$^4$ *P. berghei* sporozoites (see FIG. 12).

Example 6

Quantification of Liver Infection in Mice

Preparation of Liver Homogenates and RNA Extraction:

Mice were sacrificed 40-42 hours after infection and their livers collected. Livers were placed in 4 ml cold lysis buffer (4 M guanidine thio-cyanate, 25 mM sodium citrate, pH 7.0 and 0.5% sarcosyl) and homogenised on ice with a tissue tearer. 1 ml aliquots of liver homogenate were kept at −80° C. until RNA extraction. Total RNA was extracted from 50 µl of liver homogenate with Qiagen's RNeasy RNA extraction kit following the instructions of the manufacturer. Preparation of cDNA samples from the extracted RNA was carried out using the First Strand cDNA Synthesis Kit for RT-PCR (Roche) and following the manufacturer's instructions.

Quantification of *P. berghei* ANKA and ScarB1 in the Liver:

*P. berghei* ANKA load and ScarB1 expression in the liver was quantified by Real-Time PCR using the SYBR Green Mix (Applied Biosystems) and primers designed for the 18S RNA of the parasite and primers for ScarB1. The mouse hypoxanthine guanine phosphoribosyl transferase 1 (Hprt1) gene was used as housekeeping control to account for differential efficiencies in RNA extraction between samples (see FIGS. 5 and 13).

Example 7

Generation of dsRNA Molecules for RNAi Experiments siRNAs of a given nucleotide sequence were synthesized by Ambion, Inc. (Austin, Tex., USA), using standard methods known to the person skilled in the art of siRNA synthesis. The sequences of the two respective RNAs hybridized to each other are shown in the left and right hand panel of FIG. 9 (From left to right and from top to bottom SEQ ID NO: 3, 4, 5, 6, 7, and 8).

Example 8

Transfection of Cells with siRNAs Prior to Infection

For RNAi experiments, cells were transfected with siRNAs 24 h after cell seeding of 4000 cells per well of a 96well plate.

Each siRNA was transfected in triplicates; the transfection mix was prepared as follows:

4 µl of a 10 µM stock of siRNA was diluted with 64 µl of Opti-MEM (Invitrogen Inc.), and 1.6 µl Oligofectamine transfection reagent (Invitrogen) were diluted with 9.6 µl of Opti-MEM. For complex formation, both solutions were gently mixed and incubated for 20 min at RT.

After replacing the complete culture medium with 80 µl/well of serum free culture medium without antibiotics, 20 µl of transfection mix was added to each of 3 replicate wells.

Cells were incubated at 3TC for 4 hours and then shifted back to initial growth conditions by adding 50 µl of fresh medium, supplemented with 30% fetal calf serum and 3% Penicillin/Streptomycin.

Controls: Each 96 well screening plate contained 3 wells transfected with a control siRNA (sharing no complete sequence homology with any coding sequence in the human transcriptome) and 3 untreated wells. (FIGS. 7 and 8)

Example 9

Validation of siRNA Efficacy in Human Cells by Real-Time RT-PCR (QRT-PCR)

48 h after transfection total RNA was extracted from the cells using Invisorb 96 well kits (Invitek, Germany), following the protocol provided by the manufacturer. cDNA was synthesized using TaqMan RT reagents (Applied Biosystems, Foster City, Calif.) following the instructions provided by the manufacturer. Real-Time qPCR with gene-specific primers was performed in the following reaction mix 5.5 µl 2× SybrGreen PCR mix (ABgene, Surrey, UK)
3.0 µl cDNA
2.5 µl 2 µM primers
=11 µl total in an ABI-7900-HT real-time PCR machine (Applied Biosystems) running the following program:

50° C. 2 min-95° C. 10 min-45 cycles (95° C. 15 sec-60° C. 1 min)-95° C. 15 sec-60° C. 15 sec-95° C. 15 sec (melting curve).

In addition to expression of the gene of interest, expression level of GAPDH as a housekeeper was determined for each sample in order to account for inter-sample variability. The degree of knockdown was determined by comparing the amplification level for the gene of interest, normalized through the level of GAPDH, between samples transfected with a specific siRNA and samples transfected with unspecific control siRNAs. Dark bars delineate level of mRNA and light bars indicate number of EEFs (see FIG. 8).

Example 10

Assays to Determine Cholesterol Transport

Lipoproteins and Cells

This assay is essentially as described in WO 2004/032716. Briefly: Human HDL are isolated and labelled with either $^{125}$I ($^{125}$I-HDL), 1,1'-dioctadecyl-3,3,3',3'-tetramethylindocarbocyanine perchlorate (DiI, Molecular Probes; DiI-HDL) or [$^3$H]cholesteryl oleyl ether ([$^3$H]CE, [$^3$H]CE-HDL) (Gu, et al. (1998) *J. Biol. Chem.* 273, 26338-48; Gu, et al. (2000) *J. Biol. Chem.* 275, 29993-30001; Acton, et al. (1994) *J. Biol. Chem.* 269, 21003-9; Pitas, et al. (1981) *Arteriosclerosis* 1, 177-85). LDL receptor deficient Chinese hamster ovary cells that express low levels of endogenous ScarB1, 1d1A-7 (Kingsley, et al. (1984) *Proc. Nat. Acad. Sci. USA* 81, 5454-8), 1d1A-7 cells stably transfected to express high levels of murine ScarB1 (termed "1d1A[mSR-BI]", see Acton, et al., 1996), Y1-BS1 murine adrenocortical cells that express high levels of ScarB1 after induction with ACTH (Rigotti, et al. (1996) *J. Biol. Chem.* 271, 33545-9), monkey kidney BS-C1 cells (Kapoor, et al. (2000) *J. Cell Biol.* 150, 975-88) and HeLa cells (Temel, et al. (2002) *J. Biol. Chem.* 8, 8) are maintained as previously described.

High Throughput Screen

On day 0, 1d1A[mSR-BI] cells are plated at 15,000 cells/well in clear bottom, black wall 384-well black assay plates (Costar) in 50 µl of medium A (Ham's F12 supplemented with 2 mM L-glutamine, 50 units/ml penicillin/50 µg/ml streptomycin, and 0.25 mg/ml G418.) supplemented with 10% fetal bovine serum (medium B). On day 1, cells are washed once with medium C (medium A with 1% (w/v) bovine serum albumin (BSA) and 25 mM HEPES pH 7.4, but no G418) and supplied with 40 µl of medium C.

Test compounds are dissolved in 100% DMSO and are added manually or for high throughput screens robotically 'pin' transferred (40 nl) to each well to give a nominal concentration of 10 µM (0.01% DMSO). After a 1 hr incubation at 37° C., DiI-HDL (final concentration of 10 µg protein/ml) in 20 µl of medium C are added. Two hours later, fluorescence is measured at room temperature (approximately 2 minutes/plate) using a Analyst plate reader (Rhodamine B dichroic filter, emission 525 nm and excitation 580 nm; LJL Biosystems), both prior to removing the incubation medium (to test for autofluorescence and quenching) and after the medium removal and four washes with 80 µl of PBS/1 mM MgCl$_2$/0.1 mM CaCl$_2$ to determine cellular uptake of DiI. All compounds are sampled in duplicate on different plates, and each screen includes 1d1A-7 and 1d1A[mSR-BI] cells in the presence and/or absence of a 40-fold excess of unlabeled HDL, but with no added compounds, as controls.

Assays

For the assays, all media and buffers contain 0.5% DMSO and 0.5% bovine serum albumin to maintain compound solubility. Cells are pre-incubated with BLTs for 1 hr (or 2.5 hrs for transferrin, EGF and cholera toxin uptake experiments)

and all the experiments are performed at 37° C. Detailed characterization of the respective test compound and their effects is performed.

(i) Lipid Uptake from HDL, Cholesterol Efflux to HDL and HDL Binding Assays.

Assays for the uptake of lipids from DiI-HDL and $^3$CE-HDL, efflux of [$^3$H]cholesterol from labeled cells, and $^{125}$I-HDL binding are performed as described by Acton et al. (1996) *Science* 271:518-20; Gu, et al. (2000) *J. Biol. Chem.* 275:29993-30001; and Ji, et al. (1997) *J. Biol. Chem.* 272, 20982-5. In some experiments, values are normalized so that the 100% of control represents activity in the absence of compounds and 0% represents activity determined in the presence of a 40-fold excess of unlabeled HDL or, for Y1-BS1 cells, in the presence of a 1:500 dilution of the KKB-1 blocking antibody (Gu, et al., 2000, supra). The amounts of cell-associated [$^3$H]cholesteryl ether are expressed as the equivalent amount of [$^3$H]CE-HDL protein (ng) to permit direct comparison of the relative amounts of $^{125}$I-HDL binding and [$^3$H]CE uptake.

The rates of HDL dissociation from cells are determined by incubation of the cells with $^{123}$I-HDL (10 μg protein/ml, 2 hrs, 37° C.) with and without BLTs. The medium is then either replaced with the same medium in which the $^{125}$I-HDL is substituted by a 40-fold excess of unlabeled HDL or a 40-fold excess of unlabeled HDL is added to the labelled incubation medium. The amounts of cell-associated $^{123}$I-HDL are then determined as a function of time. Either of these methods can be used.

(ii) Fluorescence Microscopy Analysis of Intracellular Trafficking and Cytoskeletal Organization.

Receptor Mediated endocytosis of Alexa-594 labelled transferrin or FITC labelled epidermal growth factor (EGF, Molecular Probes) by HeLa cells (Spiro, et al. (1996) *Mol. Biol. Cell* 7, 355-67) and uptake of Alexa-594-labeled holocholera toxin by BSC-1 cells is detected by fluorescent microscopy. The intracellular transport of the temperature sensitive glycoprotein of vesicular stomatitis virus (VS-VG$^{ts045}$) fused at its carboxyl terminus to EGFP (VSVG$^{ts045}$-EGFP) from the endoplasmic reticulum to the plasma membrane, after a shift from 40° C. to 32° C. for 2 hrs, is determined by fluorescent microscopy. The effects of the compounds on the distribution of actin using rhodamine labeled phalloidin and tubulin using the FITC labelled DM1 monoclonal antibody (Sigma Co.) in 1d1A[mSR-BI] cells is determined as described by Rigotti, et al. (1996) *J. Biol. Chem.* 271, 33545-9 by fluorescence microscopy using an air 63* objective (Nikon).

Example 11

Knockdown Of ScarB1 in Mice by RNAi

C57B1/6 mice (male, 6-8 weeks old) were treated daily for 10 days with 200 μg/kg of the control siRNA (Negative, Ambion Inc., Texas, USA) or siRNA targeting SR-BI (ID 72593 and 152100, Ambion Inc., Texas, US). Mice were infected by intravenous injection of 2×10$^4$ *P. berghei* sporozoites. (see FIG. 13)

Example 12

Treatment Of Mouse Primary Hepatocytes with BLT-1 Prior to Infection with *P. Berghei* Sporozoites C57B1/6 freshly isolated mouse primary hepatocytes (1×10$^5$ cells per well) were seeded in 700 μl of Williams E medium supplemented with 1× glutamax (Gibco/Invitrogen), 4% fetal calf serum (Gibco/Invitrogen) and 1% penicillin/streptomycin (Gibco/Invitrogen) in 24 well plates incubated at 37° C. 5% $CO_2$.

After two days cells were treated with 10 μM BLT-1 for different time points: for the full 24 hours of infection with *P. berghei* (5×10$^5$ sporozoites), only during the first 2 hours of infection, or for the time of 2 hours after infection until evaluation at 24 hours. (see FIG. 14)

Example 13

Treatment of HEPA1-6 Cells with BLT-1 Prior to Infection with *P. yoelii* Sporozoites Cells were treated with 10 μM BLT-1 for different time points: for the full 24 hours of infection with *P. yoelii* (1×10$^5$ sporozoites), only during the first 2 hours of infection, or for the time of 2 hours after infection until evaluation of infection at 24 hours (see FIG. 15).

Example 14

Treatment of Huh-7 Cells with Various Compounds of the Invention

All compounds tested were synthesized by Tripos UK Ltd. or purchased from chemical suppliers.

Huh-7 human hepatoma cells were treated as described in examples 3 and 4. Incubation with the compounds was performed at final concentrations of 1, 2, 5, and 10 μM.

Influence of the compounds on proliferation and infection with plasmodium sporozoites was calculated as % of the plate mean for all samples, with the mean set to 100%. To assess its performance, each compound was assigned a score between 0 and 4 for inhibition of infection. A compound would score at 4, if at all 4 tested concentrations it would reduce the number of EEFs by at least 50% (corresponding to an $IC_{50}$ of 1 μM or lower), it would score at 3, if this was true for the 3 highest concentrations ($IC_{50}$ between 1 and 2 μM), and so on. (see FIG. 16).

We claim:

1. A method of treating a protozoal infection comprising the administration of an inhibitor of a scavenger receptor class protein to an individual having a protozoal infection, wherein the inhibitor of the scavenger receptor class protein has a structure according to formula (I):

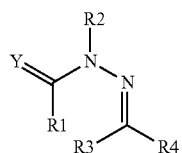

(I)

wherein,
$R^1$ is $NR^5R^6$;
$R^2$ is hydrogen or alkyl, optionally substituted;
$R^3$ and $R^4$ together form a $C_3$-, $C_4$-, $C_6$-, or $C_7$-cycloalkyl, $C_3$-, $C_5$- to $C_{10}$-heterocycloalkyl, $C_3$ to $C_{10}$-cycloalkenyl, or $C_6$-, $C_7$-, $C_9$-, $C_{10}$- heterocycloalkenyl, optionally substituted;
$R^5$ is hydrogen or alkyl, optionally substituted;
$R^6$ is hydrogen, hydroxyl, halogen, alkyl, cycloalkyl, heteroalkyl, cycloheteroalkyl, aryl, aralkyl, heteroaryl, heteroaralkyl, alkenyl, cycloalkenyl, alkynyl, alkanoyl, alkoxyalkyl; or —CO—R'; optionally substituted;
wherein
R' is hydrogen; alkyl; cycloalkyl; alkenyl; cycloalkenyl; aryl; aralkyl; heteroalkyl; cycloheteroalkyl; heteroaryl; heteroaralkyl; or alkynyl; optionally substituted;
and
Y is S,
or a pharmaceutically acceptable salt thereof.

2. The method according to claim 1, wherein the $C_3$-, $C_4$-, $C_6$-, or $C_7$-cycloalkyl is selected from the group consisting of cyclopropyl, cyclobutyl, cyclohexyl, cycloheptyl, ($C_6$- or $C_7$-)-spiroalkyl, bicyclo-[2.2.1]-heptyl, and the $C_6$-, $C_7$-, $C_9$-, or $C_{10}$-heterocycloalkyl is $C_6$-, $C_7$-, $C_9$-, or $C_{10}$-.spiroheteroalkyl.

3. The method according to claim 1, wherein the inhibitor of the scavenger receptor class protein has a structure according to formula (II)

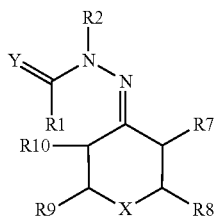

(II)

wherein,
$R^1$ is $NR^5R^6$;
$R^2$ is hydrogen or alkyl, optionally substituted;
$R^5$ is hydrogen or alkyl, optionally substituted;
$R^6$ is hydrogen, hydroxyl, halogen, alkyl, cycloalkyl, heteroalkyl, cycloheteroalkyl, aryl, aralkyl, heteroaryl, heteroaralkyl, alkenyl, cycloalkenyl, alkynyl, alkanoyl, alkoxyalkyl; or —CO—R' each of which can be optionally substituted, wherein
R' is hydrogen; alkyl; cycloalkyl; alkenyl; cycloalkenyl; aryl; aralkyl; heteroalkyl; cycloheteroalkyl; heteroaryl; heteroaralkyl; or alkynyl; each of which can be optionally substituted;
$R^7$, $R^8$, $R^9$, and $R^{10}$ are each independent of each other selected from the group consisting of hydrogen, hydroxyl, halogen, oxo, alkyl, heteroalkyl, cycloalkyl, heterocycloalkyl, alicyclic system, aryl, aralkyl, aralkenyl, aralkynyl, heteroaryl, heteroaralkyl, heteroaralkenyl, alkenyl, cycloalkenyl, heterocycloalkenyl, alkynyl, heteroaralkynyl, or $NR^{11}R^{12}$, optionally substituted and/or one or both of $R^7$ and $R^8$ or $R^9$ and $R^{10}$ are taken together to form an aryl or heteroaryl, optionally substituted;
$R^{11}$ is hydrogen or alkyl, optionally substituted;
$R^{12}$ is hydrogen, hydroxyl, halogen, alkyl, heteroalkyl, aryl, aralkyl, heteroaryl, heteroaralkyl, alkenyl, cycloalkenyl, or alkynyl, optionally substituted;
X is $CH_2$, $C_2H_4$, N, S or O; and
Y is S;
or a pharmaceutically acceptable salt thereof.

4. The method according to claim 1, wherein the compound according to formula (II) has a structure selected from the structures according to formulas (VIII) to (XXXI)

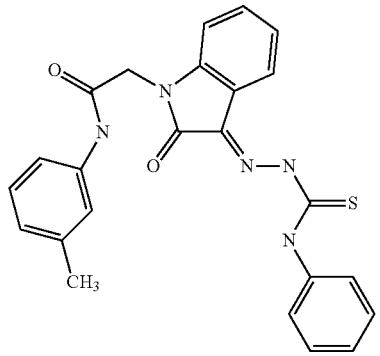

(IX)

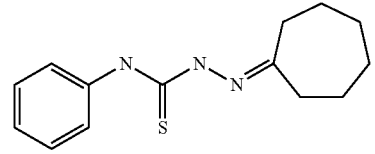

(X)

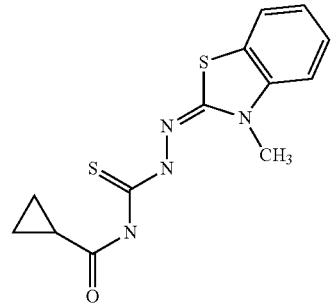

(XI)

-continued
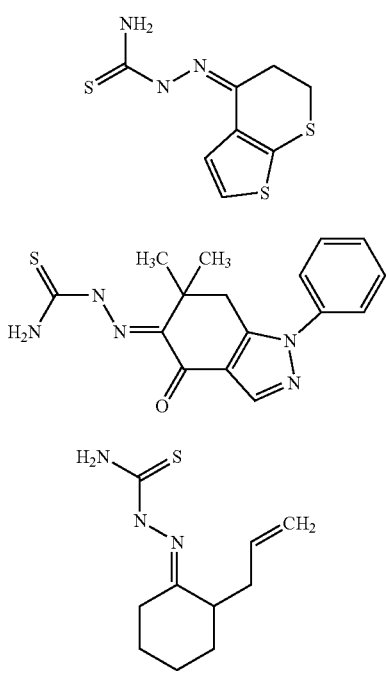
(XII)
(XIII)
(XIV)
(XV)
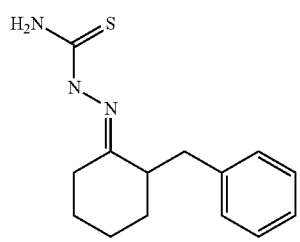
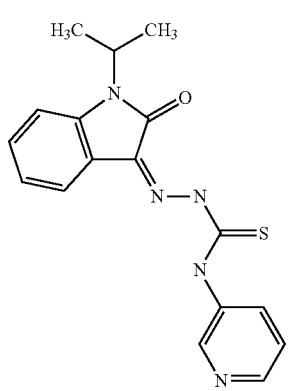
(XVII)
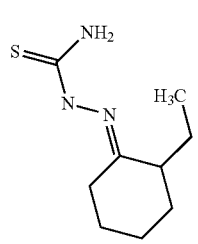
(XX)
-continued
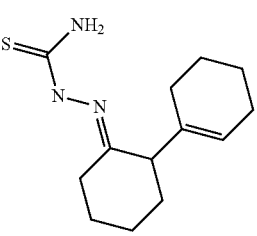
(XXI)
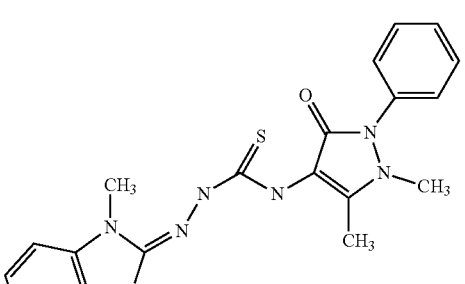
(XXIII)
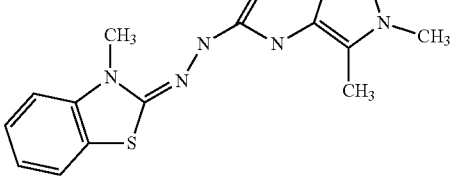
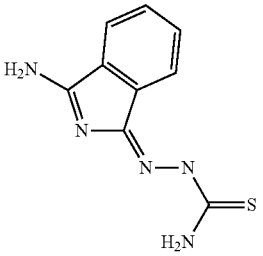
(XXIV)
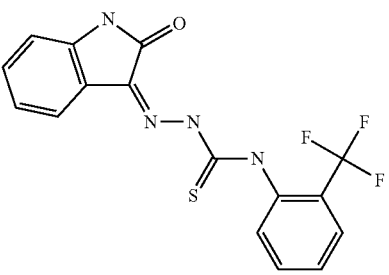
(XXV)
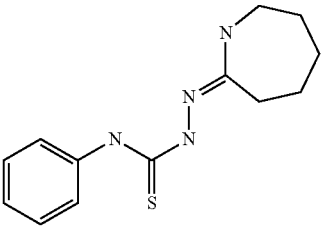
(XXVI)

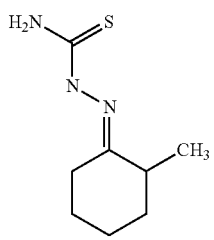

(XXVIII)

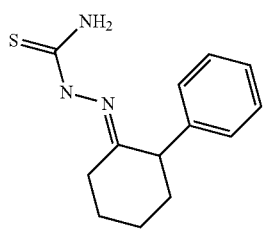

(XXIX)

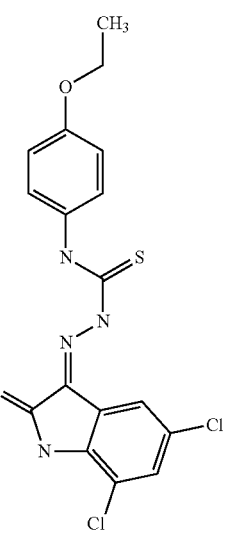

(XXXI)

each of which can be optionally substituted or pharmaceutically acceptable salts thereof.

5. The method according claim 1, wherein the protozoal infection is an infection with a protozoa selected from the group consisting of *Entomoeba histolytica, Trichomonas tenas, Trichomonas hominis, Trichomonas vaginalis, Trypanosoma gambiense, Trypanosoma rhodesiense, Trypanosoma cruzi, Leishmania donovani, Leishmania tropica, Leishmania braziliensis, Pneumocystis pneumonia, Toxoplasma gondii, Theileria lawrenci, Theileria parva, Plasmodium vivax, Plasmodium falciparum, Plasmodium berghei*, and *Plasmodium malaria*.

\* \* \* \* \*

UNITED STATES PATENT AND TRADEMARK OFFICE
CERTIFICATE OF CORRECTION

PATENT NO.       : 8,507,546 B2
APPLICATION NO.  : 13/548777
DATED            : August 13, 2013
INVENTOR(S)      : Michael Hannus et al.

It is certified that error appears in the above-identified patent and that said Letters Patent is hereby corrected as shown below:

In the Specification

Column 6,
Lines 59-60, "–$CH_2$–O–$C_3H_2$," should read -- –$CH_2$–O–$C_3H_7$,--.
Line 60, "–$C_2$–O–$C_5H_{11}$," should read -- –$CH_2$–O–$C_5H_{11}$,--.

Column 13,
Line 25, "($C_6$-$C_{10}$-" should read --($C_{6-10}$)- --.

Column 14,
Line 23, "benzothiazolyl," should read --benzotriazolyl,--.
Lines 25-26, "benzotriazinyl;" should read --1,2,4-benzotriazinyl;--.
Line 46, "$C_3$, C4," should read --$C_3$, $C_4$,--.

Column 19,
Line 14, "C9, $C_{10}$," should read --$C_9$, $C_{10}$,--.

Column 33,
Line 24, "($C_{1-6}$)" should read --($C_{1-16}$)--.

Column 36,
Line 20, "$R_{23}$, $R_{24}$, and $R^{25}$" should read --$R^{23}$, $R^{24}$, and $R_{25}$--.
Line 39, "2,1-benzisoxazoly 1;" should read --2,1-benzisoxazolyl;--.

Column 39,
Line 13, "($C_{1-4}$)alkoxy," should read --($C_{1-6}$)alkoxy,--.

Signed and Sealed this
Seventh Day of January, 2014

Margaret A. Focarino
*Commissioner for Patents of the United States Patent and Trademark Office*

CERTIFICATE OF CORRECTION (continued)
U.S. Pat. No. 8,507,546 B2

Page 2 of 8

Column 47,

MIT 9952-25, " 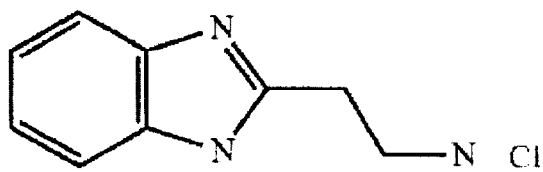 " should read

-- MIT 9952-25 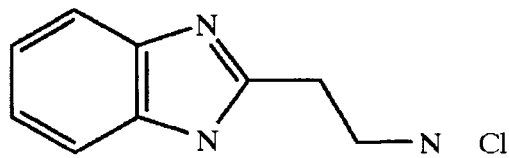 --.

Column 77,

MIT 9952-110, " 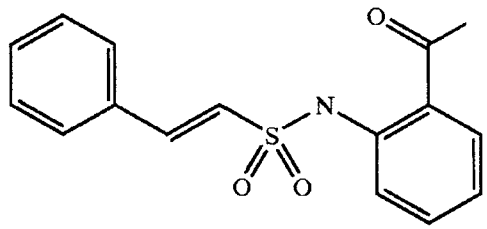 " should read

-- MIT 9952-110 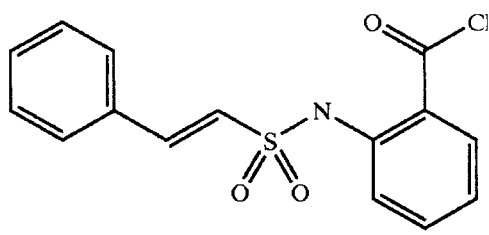 --.

Column 97,

MIT 9952-162, " 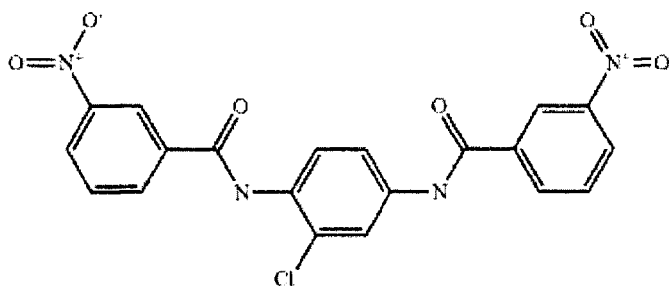 " should read

CERTIFICATE OF CORRECTION (continued)
U.S. Pat. No. 8,507,546 B2

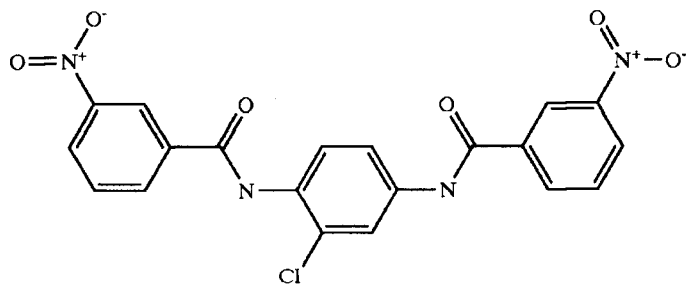

-- MIT 9952-162 --.

Column 99,

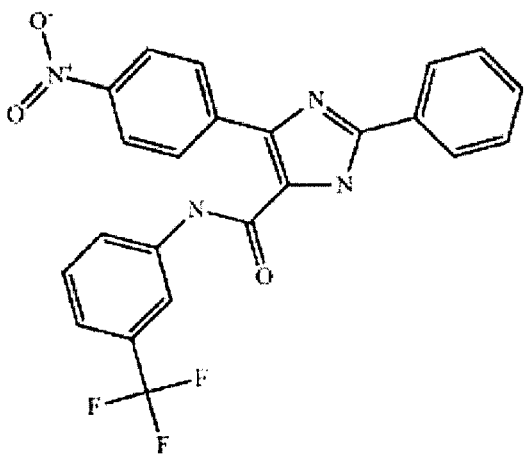

MIT 9952-166, " MIT 9952-166 " should read

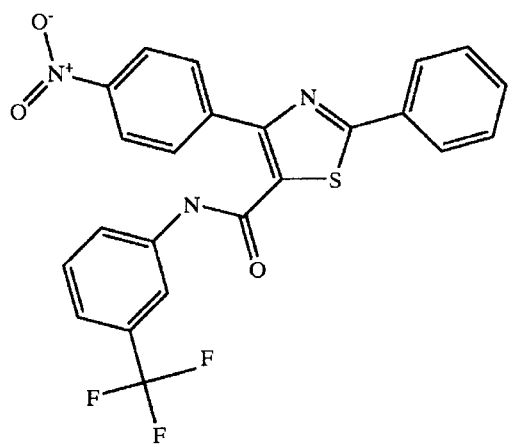

-- MIT 9952-166 --.

CERTIFICATE OF CORRECTION (continued)  Page 4 of 8
U.S. Pat. No. 8,507,546 B2

Column 147,

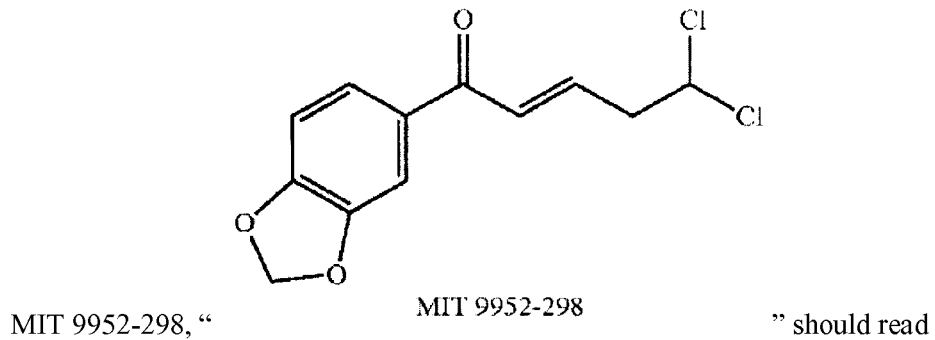

MIT 9952-298, " " should read

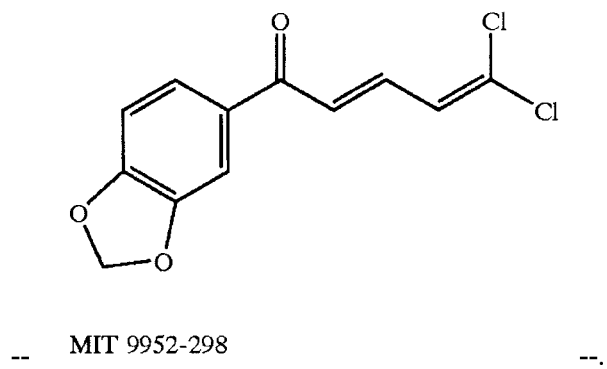

-- MIT 9952-298 --.

Column 147,

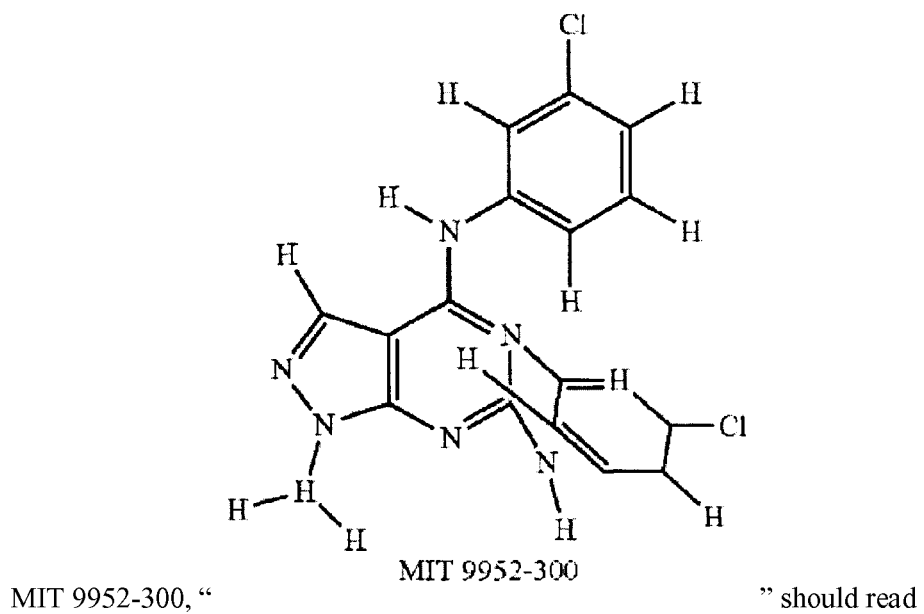

MIT 9952-300, " " should read

CERTIFICATE OF CORRECTION (continued)
U.S. Pat. No. 8,507,546 B2

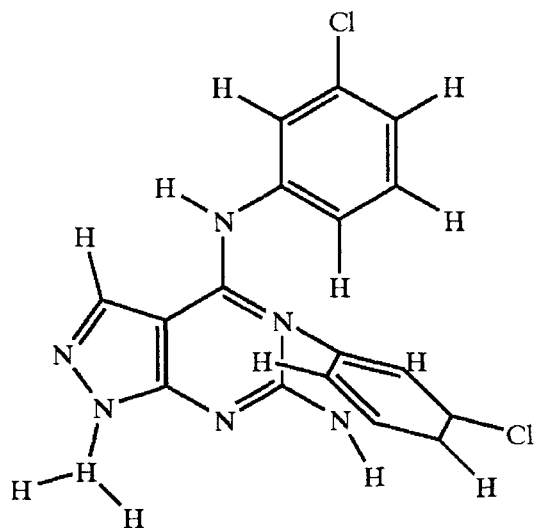

-- MIT 9952-300 --.

<u>Column 149,</u>

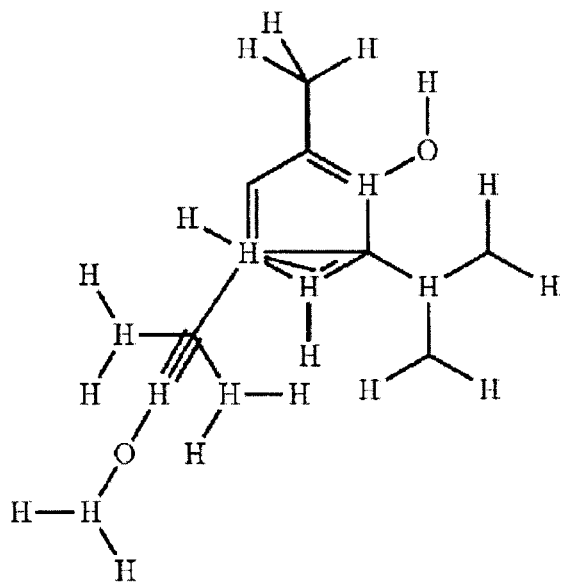

MIT 9952-307, " MIT 9952-307 " should read

CERTIFICATE OF CORRECTION (continued)
U.S. Pat. No. 8,507,546 B2

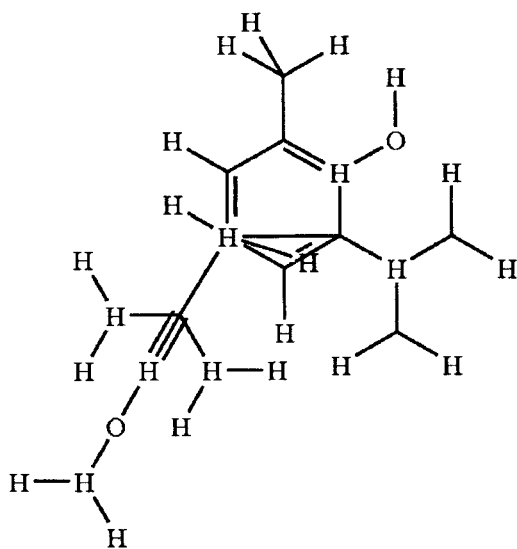

-- MIT 9952-307                    --.

Column 151,

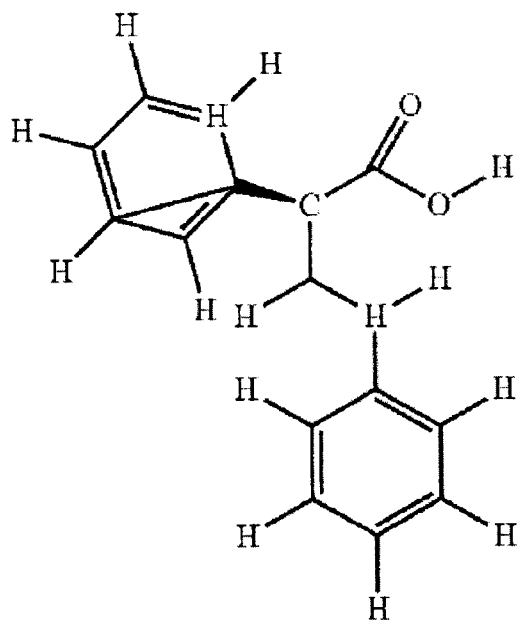

MIT 9952-310, "                MIT 9952-310                " should read

CERTIFICATE OF CORRECTION (continued)
U.S. Pat. No. 8,507,546 B2

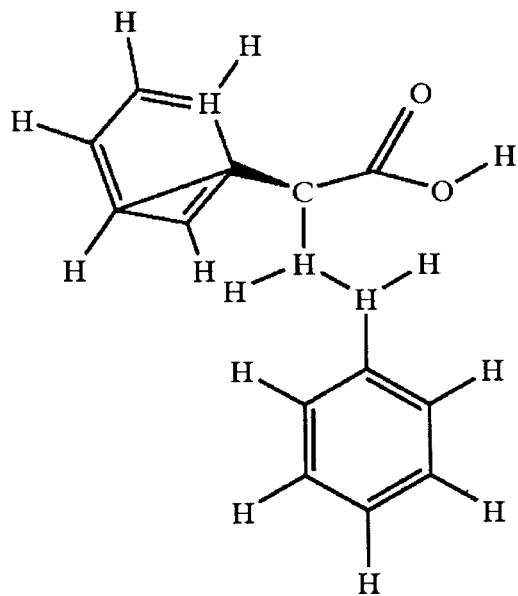

-- MIT 9952-310 --.

Column 151,

MIT 9952-311, " 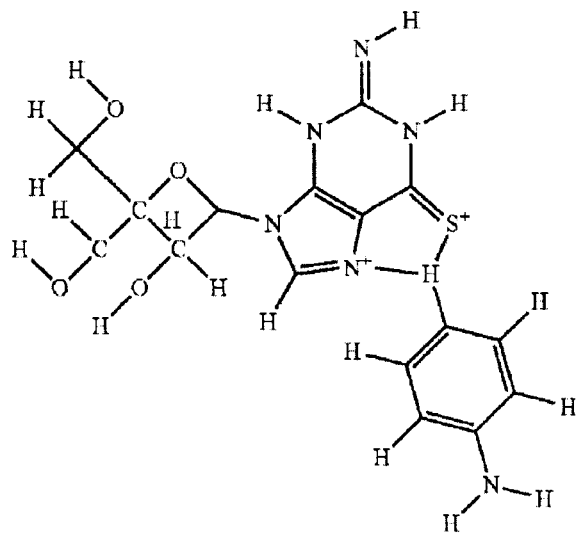 " should read

CERTIFICATE OF CORRECTION (continued)
U.S. Pat. No. 8,507,546 B2

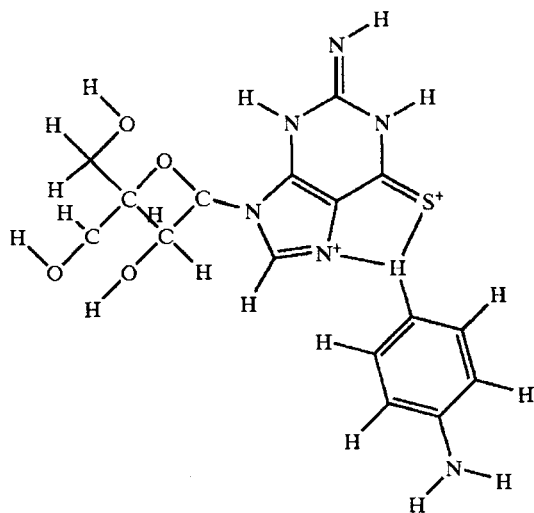

-- MIT 9952-311            --.

Column 153,

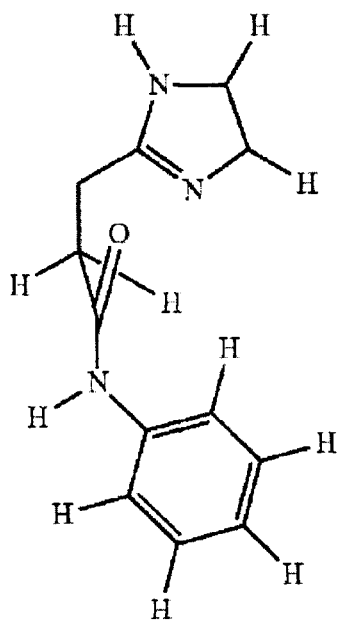
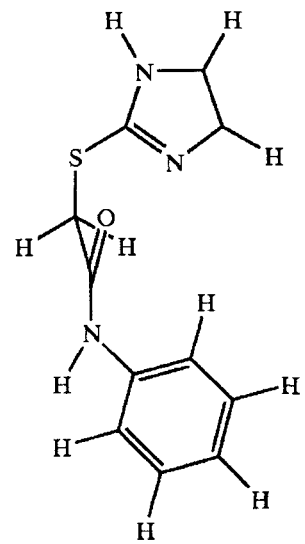

MIT 9952-314, " MIT 9952-314 " should read -- MIT 9952-314 --.

Column 177,
Line 38, "at 3TC for" should read --at 37°C for--.